(12) United States Patent
Donner et al.

(10) Patent No.: US 8,986,740 B2
(45) Date of Patent: *Mar. 24, 2015

(54) ANTI-INFECTIVE AGENTS AND USES THEREOF

(75) Inventors: Pamela L. Donner, Mundelein, IL (US); John T. Randolph, Libertyville, IL (US); Allan C. Krueger, Gurnee, IL (US); David A. Betebenner, Libertyville, IL (US); Douglas K. Hutchinson, Antioch, IL (US); Dachun Liu, Waukegan, IL (US); Yaya Liu, Buffalo Grove, IL (US); Kenton L. Longenecker, Grayslake, IL (US); Clarence J. Maring, Palatine, IL (US); John K. Pratt, Kenosha, WI (US); Todd W. Rockway, Grayslake, IL (US); Kent D. Stewart, Gurnee, IL (US); Rolf Wagner, Antioch, IL (US); Shuang Chen, Gurnee, IL (US); Yi Gao, Vernon Hills, IL (US); John E. Hengeveld, Kenosha, WI (US); Rodger F. Henry, Wildwood, IL (US); Xiaochun Lou, Long Grove, IL (US); Geoff G. Z. Zhang, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 347 days.

This patent is subject to a terminal disclaimer.

(21) Appl. No.: 13/441,528

(22) Filed: Apr. 6, 2012

(65) Prior Publication Data

US 2012/0189580 A1    Jul. 26, 2012

Related U.S. Application Data

(63) Continuation of application No. 12/212,315, filed on Sep. 17, 2008, now Pat. No. 8,178,548.

(60) Provisional application No. 60/972,887, filed on Sep. 17, 2007, provisional application No. 61/096,794, filed on Sep. 13, 2008.

(51) Int. Cl.
*A61K 9/14* (2006.01)
*A61K 31/505* (2006.01)
(Continued)

(52) U.S. Cl.
CPC ............ *C07D 239/22* (2013.01); *C07D 239/54* (2013.01); *C07D 239/553* (2013.01);
(Continued)

(58) Field of Classification Search
USPC ........................................... 514/269; 424/489
See application file for complete search history.

(56) References Cited

U.S. PATENT DOCUMENTS 4,239,888 A    12/1980  Miller
4,588,729 A     5/1986  Teranishi et al.
(Continued)

FOREIGN PATENT DOCUMENTS

JP    5213755 A    8/1993
WO   9705117 A1   2/1997
(Continued)

OTHER PUBLICATIONS

Ansel H.C., et al., Ansel's Pharmaceutical Dosage forms and Drug Delivery Systems, 8th Edition, Lippincott Williams & Wilkins, 2005, Table of Contents.
(Continued)

*Primary Examiner* — Shengjun Wang
(74) *Attorney, Agent, or Firm* — Bradley E. Davis

(57) ABSTRACT

This invention relates to: (a) compounds and salts thereof that, inter alia, inhibit HCV; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

40 Claims, 23 Drawing Sheets

(51) Int. Cl.
| | |
|---|---|
| C07D 239/22 | (2006.01) |
| C07D 239/54 | (2006.01) |
| C07D 239/553 | (2006.01) |
| C07D 401/10 | (2006.01) |
| C07D 403/10 | (2006.01) |
| C07D 405/10 | (2006.01) |
| C07D 409/10 | (2006.01) |
| C07D 413/10 | (2006.01) |

(52) U.S. Cl.
CPC ............ *C07D401/10* (2013.01); *C07D 403/10* (2013.01); *C07D 405/10* (2013.01); *C07D 409/10* (2013.01); *C07D 413/10* (2013.01)
USPC .......................................... 424/489; 514/269

(56) References Cited

U.S. PATENT DOCUMENTS

| | | | |
|---|---|---|---|
| 5,084,084 | A | 1/1992 | Satow et al. |
| 5,127,935 | A | 7/1992 | Satow et al. |
| 5,154,755 | A | 10/1992 | Satow et al. |
| 5,162,326 | A | 11/1992 | Naka et al. |
| 5,164,396 | A | 11/1992 | Grosscurt et al. |
| 6,380,387 | B1 | 4/2002 | Sidduri et al. |
| 6,537,948 | B1 | 3/2003 | Tohyama et al. |
| 8,178,548 | B2 | 5/2012 | Donner et al. |
| 8,188,104 | B2 | 5/2012 | Flengte et al. |

FOREIGN PATENT DOCUMENTS

| | | |
|---|---|---|
| WO | 0142225 A2 | 6/2001 |
| WO | 0190121 A2 | 11/2001 |
| WO | 0142225 A3 | 2/2002 |
| WO | 2005021500 A1 | 3/2005 |
| WO | 2009039127 A1 | 3/2009 |
| WO | 2009039134 A1 | 3/2009 |
| WO | 2009039135 A1 | 3/2009 |
| WO | 2010010017 A1 | 1/2010 |

OTHER PUBLICATIONS

Aulton M.E., ed., the Design of Dosage Forms : in Pharmaceutics: The Science of Dosage Form Design, 2nd Edition, Churchill Livingstone, 2004, Table of Contents.
Austin W.B., et al., "Facile Synthesis of Ethynylated Benzoic Acid Derivatives and Aromatic Compounds via Ethynyltrimethylsilane," Journal of Organic Chemistry, 1981, vol. 46 (11), pp. 2280-2286.
Baltrushis R.S., et al., "Bromo Derivatives of 1-(4-hydroxyphenyl)dihydrouracil and -(4-hydroxyphenyl)-5- or -6-Methyldihydrouracils," Chemistry of Heterocyclic Compounds, 1982, vol. 18 (9), pp. 1251-1254.
Baltrusis, et al., CAPLUS Abstract 97:216122, 1982.
Blight K.J., et al., "Efficient Initiation of HCV RNA Replication in Cell Culture," 2000, vol. 290 (5498), pp. 1972-1974.
Blight K.J., et al., "Efficient Replication of Hepatitis C Virus Genotype 1 a RNAs in Cell Culture," 2003, vol. 77 (5), pp. 3181-3190.
Camma C., et al., "The Impact of Antiviral Treatments on the Course of Chronic Hepatitis C: An Evidence-Based Approach," Current Pharmaceutical Design, 2004, vol. 10 (17), pp. 2123-2130.
De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.
De Francesco R., et al., "Challenges and Successes in Developing New Therapies for Hepatitis C," Nature, 2005, vol. 436 (7053), pp. 953-960.
European Search Report for Application No. EP12185550, mailed on Dec. 14, 2012, 1 page.

Gravel M., et al., "Practical Procedure for the Preparation of Functionalized (E)-1-Alkenylboronic Acids Including the Unprecedented 1-Alkoxycarbonyl Derivatives," 2004, vol. 36 (6), pp. 573-579.
Hilfiker R., et al., "Relevance of Solid-state Properties for Pharmaceutical Products," Polymorphism, 2006, pp. 1-19.
International Preliminary Report on Patentability and Written Opinion for Application No. PCT/US2008/076576, mailed on Feb. 12, 2010, 38 pages.
International Preliminary Report on Patentability and Written Opinion for Application No. PCT/US2008/076592, mailed on Mar. 24, 2010, 7 pages.
International Preliminary Report on Patentability and Written Opinion for Application No. PCT/US2008/076594, mailed on Mar. 24, 2010, 7 pages.
International Search Report for Application No. PCT/US2008/076576, mailed on Dec. 22, 2008, 4 pages.
International Search Report for Application No. PCT/US2008/076592, mailed on Feb. 16, 2009, 2 pages.
International Search Report for Application No. PCT/US2008/076594, mailed on Dec. 30, 2008, 2 pages.
Jacobsen M.F., et al., "Efficient N-Arylation and N-Alkenylation of the Five DNA/RNA Nucleobases," Journal of Organic Chemistry, 2006, vol. 71 (24), pp. 9183-9190.
Koch U., et al., "2-(2-Thienyl)-5,6-dihydroxy-4-carboxypyrimidines as Inhibitors of the Hepatitis C Virus NS5B Polymerase: Discovery, SAR, Modeling, and Mutagenesis," Journal of Medicinal Chemistry, 2006, vol. 49 (5), pp. 1693-1705.
Lal G.S. et al., "A Convenient Synthesis of 5-Fluoropyrimidines Using 1-(Chloromethyl)-4-fluoro- 1,4-diazabicyclo [2.2.2]octane Bis(tetrafluoroborate)-SELECTFLUOR Reagent," J. Org. Chem, vol. 60 (22), pp. 7340-7342, 1995.
Lohmann V., et al., "Replication of Subgenomic Hepatitis C Virus RNAs in a Hepatoma Cell Line," Science, 1999, vol. 285 (5424), pp. 110-113.
Mathe C., et al., "L-nucleoside Enantiomers as Antivirals Drugs: A Mini-review," Antiviral Research, 2006, vol. 71, pp. 276-281.
Miller M.W., et al., "Anticoccidial Activity of 1-Phenyluracils," Journal of Medicinal Chemistry, 1983, vol. 26 (7), pp. 1075-1076.
Morrison J.F., et al., "Approaches to the Study and Analysis of the Inhibition of Enzymes by Slow- and Tight-Binding Binding Inhibitors," Comments Molecular Cellular Biophysics, 1985, vol. 2(6), pp. 347-368.
Ohira S., "Methanolysis of Dimethyl (1-Diazo-2-Oxopropyl)Phosphonate: Generation of Dimethyl(DiazoMethyl) Phosphonate and Reaction with Carbonyl Compounds," Synthetic Communications, 1989, vol. 19 (3-4), pp. 561-564.
Onitsuka K., et al., "Living Polymerization of Bulky Aryl Isocyanide with Arylrhodium Complexes," Organometallics, 2006, vol. 25 (5), pp. 1270-1278.
Remington J.P., ed., Pharmaceutical Sciences, 15th Edition, Mack Publishing Company, 1975, pp. 411-415.
Santana L., et al., "A Slightly Shorter Route to Carbocyclic Nucleosides. Synthesis of (±)-trans- I [2-(Hydroxymethyl) cyclopentylmethyl]uracil," Journal of Heterocyclic Chemistry, 1999, vol. 36, pp. 293-295.
Supplementary International Search Report for Application No. PCT/US2008/076576, mailed on Jan. 14, 2010, 2 pages.
Taylor W.P., et al., "Quiescent Affinity Inactivators of Protein Tyrosine Phosphatases," Bioorganic & Medicinal Chemistry, 1996, vol. 4 (9), pp. 1515-1520.
Ueno Y., et al., "Synthesis and Properties of Nucleic Acid Analogues Consisting of a Benzene-Phosphate Backbone," Journal of Organic Chemistry, 2005, vol. 70 (20), pp. 7925-7935.
Zhou T., et al., "Hypervalent Iodine in Synthesis: Part 86. Selective Copper-catalyzed N-monoarylation and N1, N3 Diarylation of Uracil and its Derivatives with Diaryliodonium Salts," Helvetica Chimica Acta, 2005, vol. 88 (2), pp. 290-296.

ANTI-INFECTIVE AGENTS AND USES THEREOF

CROSS-REFERENCE TO RELATED PATENT APPLICATIONS

This patent application is a continuation of U.S. patent application Ser. No. 12/212,315 (filed Sep. 17, 2008) which claims priority to U.S. Provisional Patent Application No. 60/972,887 (filed Sep. 17, 2007) and U.S. Provisional Patent Application No. 61/096,794 (filed Sep. 13, 2008). The entire text of those applications is incorporated by reference into this application.

FIELD OF THE INVENTION

This invention is directed to: (a) compounds and salts thereof that, inter alia, are useful as hepatitis C virus (HCV) inhibitors; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

BACKGROUND OF THE INVENTION

Hepatitis C is a blood-borne, infectious, viral disease that is caused by a hepatotropic virus called HCV. At least six different HCV genotypes (with several subtypes within each genotype) are known to date. In North America, HCV genotype 1a predominates, followed by HCV genotypes 1b, 2a, 2b, and 3a. In the United States, HCV genotypes 1, 2, and 3 are the most common, with about 80% of the hepatitis C patients having HCV genotype 1. In Europe, HCV genotype 1b is predominant, followed by HCV genotypes 2a, 2b, 2c, and 3a. HCV genotypes 4 and 5 are found almost exclusively in Africa. As discussed below, the patient's HCV genotype is clinically important in determining the patient's potential response to therapy and the required duration of such therapy.

An HCV infection can cause liver inflammation (hepatitis) that is often asymptomatic, but ensuing chronic hepatitis can result in cirrhosis of the liver (fibrotic scarring of the liver), liver cancer, and/or liver failure. The World Health Organization estimates that about 170 million persons worldwide are chronically infected with HCV, and from about three to about four million persons are newly infected globally each year. According to the Centers for Disease Control and Prevention, about four million people in the United States are infected with HCV. Co-infection with the human immunodeficiency virus (HIV) is common, and rates of HCV infection among HIV positive populations are higher.

There is a small chance of clearing the virus spontaneously, but the majority of patients with chronic hepatitis C will not clear it without treatment. Indications for treatment typically include proven HCV infection and persistent abnormal liver function tests. There are two treatment regimens that are primarily used to treat hepatitis C: monotherapy (using an interferon agent—either a "conventional" or longer-acting pegylated interferon) and combination therapy (using an interferon agent and ribavirin). Interferon, which is injected into the bloodstream, works by bolstering the immune response to HCV; and ribavirin, which is taken orally, is believed to work by preventing HCV replication. Taken alone, ribavirin does not effectively suppress HCV levels, but an interferon/ribavirin combination is more effective than interferon alone. Typically, hepatitis C is treated with a combination of pegylated interferon alpha and ribavirin for a period of 24 or 48 weeks, depending on the HCV genotype.

The goal of treatment is sustained viral response—meaning that HCV is not measurable in the blood after therapy is completed. Following treatment with a combination of pegylated interferon alpha and ribavirin, sustained cure rates (sustained viral response) of about 75% or better occur in people with HCV genotypes 2 and 3 in 24 weeks of treatment, about 50% in those with HCV genotype 1 with 48 weeks of treatment, and about 65% in those with HCV genotype 4 in 48 weeks of treatment.

Treatment may be physically demanding, particularly for those with prior history of drug or alcohol abuse, because both interferon and ribavirin have numerous side effects. Common interferon-associated side effects include flu-like symptoms, extreme fatigue, nausea, loss of appetite, thyroid problems, high blood sugar, hair loss, and skin reactions at the injection site. Possible serious interferon-associated side effects include psychoses (e.g., suicidal behavior), heart problems (e.g., heart attack, low blood pressure), other internal organ damage, blood problems (e.g., blood counts falling dangerously low), and new or worsening autoimmune disease (e.g., rheumatoid arthritis). Ribavirin-associated side effects include anemia, fatigue, irritability, skin rash, nasal stuffiness, sinusitis, and cough. Ribavirin can also cause birth defects, so pregnancy in female patients and female partners of male patients must be avoided during treatment and for six months afterward.

Some patients do not complete treatment because of the serious side effects discussed above; other patients (non-responders) continue to have measurable HCV levels despite treatment; and yet other patients (relapsers) "clear" the virus during therapy, but the virus returns sometime after completion of the treatment regimen. Thus, there continues to be a need for alternative compounds, compositions, and methods of treatment (used either in combination with or in lieu of an interferon agent and/or ribavirin) to alleviate the symptoms of hepatitis C, thereby providing partial or complete relief. This invention provides compounds (including salts thereof), compositions, and methods of treatment that generally address such a need.

SUMMARY OF THE INVENTION

This invention is directed to compounds that correspond in structure to formula I:

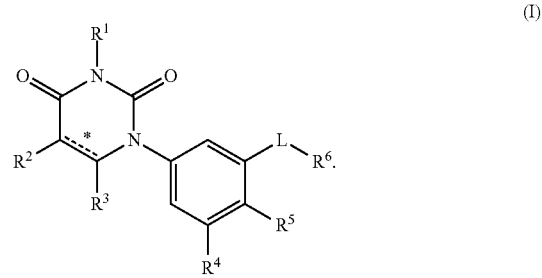

(I)

In formula I:

$\cdots$ is selected from the group consisting of single carbon-carbon bond and double carbon-carbon bond;

$R^1$ is selected from the group consisting of hydrogen, methyl, and nitrogen-protecting group;

$R^2$ is selected from the group consisting of hydrogen, halo, hydroxy, methyl, cyclopropyl, and cyclobutyl;

R³ is selected from the group consisting of hydrogen, halo, oxo, and methyl;

R⁴ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
  (a) the amino, aminocarbonyl, and aminosulfonyl optionally are substituted with:
    (1) one or two substituents independently selected from the group consisting of alkyl, alkenyl, alkynyl, and alkylsulfonyl, or
    (2) two substituents that, together with the amino nitrogen, form a single-ring heterocyclyl, and
  (b) the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
    the amino optionally is substituted with:
      (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
      (2) two substituents that, together with the amino nitrogen, form a single-ring heterocyclyl, and
  (c) the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
    the amino optionally is substituted with:
      (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
      (2) two substituents that, together with the amino nitrogen, form a single-ring heterocyclyl;

R⁵ is selected from the group consisting of hydrogen, hydroxy, alkyl, alkenyl, alkynyl, alkyloxy, alkenyloxy, alkynyloxy, alkylsulfonyloxy, carbocyclylsulfonyloxy, haloalkylsulfonyloxy, and halo;

L is selected from the group consisting of $C(R^A)=C(R^B)$, ethylene, and cyclopropyl-1,2-ene;

$R^A$ and $R^B$ are independently selected from the group consisting of hydrogen, $C_1$-$C_6$-alkyl, $C_1$-$C_6$-alkyloxy, $C_3$-$C_8$-cycloalkyl, and halo, wherein:
  the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl;

R⁶ is selected from the group consisting of $C_5$-$C_6$-carbocyclyl, 5-6-membered heterocyclyl, fused 2-ring carbocyclyl, and fused 2-ring heterocyclyl, wherein each such substituent optionally is substituted with one or more substituents independently selected from the group consisting of $R^E$, $R^F$, $R^G$, $R^H$, $R^I$, $R^J$, and $R^K$;

each $R^E$ is independently selected from the group consisting of halo, nitro, hydroxy, oxo, carboxy, cyano, amino, imino, azido, and aldehydro, wherein:
  the amino optionally is substituted with one or two substituents independently selected from the group consisting of alkyl, alkenyl, and alkynyl;

each $R^F$ is independently selected from the group consisting of alkyl, alkenyl, and alkynyl, wherein:
  each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, imino, aminosulfonyl, aminocarbonyl, carbocyclyl, and heterocyclyl optionally are substituted with one or two substituents independently selected from the group consisting of alkyl, alkenyl, alkynyl, alkylsulfonyl, alkenylsulfonyl, alkynylsulfonyl, alkylsulfonylamino, hydroxy, and alkyloxy, wherein:
      amino portion of the alkylsulfonylamino optionally is substituted with a substituent selected from the group consisting of alkyl, alkenyl, and alkynyl;

each $R^G$ is independently selected from the group consisting of carbocyclyl and heterocyclyl, wherein:
  each such substituent optionally is substituted with one or more substituents independently selected from the group consisting of alkyl, alkenyl, alkynyl, carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl;

each $R^H$ is independently selected from the group consisting of alkyloxy, alkenyloxy, alkynyloxy, alkylsulfonyloxy, alkenylsulfonyloxy, and alkynylsulfonyloxy, wherein:
  each such substituent optionally is substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl;

each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein:
  (a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and
  (b) the aminocarbonyl optionally is substituted with one or two substituents independently selected from the group consisting of alkyl, alkenyl, alkynyl, alkyloxyalkyl, carbocyclyl, heterocyclyl, alkylsulfonyl, and alkylsulfonylamino, wherein:
   the carbocyclyl and heterocyclyl optionally are substituted with one or two substituents independently selected from the group consisting of halo, alkyl, and oxo;
each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkyloxycarbonylaminoimino, alkylsulfonylaminoimino, alkenylsulfonylaminoimino, and alkynylsulfonylaminoimino, wherein:
   (a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
      (1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and
      (2) the amino portion of the aminocarbonylalkyl optionally is substituted with one or two substituents independently selected from the group consisting of alkyl, alkenyl, and alkynyl,
   (b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
      the amino optionally is substituted with one or two substituents independently selected from the group consisting of alkyl, alkenyl, alkynyl, alkyloxy, alkenyloxy, and alkynyloxy, wherein:
         the alkyl optionally is substituted with one or more hydroxy;
   (c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:
      the amino optionally is substituted with one or two substituents independently selected from the group consisting of alkyl, alkenyl, and alkynyl; and
each $R^K$ is independently selected from the group consisting of aminosulfonyl, alkylsulfonyl, alkenylsulfonyl, and alkynylsulfonyl, wherein:
   (a) the alkylsulfonyl, alkenylsulfonyl, and alkynylsulfonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
      the amino, aminosulfonyl, and aminocarbonyl optionally are substituted with one or two substituents independently selected from the group consisting of alkyl, alkenyl, and alkynyl; and
   (b) the aminosulfonyl optionally is substituted with one or two substituents independently selected from the group consisting of alkyl, alkenyl, and alkynyl.

This invention also is directed to the salts (including pharmaceutically acceptable salts) of the compounds of the invention.

This invention also is directed to compositions (including pharmaceutical compositions) that comprise one or more compounds and/or salts of the invention, and, optionally, one or more additional therapeutic agents.

This invention also is directed to kits that comprise one or more compounds and/or salts of the invention, and, optionally, one or more additional therapeutic agents.

This invention also is directed to methods of use of the compounds, salts, compositions, and/or kits of the invention to, for example, inhibit replication of an RNA virus (including HCV), treat a disease treatable by inhibiting HCV ribonucleic acid (RNA) polymerase (including hepatitis C).

This invention also is directed to a use of one or more compounds and/or salts of the invention to prepare a medicament. The medicament optionally can comprise one or more additional therapeutic agents. In some embodiments, the medicament is useful for treating hepatitis C.

Further benefits of Applicants' invention will be apparent to one skilled in the art from reading this patent application.

DETAILED DESCRIPTION OF THE INVENTION

Figure 1:
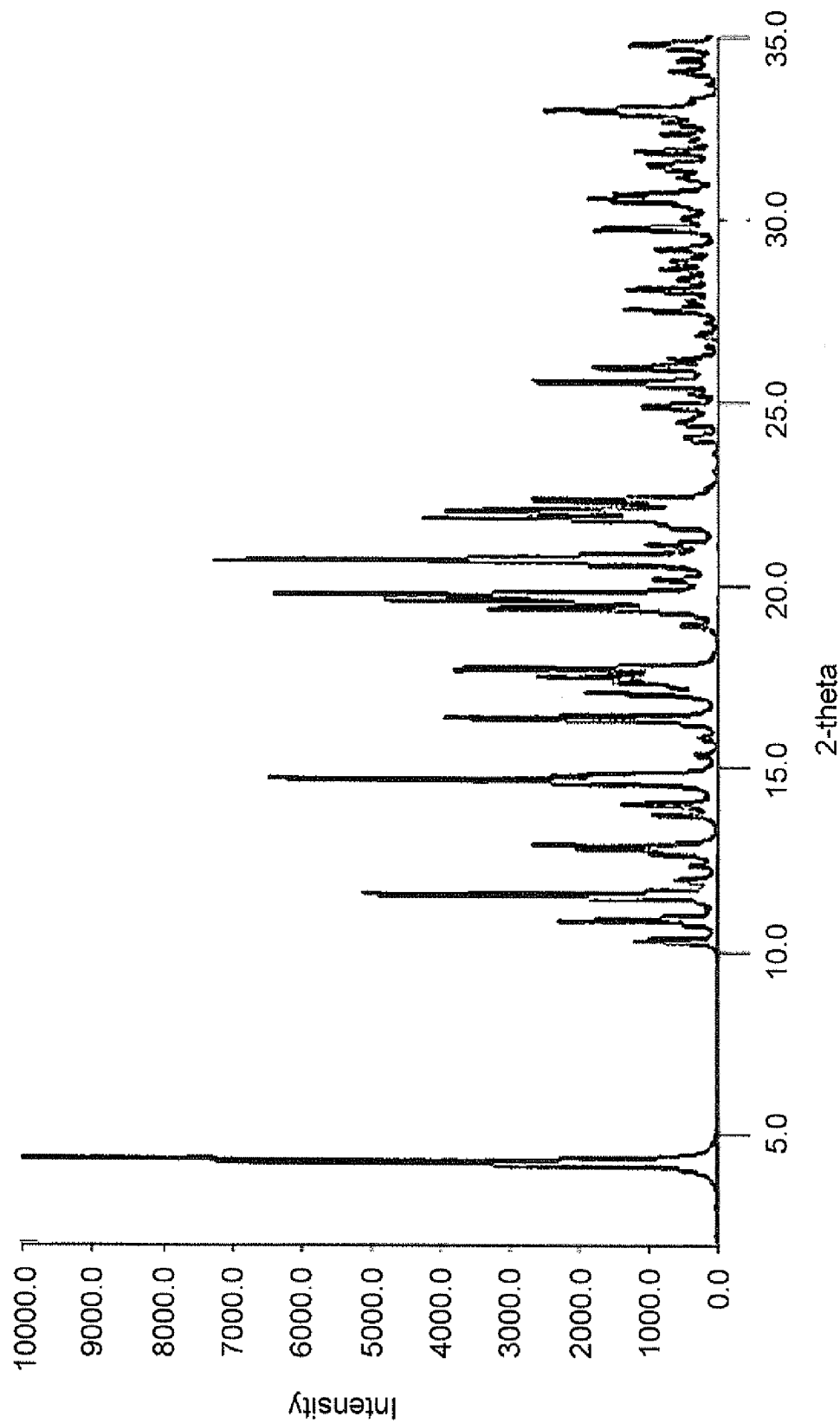
FIG. 1 shows an illustrative PXRD pattern for the disodium salt nonahydrate of compound IB-L1-1.1.

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. Definitions

The term "alkyl" (alone or in combination with another term(s)) means a straight- or branched-chain saturated hydrocarbyl substituent typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, isobutyl, sec-butyl, tert-butyl, pentyl, iso-amyl, and hexyl. As in this definition, throughout this detailed description Applicants have provided illustrative examples. The provision of such illustrative examples should not be interpreted as if the provided illustrative examples are the only options available to one skilled in the art.

The term "alkenyl" (alone or in combination with another term(s)) means a straight- or branched-chain hydrocarbyl substituent containing one or more double bonds and typically from 2 to about 20 carbon atoms, more typically from about 2 to about 8 carbon atoms, and even more typically from about 2 to about 6 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, 2-butynyl, and 3-butynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single ring, which typically contains from 3 to 6 ring atoms. Examples of such single-ring carbocyclyls include cyclopropyl (cyclopropanyl), cyclobutyl (cyclobutanyl), cyclopentyl(cyclopentanyl), cyclopentenyl, cyclopentadienyl, cyclohexyl (cyclohexanyl), cyclohexenyl, cyclohexadienyl, and phenyl. A carbocyclyl alternatively may be 2 or 3 rings fused together, such as naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 6 carbon ring atoms. Examples of single-ring cycloalkyls include cyclopropyl, cyclobutyl, cyclopentyl, and cyclohexyl. A cycloalkyl alternatively may be 2 or 3 carbon rings fused together, such as, decalinyl.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "nitro" (alone or in combination with another term(s)) means —$NO_2$.

The term "cyano" (alone or in combination with another term(s)) means —CN, which also may be depicted as —C≡N.

The term "keto" (alone or in combination with another term(s)) means an oxo radical, and may be depicted as =O.

The term "carboxy" (alone or in combination with another term(s)) means —C(O)—OH.

The term "amino" (alone or in combination with another term(s)) means —$NH_2$.

The term "imino" (alone or in combination with another term(s)) means =NH.

The term "aminoimino" (alone or in combination with another term(s)) means =$NNH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxy" (alone or in combination with another term(s)) means an ether substituent, and may be depicted as —O—.

The term "alkoxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkoxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkoxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydropyranyl, tetrahydrofuranyl, thiophenyl (thiopyranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl alternatively may be 2 or 3 rings fused together, such as, for example, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "2-fused ring" heterocyclyl (alone or in combination with another term(s)) means a saturated, partially saturated, or aryl heterocyclyl containing 2 fused rings. Examples of 2-fused-ring heterocyclyls include indolizinyl, quinolizinyl, purinyl, naphthyridinyl, pteridinyl, indolyl, isoindolyl, indoleninyl, isoindazolyl, phthalazinyl, quinoxalinyl, quinazolinyl, benzodiazinyl, benzopyranyl, benzothiopyranyl, benzoxazolyl, anthranilyl, benzodioxolyl, benzodioxanyl, benzoxadiazolyl, benzopyranyl, isobenzofuranyl, benzothiazolyl, benzothiadiazolyl, benzimidazolyl, benzotriazolyl, benzoxazinyl, and tetrahydroisoquinolinyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent therefore may be identical to or different from the other substituent(s).

When words are used to describe a substituent, the rightmost-described component of the substituent is the component that has the free valence.

When a chemical formula is used to describe a substituent, the dash on the left side of the formula indicates the portion of the substituent that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X-L-Y and L is described as —C(O)—N(H)—, then the chemical would be X—C(O)—N(H)—Y.

With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below.

ChemDraw software has been used to generate the compound names in this patent application.

The term "amorphous" as applied to a compound refers to a solid-state in which the compound molecules are present in a disordered arrangement and do not form a distinguishable crystal lattice or unit cell. When subjected to X-ray powder diffraction, an amorphous compound does not produce any characteristic crystalline peaks.

The term "crystalline form" as applied to a compound refers to a solid-state in which the compound molecules are arranged to form a distinguishable crystal lattice (i) comprising distinguishable unit cells, and (ii) yielding diffraction pattern peaks when subjected to X-ray radiation.

The term "purity", unless otherwise qualified, means the chemical purity of a compound according to conventional HPLC assay.

The term "phase purity" means the solid-state purity of a compound with regard to a particular crystalline or amorphous form of the compound as determined by X-ray powder diffraction analytical methods.

The term "phase pure" refers to purity with respect to other solid-state forms of the compound, and does not necessarily imply a high degree of chemical purity with respect to other compounds.

The term "PXRD" means X-ray powder diffraction.
The term "TGA" means thermogravimetric analysis.
The term "DSC" means differential scanning calorimetry.

B. Compounds

This invention is directed, in part, to compounds that are phenyl-uracil derivatives that correspond in structure to formula I:

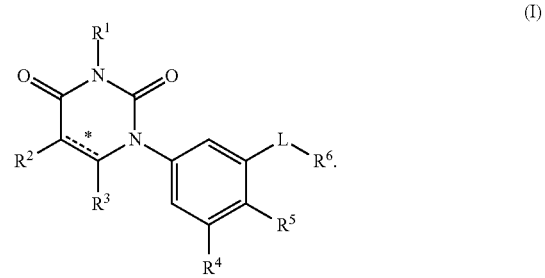

In these compounds, ⋯⋆⋯ is selected from the group consisting of single carbon-carbon bond and double carbon-carbon bond.

In some embodiments, ⋯⋆⋯ is a single carbon-carbon bond. In these embodiments, the compounds of formula I correspond in structure to the following formula (i.e., formula IA):

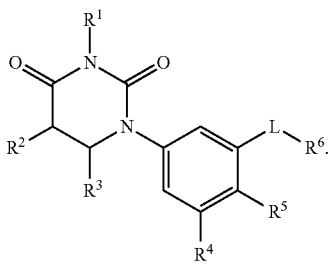

In other embodiments, ⋯⋆⋯ is a double carbon-carbon bond. In these embodiments, the compounds of formula I correspond in structure to the following formula (i.e., formula IB):

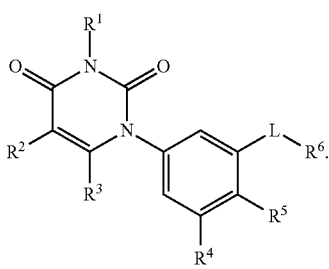

B1. Substituent $R^1$ $R^1$ is selected from the group consisting of hydrogen, methyl, and nitrogen-protecting group.

In some embodiments, $R^1$ is hydrogen.
In some embodiments, $R^1$ is methyl.
In some embodiments, $R^1$ is selected from the group consisting of hydrogen and methyl.

In some embodiments, $R^1$ is a nitrogen-protecting group. In these embodiments, the compounds are useful as intermediates for the preparation of compounds of formula I. Nitrogen-protecting groups suitable for preparing compounds of formula I are known to those skilled in the art.

B2. Substituent $R^2$ $R^2$ is selected from the group consisting of hydrogen, halo, hydroxy, methyl, cyclopropyl, and cyclobutyl.

In some embodiments, $R^2$ is hydrogen.
In some embodiments, $R^2$ is halo. In some such embodiments, $R^2$ is selected from the group consisting of fluoro and chloro. In other such embodiments, $R^2$ is fluoro. In yet other such embodiments, $R^2$ is chloro. In yet other such embodiments, $R^2$ is bromo. In further such embodiments, $R^2$ is iodo.
In some embodiments, $R^2$ is hydroxy.
In some embodiments, $R^2$ is methyl.
In some embodiments, $R^2$ is cyclopropyl.
In some embodiments, $R^2$ is cyclobutyl.

In some embodiments, $R^2$ is selected from the group consisting of hydrogen, methyl, hydroxy, and halo. In some such embodiments, $R^2$ is selected from the group consisting of hydrogen, methyl, hydroxy, fluoro, and chloro. In other such embodiments, $R^2$ is selected from the group consisting of hydrogen, methyl, hydroxy, and fluoro. In yet other such embodiments, $R^2$ is selected from the group consisting of hydrogen, methyl, hydroxy, and chloro. In yet other such embodiments, $R^2$ is selected from the group consisting of hydrogen, methyl, hydroxy, and bromo. In further such embodiments, $R^2$ is selected from the group consisting of hydrogen, methyl, hydroxy, and iodo.

In some embodiments, $R^2$ is selected from the group consisting of hydrogen, methyl, and halo. In some such embodiments, $R^2$ is selected from the group consisting of hydrogen, methyl, fluoro, and chloro. In other such embodiments, $R^2$ is selected from the group consisting of hydrogen, methyl, and fluoro. In yet other such embodiments, $R^2$ is selected from the group consisting of hydrogen, methyl, and chloro. In yet other such embodiments, $R^2$ is selected from the group consisting of hydrogen, methyl, and bromo. In further such embodiments, $R^2$ is selected from the group consisting of hydrogen, methyl, and iodo.

In some embodiments, $R^2$ is selected from the group consisting of hydrogen and halo. In some such embodiments, $R^2$ is selected from the group consisting of hydrogen, fluoro, and chloro. In other such embodiments, $R^2$ is selected from the group consisting of hydrogen and fluoro. In yet other such embodiments, $R^2$ is selected from the group consisting of hydrogen and chloro. In yet other such embodiments, $R^2$ is selected from the group consisting of hydrogen and bromo. In further such embodiments, $R^2$ is selected from the group consisting of hydrogen and iodo.

B3. Substituent $R^3$ $R^3$ is selected from the group consisting of hydrogen, halo, oxo, and methyl. In some such embodiments, $R^3$ is selected from the group consisting of hydrogen, fluoro, oxo, and methyl. In other such embodiments, $R^3$ is selected from the group consisting of hydrogen, chloro, oxo, and methyl. In yet other such embodiments, $R^3$ is selected from the group consisting of hydrogen, bromo, oxo, and methyl. In yet other such embodiments, $R^3$ is selected from the group consisting of hydrogen, iodo, oxo, and methyl.

In some embodiments, $R^3$ is selected from the group consisting of hydrogen, halo, and oxo. In some such embodiments, $R^3$ is selected from the group consisting of hydrogen, fluoro, and oxo. In other such embodiments, $R^3$ is selected from the group consisting of hydrogen, chloro, and oxo. In yet other such embodiments, $R^3$ is selected from the group consisting of hydrogen, bromo, and oxo. In yet other such embodiments, $R^3$ is selected from the group consisting of hydrogen, iodo, and oxo.

In some embodiments, $R^3$ is selected from the group consisting of hydrogen and methyl.

In some embodiments, $R^3$ is hydrogen.
In some embodiments, $R^3$ is methyl.
In some embodiments, $R^3$ is oxo.
In some embodiments, $R^3$ is halo. In some such embodiments, $R^3$ is fluoro. In other such embodiments, $R^3$ is chloro. In yet other such embodiments, $R^3$ is bromo. In further such embodiments, $R^3$ is iodo.

B4. Substituent $R^4$ $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
  (a) the amino, aminocarbonyl, and aminosulfonyl optionally are substituted with:
    (1) one or two substituents independently selected from the group consisting of alkyl, alkenyl, alkynyl, and alkylsulfonyl, or
    (2) two substituents that, together with the amino nitrogen, form a single-ring heterocyclyl,
  (b) the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
    the amino optionally is substituted with:
      (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
      (2) two substituents that, together with the amino nitrogen, form a single-ring heterocyclyl, and
  (c) the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
    the amino optionally is substituted with:
      (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
      (2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
  the amino, aminocarbonyl, and aminosulfonyl optionally are substituted with:
    (1) one or two substituents independently selected from the group consisting of alkyl, alkenyl, alkynyl, and alkylsulfonyl, or
    (2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
  the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
    the amino optionally is substituted with:
      (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
      (2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
  the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
    the amino optionally is substituted with:
      (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
      (2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
  (a) the amino, aminocarbonyl, and aminosulfonyl optionally are substituted with:
    (1) one or two substituents independently selected from the group consisting of alkyl, alkenyl, and alkynyl, or,
    (2) two substituents that, together with the amino nitrogen, form a single-ring heterocyclyl; and
  (b) the alkyl, alkenyl, alkynyl, alkyloxy, alkenyloxy, alkynyloxy, alkylsulfonyl, carbocyclyl, and heterocyclyl optionally are substituted with up to three substituents independently selected from the group consisting of halo, oxo, nitro, cyano, azido, hydroxy, amino, alkyloxy, carbocyclyl, and heterocyclyl, wherein the amino optionally is substituted with:
    (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or,
    (2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
  the amino, aminocarbonyl, and aminosulfonyl optionally are substituted with:
    (1) one or two substituents independently selected from the group consisting of alkyl, alkenyl, and alkynyl, or,
    (2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
  the alkyl, alkenyl, alkynyl, alkyloxy, alkenyloxy, alkynyloxy, alkylsulfonyl, carbocyclyl, and heterocyclyl optionally are substituted with up to three substituents independently selected from the group consisting of halo, oxo, nitro, cyano, azido, hydroxy, amino, alkyloxy, carbocyclyl, and heterocyclyl, wherein the amino optionally is substituted with:

(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or,
(2) two substituents that, together with the amino nitrogen, form a single-ring heterocyclyl.

In some embodiments, $R^4$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl, wherein:
(a) the amino optionally is substituted with one or two substituents independently selected from the group consisting of alkyl, alkenyl, alkynyl, and alkylsulfonyl,
(b) the $C_1$-$C_4$-alkyl, $C_2$-$C_4$-alkenyl, and $C_2$-$C_4$-alkynyl optionally are substituted with one or more substituents independently selected from the group consisting of halo, oxo, hydroxy, alkyloxy, and trimethylsilyl, and
(c) the $C_3$-$C_6$-carbocyclyl and 5-6-membered heterocyclyl optionally are substituted with up to three substituents independently selected from the group consisting of alkyl, alkenyl, alkynyl, halo, and amino, wherein:
the amino optionally is substituted with one or two substituents independently selected from the group consisting of alkyl, alkenyl, alkynyl, and alkylsulfonyl.

In some embodiments, $R^4$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl, wherein:
(a) the amino optionally is substituted with one or two substituents independently selected from the group consisting of alkyl, alkenyl, alkynyl, and alkylsulfonyl,
(b) the $C_1$-$C_4$-alkyl, $C_2$-$C_4$-alkenyl, and $C_2$-$C_4$-alkynyl optionally are substituted with one or more substituents independently selected from the group consisting of halo, oxo, hydroxy, alkyloxy, and trimethylsilyl, and
(c) the $C_3$-$C_6$-carbocyclyl and 5-6-membered heterocyclyl optionally are substituted with up to three substituents independently selected from the group consisting of alkyl, alkenyl, alkynyl, halo, and amino, wherein:
the amino optionally is substituted with one or two substituents independently selected from the group consisting of alkyl, alkenyl, alkynyl, and alkylsulfonyl.

In some embodiments, $R^4$ is selected from the group consisting of halo, $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with one or two substituents independently selected from the group consisting of alkyl, halo, and alkylsulfonylamino.

In some embodiments, $R^4$ is selected from the group consisting of halo, $C_1$-$C_4$-alkyl, $C_3$-$C_6$-carbocyclyl, and 5-6-membered heterocyclyl, wherein:
(a) the $C_1$-$C_4$-alkyl optionally is substituted with one or two substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with a substituent selected from the group consisting of alkyl, halo, and alkylsulfonylamino.

In some embodiments, $R^4$ is selected from the group consisting of $C_1$-$C_4$-alkyl, $C_3$-$C_6$-carbocyclyl, and 5-6-membered heterocyclyl, wherein:

(a) the $C_1$-$C_4$-alkyl optionally is substituted with up to three substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with one or two substituents independently selected from the group consisting of alkyl, halo, and alkylsulfonylamino.

In some embodiments, $R^4$ is selected from the group consisting of halo, tert-butyl, $C_3$-$C_6$-carbocyclyl, and 5-6-membered heterocyclyl, wherein:
the $C_3$-$C_6$-carbocyclyl and 5-6-membered heterocyclyl optionally are substituted with a substituent selected from the group consisting of alkyl, halo, and alkylsulfonylamino.

In some embodiments, $R^4$ is selected from the group consisting of tert-butyl, $C_3$-$C_6$-carbocyclyl, and 5-6-membered heterocyclyl, wherein:
the $C_3$-$C_6$-carbocyclyl and 5-6-membered heterocyclyl optionally are substituted with a substituent selected from the group consisting of alkyl, halo, and alkylsulfonylamino.

In some embodiments, $R^4$ is selected from the group consisting of halo, alkyl, haloalkyl, carboxyalkyl, hydroxyalkyl, alkyloxyalkyl, trimethylsilylalkynyl, alkylcarbocyclyl, carbocyclyl, alkylheterocyclyl, heterocyclyl, halocarbocyclyl, alkylsulfonylamino, and alkylsulfonyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl.

In some embodiments, $R^4$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl. In some such embodiment, $R^4$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_6$-carbocyclyl, and 5-6-membered heterocyclyl. In other such embodiment, $R^4$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, phenyl, and 5-6-membered heteroaryl.

In some embodiments, $R^4$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl. In some such embodiment, $R^4$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_6$-carbocyclyl, and 5-6-membered heterocyclyl. In other such embodiment, $R^4$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, phenyl, and 5-6-membered heteroaryl.

In some embodiments, $R^4$ is selected from the group consisting of halo, $C_1$-$C_4$-alkyl, $C_3$-$C_6$-carbocyclyl, and 5-6-membered heterocyclyl. In some such embodiments, $R^4$ is selected from the group consisting of halo, $C_1$-$C_4$-alkyl, $C_6$-carbocyclyl, and 5-6-membered heterocyclyl. In other such embodiments, $R^4$ is selected from the group consisting of halo, $C_1$-$C_4$-alkyl, phenyl, and 5-6-membered heteroaryl.

In some embodiments, $R^4$ is selected from the group consisting of $C_1$-$C_4$-alkyl, $C_3$-$C_6$-carbocyclyl, and 5-6-membered heterocyclyl. In some such embodiments, $R^4$ is selected from the group consisting of $C_1$-$C_4$-alkyl, $C_6$-carbocyclyl, and 5-6-membered heterocyclyl. In other such embodiments, $R^4$ is selected from the group consisting of $C_1$-$C_4$-alkyl, phenyl, and 5-6-membered heteroaryl.

In some embodiments, $R^4$ is selected from the group consisting of halo, tert-butyl, $C_3$-$C_6$-carbocyclyl, and 5-6-membered heterocyclyl. In some such embodiments, R⁴ is selected from the group consisting of halo, tert-butyl, C₆-carbocyclyl, and 5-6-membered heterocyclyl. In other such embodiments, R⁴ is selected from the group consisting of halo, tert-butyl, phenyl, and 5-6-membered heteroaryl.

In some embodiments, R⁴ is selected from the group consisting of tert-butyl, C₃-C₆-carbocyclyl, and 5-6-membered heterocyclyl. In some such embodiments, R⁴ is selected from the group consisting of tert-butyl, C₆-carbocyclyl, and 5-6-membered heterocyclyl. In other such embodiments, R⁴ is selected from the group consisting of tert-butyl, phenyl, and 5-6-membered heteroaryl.

In some embodiments, R⁴ is selected from the group consisting of C₃-C₆-carbocyclyl and 5-6-membered heterocyclyl. In some such embodiments, R⁴ is selected from the group consisting of C₆-carbocyclyl, and 5-6-membered heterocyclyl. In other such embodiments, R⁴ is selected from the group consisting of phenyl and 5-6-membered heteroaryl.

Suitable carbocyclyls for the above embodiments include, for example, cyclopropyl and phenyl. Suitable heterocyclyls for the above embodiments include, for example, furanyl, thienyl, and pyridinyl.

In some embodiments, R⁴ is selected from the group consisting of halo, alkyl, and alkyloxy.

In some embodiments, R⁴ is alkyl.

In some embodiments, R⁴ is tert-butyl.

B5. Substituent R⁵

R⁵ is selected from the group consisting of hydrogen, hydroxy, alkyl, alkenyl, alkynyl, alkyloxy, alkenyloxy, alkynyloxy, alkylsulfonyloxy, carbocyclylsulfonyloxy, haloalkylsulfonyloxy, and halo.

In some embodiments, R⁵ is selected from the group consisting of hydrogen, hydroxy, alkyloxy, and halo. In some such embodiments, R⁵ is selected from the group consisting of hydrogen, hydroxy, alkyloxy, and fluoro. In other such embodiments, R⁵ is selected from the group consisting of hydrogen, hydroxy, alkyloxy, and fluoro. In yet other such embodiments, R⁵ is selected from the group consisting of hydrogen, hydroxy, alkyloxy, and chloro. In yet other such embodiments, R⁵ is selected from the group consisting of hydrogen, hydroxy, alkyloxy, and bromo. In further such embodiments, R⁵ is selected from the group consisting of hydrogen, hydroxy, alkyloxy, and iodo.

In some embodiments, R⁵ is selected from the group consisting of hydrogen, hydroxy, methoxy, and halo. In some such embodiments, R⁵ is selected from the group consisting of hydrogen, hydroxy, methoxy, and fluoro. In other such embodiments, R⁵ is selected from the group consisting of hydrogen, hydroxy, methoxy, and chloro. In yet other such embodiments, R⁵ is selected from the group consisting of hydrogen, hydroxy, methoxy, and bromo. In further such embodiments, R⁵ is selected from the group consisting of hydrogen, hydroxy, methoxy, and iodo.

In some embodiments, R⁵ is selected from the group consisting of hydrogen, hydroxy, and alkyloxy. In some such embodiments, R⁵ is selected from the group consisting of hydrogen, hydroxy, methoxy, and ethoxy.

In some embodiments, R⁵ is s hydrogen.
In some embodiments, R⁵ is hydroxy.
In some embodiments, R⁵ is alkyloxy.
In some embodiments, R⁵ is methoxy.
In some embodiments, R⁵ is ethoxy.

B6. Substituent L

L is selected from the group consisting of C(R^A)=C(R^B), ethylene, and cyclopropyl-1,2-ene, wherein R^A and R^B are as discussed below.

In some embodiments, L is C(R^A)=C(R^B), wherein R^A and R^B are as discussed below. In these embodiments, the compounds of formula I correspond in structure to formula I-L1:

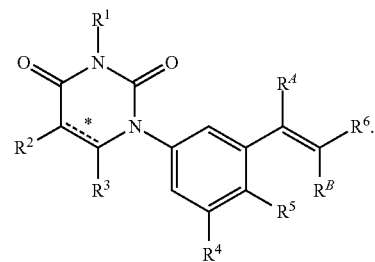

(I-L1)

In some such embodiments, the compounds correspond in structure to formula IA-L1:

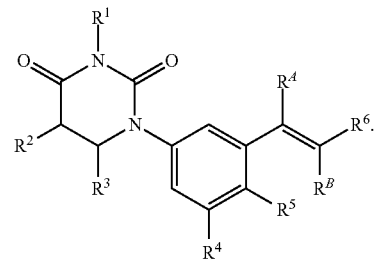

(IA-L1)

In other such embodiments, the compounds correspond in structure to formula IB-L1:

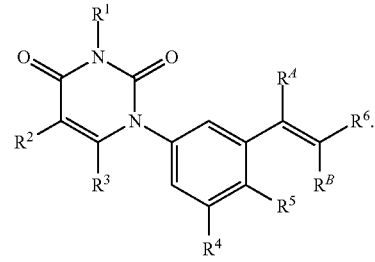

(IB-L1)

Typically, the compounds of formula I-L1 are more potent if R⁶ and the phenyl-uracil are on opposite sides of the double bond (i.e., in trans configuration in relation to the double bond).

In some embodiments, L is ethylene. In these embodiments, the compounds of formula I correspond in structure to I-L5-2:

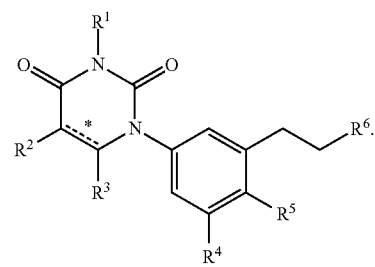

(I-L5-2)

In some such embodiments, the compounds correspond in structure to formula IA-L5-2:

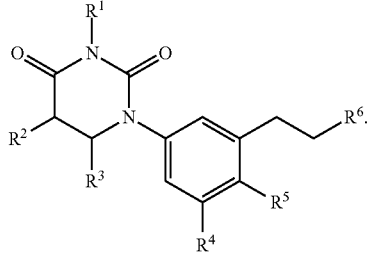

(IA-L5-2)

In other such embodiments, the compounds correspond in structure to formula IB-L5-2:

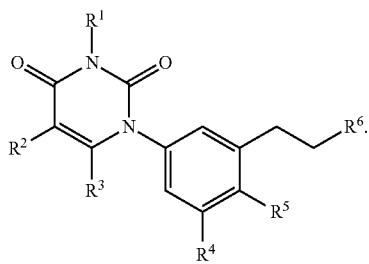

(IB-L5-2)

In some embodiments, L is cyclopropyl-1,2-ene. In these embodiments, the compounds of formula I correspond in structure to formula I-L8:

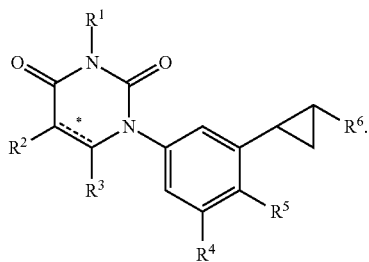

(I-L8)

In some such embodiments, the compounds correspond in structure to formula IA-L8:

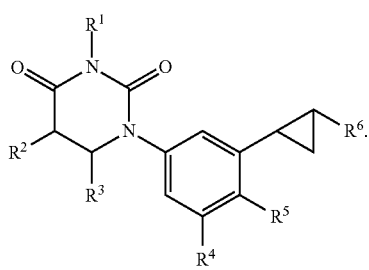

(IA-L8)

In other such embodiments, the compounds correspond in structure to formula IB-L8:

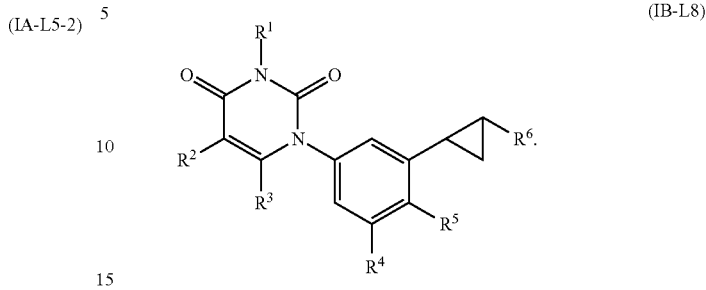

(IB-L8)

B7. Substituents $R^A$ and $R^B$ $R^A$ and $R^B$ are independently selected from the group consisting of hydrogen, $C_1$-$C_6$-alkyl, $C_1$-$C_6$-alkyloxy, $C_3$-$C_8$-cycloalkyl, and halo, wherein:
the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, one of $R^A$ and $R^B$ is hydrogen, and the other is selected from the group consisting of $C_1$-$C_6$-alkyl, $C_1$-$C_6$-alkyloxy, $C_3$-$C_8$-cycloalkyl, and halo, wherein:
the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^A$ and $R^B$ are independently selected from the group consisting of hydrogen, $C_1$-$C_6$-alkyl, $C_1$-$C_6$-alkyloxy, $C_3$-$C_8$-cycloalkyl, and halo.

In some of the above embodiments, $R^A$ is hydrogen. In other of the above embodiments, $R^B$ is hydrogen.

In some embodiment, one of $R^A$ and $R^B$ is hydrogen, and the other is selected from the group consisting of hydrogen, methyl, methoxy, and halo.

In some embodiments, $R^A$ is hydrogen, and $R^B$ is selected from the group consisting of methyl, methoxy, and halo. In some such embodiments, $R^B$ is selected from the group consisting of methyl, methoxy, and fluoro. In other such embodiments, $R^B$ is selected from the group consisting of methyl, methoxy, and chloro. In yet other such embodiments, $R^B$ is selected from the group consisting of methyl, methoxy, and bromo. In further such embodiments, $R^B$ is selected from the group consisting of methyl, methoxy, and iodo. In yet further such embodiments, $R^B$ is selected from the group consisting of methyl, methoxy, chloro, and fluoro.

In some embodiments, $R^B$ is hydrogen, and $R^A$ is selected from the group consisting of methyl, methoxy, and halo. In some such embodiments, $R^A$ is selected from the group consisting of methyl, methoxy, and fluoro. In other such embodiments, $R^A$ is selected from the group consisting of methyl, methoxy, and chloro. In yet other such embodiments, $R^A$ is selected from the group consisting of methyl, methoxy, and bromo. In further such embodiments, $R^A$ is selected from the group consisting of methyl, methoxy, and iodo. In yet further such embodiments, $R^A$ is selected from the group consisting of methyl, methoxy, chloro, and fluoro.

In some embodiments, $R^A$ is hydrogen, and $R^B$ is hydrogen.

B8. Substituent $R^6$ $R^6$ is selected from the group consisting of $C_5$-$C_6$-carbocyclyl, 5-6-membered heterocyclyl, fused 2-ring carbocyclyl, and fused 2-ring heterocyclyl, wherein each such substituent optionally is substituted with one or more substituents independently selected from the group consisting of $R^E$, $R^F$, $R^G$, $R^H$, $R^I$, $R^J$, and $R^K$, wherein $R^E$, $R^F$, $R^G$, $R^H$, $R^I$, $R^J$, and $R^K$ are as described below. In some such embodiments, the $C_5$-$C_6$-carbocyclyl, 5-6-membered heterocyclyl, fused 2-ring carbocyclyl, and fused 2-ring heterocyclyl are not substituted. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, $R^G$, $R^H$, $R^I$, $R^J$, and $R^K$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, $R^I$, $R^J$, and $R^K$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, and $R^J$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^F$ and $R^J$. In other such embodiments, the $C_5$-$C_6$-carbocyclyl, 5-6-membered heterocyclyl, fused 2-ring carbocyclyl, and fused 2-ring heterocyclyl are substituted with $R^J$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, $R^G$, $R^H$, $R^I$, $R^J$, and $R^K$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, $R^I$, $R^J$, and $R^K$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, and $R^J$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^F$ and $R^J$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, and $R^J$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^F$ and $R^J$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, $R^G$, $R^H$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, and $R^J$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^F$ and $R^J$.

In some embodiments, $R^6$ is selected from the group consisting of $C_5$-$C_6$-carbocyclyl and 5-6-membered heterocyclyl, wherein each such substituent optionally is substituted with one or more substituents independently selected from the group consisting of $R^E$, $R^F$, $R^G$, $R^H$, $R^I$, $R^J$, and $R^K$. In some such embodiments, the $C_5$-$C_6$-carbocyclyl and 5-6-membered heterocyclyl are not substituted. In other such embodiments, the $C_5$-$C_6$-carbocyclyl and 5-6-membered heterocyclyl are substituted with a substituent selected from the group consisting of $R^E$, $R^F$, $R^G$, $R^H$, $R^I$, $R^J$, and $R^K$. In yet other such embodiments, the $C_5$-$C_6$-carbocyclyl and 5-6-membered heterocyclyl are substituted with two substituents independently selected from the group consisting of $R^E$, $R^F$, $R^G$, $R^H$, $R^I$, $R^J$, and $R^K$. In further such embodiments, the $C_5$-$C_6$-carbocyclyl and 5-6-membered heterocyclyl are substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl and 5-6-membered heterocyclyl are substituted with one, two, or three substituents independently selected from the group consisting of $R^E$, $R^F$, $R^G$, $R^H$, $R^I$, $R^J$, and $R^K$.

In some embodiments, $R^6$ is $C_5$-$C_6$-carbocyclyl optionally substituted with one or more substituents independently selected from the group consisting of $R^E$, $R^F$, $R^G$, $R^H$, $R^I$, $R^J$, and $R^K$. In some such embodiments, the $C_5$-$C_6$-carbocyclyl is not substituted. In other such embodiments, the $C_5$-$C_6$-carbocyclyl is substituted with a substituent selected from the group consisting of $R^E$, $R^F$, $R^G$, $R^H$, $R^I$, $R^J$, and $R^K$. In yet other such embodiments, the $C_5$-$C_6$-carbocyclyl is substituted with two substituents independently selected from the group consisting of $R^E$, $R^F$, $R^G$, $R^H$, $R^I$, $R^J$, and $R^K$. In further such embodiments, the $C_5$-$C_6$-carbocyclyl is substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl is substituted with one, two, or three substituents independently selected from the group consisting of $R^E$, $R^F$, $R^G$, $R^H$, $R^I$, $R^J$, and $R^K$.

In some embodiments, $R^6$ is 5-6-membered heterocyclyl optionally substituted with one or more substituents independently selected from the group consisting of $R^E$, $R^F$, $R^G$, $R^H$, $R^I$, $R^J$, and $R^K$. In some such embodiments, the 5-6-membered heterocyclyl is not substituted. In other such embodiments, the 5-6-membered heterocyclyl is substituted with a substituent selected from the group consisting of $R^E$, $R^F$, $R^G$, $R^H$, $R^I$, $R^J$, and $R^K$. In yet other such embodiments, the 5-6-membered heterocyclyl is substituted with two substituents independently selected from the group consisting of $R^E$, $R^F$, $R^G$, $R^H$, $R^I$, $R^J$, and $R^K$. In further such embodiments, the 5-6-membered heterocyclyl is substituted with three substituents independently selected from the group consisting of $R^E$, $R^F$, $R^G$, $R^H$, $R^I$, $R^J$, and $R^K$. In further such embodiments, the 5-6-membered heterocyclyl is substituted with one, two, or three substituents independently selected from the group consisting of $R^E$, $R^F$, $R^G$, $R^H$, $R^I$, $R^J$, and $R^K$.

In some embodiments, $R^6$ is selected from the group consisting of fused 2-ring carbocyclyl and fused 2-ring heterocyclyl, wherein each such substituent optionally is substituted with one or more substituents independently selected from the group consisting of $R^E$, $R^F$, $R^G$, $R^H$, $R^I$, $R^J$, and $R^K$. In some such embodiments, the fused 2-ring carbocyclyl and fused 2-ring heterocyclyl are not substituted. In other such embodiments, the fused 2-ring carbocyclyl and fused 2-ring heterocyclyl are substituted with a substituent selected from the group consisting of $R^E$, $R^F$, $R^G$, $R^H$, $R^I$, $R^J$, and $R^K$. In yet other such embodiments, the fused 2-ring carbocyclyl and fused 2-ring heterocyclyl are substituted with two substituents independently selected from the group consisting of $R^E$, $R^F$, $R^G$, $R^H$, $R^I$, $R^J$, and $R^K$. In further such embodiments, the fused 2-ring carbocyclyl and fused 2-ring heterocyclyl are substituted with three substituents independently selected from the group consisting of $R^E$, $R^F$, $R^G$, $R^H$, $R^I$, $R^J$, and $R^K$. In further such embodiments, the fused 2-ring carbocyclyl and fused 2-ring heterocyclyl are substituted with one, two, or three substituents independently selected from the group consisting of $R^E$, $R^F$, $R^G$, $R^H$, $R^I$, $R^J$, and $R^K$.

In some embodiments, $R^6$ is fused 2-ring carbocyclyl optionally substituted with one or more substituents independently selected from the group consisting of $R^E$, $R^F$, $R^G$, $R^H$, $R^I$, $R^J$, and $R^K$. In some such embodiments, the fused 2-ring carbocyclyl is not substituted. In other such embodiments, the fused 2-ring carbocyclyl is substituted with a substituent selected from the group consisting of $R^E$, $R^F$, $R^G$, $R^H$, $R^I$, $R^J$, and $R^K$. In yet other such embodiments, the fused 2-ring carbocyclyl is substituted with two substituents independently selected from the group consisting of $R^E$, $R^F$, $R^G$, $R^H$, $R^I$, $R^J$, and $R^K$. In further such embodiments, the fused 2-ring carbocyclyl is substituted with three substituents independently selected from the group consisting of $R^E$, $R^F$, $R^G$, $R^H$, $R^I$, $R^J$, and $R^K$. In further such embodiments, the fused 2-ring carbocyclyl is substituted with one, two, or three substituents independently selected from the group consisting of $R^E$, $R^F$, $R^G$, $R^H$, $R^I$, $R^J$, and $R^K$.

In some embodiments, $R^6$ is fused 2-ring heterocyclyl optionally substituted with one or more substituents independently selected from the group consisting of $R^E$, $R^F$, $R^G$, $R^H$, $R^I$, $R^J$, and $R^K$. In some such embodiments, the fused 2-ring heterocyclyl is not substituted. In other such embodiments, the fused 2-ring heterocyclyl is substituted with a substituent selected from the group consisting of $R^E$, $R^F$, $R^G$, $R^H$, $R^I$, $R^J$, and $R^K$. In yet other such embodiments, the fused 2-ring heterocyclyl is substituted with two substituents independently selected from the group consisting of $R^E$, $R^F$, $R^G$, $R^H$, $R^I$, $R^J$, and $R^K$. In further such embodiments, the fused 2-ring heterocyclyl is substituted with three substituents independently selected from the group consisting of $R^E$, $R^F$, $R^G$, $R^H$, $R^I$, $R^J$, and $R^K$. In further such embodiments, the fused 2-ring heterocyclyl is substituted with one, two, or three substituent independently selected from the group consisting of $R^E$, $R^F$, $R^G$, $R^H$, $R^I$, $R^J$, and $R^K$.

In some of the above embodiments, the optionally substituted $C_5$-$C_6$-carbocyclyl is selected from the group consisting of cyclopentyl, cyclopentenyl, cyclopentadienyl, cyclohexyl, cyclohexenyl, cyclohexadienyl, and phenyl. In some such embodiments, the optionally substituted $C_5$-$C_6$-carbocyclyl is phenyl.

In some of the above embodiments, the optionally substituted $C_5$-$C_6$-carbocyclyl is $C_5$-carbocyclyl. Examples of $C_5$-carbocyclyls include cyclopentyl, cyclopentenyl, and cyclopentadienyl.

In other of the above embodiments, the optionally substituted $C_5$-$C_6$-carbocyclyl is $C_6$-carbocyclyl. Examples of $C_6$-carbocyclyls include cyclohexyl, cyclohexenyl, cyclohexadienyl, and phenyl.

In some of the above embodiments, the optionally substituted 5-6-membered-heterocyclyl is selected from the group consisting of furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, dioxazolidinyl, pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

In some of the above embodiments, the optionally substituted 5-6-membered-heterocyclyl is 5-membered heterocyclyl. Examples of such 5-membered heterocyclyl include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, and dioxazolidinyl.

In other of the above embodiments, the optionally substituted 5-6-membered-heterocyclyl is 6-membered heterocyclyl. Examples of 6-membered heterocyclyls include pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

In some of the above embodiments, the optionally substituted fused 2-ring carbocyclyl is selected from the group consisting of naphthalenyl, dihydronaphthalenyl, tetrahydronaphthalenyl, hexahydronaphthalenyl, octahydronaphthalenyl, decahydronaphthalenyl, indenyl, dihydroindenyl, hexahydroindenyl, octahydroindenyl, pentalenyl, octahydropentalenyl, and hexahydropentalenyl. In some such embodiments, the optionally substituted fused 2-ring carbocyclyl is selected from the group consisting of naphthalenyl and dihydroindenyl. In some such embodiments, the optionally substituted fused 2-ring carbocyclyl is naphthalenyl. In other such embodiments, the optionally substituted fused 2-ring carbocyclyl is dihydroindenyl. In further such embodiments, the optionally substituted fused 2-ring carbocyclyl is indenyl.

In some of the above embodiments, the optionally substituted fused 2-ring heterocyclyl is selected from the group consisting of

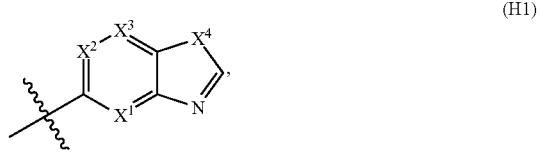

(H1)

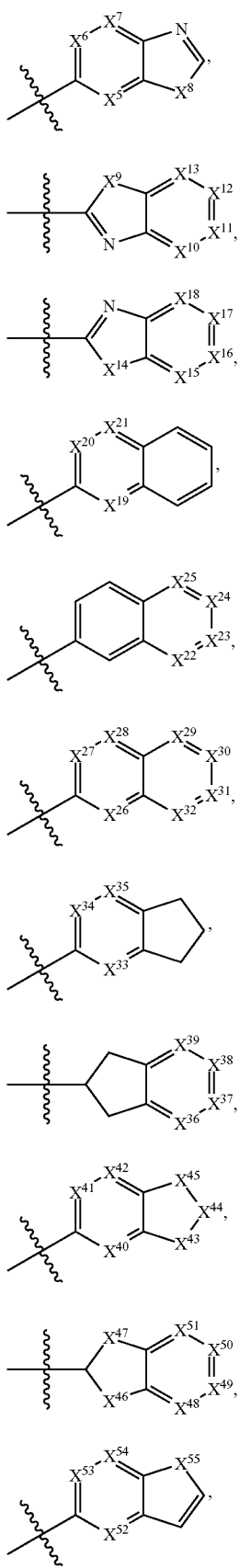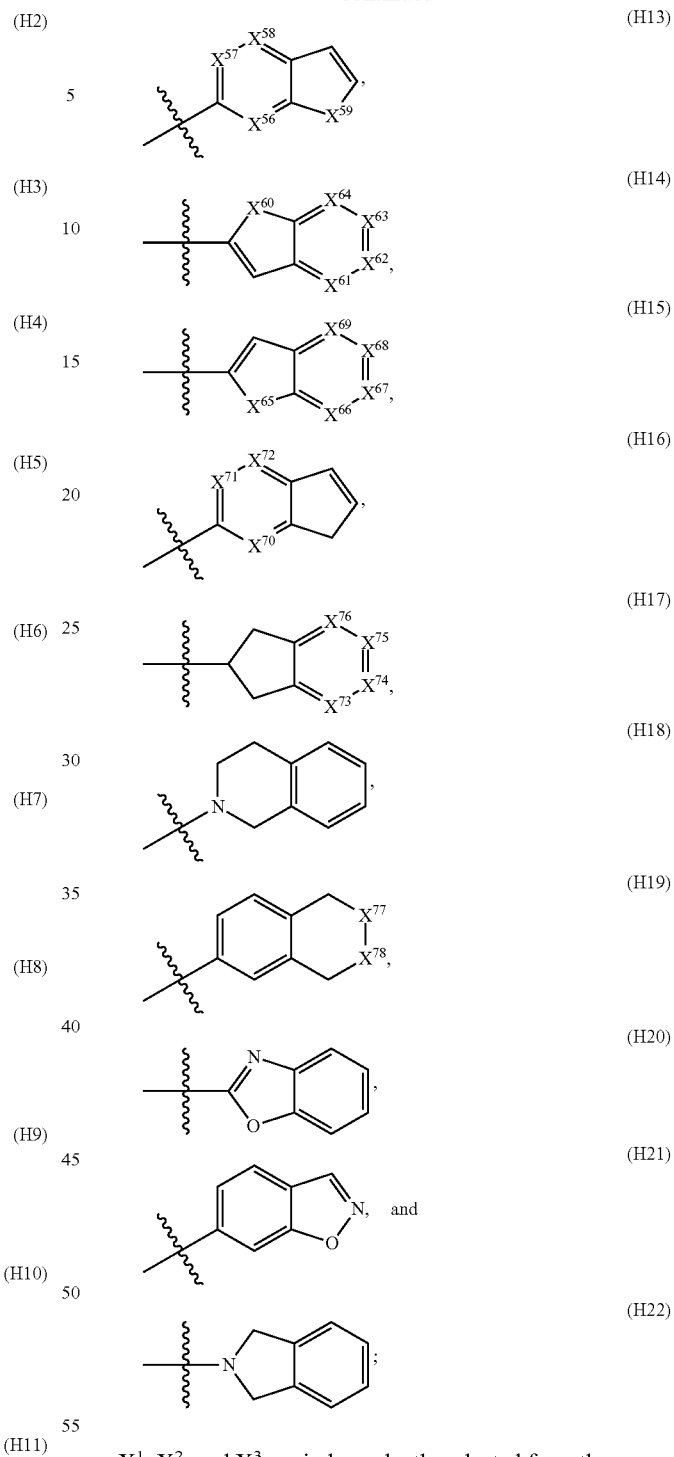

$X^1$, $X^2$, and $X^3$ are independently selected from the group consisting of N and C(H);
$X^4$ is selected from the group consisting of N(H), O, and S;
$X^5$, $X^6$, and $X^7$ are independently selected from the group consisting of N and C(H);
$X^8$ is selected from the group consisting of N(H), O, and S;
$X^9$ is selected from the group consisting of N(H), O, and S;
$X^{10}$, $X^{11}$, $X^{12}$, and $X^{13}$ are independently selected from the group consisting of N and C(H);
$X^{14}$ is selected from the group consisting of N(H), O, and S;
$X^{15}$, $X^{16}$, $X^{17}$, and $X^{18}$ are independently selected from the group consisting of N and C(H);

one or more of $X^{19}$, $X^{20}$, and $X^{21}$ is N, and the remaining one(s) is/are C(H);

one or more of $X^{22}$, $X^{23}$, $X^{24}$, and $X^{25}$ is N, and the remaining one(s) is/are C(H);

one or more of $X^{26}$, $X^{27}$, and $X^{28}$ is N, and the remaining one(s) is/are C(H);

one or more of $X^{29}$, $X^{30}$, $X^{31}$, and $X^{32}$ is N, and the remaining one(s) is/are C(H);

one or more of $X^{33}$, $X^{34}$, and $X^{35}$ is N, and the remaining one(s) is/are C(H);

one or more of $X^{36}$, $X^{37}$, $X^{38}$, and $X^{39}$ is N, and the remaining one(s) is/are C(H); $X^{40}$, $X^{41}$, and $X^{42}$ are independently selected from the group consisting of N and C(H);

one of $X^{43}$, $X^{44}$, and $X^{45}$ is selected from the group consisting of N(H), O, and S, and the remaining two are $C(H)_2$;

one of $X^{46}$ and $X^{47}$ is selected from the group consisting of N(H), O, and S, and the other one is $C(H)_2$;

$X^{48}$, $X^{49}$, $X^{50}$, and $X^{51}$ are independently selected from the group consisting of N and C(H);

$X^{52}$, $X^{53}$, and $X^{54}$ are independently selected from the group consisting of N and C(H);

$X^{55}$ is selected from the group consisting of N(H), O, and S;

$X^{56}$, $X^{57}$, and $X^{58}$ are independently selected from the group consisting of N and C(H);

$X^{59}$ is selected from the group consisting of N(H), O, and S;

$X^{60}$ is selected from the group consisting of N(H), O, and S;

$X^{61}$, $X^{62}$, $X^{63}$, and $X^{64}$ are independently selected from the group consisting of N and C(H);

$X^{65}$ is selected from the group consisting of N(H), O, and S;

$X^{66}$, $X^{67}$, $X^{68}$, and $X^{69}$ are independently selected from the group consisting of N and C(H);

one or more of $X^{70}$, $X^{71}$, and $X^{72}$ is N, and the remaining one(s) is/are C(H);

one or more of $X^{73}$, $X^{74}$, $X^{75}$, and $X^{76}$ is N, and the remaining one(s) is/are C(H); and one of $X^{77}$ and $X^{78}$ is N(H), and the remaining one is $C(H)_2$.

In some of the above embodiments, the optionally substituted fused 2-ring heterocyclyl is selected from the group consisting of

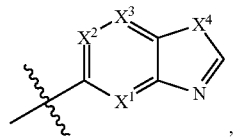
(H1)

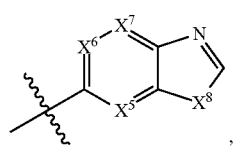
(H2)

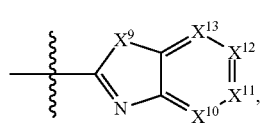
(H3)

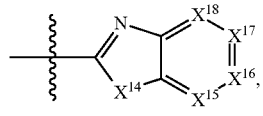
(H4)

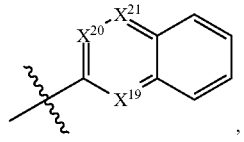
(H5)

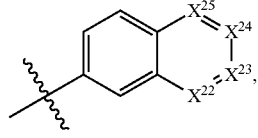
(H6)

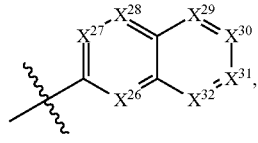
(H7)

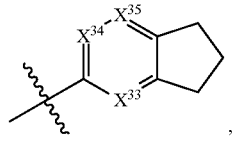
(H8)

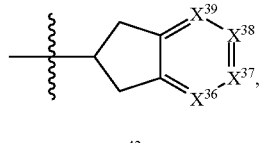
(H9)

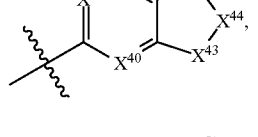
(H10)

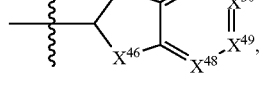
(H11)

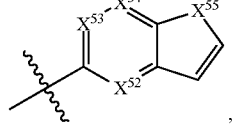
(H12)

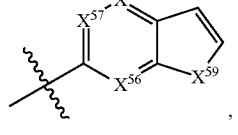
(H13)

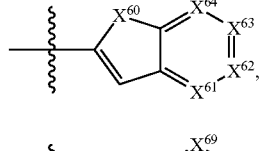
(H14)

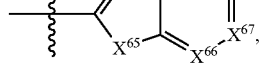
(H15)

-continued

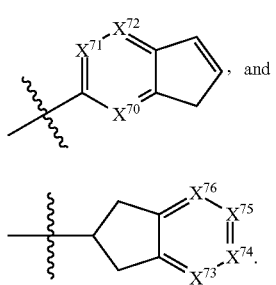
(H16)

In some of the above embodiments, the optionally substituted fused 2-ring heterocyclyl is selected from the group consisting of:

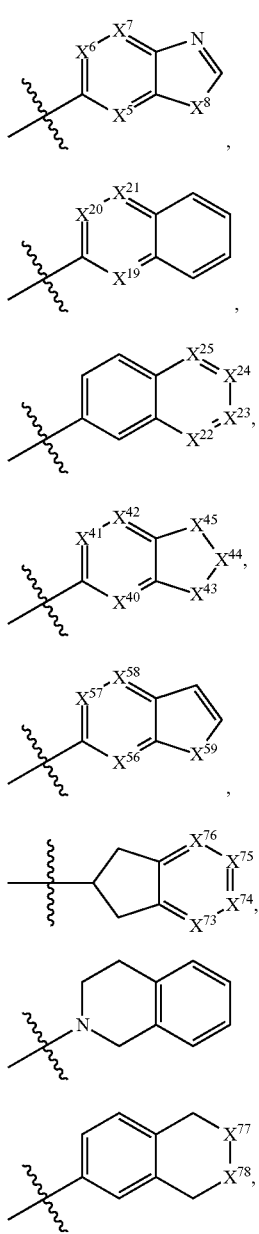

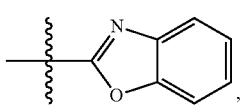
(H20)

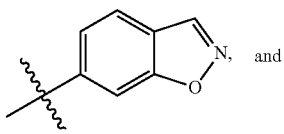
(H21)

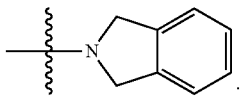
(H22)

In some of the above embodiments, $X^1$, $X^2$, and $X^3$ are C(H).

In some of the above embodiments, $X^5$, $X^6$, and $X^7$ are C(H).

In some of the above embodiments, $X^{10}$, $X^{11}$, $X^{12}$, and $X^{13}$ are C(H).

In some of the above embodiments, $X^{15}$, $X^{16}$, $X^{17}$, and $X^{18}$ are C(H).

In some of the above embodiments, one of $X^{19}$, $X^{20}$, and $X^{21}$ is N.

In some of the above embodiments, one of $X^{22}$, $X^{23}$, $X^{24}$, and $X^{25}$ is N.

In some of the above embodiments, one of $X^{26}$, $X^{27}$, and $X^{28}$ is N, and one of $X^{29}$, $X^{30}$, $X^{31}$, and $X^{32}$ is N.

In some of the above embodiments, $X^{40}$, $X^{41}$, and $X^{42}$ are C(H).

In some of the above embodiments, $X^{48}$, $X^{49}$, $X^{50}$, and $X^{51}$ are C(H).

In some of the above embodiments, $X^{52}$, $X^{53}$, and $X^{54}$ are C(H).

In some of the above embodiments, $X^{56}$, $X^{57}$, and $X^{58}$ are C(H).

In some of the above embodiments, $X^{61}$, $X^{62}$, $X^{63}$, and $X^{64}$ are C(H).

In some of the above embodiments, $X^{66}$, $X^{67}$, $X^{68}$ and $X^{69}$ are C(H).

In some of the above embodiments, one or more of $X^{70}$, $X^{71}$, and $X^{72}$ is N, and the remaining one(s) is/are C(H).

In some of the above embodiments, one or more of $X^{73}$, $X^{74}$, $X^{75}$, and $X^{76}$ is N, and the remaining one(s) is/are C(H).

B9. Substituent $R^E$

Each $R^E$ is independently selected from the group consisting of halo, nitro, hydroxy, oxo, carboxy, cyano, amino, imino, azido, and aldehydro, wherein the amino optionally is substituted with one or two substituents independently selected from the group consisting of alkyl, alkenyl, and alkynyl.

In some embodiment, each $R^E$ is independently selected from the group consisting of halo, nitro, hydroxy, oxo, carboxy, amino, imino, and aldehydro, wherein the amino optionally is substituted with one or two independently selected alkyl.

In some embodiment, each $R^E$ is independently selected from the group consisting of halo, nitro, hydroxy, oxo, carboxy, amino, imino, aldehydro, and alkylamino.

In some embodiment, each $R^E$ is independently selected from the group consisting of chloro, fluoro, nitro, hydroxy, oxo, carboxy, amino, imino, aldehydro, and alkylamino.

In some embodiment, each $R^E$ is independently selected from the group consisting of halo, nitro, hydroxy, oxo, carboxy, cyano, amino, imino, and azido. In some such embodiments, each $R^E$ is halo. In other such embodiments, each $R^E$ is nitro. In yet other such embodiments, each $R^E$ is hydroxy. In yet other such embodiments, each $R^E$ is oxo. In yet other such embodiments, each $R^E$ is carboxy. In yet other such embodiments, each $R^E$ is cyano. In yet other such embodiments, each $R^E$ is amino. In further such embodiments, each $R^E$ is imino. In yet further such embodiments, each $R^E$ is and azido.

In some embodiments, each $R^E$ is independently selected from the group consisting of halo, nitro, hydroxy, oxo, carboxy, cyano, amino, and imino.

B10. Substituent

Each $R^F$ is independently selected from the group consisting of alkyl, alkenyl, and alkynyl, wherein:
  each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, imino, aminosulfonyl, aminocarbonyl, carbocyclyl, and heterocyclyl optionally are substituted with one or two substituents independently selected from the group consisting of alkyl, alkenyl, alkynyl, alkylsulfonyl, alkenylsulfonyl, alkynylsulfonyl, alkylsulfonylamino, hydroxy, and alkyloxy,
    wherein:
      amino portion of the alkylsulfonylamino optionally is substituted with a substituent selected from the group consisting of alkyl, alkenyl, and alkynyl.

In some embodiment, each $R^F$ is independently selected from the group consisting of alkyl, alkenyl, and alkynyl, wherein:
  each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, imino, aminosulfonyl, and aminocarbonyl optionally are substituted with one or two substituents independently selected from the group consisting of alkyl, alkenyl, alkynyl, alkylsulfonyl, alkenylsulfonyl, alkynylsulfonyl, and alkylsulfonylamino, wherein:
      amino portion of the alkylsulfonylamino optionally is substituted with a substituent selected from the group consisting of alkyl, alkenyl, and alkynyl.

In some of the above embodiments, each $R^F$ is independently selected from the group consisting of the alkyl, alkynyl, and alkynyl, wherein such substituents are not substituted.

In some embodiments, each $R^F$ is independently selected from the group consisting of alkyl, alkenyl, and alkynyl, wherein:
  each such substituent optionally is substituted with one or two substituents independently selected from the group consisting of carboxy, hydroxy, halo, amino, imino, nitro, oxo, aminosulfonyl, alkylsulfonyl, alkyloxycarbonyl, alkylcarbonyloxy, alkyloxy, carbocyclyl, heterocyclyl, cyano, and aminocarbonyl, wherein:
    the amino, imino, aminosulfonyl, and aminocarbonyl optionally are substituted with one or two substituents independently selected from the group consisting of alkyl, alkylsulfonyl, and alkylsulfonylamino,
    wherein:
      amino portion of the alkylsulfonylamino optionally is substituted with alkyl.

In some embodiments, each $R^F$ is an independently selected alkyl optionally substituted with a substituent selected from the group consisting of carboxy, hydroxy, halo, amino, imino, nitro, oxo, aminosulfonyl, alkylsulfonyl, alkyloxycarbonyl, alkylcarbonyloxy, alkyloxy, carbocyclyl, heterocyclyl, cyano, and aminocarbonyl, wherein:
  the amino, imino, aminosulfonyl, and aminocarbonyl optionally are substituted with one or two substituents independently selected from the group consisting of alkyl, alkylsulfonyl, and alkylsulfonylamino, wherein:
    amino portion of the alkylsulfonylamino optionally is substituted with alkyl.

In some embodiments, each $R^F$ is an independently selected alkyl optionally substituted with a substituent selected from the group consisting of carboxy, halo, amino, imino, and aminosulfonyl, wherein:
  the amino, imino, and aminosulfonyl optionally are substituted with one or two substituents independently selected from the group consisting of alkyl, alkylsulfonyl, and alkylsulfonylamino.

In some embodiments, each $R^F$ is an independently selected alkyl optionally substituted with amino, wherein the amino optionally is substituted with alkylsulfonyl.

In some embodiments, each $R^F$ is an independently selected alkyl substituted with amino, wherein the amino is substituted with alkylsulfonyl. In some such embodiments, each $R^F$ is methylsulfonylaminomethyl.

In some embodiments, each $R^F$ is independently selected from the group consisting of alkyl, alkenyl, and alkynyl, wherein:
  each such substituent optionally is substituted with one, two, or three substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl.

In some embodiments, each $R^F$ is independently selected alkyl substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl.

B11. Substituent $R^G$

Each $R^G$ is independently selected from the group consisting of carbocyclyl and heterocyclyl, wherein:
  each such substituent optionally is substituted with one or more substituents independently selected from the group consisting of alkyl, alkenyl, alkynyl, carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl.

In some of the above embodiments, each $R^G$ is independently selected from the group consisting of carbocyclyl and heterocyclyl, wherein such substituents are not substituted.

In some embodiments, each $R^G$ is independently selected from the group consisting of carbocyclyl and heterocyclyl, wherein:
each such substituent optionally is substituted with one or two substituents independently selected from the group consisting of alkyl, carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl and alkylsulfonyl.

In some of the above embodiments, the carbocyclyl is $C_3$-$C_6$-carbocyclyl.

In some of the above embodiments, the heterocyclyl is 5-6-membered heterocyclyl.

B12. Substituent

Each $R^H$ is independently selected from the group consisting of alkyloxy, alkenyloxy, alkynyloxy, alkylsulfonyloxy, alkenylsulfonyloxy, and alkynylsulfonyloxy, wherein:
each such substituent optionally is substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl.

In some of the above embodiments, each $R^H$ is independently selected from the group consisting of alkyloxy, alkenyloxy, alkynyloxy, alkylsulfonyloxy, alkenylsulfonyloxy, and alkynylsulfonyloxy, wherein such substituents are not substituted.

In some embodiments, each $R^H$ is independently selected from the group consisting of alkyloxy and alkylsulfonyloxy, wherein:
each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl and alkylsulfonyl.

In some embodiments, each $R^H$ is independently selected from the group consisting of alkyloxy and alkylsulfonyloxy, wherein:
each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl, wherein:
the amino, aminosulfonyl, and aminocarbonyl optionally are substituted with one or two substituents independently selected from the group consisting of alkyl and alkylsulfonyl.

In some embodiments, each $R^H$ is independently selected from the group consisting of alkyloxy and alkylsulfonyloxy, wherein:
each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl.

In some embodiments, each $R^H$ is independently selected alkyloxy.

In some embodiments, each $R^H$ is independently selected alkylsulfonyloxy.

B13. Substituent $R^1$

Each $R^1$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein:
(a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and
(b) the aminocarbonyl optionally is substituted with one or two substituents independently selected from the group consisting of alkyl, alkenyl, alkynyl, alkyloxyalkyl, carbocyclyl, heterocyclyl, alkylsulfonyl, and alkylsulfonylamino, wherein:
the carbocyclyl and heterocyclyl optionally are substituted with one or two substituents independently selected from the group consisting of halo, alkyl, and oxo.

In some embodiments, each $R^1$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein such substituents are not substituted.

In some embodiments, each $R^1$ is independently selected from the group consisting of alkylcarbonyl, aminocarbonyl, alkyloxycarbonyl, carbocyclylcarbonyl, and heterocyclylcarbonyl, wherein:
(a) the alkylcarbonyl optionally is substituted with a substituent selected from the group consisting of carboxy, hydroxy, halo, amino, nitro, oxo, aminosulfonyl, alkyloxycarbonyl, alkylcarbonyloxy, alkyloxy, and aminocarbonyl, and
(b) the aminocarbonyl optionally is substituted with a substituent selected from the group consisting of alkyl, alkyloxyalkyl, alkylsulfonyl, and alkylsulfonylamino.

In some embodiments, each $R^1$ is independently selected from the group consisting of alkylcarbonyl and aminocarbonyl, wherein:
 the aminocarbonyl optionally is substituted with a substituent selected from the group consisting of alkyl, alkyloxyalkyl, alkylsulfonyl, and alkylsulfonylamino.

In some embodiment, each $R^1$ is independently selected from the group consisting of alkylcarbonyl, alkenylcarbonyl, alkynylcarbonyl, and aminocarbonyl, wherein:
 (a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and
 (b) the aminocarbonyl optionally is substituted with one or two substituents independently selected from the group consisting of alkyl, alkenyl, alkynyl, and alkylsulfonylamino.

In some of the above embodiments, each $R^1$ is independently selected from the group consisting of alkylcarbonyl, alkenylcarbonyl, alkynylcarbonyl, and aminocarbonyl, wherein such substituents are not substituted.

In some embodiments, each $R^1$ is independently selected from the group consisting of alkylcarbonyl and aminocarbonyl, wherein:
 (a) the alkylcarbonyl optionally is substituted with one or two substituents independently selected from the group consisting of carboxy, hydroxy, halo, amino, nitro, azido, oxo, aminosulfonyl, alkyloxycarbonyl, alkylcarbonyloxy, alkyloxy, carbocyclyl, heterocyclyl, cyano, and aminocarbonyl, and
 (b) the aminocarbonyl optionally is substituted with one or two substituents independently selected from the group consisting of alkyl and alkylsulfonylamino.

In some embodiments, each $R^I$ is independently selected from the group consisting of alkylcarbonyl and aminocarbonyl, wherein:
 (a) the alkylcarbonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl, and
 (b) the aminocarbonyl optionally is substituted with one or two substituents independently selected from the group consisting of alkyl and alkylsulfonylamino.

In some embodiments, each $R^I$ is independently selected from the group consisting of alkylcarbonyl and aminocarbonyl, wherein:
 the alkylcarbonyl optionally is substituted with one or two substituents independently selected from the group consisting of carboxy, hydroxy, halo, amino, nitro, azido, oxo, aminosulfonyl, alkyloxycarbonyl, alkylcarbonyloxy, alkyloxy, carbocyclyl, heterocyclyl, cyano, and aminocarbonyl.

In some embodiments, each $R^I$ is independently selected alkylcarbonyl.

In some embodiments, each $R^1$ is independently selected aminocarbonyl.

B14. Substituent $R^1$

Each $R^1$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkyloxycarbonylaminoimino, alkylsulfonylaminoimino, alkenylsulfonylaminoimino, and alkynylsulfonylaminoimino, wherein:
 (a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
  (1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and
  (2) the amino portion of the aminocarbonylalkyl optionally is substituted with one or two substituents independently selected from the group consisting of alkyl, alkenyl, and alkynyl,
 (b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
  the amino optionally is substituted with one or two substituents independently selected from the group consisting of alkyl, alkenyl, alkynyl, alkyloxy, alkenyloxy, and alkynyloxy, wherein:
   the alkyl optionally is substituted with one or more hydroxy;
 (c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:
  the amino optionally is substituted with one or two substituents independently selected from the group consisting of alkyl, alkenyl, and alkynyl.

In some embodiment, each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkylsulfonylaminoimino, alkenylsulfonylaminoimino, and alkynylsulfonylaminoimino, wherein:
 (a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
  (1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and (2) the amino portion of the aminocarbonylalkyl optionally is substituted with one or two substituents independently selected from the group consisting of alkyl, alkenyl, and alkynyl, (b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl, alkenyl, alkynyl, alkyloxy, alkenyloxy, and alkynyloxy, wherein:

the alkyl optionally is substituted with one or more hydroxy;

(c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:

the amino optionally is substituted with one or two substituents independently selected from the group consisting of alkyl, alkenyl, and alkynyl; and In some of the above embodiments, each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkylsulfonylaminoimino, alkenylsulfonylaminoimino, and alkynylsulfonylaminoimino, wherein such substituents are not substituted.

In some embodiments, each $R^J$ is independently selected from the group consisting of carbocyclylsulfonylamino, heterocyclylsulfonylamino, alkylcarbonylamino, alkyloxycarbonylamino, alkylsulfonylamino, aminocarbonylamino, and alkylsulfonylaminoimino, wherein:

(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl, (b) the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:

the alkyl optionally is substituted with one or more hydroxy;

(c) the carbocyclyl and heterocyclyl portions of such substituents optionally are substituted with one or two substituents independently selected from the group consisting of alkyl, carboxy, hydroxy, alkyloxy, halo, nitro, cyano, and amino, wherein:

the amino optionally is substituted with one or two substituents independently selected alkyl.

In some embodiments, each $R^J$ is independently selected from the group consisting of carbocyclylsulfonylamino, heterocyclylsulfonylamino, alkylsulfonylamino, and alkylsulfonylaminoimino, wherein:

(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl, (b) the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:

the alkyl optionally is substituted with one or more hydroxy;

(c) the carbocyclyl and heterocyclyl portions of such substituents optionally are substituted with one or two substituents independently selected from the group consisting of alkyl, carboxy, hydroxy, alkyloxy, halo, nitro, cyano, and amino, wherein:

the amino optionally is substituted with one or two substituents independently selected alkyl.

In some embodiments, each $R^J$ is independently selected from the group consisting of carbocyclylsulfonylamino, heterocyclylsulfonylamino, alkylsulfonylamino, and alkylsulfonylaminoimino, wherein:

the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl.

In some embodiments, each $R^J$ is independently selected from the group consisting of carbocyclylsulfonylamino, heterocyclylsulfonylamino, alkylsulfonylamino, and alkylsulfonylaminoimino, wherein:

the alkyl portion of the alkylsulfonylamino and alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:

the alkyl optionally is substituted with one or more hydroxy.

In some embodiments, each $R^J$ is independently selected from the group consisting of carbocyclylsulfonylamino, heterocyclylsulfonylamino, alkylsulfonylamino, and alkylsulfonylaminoimino, wherein:

the carbocyclyl and heterocyclyl portions of such substituents optionally are substituted with one or two substituents independently selected from the group consisting of alkyl, carboxy, hydroxy, alkyloxy, halo, nitro, cyano, and amino.

In some embodiments, each $R^1$ is independently selected from the group consisting of carbocyclylsulfonylamino and heterocyclylsulfonylamino, wherein:

the carbocyclyl and heterocyclyl portions of such substituents optionally are substituted with one or two substituents independently selected from the group consisting of alkyl, carboxy, hydroxy, alkyloxy, halo, nitro, cyano, and amino.

In some embodiments, each $R^J$ is independently selected from the group consisting of alkylsulfonylamino, alkenylsulfonylamino, alkynylsulfonylamino, and alkylsulfonylaminoimino, wherein:

(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl, (b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:

the alkyl optionally is substituted with one or more hydroxy.

In some embodiments, each $R^J$ is an independently selected alkylsulfonylamino, wherein:

(a) the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl, (b) the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:

the alkyl optionally is substituted with one or more hydroxy.

In some embodiments, each $R^J$ is an independently selected alkylsulfonylamino, wherein:

the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl.

In some embodiments, each $R^1$ is an independently selected alkylsulfonylamino, wherein:

the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl.

In some embodiments, each $R^J$ is an independently selected alkylsulfonylamino, wherein:

the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano,
wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylamino, wherein:
the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

In some embodiments, each $R^J$ is an independently selected alkylsulfonylamino. In some such embodiments, each $R^J$ is methylsulfonylamino.

In some embodiments, each $R^J$ is an independently selected alkylsulfonylaminoimino, wherein:
(a) the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylaminoimino, wherein:
the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl.

In some embodiments, each $R^J$ is an independently selected alkylsulfonylaminoimino, wherein:
the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbony l, alkyloxyalkyloxycarbonyl, alkylcarbonyloxyalkyl, and alkylsulfonyl.

In some embodiments, each is an independently selected alkylsulfonylaminoimino, wherein:
the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylaminoimino, wherein:
the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

In some embodiments, each $R^J$ is an independently selected alkylsulfonylaminoimino. In some such embodiments, each $R^J$ is methylsulfonylaminoimino.

In some embodiments, each $R^J$ is independently selected from the group consisting of alkylcarbonylamino and alkyloxycarbonylamino, wherein:
the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

B15. Substituent $R^K$

Each $R^K$ is independently selected from the group consisting of aminosulfonyl, alkylsulfonyl, alkenylsulfonyl, and alkynylsulfonyl, wherein:
(a) the alkylsulfonyl, alkenylsulfonyl, and alkynylsulfonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl, alkenyl, and alkynyl; and
(b) the aminosulfonyl optionally is substituted with one or two substituents independently selected from the group consisting of alkyl, alkenyl, and alkynyl.

In some of the above embodiments, each $R^K$ is independently selected from the group consisting of aminosulfonyl, alkylsulfonyl, alkenylsulfonyl, and alkynylsulfonyl, wherein such substituents are not substituted.

In some embodiments, each $R^K$ is independently selected from the group consisting of aminosulfonyl and alkylsulfonyl, wherein:
(a) the alkylsulfonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl; and
(b) the aminosulfonyl optionally is substituted with one or two substituents independently selected alkyl.

In some embodiments, each $R^K$ is independently selected from the group consisting of aminosulfonyl and alkylsulfonyl.

C. Embodiments of Compounds of Formula I

Various embodiments of substituents $R^1$, $R^2$, $R^3$, $R^4$, $R^5$, L, $R^A$, $R^B$, $R^C$, $R^D$, $R^6$, $R^E$, $R^F$, $R^G$, $R^H$, $R^I$, $R^J$, and $R^K$ have been discussed above. These substituent embodiments can be combined to form various embodiments of compounds of formula I. All embodiments of compounds of formula I formed by combining the substituent embodiments discussed above are within the scope of Applicants' invention, and some illustrative embodiments of the compounds of formula I are provided below.

In some embodiments, in the compounds of formula I:
⸺⸺ is selected from the group consisting of single carbon-carbon bond and double carbon-carbon bond;
$R^1$ is selected from the group consisting of hydrogen and methyl;
$R^2$ is selected from the group consisting of hydrogen and halo;
$R^3$ is selected from the group consisting of hydrogen and halo;
$R^4$ is selected from the group consisting of $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with one or two substituents independently selected from the group consisting of alkyl, halo, and alkylsulfonylamino;
$R^5$ is selected from the group consisting of hydrogen, hydroxy, alkyloxy, and halo;
L is selected from the group consisting of $C(R^A)=C(R^B)$, ethylene, and cyclopropyl-1,2-ene; one of $R^A$ and $R^B$ is hydrogen, and the other is selected from the group consisting of hydrogen, methyl, methoxy, and halo;
$R^6$ is selected from the group consisting of $C_5$-$C_6$-carbocyclyl and 5-6-membered heterocyclyl, wherein each such substituent is substituted with one, two, or three substituents independently selected from the group consisting of $R^E$, $R^F$, and $R^J$;
each $R^E$ is independently selected from the group consisting of chloro, fluoro, nitro, hydroxy, oxo, carboxy, amino, imino, aldehydro, and alkylamino;
each $R^F$ is an independently selected alkyl optionally substituted with a substituent selected from the group consisting of carboxy, halo, amino, imino, and aminosulfonyl, wherein:

the amino, imino, and aminosulfonyl optionally are substituted with one or two substituents independently selected from the group consisting of alkyl, alkylsulfonyl, and alkylsulfonylamino;
each $R^I$ is independently selected from the group consisting of alkylcarbonyl and aminocarbonyl, wherein:
the aminocarbonyl optionally is substituted with a substituent selected from the group consisting of alkyl, alkyloxyalkyl, alkylsulfonyl, and alkylsulfonylamino; and
each $R^J$ is independently selected from the group consisting of alkylsulfonylamino, alkenylsulfonylamino, alkynylsulfonylamino, and alkylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein the alkyl optionally is substituted with one or more hydroxy.

Examples of compounds of formula I (and salts thereof) are shown in Tables 1-7 below. The synthesis examples below provide step-by-step preparation instructions for some of these compounds. The remaining compounds were prepared utilizing the general method-of-preparation discussion, specific synthesis examples below, and/or the discussion throughout this application.

TABLE 1

| compound | $R^5$ | $R^B$ | substituent(s) |
|---|---|---|---|
| IA-L1-1.3 | —OCH$_3$ | —Cl | 4-N(H)S(O)$_2$CH$_3$ [Z] |
| IA-L1-1.4 | —OCH$_3$ | —F | 4-N(H)S(O)$_2$CH$_3$ [Z] |
| IA-L1-1.5 | —OCH$_3$ | —F | 4-N(H)S(O)$_2$CH$_3$ [E] |
| IA-L1-1.6 | —OCH$_3$ | —CH$_3$ | 4-N(H)S(O)$_2$CH$_3$ [E] |

TABLE 1-continued

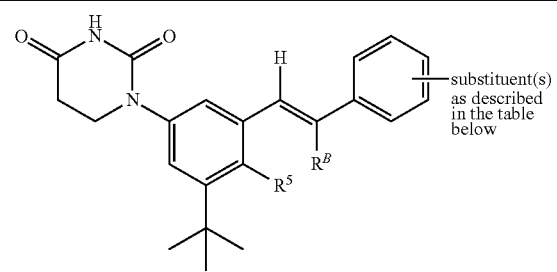

| compound | $R^5$ | $R^B$ | substituent(s) |
|---|---|---|---|
| IA-L1-1.9 | —OCH$_3$ | —H | -4-N(H)S(O)$_2$CH$_3$ [E] |
| IA-L1-1.10 | —OCH$_3$ | —H | -4-N(H)S(O)$_2$CH$_3$ [Z] |
| IA-L1-1.11 | —OCH$_3$ | —H | -4-N[C(O)CH$_3$]S(O)$_2$CH$_3$ [E] |
| IA-L1-1.12 | —OCH$_3$ | —H | -4-F [E] |
| IA-L1-1.13 | —OCH$_3$ | —H | -4-NH$_2$ [E] |
| IA-L1-1.14 | —OCH$_3$ | —H | -4-OCH$_3$ [E] |
| IA-L1-1.16 | —H | —H | -4-N(H)S(O)$_2$CH$_3$ [E] |
| IA-L1-1.17 | —OCH$_3$ | —OCH$_3$ | -4-N(H)S(O)$_2$CH$_3$ [Z] |
| IA-L1-1.18 | —OCH$_3$ | —H | — [E] |
| IA-L1-1.20 | —OCH$_3$ | —H | -4-N(H)S(O)$_2$CH$_3$ [Z] |
| IA-L1-1.21 | —OCH$_3$ | —F | -4-N(H)S(O)$_2$CH$_3$ [Z]:[E] (1:1) |
| IA-L1-1.22 | —OCH$_3$ | —H | -4-NO$_2$ [E] |
| IA-L1-1.23 | —OCH$_3$ | —Cl | -4-NO$_2$ [Z] |
| IA-L1-1.24 | —OCH$_3$ | —CH$_3$ | -4-NO$_2$ [E] |
| IA-L1-1.25 | —H | —H | -4-NO$_2$ [E] |
| IA-L1-1.26 | —OCH$_3$ | —H | -3-F and -4-N(H)S(O)$_2$CH$_3$ [E] |
| IA-L1-1.27 | —OCH$_3$ | —H | -2-OCH$_3$ and -4-N(H)S(O)$_2$CH$_3$ [E] |

TABLE 2

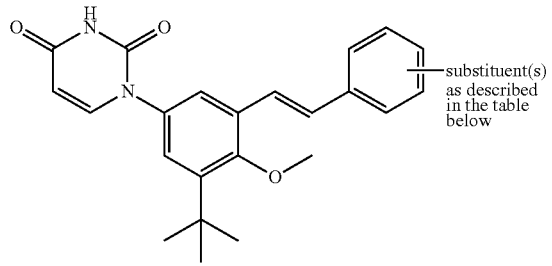

| compound | substituent(s) |
|---|---|
| 1B-L1-1.1 | -4-N(H)S(O)$_2$CH$_3$ [E] |
| 1B-L1-1.4 | -2-C(O)OH and -4-N(H)S(O)$_2$CH$_3$ [E] |
| 1B-L1-1.5 | -3-F and -4-N(H)S(O)$_2$CH$_3$ [E] |
| 1B-L1-1.6 | -2-C(O)H and -4-N(H)S(O)$_2$CH$_3$ [E] |
| 1B-L1-1.7 | -2-C(O)OCH$_3$ and -4-N(H)S(O)$_2$CH$_3$ [E] |
| 1B-L1-1.8 | -2-C(H)=N(OH) and -4-N(H)S(O)$_2$CH$_3$ [E] |
| 1B-L1-1.9 | -2-C(O)N(H)CH$_2$CH$_2$OCH$_3$ and -4-N(H)S(O)$_2$CH$_3$ [E] |
| 1B-L1-1.10 | -2-CH$_2$OH and -4-N(H)S(O)$_2$CH$_3$ [E] |
| 1B-L1-1.11 | -2-C(O)OC(H)$_2$CH$_3$ and -4-N(H)S(O)$_2$CH$_3$ [E] |
| 1B-L1-1.13 | -2-C(H)$_2$OCH$_3$ and -4-N(H)S(O)$_2$CH$_3$ [E] |
| 1B-L1-1.14 | -2-C(O)N(CH$_3$)$_2$ and -4-N(H)S(O)$_2$CH$_3$ [E] |
| 1B-L1-1.15 | -2-CH$_3$ and -4-N(H)S(O)$_2$CH$_3$ and -5-F [E] |
| 1B-L1-1.16 | imidazol-2-yl and -4-N(H)S(O)$_2$CH$_3$ [E] |
| 1B-L1-1.17 | -2-C(O)N(H)CH$_3$ and -4-N(H)S(O)$_2$CH$_3$ [E] |
| 1B-L1-1.18 | 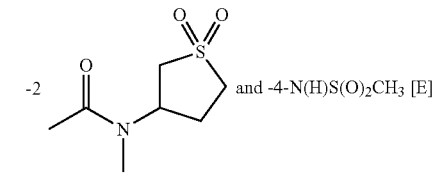 and -4-N(H)S(O)$_2$CH$_3$ [E] |

TABLE 2-continued

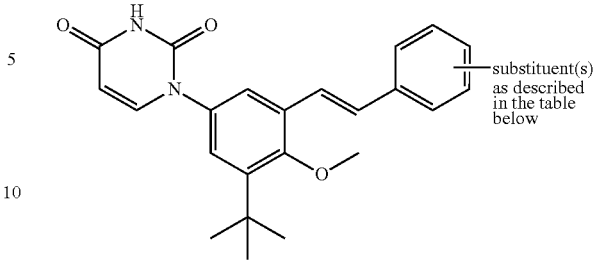

| compound | substituent(s) |
|---|---|
| 1B-L1-1.19 | -2-C(H)=NOCH$_3$ and -4-N(H)S(O)$_2$CH$_3$ [E] |
| 1B-L1-1.21 | -2-C(O)NH$_2$ and -4-N(H)S(O)$_2$CH$_3$ [E] |
| 1B-L1-1.22 | -2-[azetidinyl acetyl] and -4-N(H)S(O)$_2$CH$_3$ [E] |
| 1B-L1-1.23 | -2-[morpholinyl acetyl] and -4-N(H)S(O)$_2$CH$_3$ [E] |
| 1B-L1-1.24 | -2-C(O)N(CH$_3$)C(H)$_2$C(H)$_2$OCH$_3$ and -4-N(H)S(O)$_2$CH$_3$ [E] |
| 1B-L1-1.25 | -2-C(H)$_2$OC(H)(CH$_3$)$_2$ and -4-N(H)S(O)$_2$CH$_3$ (E) |
| 1B-L1-1.26 | -2-[2-methyloxazolyl] and -4-N(H)S(O)$_2$CH$_3$ [E] |
| 1B-L1-1.27 | -2-[pyrrolidinyl acetyl] and -4-N(H)S(O)$_2$CH$_3$ [E] |
| 1B-L1-1.28 | -2-NH$_2$ and -4-N(H)S(O)$_2$CH$_3$ [E] |
| 1B-L1-1.29 | -2-[3-hydroxy-azetidinyl methyl] and -4-N(H)S(O)$_2$CH$_3$ [E] |
| 1B-L1-1.31 | -2-C(H)$_2$N(H)C(H)$_2$C(H)$_2$C(H)(CH$_3$)$_2$ and -4-N(H)S(O)$_2$CH$_3$ [E] |
| 1B-L1-1.32 | -2-N(H)C(O)OC(CH$_3$)$_3$ and -4-N(H)S(O)$_2$CH$_3$ [E] |
| 1B-L1-1.33 | -2-[pyrrolidinyl methyl] and -4-N(H)S(O)$_2$CH$_3$ [E] |
| 1B-L1-1.34 | -4-N(H)S(O)$_2$CH$_3$ [Z] |

TABLE 3

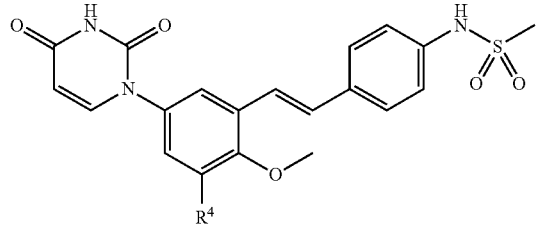

| compound | R⁴ |
|---|---|
| 1B-L1-1.45 | —C(CH₃)₂C(H)₂OH [E] |
| 1B-L1-1.46 | furan-2-yl [E] |
| 1B-L1-1.47 | 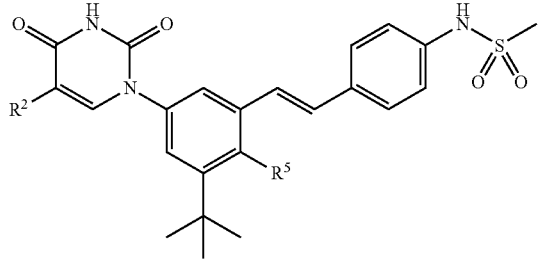 [E] (thiophen-3-yl) |
| 1B-L1-1.48 | (thiophen-2-yl) [E] |
| 1B-L1-1.49 | —S(O)₂CH₃ [E] |
| 1B-L1-1.50 | furan-3-yl [E] |
| 1B-L1-1.51 | —I [E] |
| 1B-L1-1.52 | —Br [E] |
| 1B-L1-1.53 | pyridin-3-yl [E] |
| 1B-L1-1.55 | pyridin-4-yl [E] |

TABLE 4

| compound | R² | R⁵ |
|---|---|---|
| 1B-L1-1.2 | —F | —OCH₃ [E] |
| 1B-L1-1.12 | —H | —Cl [E] |
| 1B-L1-1.20 | —Cl | —OCH₃ [E] |
| 1B-L1-1.30 | —H | —OCH₂CH₃ [E] |

TABLE 5

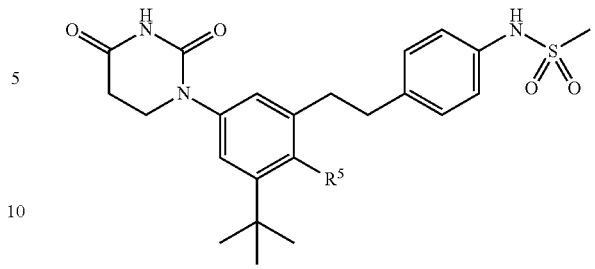

| compound | R⁵ |
|---|---|
| IA-L5-2-1.1 | —OCH₃ |
| IA-L5-2-1.2 | —H |

TABLE 6

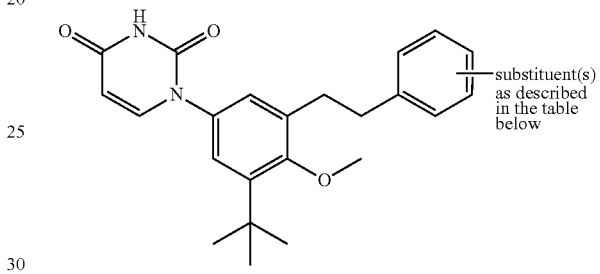

| compound | substituent(s) |
|---|---|
| 1B-L5-2-1.1 | -2-C(O)OCH₃ and -4-N(H)S(O)₂CH₃ |
| 1B-L5-2-1.2 | -4-N(H)S(O)₂CH₃ |

TABLE 7

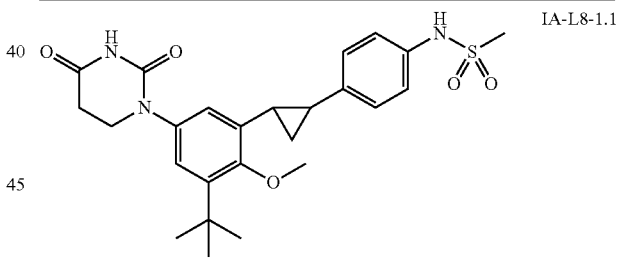

IA-L8-1.1

D. Isomers

This invention also is directed, in part, to all isomers of the compounds of formula I (and their salts) (i.e., structural and stereoisomers). Structural isomers include chain and position isomers. Stereoisomers include E/Z isomers (i.e., isomers with regard to one or more double bonds), enantiomers (i.e., stereo-isomers that have opposite configurations at all stereogenic centers), and diastereoisomers (i.e., stereo-isomers that have the same configuration at one or more stereogenic centers, but differ at other stereogenic centers).

E. Salts

This invention also is directed, in part, to all salts of the compounds of formula I. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula I can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula I include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In some embodiments, the salt is sodium salt of (E)-N-(4-(3-tert-butyl-5-(2,4-dioxo-3,4-dihydro-pyrimidin-1(2H)-yl)-2-methoxystyryl)phenyl)methanesulfonamide.

In some embodiments, the salt is disodium salt of (E)-N-(4-(3-tert-butyl-5-(2,4-dioxo-3,4-dihydropyrimidin-1(2H)-yl)-2-methoxystyryl)phenyl)methanesulfonamide.

In some embodiments, the salt is potassium salt of (E)-N-(4-(3-tert-butyl-5-(2,4-dioxo-3,4-dihydropyrimidin-1(2H)-yl)-2-methoxystyryl)phenyl)methanesulfonamide.

In some embodiments, the salt is monopotassium salt of (E)-N-(4-(3-tert-butyl-5-(2,4-dioxo-3,4-dihydropyrimidin-1(2H)-yl)-2-methoxystyryl)phenyl)methanesulfonamide.

F. Purity

Compounds of formula I (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

G. Crystalline Forms of Some Specific Compounds and Salts of the Invention

G1. Crystalline Forms of (E)-N-(4-(3-tert-butyl-5-(2,4-dioxo-3,4-dihydropyrimidin-1(2H)-yl)-2-methoxystytyl)phenyl)methanesulfonamide Disodium Salt This invention also relates, in part, to crystalline forms of (E)-N-(4-(3-tert-butyl-5-(2,4-dioxo-3,4-dihydropyrimidin-1(2H)-yl)-2-methoxystyryl)phenyl)methanesulfonamide disodium salt, namely the nonahydrate and tetrahydrate crystalline forms discussed below.

This invention relates, in part, to a nonahydrate crystalline disodium salt. The crystallographic unit cell parameters of the nonahydrate crystalline disodium salt have been determined to be as follows: a is 8.9 Å, b is 9.4 Å, and c is 20.7 Å (more precisely, a is 8.926(2)Å, b is 9.415(2)Å, and c is 20.674(5) Å); the cell angles are: α—94.8°, β—93.3°, and γ—107.0° (more precisely, a is 94.796(4)°, β is 93.345(4)°, and γ is 107.013(4)°); and the cell volume is 1649 Å$^3$ (more precisely, 1649.3(7)Å$^3$). The salt crystallizes in the P-1 space group.

In some embodiments, the disodium salt nonahydrate has an X-ray powder diffraction pattern comprising one or more peaks selected from the group consisting of 4.3±0.2, 10.4±0.2, 10.9±0.2, 11.6±0.2, 12.9±0.2, 14.7±0.2, 16.4±0.2, 17.8±0.2, 19.4±0.2, 19.8±0.2, 20.8±0.2, 21.9±0.2, and 23.5±0.2 degrees 2θ. In some such embodiments, the disodium salt nonahydrate has an X-ray powder diffraction pattern comprising three or more peaks selected from the group consisting of 4.3±0.2, 10.4±0.2, 10.9±0.2, 11.6±0.2, 12.9±0.2, 14.7±0.2, 16.4±0.2, 17.8±0.2, 19.4±0.2, 19.8±0.2, 20.8±0.2, 21.9±0.2, and 23.5±0.2 degrees 2θ. In other such embodiments, the disodium salt nonahydrate has an X-ray powder diffraction pattern comprising five or more peaks selected from the group consisting of 4.3±0.2, 10.4±0.2, 10.9±0.2, 11.6±0.2, 12.9±0.2, 14.7±0.2, 16.4±0.2, 17.8±0.2, 19.4±0.2, 19.8±0.2, 20.8±0.2, 21.9±0.2, and 23.5±0.2 degrees 2θ.

In some embodiments, the disodium salt nonahydrate has an X-ray powder diffraction pattern comprising one or more peaks selected from the group consisting of 4.3±0.2, 10.4±0.2, 10.9±0.2, 11.6±0.2, 12.9±0.2, 14.7±0.2, 14.9±0.2, 16.4±0.2, 17.8±0.2, 19.4±0.2, 19.7±0.2, 19.8±0.2, 20.8±0.2, 20.9±0.2, 21.9±0.2, 22.1±0.2, and 23.5±0.2 degrees 2θ. In some such embodiments, the disodium salt nonahydrate has an X-ray powder diffraction pattern comprising three or more peaks selected from the group consisting of 4.3±0.2, 10.4±0.2, 10.9±0.2, 11.6±0.2, 12.9±0.2, 14.7±0.2, 14.9±0.2, 16.4±0.2, 17.8±0.2, 19.4±0.2, 19.7±0.2, 19.8±0.2, 20.8±0.2, 20.9±0.2, 21.9±0.2, 22.1±0.2, and 23.5±0.2 degrees 2θ. In other such embodiments, the disodium salt nonahydrate has an X-ray powder diffraction pattern comprising five or more peaks selected from the group consisting of 4.3±0.2, 10.4±0.2, 10.9±0.2, 11.6±0.2, 12.9±0.2, 14.7±0.2, 14.9±0.2, 16.4±0.2, 17.8±0.2, 19.4±0.2, 19.7±0.2, 19.8±0.2, 20.8±0.2, 20.9±0.2, 21.9±0.2, 22.1±0.2, and 23.5±0.2 degrees 2θ.

In some embodiments, the disodium salt nonahydrate has an X-ray powder diffraction pattern substantially as shown in FIG. 1. The 2θ values for the peaks in FIG. 1 (and their intensities) are as follows: 4.31 (100), 10.36 (12), 10.91 (23), 11.61 (52), 12.93 (24), 14.73 (65), 14.89 (20), 16.44 (41), 17.80 (38), 19.44 (26), 19.67 (37), 19.83 (59), 20.75 (69), 20.89 (21), 21.92 (43), 22.13 (40), and 22.42 (24).

This invention also relates, in part, to a process for preparing the disodium salt nonahydrate. It was prepared in aqueous medium. Aqueous NaOH (1M, 1.18 ml) was added to (E)-N-(4-(3-tert-butyl-5-(2,4-dioxo-3,4-dihydropyrimidin-1(2H)-yl)-2-methoxystyryl)phenyl)methanesulfonamide (compound IB-L1-1.1) (27.82 mg) (molar ratio 1:20 acid:base). The resulting suspension was equilibrated at ambient conditions. The disodium salt nonahydrate formed seven days later through a solution-mediated process. Alternatively, the disodium salt nonahydrate was prepared by suspending 278.8 mg of compound IB-L1-1.1 in 1.25 ml THF while heated to about 50° C. Aqueous NaOH (1N, 1.5 ml, 2.2 molar equivalents) was added. The solid dissolved completely to yield a clear solution, which was naturally cooled to ambient temperatures. The salt crystallized spontaneously. The molecular structure was determined by single crystal diffractometry.

This invention relates, in part, to a tetrahydrate crystalline disodium salt.

In some embodiments, the disodium salt tetrahydrate has an X-ray powder diffraction pattern comprising one or more peaks selected from the group consisting of 4.8±0.2, 12.1±0.2, 14.0±0.2, 17.0±0.2, 17.5±0.2, 20.9±0.2, 21.6±0.2, 25.0±0.2, and 29.5±0.2 degrees 2θ. In some such embodiments, the disodium salt tetrahydrate has an X-ray powder diffreaction pattern comprising three or more peaks selected from the group consisting of 4.8±0.2, 12.1±0.2, 14.0±0.2, 17.0±0.2, 17.5±0.2, 20.9±0.2, 21.6±0.2, 25.0±0.2, and 29.5±0.2 degrees 2θ. In other such embodiments, the disodium salt tetrahydrate has an X-ray powder diffraction pattern comprising five or more peaks selected from the group consisting of 4.8±0.2, 12.1±0.2, 14.0±0.2, 17.0±0.2, 17.5±0.2, 20.9±0.2, 21.6±0.2, 25.0±0.2, and 29.5±0.2 degrees 2θ.

In some embodiments, the disodium salt tetrahydrate has an X-ray powder diffraction pattern comprising one or more peaks selected from the group consisting of 4.8±0.2, 12.1±0.2, 14.0±0.2, 14.4±0.2, 17.0±0.2, 17.5±0.2, 20.9±0.2, 21.6±0.2, 25.0±0.2, 29.5±0.2, and 34.2±0.2 degrees 2θ. In some embodiments, the disodium salt tetrahydrate has an X-ray powder diffraction pattern comprising three or more peaks selected from the group consisting of 4.8±0.2, 12.1±0.2, 14.0±0.2, 14.4±0.2, 17.0±0.2, 17.5±0.2, 20.9±0.2, 21.6±0.2, 25.0±0.2, 29.5±0.2, and 34.2±0.2 degrees 2θ. In other such embodiments, the disodium salt tetrahydrate has an X-ray powder diffraction pattern comprising five or more peaks selected from the group consisting of 4.8±0.2, 12.1±0.2, 14.0±0.2, 14.4±0.2, 17.0±0.2, 17.5±0.2, 20.9±0.2, 21.6±0.2, 25.0±0.2, 29.5±0.2, and 34.2±0.2 degrees 2θ.

Figure 2:
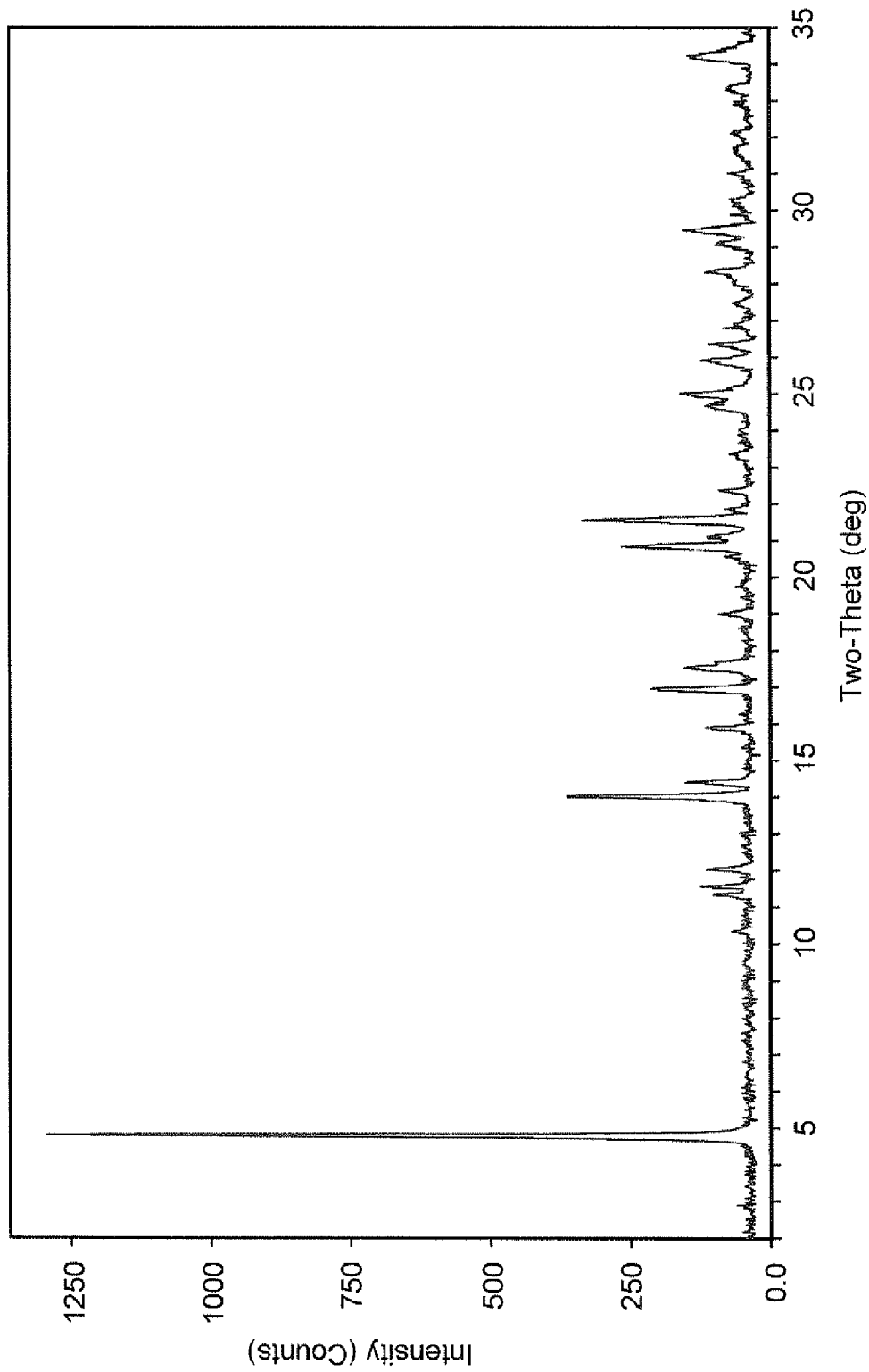
FIG. 2 shows an illustrative PXRD pattern for the disodium salt tetrahydrate of compound IB-L1-1.1.
Figure 3:
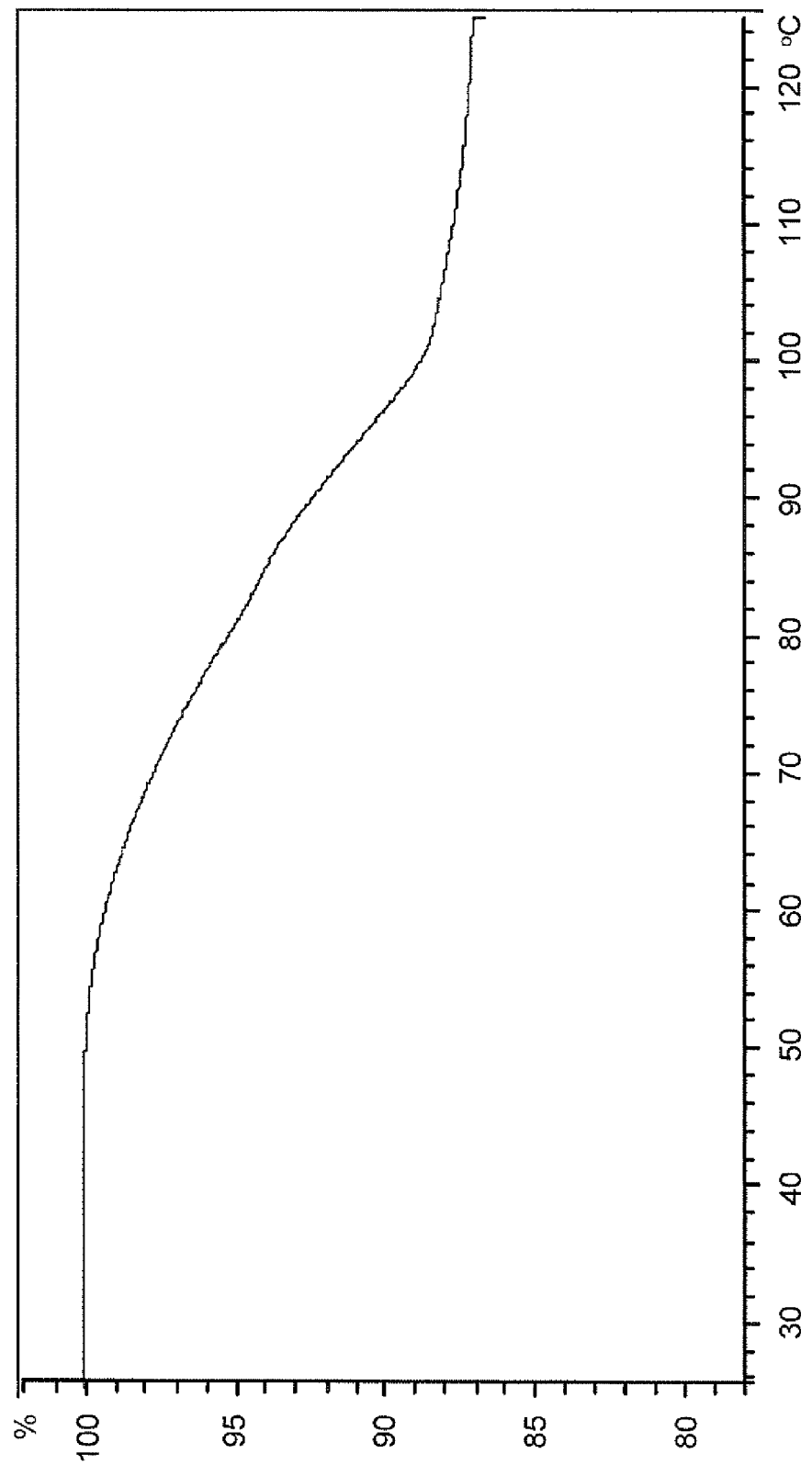
FIG. 3 shows an illustrative TGA profile of the disodium salt tetrahydrate of compound IB-L1-1.1.

In some embodiments, the disodium salt tetrahydrate has an X-ray powder diffraction pattern substantially as shown in FIG. 2. The 2θ values for the peaks in FIG. 2 (and their intensities) are as follows: 4.81 (100), 12.07 (7), 14.01 (27), 14.41 (8), 16.96 (18), 17.53 (11), 20.87 (18), 21.58 (22), 24.99 (11), 29.47 (9), and 34.20 (9).

This invention also relates, in part, to a process for preparing the disodium salt tetrahydrate by suspending the nonahydrate disodium salt in an organic solvent (e.g., ethanol, 1-propanol, or 2-propanol).

G2. Crystalline Form of (E)-N-(4-(3-tert-butyl-5-(2,4-dioxo-3,4-dihydropyrimidin-1(2H)-yl)-2-methoxystyryl)phenyl)methanesulfonamide Dipotassium Salt This invention also relates, in part, to a crystalline (E)-N-(4-(3-tert-butyl-5-(2,4-dioxo-3,4-dihydropyrimidin-1(2H)-yl)-2-methoxystyryl)phenyl)methanesulfonamide dipotassium salt tetrahydrate.

The crystallographic unit cell parameters of the dipotassium salt tetrahydrate have been determined to be as follows: a is 14.5 Å, b is 10.8 Å, and c is 35.8 Å (more precisely, a is 14.454(14)Å, b is 10.763(14)Å, and c is 35.75(4)Å); the cell angle is: β—98.8° (more precisely, β is 98.82(3)°; and the cell volume is 5499 Å$^3$ (more precisely, 5499(11)Å$^3$). The salt crystallizes in the C2/c space group.

In some embodiments, the dipotassium salt tetrahydrate has an X-ray powder diffraction pattern comprising one or more peaks selected from the group consisting of 5.0±0.2, 11.9±0.2, 12.4±0.2, 13.7±0.2, 15.0±0.2, 16.5±0.2, 17.1±0.2, 20.8±0.2, 21.3±0.2, 22.2±0.2, 24.0±0.2, 26.4±0.2, and 29.3±0.2 degrees 2θ. In some such embodiments, the dipotassium salt tetrahydrate has an X-ray powder diffraction pattern comprising three or more peaks selected from the group consisting of 5.0±0.2, 11.9±0.2, 12.4±0.2, 13.7±0.2, 15.0±0.2, 16.5±0.2, 17.1±0.2, 20.8±0.2, 21.3±0.2, 22.2±0.2, 24.0±0.2, 26.4±0.2, and 29.3±0.2 degrees 2θ. In other such embodiments, the dipotassium salt tetrahydrate has an X-ray powder diffraction pattern comprising five or more peaks selected from the group consisting of 5.0±0.2, 11.9±0.2, 12.4±0.2, 13.7±0.2, 15.0±0.2, 16.5±0.2, 17.1±0.2, 20.8±0.2, 21.3±0.2, 22.2±0.2, 24.0±0.2, 26.4±0.2, and 29.3±0.2 degrees 2θ.

In some embodiments, the dipotassium salt tetrahydrate has an X-ray powder diffraction pattern comprising one or more peaks selected from the group consisting of 5.0±0.2, 11.9±0.2, 12.4±0.2, 12.6±0.2, 13.7±0.2, 15.0±0.2, 16.5±0.2, 16.7±0.2, 17.1±0.2, 20.7±0.2, 20.8±0.2, 21.3±0.2, 22.2±0.2, 22.4±0.2, 24.0±0.2, 26.4±0.2, and 29.3±0.2 degrees 2θ. In some such embodiments, the dipotassium salt tetrahydrate has an X-ray powder diffraction pattern comprising three or more peaks selected from the group consisting of 5.0±0.2, 11.9±0.2, 12.4±0.2, 12.6±0.2, 13.7±0.2, 15.0±0.2, 16.5±0.2, 16.7±0.2, 17.1±0.2, 20.7±0.2, 20.8±0.2, 21.3±0.2, 22.2±0.2, 22.4±0.2, 24.0±0.2, 26.4±0.2, and 29.3±0.2 degrees 2θ.

In other such embodiments, the dipotassium salt tetrahydrate has an X-ray powder diffraction pattern comprising five or more peaks selected from the group consisting of 5.0±0.2, 11.9±0.2, 12.4±0.2, 12.6±0.2, 13.7±0.2, 15.0±0.2, 16.5±0.2, 16.7±0.2, 17.1±0.2, 20.7±0.2, 20.8±0.2, 21.3±0.2, 22.2±0.2, 22.4±0.2, 24.0±0.2, 26.4±0.2, and 29.3±0.2 degrees 2θ.

Figure 4:
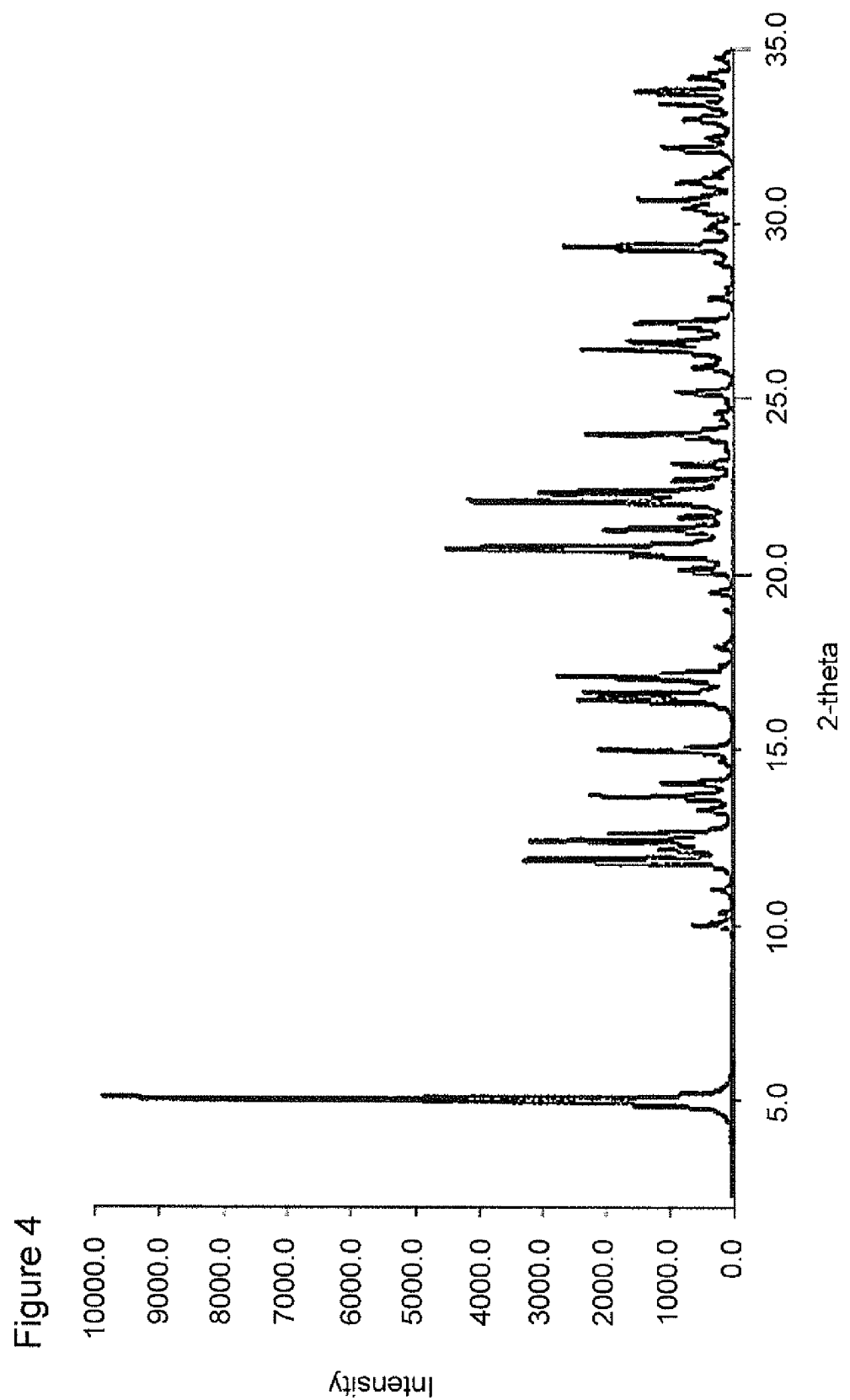
FIG. 4 shows an illustrative PXRD pattern for the dipotassium salt tetrahydrate of compound IB-L1-1.1.

In some embodiments, the dipotassium salt tetrahydrate has an X-ray powder diffraction pattern substantially as shown in FIG. 4. The 2θ values for the peaks in FIG. 4 (and their intensities) are as follows: 5.00 (100), 11.86 (34), 12.39 (32), 12.64 (19), 13.70 (23), 15.03 (21), 16.47 (24), 16.66 (24), 17.12 (28), 20.75 (29), 20.81 (33), 21.34 (22), 22.15 (46), 22.38 (31), 24.02 (24), 26.44 (24), and 29.32 (21).

This invention also relates, in part, to a process for preparing the dipotassium salt tetrahydrate by suspending compound IB-L1-1.1 (261.13 mg) in 1.25 ml THF while heated to about 50° C. Aqueous KOH (1N, 1.3 ml, 2.2 molar equivalent) was added. The solid dissolved completely to yield a clear solution, which was naturally cooled to ambient temperatures. Crystallization occurred during the slow evaporation process.

G3. Crystalline Forms of (E)-N-(4-(3-tert-butyl-5-(2,4-dioxo-3,4-dihydropyrimidin-1(2H)-yl)-2-methoxystytyl)phenyl)methanesulfonamide Monopotassium Salt This invention also relates, in part, to crystalline forms of (E)-N-(4-(3-tert-butyl-5-(2,4-dioxo-3,4-dihydropyrimidin-1(2H)-yl)-2-methoxystyryl)phenyl)methanesulfonamide monopotassium salt, namely the trihydrate and dihydrate crystalline forms discussed below.

This invention relates, in part, to a monopotassium salt trihydrate. The crystallographic unit cell parameters of the trihydrate crystalline monopotassium salt have been determined to be as follows: a is 9.0 Å, b is 8.3 Å, and c is 18.6 Å (more precisely, a is 9.0393(16)Å, b is 8.3332(15)Å, and c is 18.582(3)Å); the cell angles are: $\alpha$—80.5°, $\beta$—85.1°, and $\gamma$—80.5° (more precisely, a is 80.511(2)°, $\beta$ is 85.134(3)°, and $\gamma$ is 80.531(2)°); and the cell volume is 1359 Å$^3$ (more precisely, 1359.3(4)Å$^3$). The salt crystallizes in the P-1 space group.

In some embodiments, the monopotassium salt trihydrate has an X-ray powder diffraction pattern comprising one or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ. In some such embodiments, the monopotassium salt trihydrate has an X-ray powder diffraction pattern comprising three or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ. In other such embodiments, the monopotassium salt trihydrate has an X-ray powder diffraction pattern comprising five or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ.

In some embodiments, the monopotassium salt trihydrate has an X-ray powder diffraction pattern comprising one or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 21.7±0.2, 22.1±0.2, 22.5±0.2, 22.6±0.2, and 23.0±0.2 degrees 2θ. In some such embodiments, the monopotassium salt trihydrate has an X-ray powder diffraction pattern comprising three or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 21.7±0.2, 22.1±0.2, 22.5±0.2, 22.6±0.2, and 23.0±0.2 degrees 2θ. In other such embodiments, the monopotassium salt trihydrate has an X-ray powder diffraction pattern comprising five or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 21.7±0.2, 22.1±0.2, 22.5±0.2, 22.6±0.2, and 23.0±0.2 degrees 2θ.

In some embodiments, the monopotassium salt trihydrate has an X-ray powder diffreaction pattern comprising one or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 21.7±0.2, 22.1±0.2, 22.5±0.2, 22.6±0.2, and 23.0±0.2 degrees 2θ. In some such embodiments, the monopotassium salt trihydrate has an X-ray powder diffraction pattern comprising three or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ. In other such embodiments, the monopotassium salt trihydrate has an X-ray powder diffraction pattern comprising five or more peaks selected from the group consisting of 4.8±0.2, 10.8±0.2, 11.3±0.2, 13.4±0.2, 15.3±0.2, 16.9±0.2, 21.1±0.2, 21.7±0.2, 22.1±0.2, 22.5±0.2, and 23.0±0.2 degrees 2θ.

Figure 5:
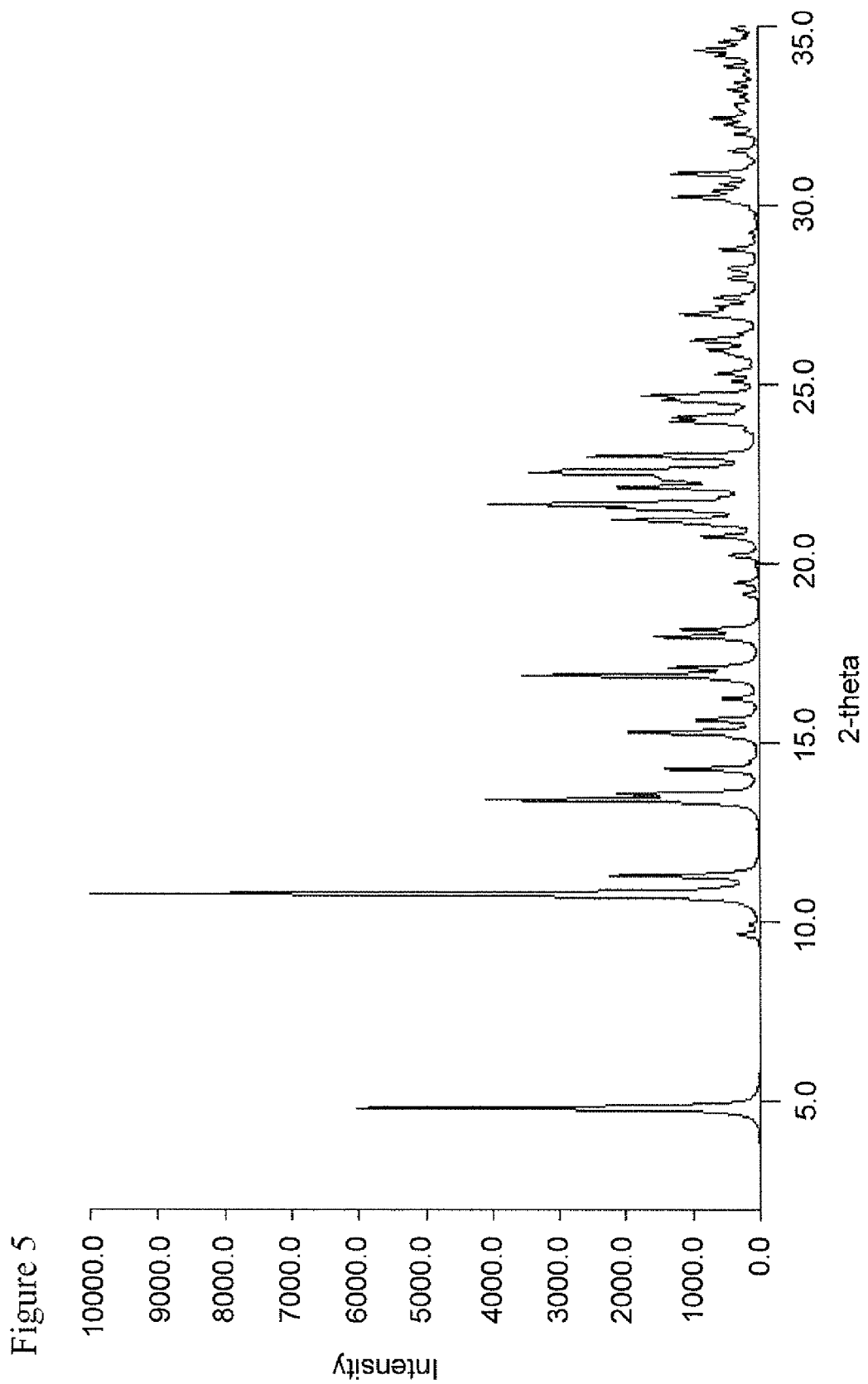
FIG. 5 shows an illustrative PXRD pattern for the monopotassium salt trihydrate of compound IB-L1-1.1.

In some embodiments, the monopotassium salt trihydrate has an X-ray powder diffraction pattern substantially as shown in FIG. 5. The 2θ values for the peaks in FIG. 5 (and their intensities) are as follows: 4.83 (60), 10.79 (100), 11.31 (22), 13.42 (41), 13.59 (18), 15.32 (21), 16.90 (38), 21.24 (22), 21.68 (20), 21.68 (21), 22.15 (22), 22.55 (29), 22.63 (23), and 23.02 (27).

This invention also relates, in part, to a process for preparing the monopotassium salt trihydrate. It was prepared by suspending compound IB-L1-1.1 (108.81 mg) in 0.4 ml THF while heated to about 50° C. Aqueous KOH solution (1N, 0.278 ml, 1.2 molar equivalent) was added. The solid dissolved completely to yield a clear solution. Additional 1.6 ml THF was added to the solution, which was then naturally cooled to ambient temperatures and crystallization was observed. Alternatively, the monopotassium salt trihydrate was prepared by suspending compound IB-L1-1.1 (343.89 mg) in 1.0 ml THF while heated to 50° C. Aqueous KOH (1 N, 0.878 ml, 1.2 molar equivalent) was added. The solid dissolved completely to yield a clear solution. Ethanol was added to the solution dropwise to a total volume of 4.0 ml. The solution was then naturally cooled to ambient temperature and crystallization was observed.

This invention relates, in part, to a monopotassium salt dihydrate.

In some embodiments, the monopotassium salt dihydrate has an X-ray powder diffraction pattern comprising one or more peaks selected from the group consisting of 7.7±0.2, 8.8±0.2, 16.1±0.2, and 19.7±0.2 degrees 2θ. In some such embodiments, the monopotassium salt dihydrate has an X-ray powder diffraction pattern comprising three or more peaks selected from the group consisting of degrees 2θ.

In some embodiments, the monopotassium salt dihydrate has an X-ray powder diffraction pattern comprising one or more peaks selected from the group consisting of 7.7±0.2, 8.8±0.2, 12.4±0.2, 14.0±0.2, 16.1±0.2, 17.7±0.2, 19.2±0.2, 19.7±0.2, 23.1±0.2, and 29.2±0.2 degrees 2θ. In some such embodiments, the monopotassium salt dihydrate has an X-ray powder diffraction pattern comprising three or more peaks selected from the group consisting of 7.7±0.2, 8.8±0.2, 12.4±0.2, 14.0±0.2, 16.1±0.2, 17.7±0.2, 19.2±0.2, 19.7±0.2, 23.1±0.2, and 29.2±0.2 degrees 2θ. In other such embodiments, the monopotassium salt dihydrate has an X-ray powder diffraction pattern comprising five or more peaks selected from the group consisting of 7.7±0.2, 8.8±0.2, 12.4±0.2, 14.0±0.2, 16.1±0.2, 17.7±0.2, 19.2±0.2, 19.7±0.2, 23.1±0.2, and 29.1±0.2 degrees 2θ.

Figure 6:
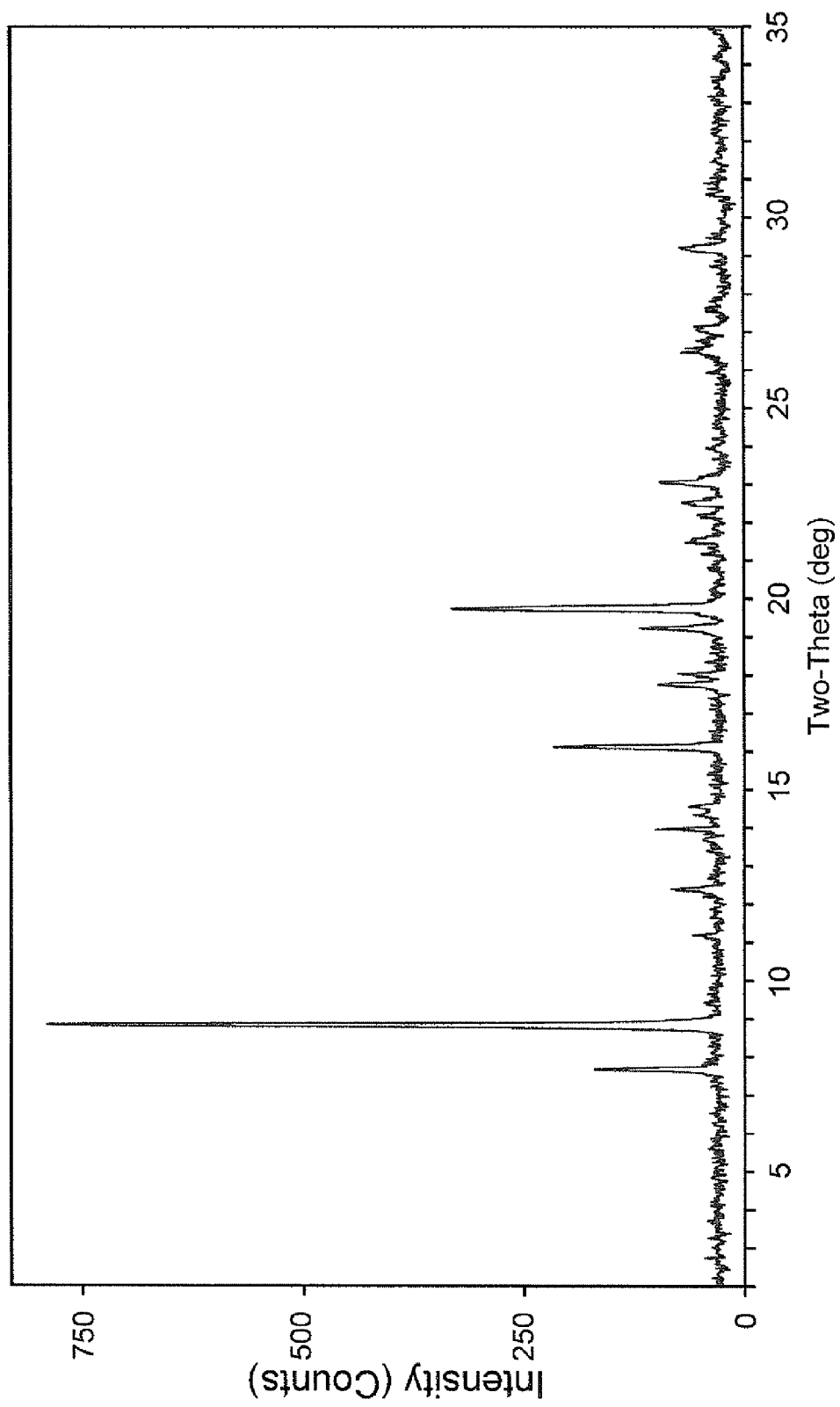
FIG. 6 shows an illustrative PXRD pattern for the monopotassium salt dihydrate of compound IB-L1-1.1.
Figure 7:
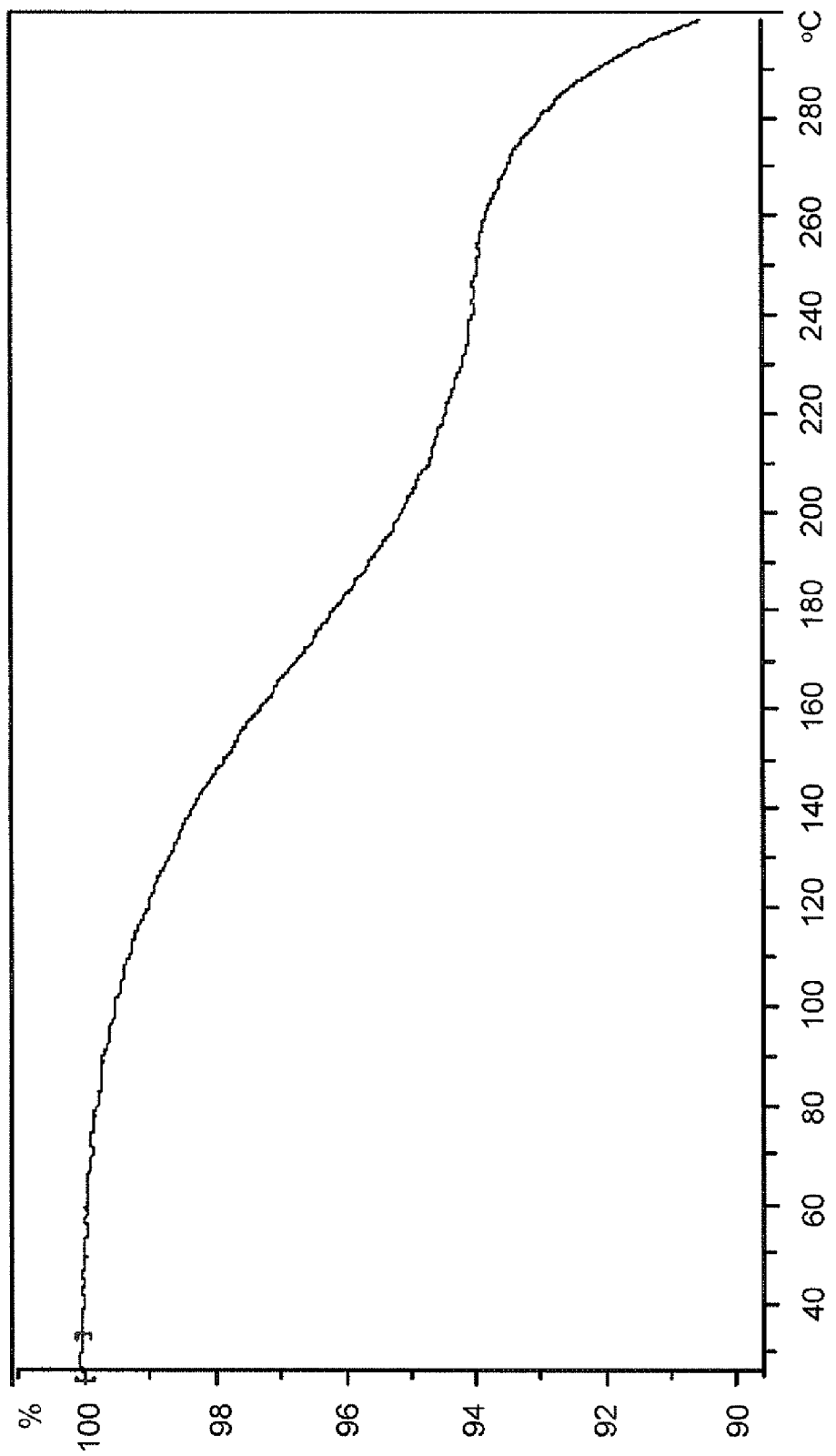
FIG. 7 shows an illustrative TGA profile of the monopotassium salt dihydrate of compound IB-L1-1.1.

In some embodiments, the monopotassium salt dihydrate has an X-ray powder diffraction pattern substantially as shown in FIG. 6. The 2θ values for the peaks in FIG. 6 (and their intensities) are as follows: 7.68 (19), 8.83 (100), 12.40 (7), 13.97 (10), 16.12 (25), 17.75 (9), 19.22 (12), 19.73 (40), 23.05 (9), and 29.21 (7).

This invention also relates, in part, to a process for preparing the monopotassium salt dihydrate. It was prepared by suspending the monopotassium salt trihydrate in media of low water activity, such as an ethanol/H$_2$O mixture (50/1 v/v). Alternatively, the monopotassium salt dihydrate was prepared by dissolving potassium trihydrate solid (1.8 g) in 36 mL of IPA and 4 ml water at 80° C. The resulting solution was cooled to 55° C. over 1 h. The solution was then seeded with 7.5 mg of dihydrate crystals at 55° C. and maintained at 55° C. for 1 h. Heptane (36 ml) was then added over 3 h. The reaction mixture was cooled to 0° C., and filtration yielded a material containing both di- and trihydrate crystals. The solid was then reslurried in 20 mL of 10:1 v/v EtOH/H$_2$O at 50° C. for 3 h and cooled to 25° C. over 5 h. The slurry was then mixed at 25° C. for additional 3 days and cooled to 0° C. over 3 h and held at this temperature for 2 h. The resulting crystals were filtered and air-dried on filter funnel for 1 h to give dihydrate. The dihydrate monopotassium salt was also prepared by slurrying a mixture of dihydrate and trihydrate crystals in 10:1 v/v EtOH/H$_2$O at 80° C. for 2 days. The potassium content was confirmed by ion chromatography.

G4. Crystalline Form of (E)-N-(4-(3-tert-butyl-5-(2,4-dioxo-3,4-dihydropyrimidin-1(2H)-yl)-2-methoxystyyl)phenyl)methanesulfonamide 1/7 Potassium Salt This invention also relates, in part, to a crystalline form of (E)-N-(4-(3-tert-butyl-5-(2,4-dioxo-3,4-dihydropyrimidin-1(2H)-yl)-2-methoxystyryl)phenyl)methanesulfonamide 1/7 potassium salt.

In some embodiments, the 1/7 potassium salt has an X-ray powder diffraction pattern comprising one or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 21.2±0.2, 22.1±0.2, and 22.9±0.2 degrees 2θ. In some such embodiments, the 1/7 potassium salt has an X-ray powder diffraction pattern comprising three or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 21.2±0.2, 22.1±0.2, and 22.9±0.2 degrees 2θ. In other such embodiments, the 1/7 potassium salt has an X-ray powder diffraction pattern comprising five or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 21.2±0.2, 22.1±0.2, and 22.9±0.2 degrees 2θ. In some embodiments, the 1/7 potassium salt has an X-ray powder diffraction pattern comprising one or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 20.8±0.2, 21.2±0.2, 22.1±0.2, 22.9±0.2, 24.3±0.2, 24.9±0.2, and 25.1±0.2 degrees 2θ. In some such embodiments, the 1/7 potassium salt has an X-ray powder diffraction pattern comprising three or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 20.8±0.2, 21.2±0.2, 22.1±0.2, 22.9±0.2, 24.3±0.2, 24.9±0.2, and 25.1±0.2 degrees 2θ. In other such embodiments, the 1/7 potassium salt has an X-ray powder diffraction pattern comprising five or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 20.8±0.2, 21.2±0.2, 22.1±0.2, 22.9±0.2, 24.3±0.2, 24.9±0.2, and 25.1±0.2 degrees 2θ.

Figure 8:
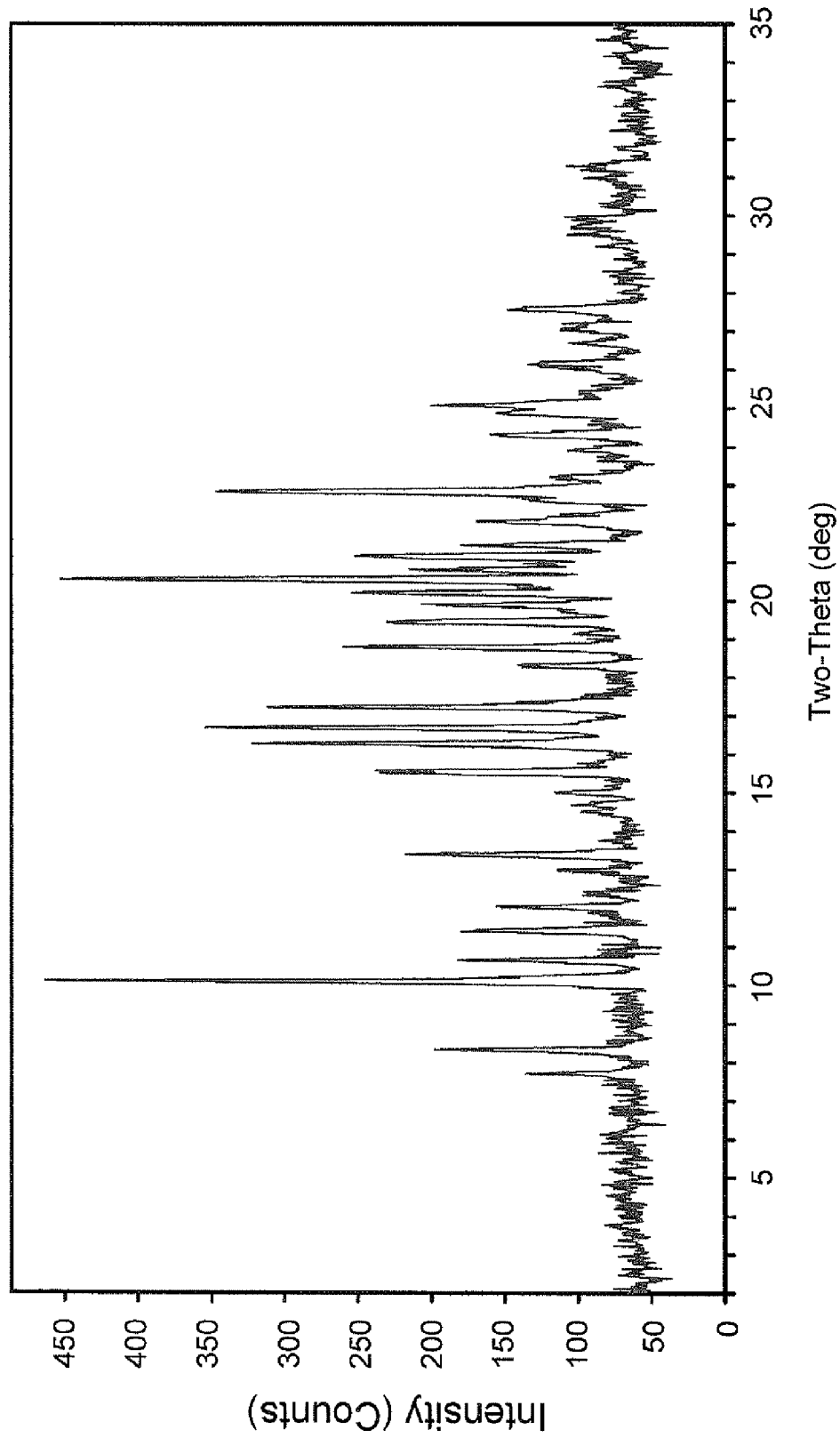
FIG. 8 shows an illustrative PXRD pattern for the 1/7 potassium salt of compound IB-L1-1.1.

In some embodiments, the 1/7 potassium salt has an X-ray powder diffraction pattern substantially as shown in FIG. 8. The 2θ values for the peaks in FIG. 8 (and their intensities) are as follows: 7.71 (19), 8.33 (34), 10.10 (100), 10.66 (29), 11.39 (27), 12.04 (22), 13.39 (39), 15.56 (41), 16.27 (62), 16.69 (70), 17.22 (59), 18.31 (18), 18.78 (47), 19.44 (36), 19.89 (28), 20.19 (33), 20.54 (87), 20.80 (33), 21.15 (47), 22.05 (24), 22.82 (67), 24.32 (22), 24.87 (22), and 25.07 (33).

This invention also relates, in part, to a process for preparing the 1/7 potassium salt. It was prepared by suspending compound IB-L1-1.1 (2 g) 6 ml THF at 50° C. One molar equivalent of KOH dissolved in 4.3 ml water was added, and the reaction mixture was heated to 65° C. to dissolve all solids. The solution was then cooled to ambient temperatures over 2 h and spontaneous crystallization took place. The slurry was then cooled to 5° C. and held at that temperature for 2 h. The pale yellow crystals were filtered and air-dried for 24 h at ambient conditions. The potassium content was determined by ion chromatography.

G5. Crystalline Form of (E)-N-(4-(3-tert-butyl-5-(2,4-dioxo-3,4-dihydropyrimidin-1(2H)-yl)-2-methoxystyryl)phenyl)methanesulfonamide Monodiethylamine Salt Tetrahydrate This invention also relates, in part, to crystalline (E)-N-(4-(3-tert-butyl-5-(2,4-dioxo-3,4-dihydropyrimidin-1(2H)-yl)-2-methoxystyryl)phenyl)methanesulfonamide monodiethylamine salt tetrahydrate.

In some embodiments, the monodiethylamine salt tetrahydrate has an X-ray powder diffraction pattern comprising one or more peaks selected from the group consisting of 9.5±0.2, 10.0±0.2, 11.8±0.2, 12.1±0.2, 14.4±0.2, 16.8±0.2, 17.6±0.2, 19.8±0.2, 20.8±0.2, 21.4±0.2, 21.8±0.2, and 29.8±0.2 degrees 2θ. In some such embodiments, the monodiethylamine salt tetrahydrate has an X-ray powder diffraction pattern comprising three or more peaks selected from the group consisting of 9.5±0.2, 10.0±0.2, 11.8±0.2, 12.1±0.2, 14.4±0.2, 16.8±0.2, 17.6±0.2, 19.8±0.2, 20.8±0.2, 21.4±0.2, 21.8±0.2, and 29.8±0.2 degrees 2θ. In other such embodiments, the monodiethylamine salt tetrahydrate has an X-ray powder diffraction pattern comprising five or more peaks selected from the group consisting of 9.5±0.2, 10.0±0.2, 11.8±0.2, 12.1±0.2, 14.4±0.2, 16.8±0.2, 17.6±0.2, 19.8±0.2, 20.8±0.2, 21.4±0.2, 21.8±0.2, and 29.8±0.2 degrees 2θ.

In some embodiments, the monodiethylamine salt tetrahydrate has an X-ray powder diffraction pattern comprising one or more peaks selected from the group consisting of 9.5±0.2, 10.0±0.2, 11.8±0.2, 12.1±0.2, 14.4±0.2, 16.8±0.2, 17.6±0.2, 19.4±0.2, 19.8±0.2, 20.8±0.2, 21.4±0.2, 21.8±0.2, 21.9±0.2, and 29.8±0.2 degrees 2θ. In some such embodiments, the monodiethylamine salt tetrahydrate has an X-ray powder diffraction pattern comprising three or more peaks selected from the group consisting of 9.5±0.2, 10.0±0.2, 11.8±0.2, 12.1±0.2, 14.4±0.2, 16.8±0.2, 17.6±0.2, 19.4±0.2, 19.8±0.2, 20.8±0.2, 21.4±0.2, 21.8±0.2, 21.9±0.2, and 29.8±0.2 degrees 2θ. In other such embodiments, the monodiethylamine salt tetrahydrate has an X-ray powder diffraction pattern comprising five or more peaks selected from the group consisting of 9.5±0.2, 10.0±0.2, 11.8±0.2, 12.1±0.2, 14.4±0.2, 16.8±0.2, 17.6±0.2, 19.4±0.2, 19.8±0.2, 20.8±0.2, 21.4±0.2, 21.8±0.2, 21.9±0.2, and 29.8±0.2 degrees 2θ.

Figure 9:
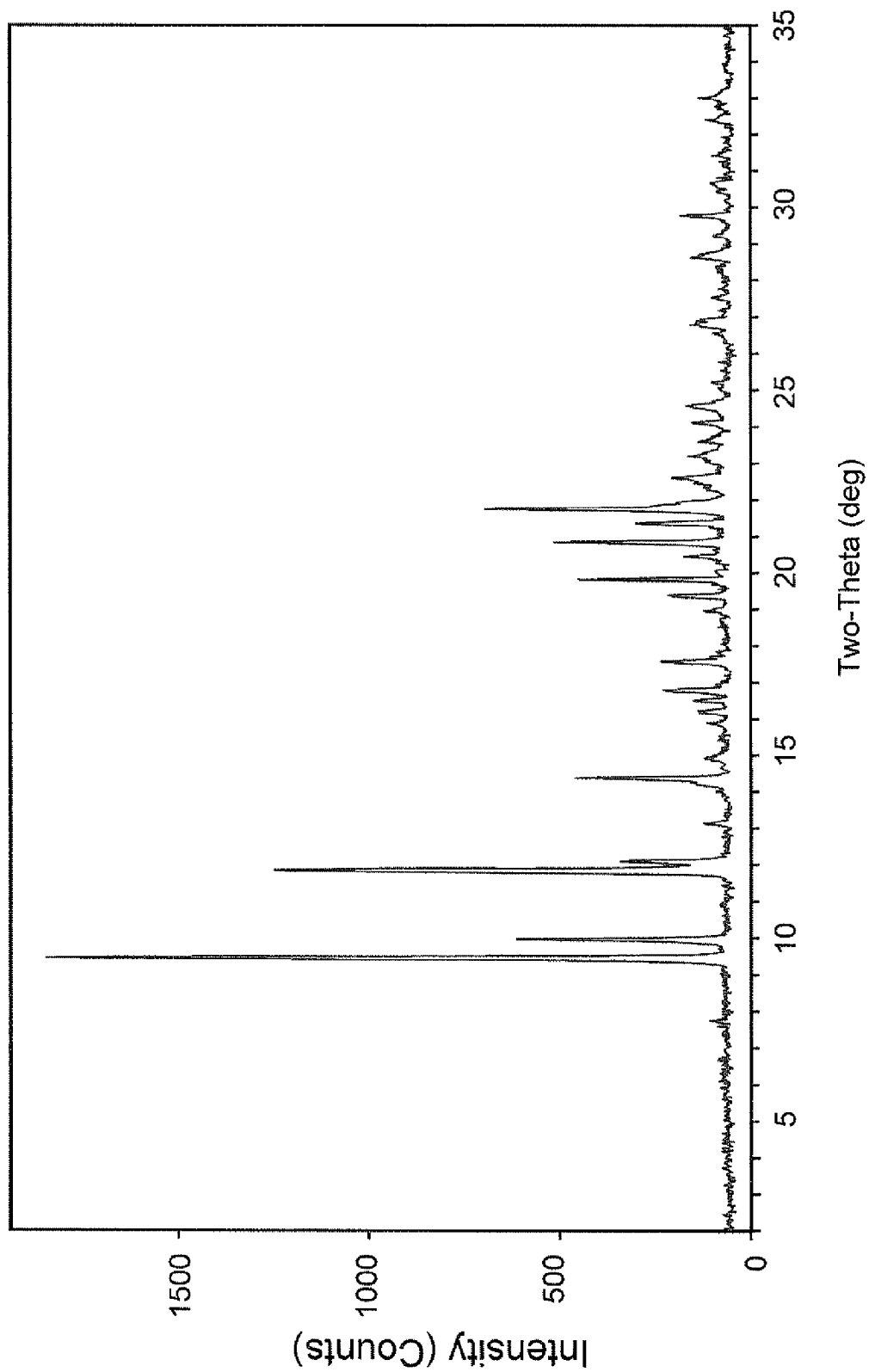
FIG. 9 shows an illustrative PXRD pattern for the monodiethylamine salt tetrahydrate of compound IB-L1-1.1.
Figure 10:
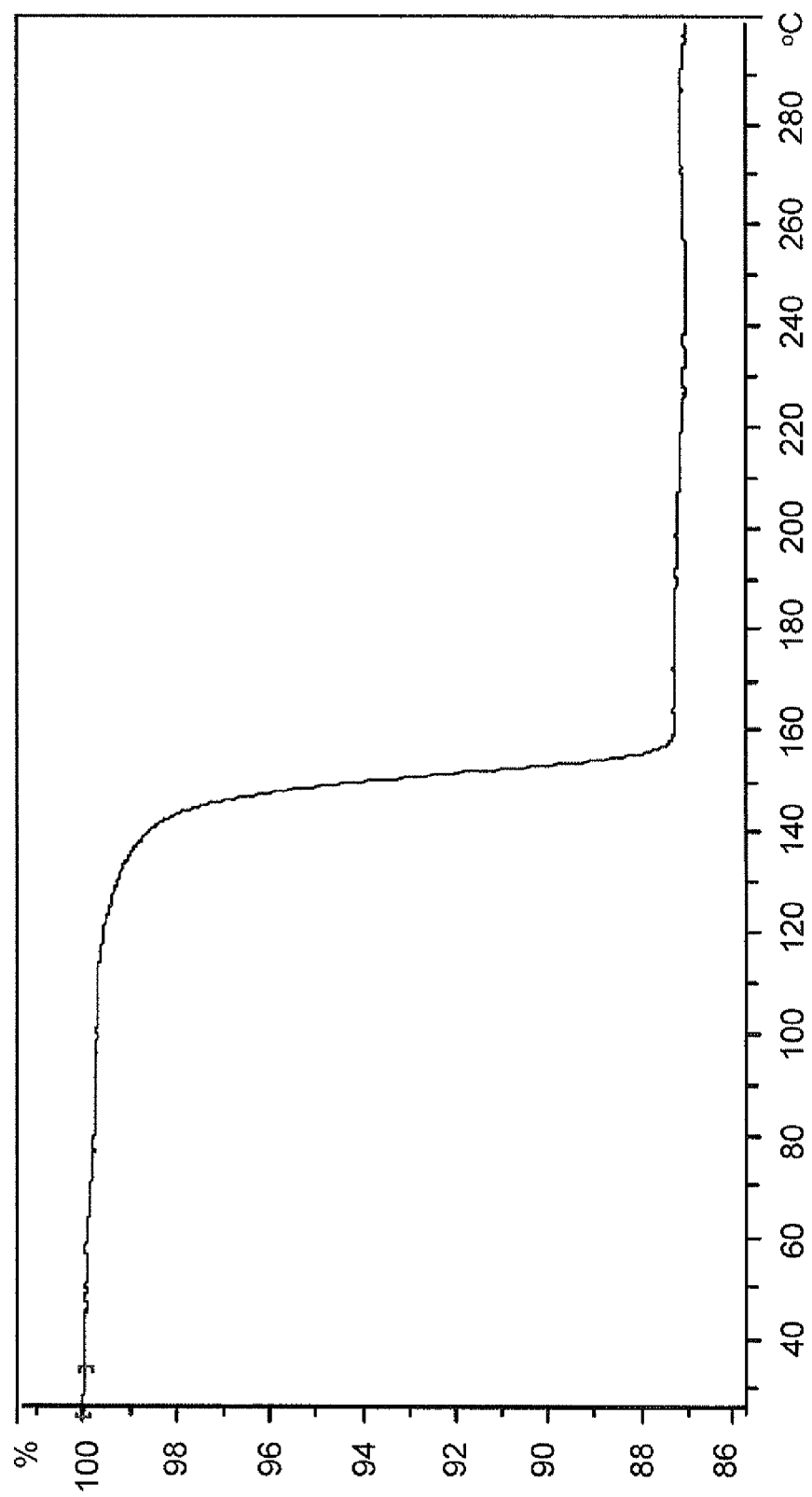
FIG. 10 shows an illustrative TGA profile of the monodiethylamine salt tetrahydrate of compound IB-L1-1.1.

In some embodiments, the monodiethylamine salt tetrahydrate has an X-ray powder diffraction pattern substantially as shown in FIG. 9. The 2θ values for the peaks in FIG. 9 (and their intensities) are as follows: 9.45 (100), 9.97 (31), 11.85 (67), 12.09 (16), 14.38 (22), 16.80 (9), 17.59 (10), 19.39 (8), 19.83 (21), 20.85 (25), 21.37 (12), 21.75 (34), 21.87 (8), and 29.78 (7).

This invention also relates, in part, to a process for preparing the monodiethylamine salt tetrahydrate. It was prepared in aqueous medium. Compound IB-L1-1.1 was slowly added to 500 ul of 1M diethylamine until no more solid can be dissolved into the solution. The solution was then evaporated slowly at ambient temperatures and the salt crystallized 2 days later. Alternatively, the monodiethylamine salt tetrahydrate was prepared by suspending 64.15 mg of compound IB-L1-1.1 in 400 ul 1M diethylamine while heated to 50° C. About 5 drops of THF (~20 ul) was added. The solid dissolved completely upon addition to yield a clear solution. The solution was then evaporated at ambient temperature, and the salt crystallized 4 days later. The stoichiometry of the salt was confirmed by solution $^1$H NMR.

G6. Crystalline Forms of (E)-N-(4-(3-tert-butyl-5-(2,4-dioxo-3,4-dihydropyrimidin-1(2H)-yl)-2-methoxystyryl)phenyl)methanesulfonamide (compound IB-L1-1.1).

This invention also relates, in part, to crystalline forms of (E)-N-(4-(3-tert-butyl-5-(2,4-dioxo-3,4-dihydropyrimidin-1(2H)-yl)-2-methoxystyryl)phenyl)methanesulfonamide (compound IB-L1-1.1), namely the true polymorphs (pattern A, pattern B, pattern C, and pattern D) and hydrate (pattern AH, pattern BH, pattern CH, and pattern DH) crystalline forms discussed below.

G6A. IB-L1-1.1 True Polymorphs

This invention relates, in part, to pattern A crystalline (E)-N-(4-(3-tert-butyl-5-(2,4-dioxo-3,4-dihydropyrimidin-1(2H)-yl)-2-methoxystyryl)phenyl)methanesulfonamide.

In some embodiments, the pattern A polymorph has an X-ray powder diffraction pattern comprising one or more peaks selected from the group consisting of 5.8±0.2, 9.9±0.2, 11.8±0.2, 12.4±0.2, 14.5±0.2, 18.8±0.2, 22.7±0.2, and 29.2±0.2 degrees 2θ. In some such embodiments, the pattern A polymorph has an X-ray powder diffraction pattern comprising three or more peaks selected from the group consisting of 5.8±0.2, 9.9±0.2, 11.8±0.2, 12.4±0.2, 14.5±0.2, 18.8±0.2, 22.7±0.2, and 29.2±0.2 degrees 2θ. In other such embodiments, the pattern A polymorph has an X-ray powder diffraction pattern comprising five or more peaks selected from the group consisting of 5.8±0.2, 9.9±0.2, 11.8±0.2, 12.4±0.2, 14.5±0.2, 18.8±0.2, 22.7±0.2, and 29.2±0.2 degrees 2θ.

In some embodiments, the pattern A polymorph has an X-ray powder diffraction pattern comprising one or more peaks selected from the group consisting of 5.8±0.2, 9.9±0.2, 11.8±0.2, 12.4±0.2, 14.0±0.2, 14.5±0.2, 15.3±0.2, 18.5±0.2, 18.8±0.2, 22.2±0.2, 22.7±0.2, 23.8±0.2, 26.0±0.2, and 29.2±0.2 degrees 2θ. In some such embodiments, the pattern A polymorph has an X-ray powder diffraction pattern comprising three or more peaks selected from the group consisting of 5.8±0.2, 9.9±0.2, 11.8±0.2, 12.4±0.2, 14.0±0.2, 14.5±0.2, 15.3±0.2, 18.5±0.2, 18.8±0.2, 22.2±0.2, 22.7±0.2, 23.8±0.2, 26.0±0.2, and 29.2±0.2 degrees 2θ. In other such embodiments, the pattern A polymorph has an X-ray powder diffraction pattern comprising five or more peaks selected from the group consisting of 5.8±0.2, 9.9±0.2, 11.8±0.2, 12.4±0.2, 14.0±0.2, 14.5±0.2, 15.3±0.2, 18.5±0.2, 18.8±0.2, 22.2±0.2, 22.7±0.2, 23.8±0.2, 26.0±0.2, and 29.2±0.2 degrees 2θ.

Figure 11:
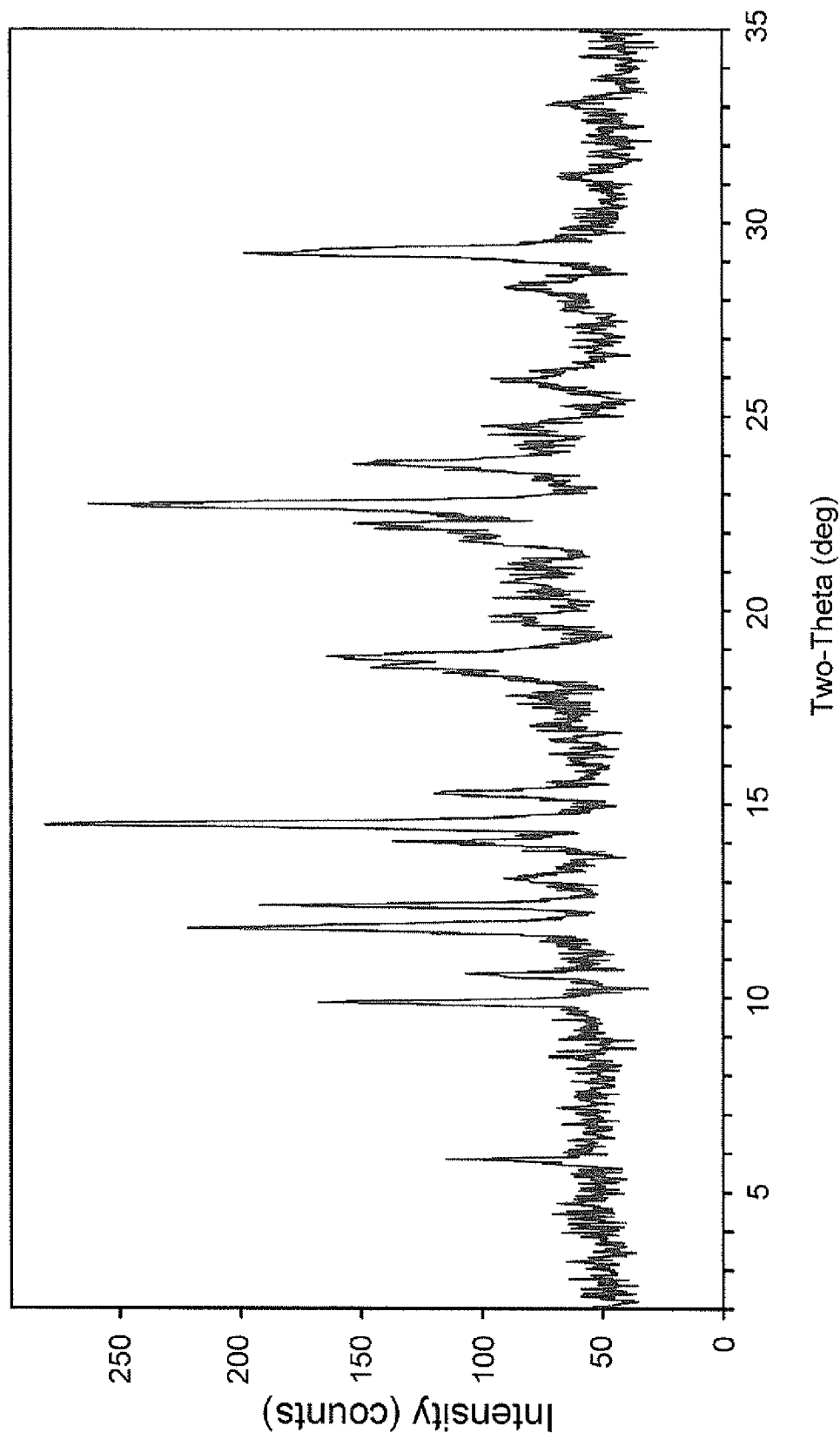
FIG. 11 shows an illustrative PXRD pattern for the pattern A polymorph of compound IB-L1-1.1.
Figure 12:
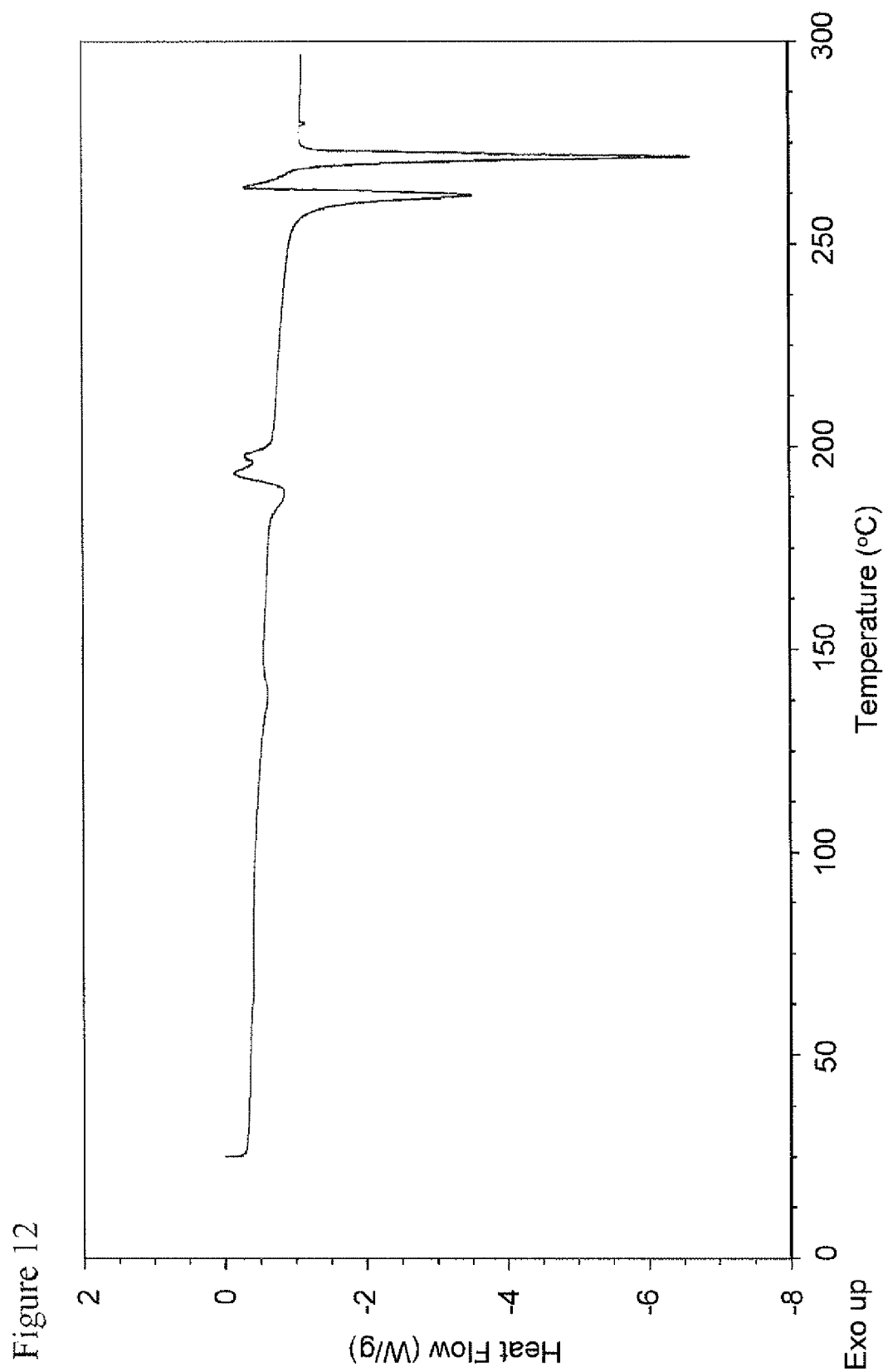
FIG. 12 shows an illustrative DSC profile of the pattern A polymorph of compound IB-L1-1.1.

In some embodiments, the pattern A polymorph has an X-ray powder diffraction pattern substantially as shown in FIG. 11. The 2θ values for the peaks in FIG. 11 (and their intensities) are as follows: 5.85 (28), 9.88 (51), 11.79 (73), 12.38 (56), 14.03 (38), 14.45 (100), 15.27 (29), 18.52 (39), 18.80 (47), 22.24 (40), 22.72 (77), 23.76 (39), 25.98 (22), and 29.21 (64).

This invention also relates, in part, to a process for preparing pattern A polymorph. Pattern A polymorph was prepared as discussed in Example E below.

This invention relates, in part, to pattern B crystalline (E)-N-(4-(3-tert-butyl-5-(2,4-dioxo-3,4-dihydropyrimidin-1(2H)-yl)-2-methoxystyryl)phenyl)methanesulfonamide.

In some embodiments, the pattern B polymorph has an X-ray powder diffraction pattern comprising one or more peaks selected from the group consisting of 11.5±0.2, 13.3±0.2, 15.4±0.2, 16.4±0.2, 17.1±0.2, 18.6±0.2, 19.4±0.2, 20.4±0.2, 21.6±0.2, 22.4±0.2, 24.0±0.2, 26.8±0.2, and 29.0±0.2 degrees 2θ. In some such embodiments, the pattern B polymorph has an X-ray powder diffraction pattern comprising three or more peaks selected from the group consisting of 11.5±0.2, 13.3±0.2, 15.4±0.2, 16.4±0.2, 17.1±0.2, 18.6±0.2, 19.4±0.2, 20.4±0.2, 21.6±0.2, 22.4±0.2, 24.0±0.2, 26.8±0.2, and 29.0±0.2 degrees 2θ. In other such embodiments, the pattern B polymorph has an X-ray powder diffraction pattern comprising five or more peaks selected from the group consisting of 11.5±0.2, 13.3±0.2, 15.4±0.2, 16.4±0.2, 17.1±0.2, 18.6±0.2, 19.4±0.2, 20.4±0.2, 21.6±0.2, 22.4±0.2, 24.0±0.2, 26.8±0.2, and 29.0±0.2 degrees 2θ.

Figure 13:
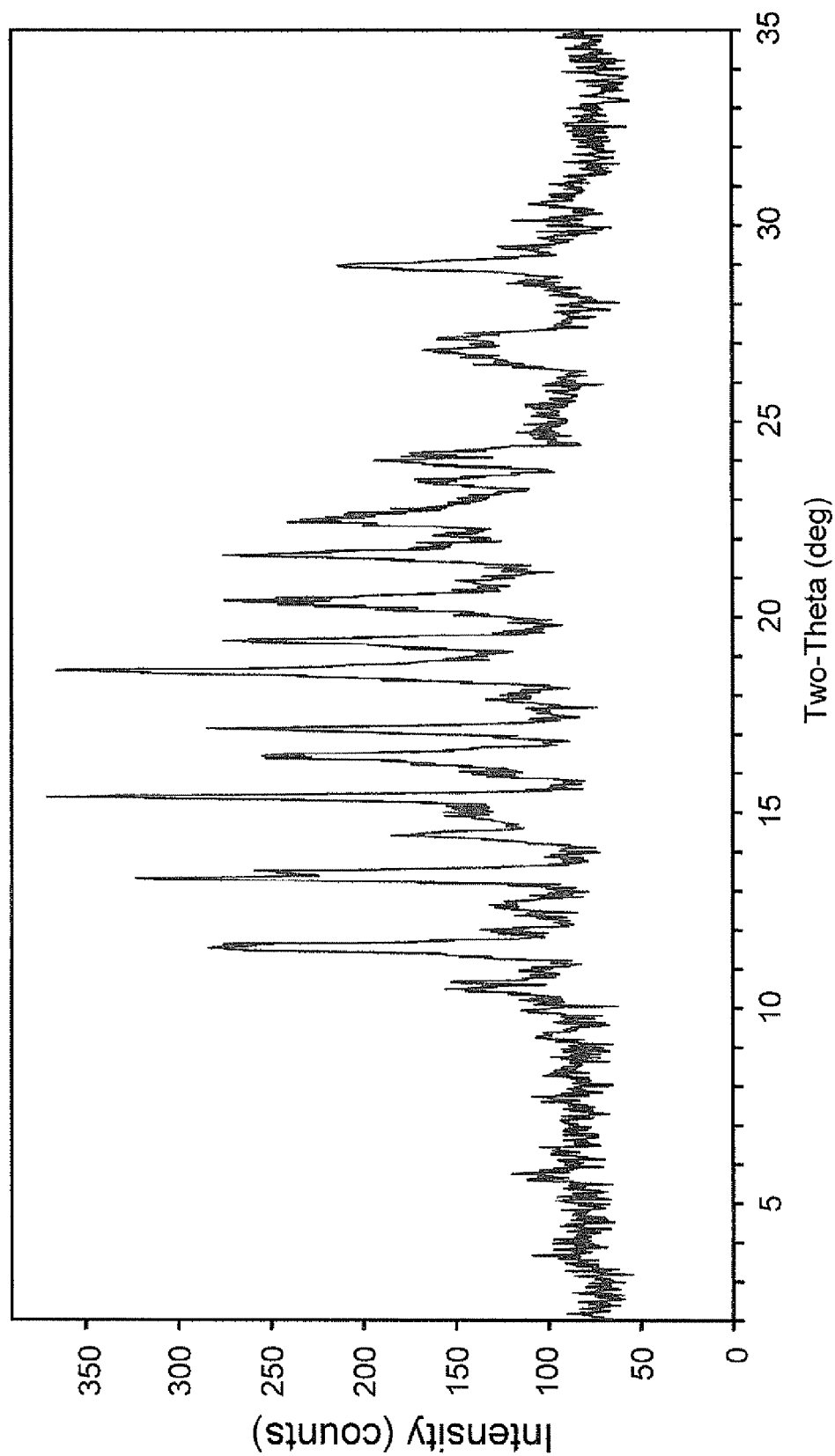
FIG. 13 shows an illustrative PXRD pattern for the pattern B polymorph of compound IB-L1-1.1.

In some embodiments, the pattern B polymorph has an X-ray powder diffraction pattern substantially as shown in FIG. 13. The 2θ values for the peaks in FIG. 13 (and their intensities) are as follows: 11.52 (71), 13.30 (87), 15.37 (100), 16.42 (60), 17.13 (69), 18.60 (97), 19.37 (56), 20.40 (62), 21.55 (55), 22.41 (39), 23.99 (33), 26.81 (31), and 28.98 (50).

This invention relates, in part, to pattern C crystalline (E)-N-(4-(3-tert-butyl-5-(2,4-dioxo-3,4-dihydropyrimidin-1(2H)-yl)-2-methoxystyryl)phenyl)methanesulfonamide.

In some embodiments, the pattern C polymorph has an X-ray powder diffraction pattern comprising one or more peaks selected from the group consisting of 7.7±0.2, 10.1±0.2, 10.6±0.2, 12.0±0.2, 13.4±0.2, 16.1±0.2, 19.4±0.2, 20.5±0.2, 21.4±0.2, 22.0±0.2, 22.6±0.2, 24.3±0.2, and 27.6±0.2 degrees 2θ. In some such embodiments, the pattern C polymorph has an X-ray powder diffraction pattern comprising three or more peaks selected from the group consisting of 7.7±0.2, 10.1±0.2, 10.6±0.2, 12.0±0.2, 13.4±0.2, 16.2±0.2, 19.4±0.2, 20.5±0.2, 21.4±0.2, 22.0±0.2, 22.6±0.2, 24.3±0.2, and 27.6±0.2 degrees 2θ. In other such embodiments, the pattern C polymorph has an X-ray powder diffraction pattern comprising five or more peaks selected from the group consisting of 7.7±0.2, 10.1±0.2, 10.6±0.2, 12.0±0.2, 13.4±0.2, 16.2±0.2, 19.4±0.2, 20.5±0.2, 21.4±0.2, 22.0±0.2, 22.6±0.2, 24.3±0.2, and 27.6±0.2 degrees 2θ.

Figure 14:
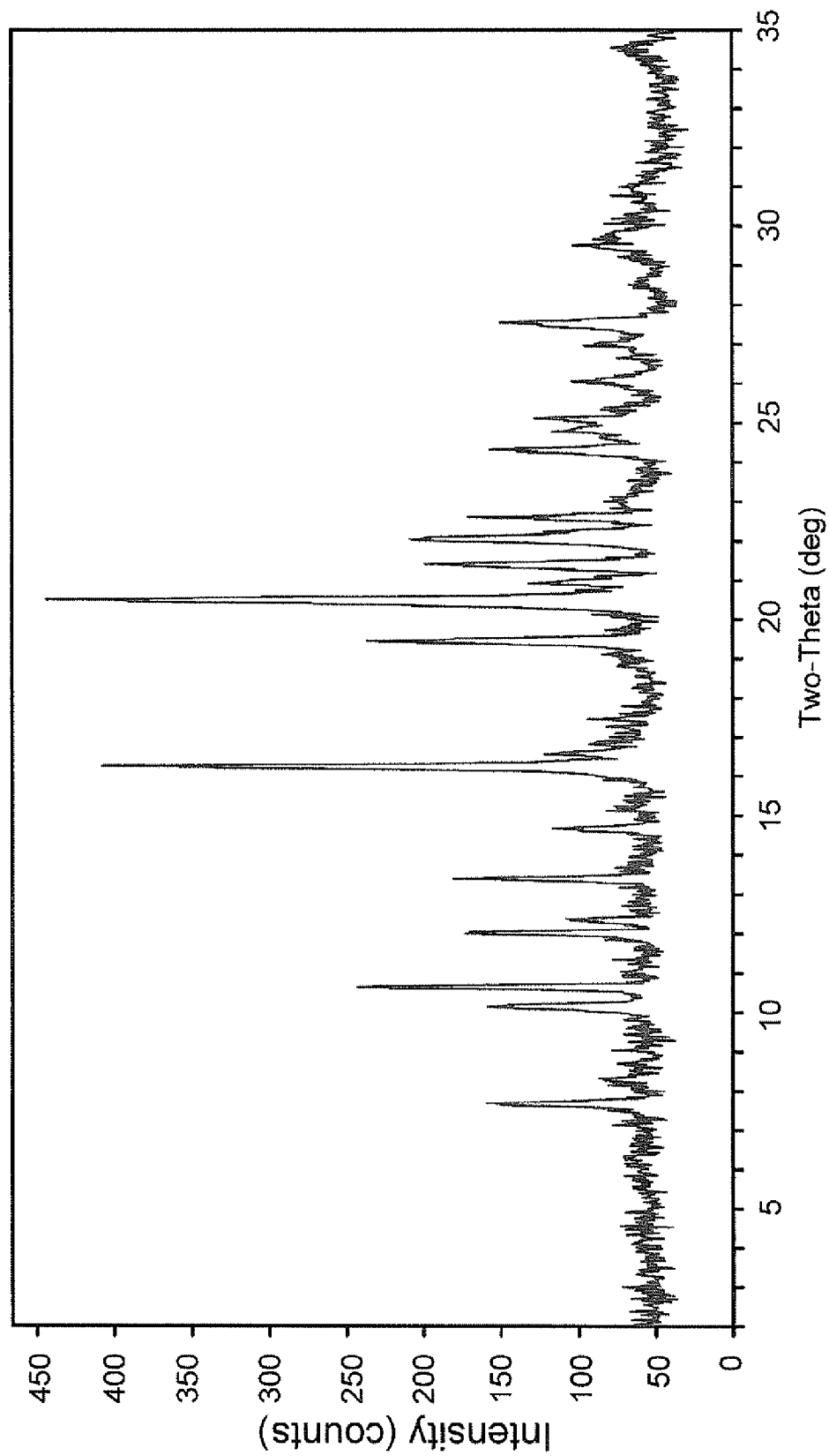
FIG. 14 shows an illustrative PXRD pattern for the pattern C polymorph of compound IB-L1-1.1.

In some embodiments, the pattern C polymorph has an X-ray powder diffraction pattern substantially as shown in FIG. 14. The 2θ values for the peaks in FIG. 14 (and their intensities) are as follows: 7.69 (27), 10.13 (27), 10.64 (49), 12.01 (31), 13.39 (33), 16.25 (91), 19.44 (46), 20.49 (100), 21.40 (35), 22.03 (37), 22.60 (30), 24.32 (23), and 27.55 (27).

This invention relates, in part, to pattern D crystalline (E)-N-(4-(3-tert-butyl-5-(2,4-dioxo-3,4-dihydropyrimidin-1(2H)-yl)-2-methoxystyryl)phenyl)methanesulfonamide.

In some embodiments, the pattern D polymorph has an X-ray powder diffraction pattern comprising one or more peaks selected from the group consisting of 5.8±0.2, 10.7±0.2, 11.2±0.2, 15.2±0.2, 16.1±0.2, 16.9±0.2, 19.9±0.2, 22.1±0.2, 24.7±0.2, and 26.0±0.2 degrees 2θ. In some such embodiments, the pattern D polymorph has an X-ray powder diffraction pattern comprising three or more peaks selected from the group consisting of 5.8±0.2, 10.7±0.2, 11.2±0.2, 15.2±0.2, 16.1±0.2, 16.9±0.2, 19.9±0.2, 22.1±0.2, 24.7±0.2, and 26.0±0.2 degrees 2θ. In other such embodiments, the pattern D polymorph has an X-ray powder diffraction pattern comprising five or more peaks selected from the group consisting of 5.8±0.2, 10.7±0.2, 11.2±0.2, 15.2±0.2, 16.1±0.2, 16.9±0.2, 19.9±0.2, 22.1±0.2, 24.7±0.2, and 26.0±0.2 degrees 2θ.

In some embodiments, the pattern D polymorph has an X-ray powder diffraction pattern comprising one or more peaks selected from the group consisting of 5.8±0.2, 10.7±0.2, 11.2±0.2, 15.2±0.2, 16.1±0.2, 16.9±0.2, 17.1±0.2, 19.9±0.2, 20.1±0.2, 22.1±0.2, 24.7±0.2, and 26.0±0.2 degrees 2θ. In some such embodiments, the pattern D polymorph has an X-ray powder diffraction pattern comprising three or more peaks selected from the group consisting of 5.8±0.2, 10.7±0.2, 11.2±0.2, 15.2±0.2, 16.1±0.2, 16.9±0.2, 17.1±0.2, 19.9±0.2, 20.1±0.2, 22.1±0.2, 24.7±0.2, and 26.0±0.2 degrees 2θ. In other such embodiments, the pattern D polymorph has an X-ray powder diffraction pattern comprising five or more peaks selected from the group consisting of 5.8±0.2, 10.7±0.2, 11.2±0.2, 15.2±0.2, 16.1±0.2, 16.9±0.2, 17.1±0.2, 19.9±0.2, 20.1±0.2, 22.1±0.2, 24.7±0.2, and 26.0±0.2 degrees 2θ.

Figure 15:
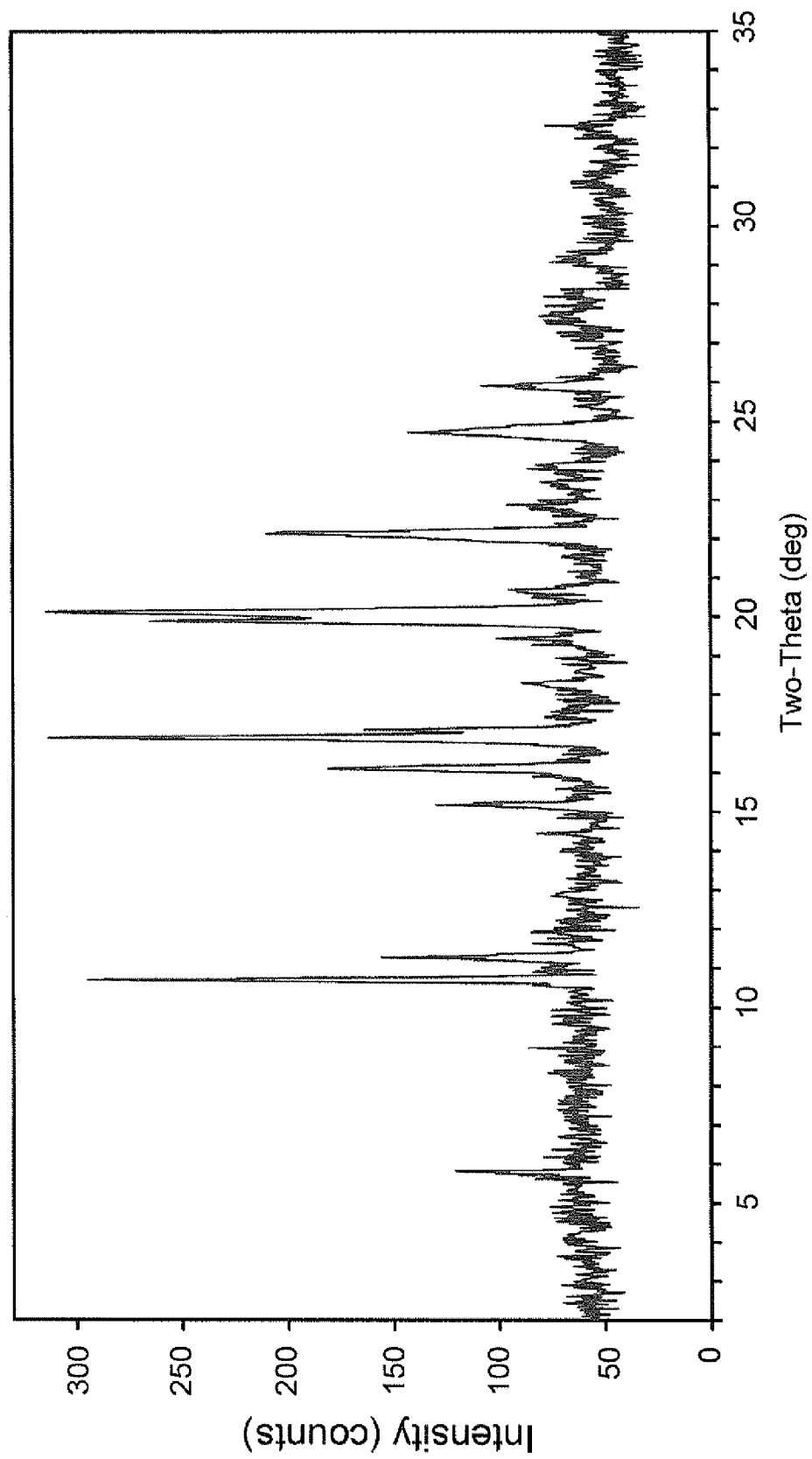
FIG. 15 shows an illustrative PXRD pattern for the pattern D polymorph of compound IB-L1-1.1.

In some embodiments, the pattern D polymorph has an X-ray powder diffraction pattern substantially as shown in FIG. 15. The 2θ values for the peaks in FIG. 15 (and their intensities) are as follows: 5.81 (24), 10.70 (91), 11.23 (60), 15.17 (28), 16.10 (48), 16.89 (100), 17.10 (42), 19.88 (81), 20.12 (100), 22.12 (59), 24.72 (37), and 25.91 (24).

This invention also relates, in part, to a process for preparing pattern B, C, and D polymorphs by heating pattern A polymorph to about 160, about 225, and about 268° C., respectively using DSC.

G6B. IB-L1-1.1 Hydrates.

This invention also relates, in part, to hydrates of compound IB-L1-1.1, namely to hydrates A, B, C, D, and E discussed below.

This invention relates, in part, to a pattern A (E)-N-(4-(3-tert-butyl-5-(2,4-dioxo-3,4-dihydro-pyrimidin-1(2H)-yl)-2-methoxystyryl)phenyl)methanesulfonamide hydrate.

In some embodiments, the pattern A hydrate has an X-ray powder diffraction pattern comprising one or more peaks selected from the group consisting of 5.1±0.2, 7.9±0.2, 9.5±0.2, 10.3±0.2, 13.7±0.2, 16.5±0.2, 17.1±0.2, 17.5±0.2, 18.8±0.2, 19.2±0.2, 20.7±0.2, 21.3±0.2, 21.6±0.2, 25.8±0.2, 26.8±0.2, and 28.4±0.2 degrees 2θ. In some such embodiments, the pattern A hydrate has an X-ray powder diffraction pattern comprising three or more peaks selected from the group consisting of 5.1±0.2, 7.9±0.2, 9.5±0.2, 10.3±0.2, 13.7±0.2, 16.5±0.2, 17.1±0.2, 17.5±0.2, 18.8±0.2, 19.2±0.2, 20.7±0.2, 21.3±0.2, 21.6±0.2, 25.8±0.2, 26.8±0.2, and 28.4±0.2 degrees 2θ. In other such embodiments, the pattern A hydrate has an X-ray powder diffraction pattern comprising five or more peaks selected from the group consisting of 5.1±0.2, 7.9±0.2, 9.5±0.2, 10.3±0.2, 13.7±0.2, 16.5±0.2, 17.1±0.2, 17.5±0.2, 18.8±0.2, 19.2±0.2, 20.7±0.2, 21.3±0.2, 21.6±0.2, 25.8±0.2, 26.8±0.2, and 28.4±0.2 degrees 2θ.

Figure 16:
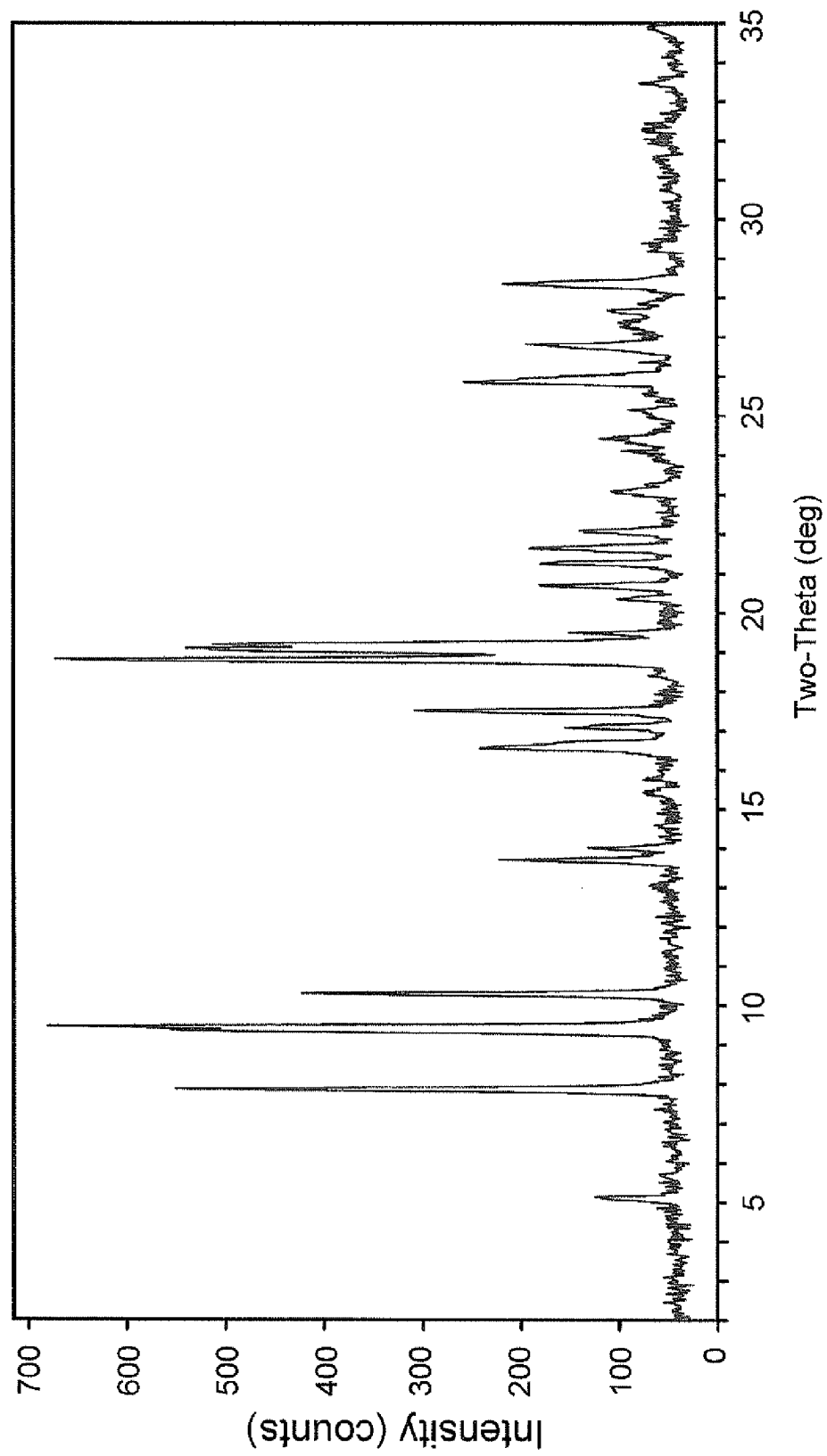
FIG. 16 shows an illustrative PXRD pattern for the pattern A hydrate of compound IB-L1-1.1.
Figure 17:
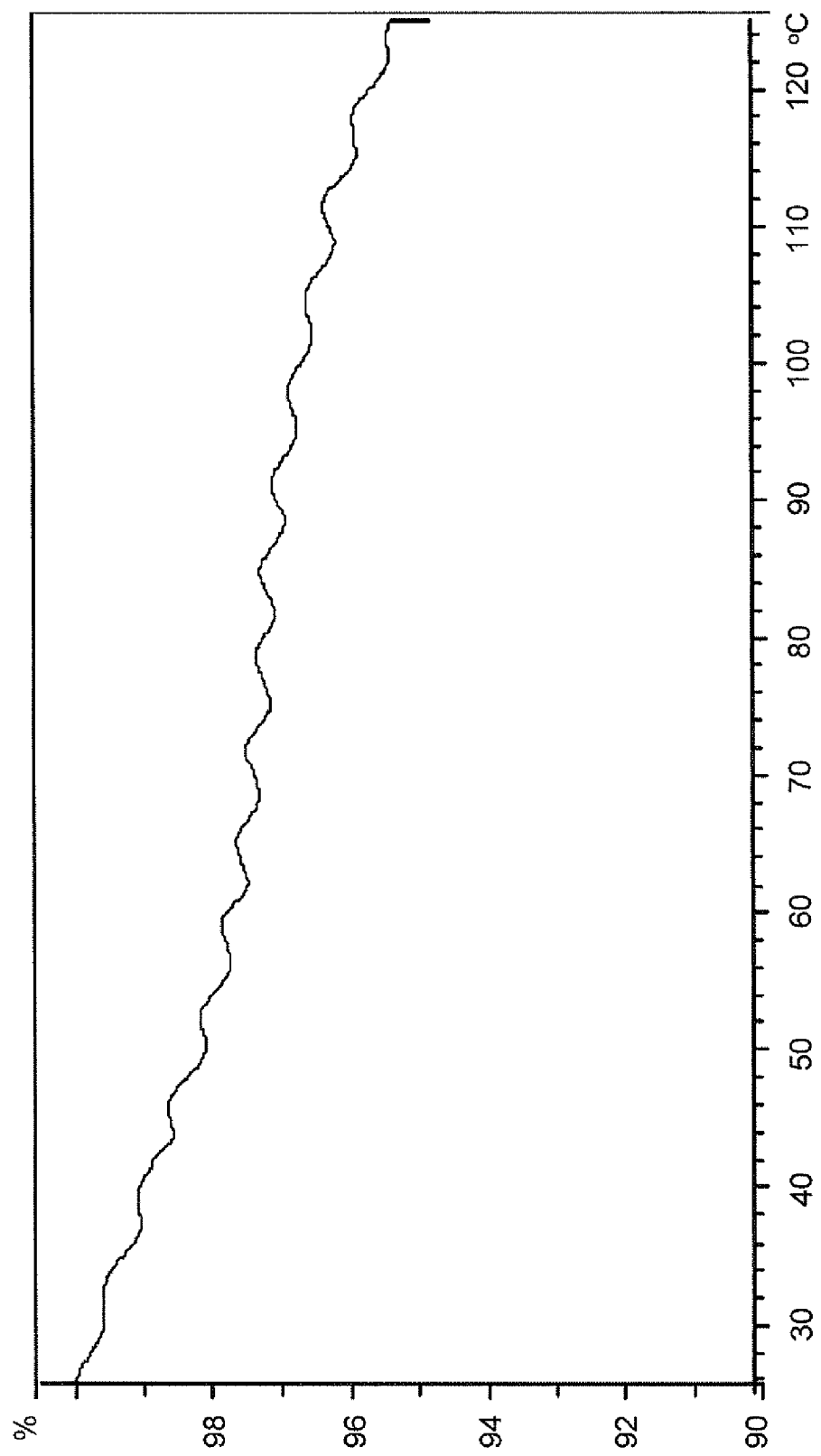
FIG. 17 shows an illustrative TGA profile of the pattern A hydrate of compound IB-L1-1.1.

In some embodiments, the pattern A hydrate has an X-ray powder diffraction pattern substantially as shown in FIG. 16. The 2θ values for the peaks in FIG. 16 (and their intensities) are as follows: 5.13 (13), 7.87 (80), 9.45 (100), 10.29 (60), 13.7 (28), 16.54 (30), 17.07 (17), 17.51 (40), 18.80 (99), 19.18 (74), 20.69 (21), 21.25 (21), 21.63 (23), 25.85 (32), 26.81 (20), and 28.35 (27).

This invention also relates, in part, to a process for preparing the pattern A hydrate by suspending pattern A polymorph (discussed above) in ethyl acetate. The recovered pattern A hydrate contains ~1 water molecules per molecule of compound IB-L1-1.1.

This invention also relates, in part, to a pattern B (E)-N-(4-(3-tert-butyl-5-(2,4-dioxo-3,4-dihydro-pyrimidin-1(2H)-yl)-2-methoxystyryl)phenyl)methanesulfonamide hydrate.

In some embodiments, the pattern B hydrate has an X-ray powder diffraction pattern comprising one or more peaks selected from the group consisting of 6.3±0.2, 7.7±0.2, 10.4±0.2, 12.7±0.2, 13.3±0.2, 14.9±0.2, 15.4±0.2, 16.4±0.2, 18.6±0.2, 18.9±0.2, 19.4±0.2, 22.5±0.2, 23.5±0.2, 24.0±0.2, 26.8±0.2, and 29.0±0.2 degrees 2θ. In some such embodiments, the pattern B hydrate has an X-ray powder diffraction pattern comprising three or more peaks selected from the group consisting of 6.3±0.2, 7.7±0.2, 10.4±0.2, 12.7±0.2, 13.3±0.2, 14.9±0.2, 15.4±0.2, 16.4±0.2, 18.6±0.2, 18.9±0.2, 19.4±0.2, 22.5±0.2, 23.5±0.2, 24.0±0.2, 26.8±0.2, and 29.0±0.2 degrees 2θ. In other such embodiments, the pattern B hydrate has an X-ray powder diffraction pattern comprising five or more peaks selected from the group consisting of 6.3±0.2, 7.7±0.2, 10.4±0.2, 12.7±0.2, 13.3±0.2, 14.9±0.2, 15.4±0.2, 16.4±0.2, 18.6±0.2, 18.9±0.2, 19.4±0.2, 22.5±0.2, 23.5±0.2, 24.0±0.2, 26.8±0.2, and 29.0±0.2 degrees 2θ.

In some embodiments, the pattern B hydrate has an X-ray powder diffraction pattern comprising one or more peaks selected from the group consisting of 6.3±0.2, 7.7±0.2, 10.4±0.2, 12.7±0.2, 13.3±0.2, 13.5±0.2, 14.9±0.2, 15.4±0.2, 16.4±0.2, 18.5±0.2, 18.6±0.2, 18.9±0.2, 19.4±0.2, 22.5±0.2, 23.5±0.2, 24.0±0.2, 26.8±0.2, and 29.0±0.2 degrees 2θ. In some such embodiments, the pattern B hydrate has an X-ray powder diffraction pattern comprising three or more peaks selected from the group consisting of 6.3±0.2, 7.7±0.2, 10.4±0.2, 12.7±0.2, 13.3±0.2, 13.5±0.2, 14.9±0.2, 15.4±0.2, 16.4±0.2, 18.5±0.2, 18.6±0.2, 18.9±0.2, 19.4±0.2, 22.5±0.2, 23.5±0.2, 24.0±0.2, 26.8±0.2, and 29.0±0.2 degrees 2θ. In other such embodiments, the pattern B hydrate has an X-ray powder diffraction pattern comprising five or more peaks selected from the group consisting of 6.3±0.2, 7.7±0.2, 10.4±0.2, 12.7±0.2, 13.3±0.2, 13.5±0.2, 14.9±0.2, 15.4±0.2, 16.4±0.2, 18.5±0.2, 18.6±0.2, 18.9±0.2, 19.4±0.2, 22.5±0.2, 23.5±0.2, 24.0±0.2, 26.8±0.2, and 29.0±0.2 degrees 2θ.

Figure 18:
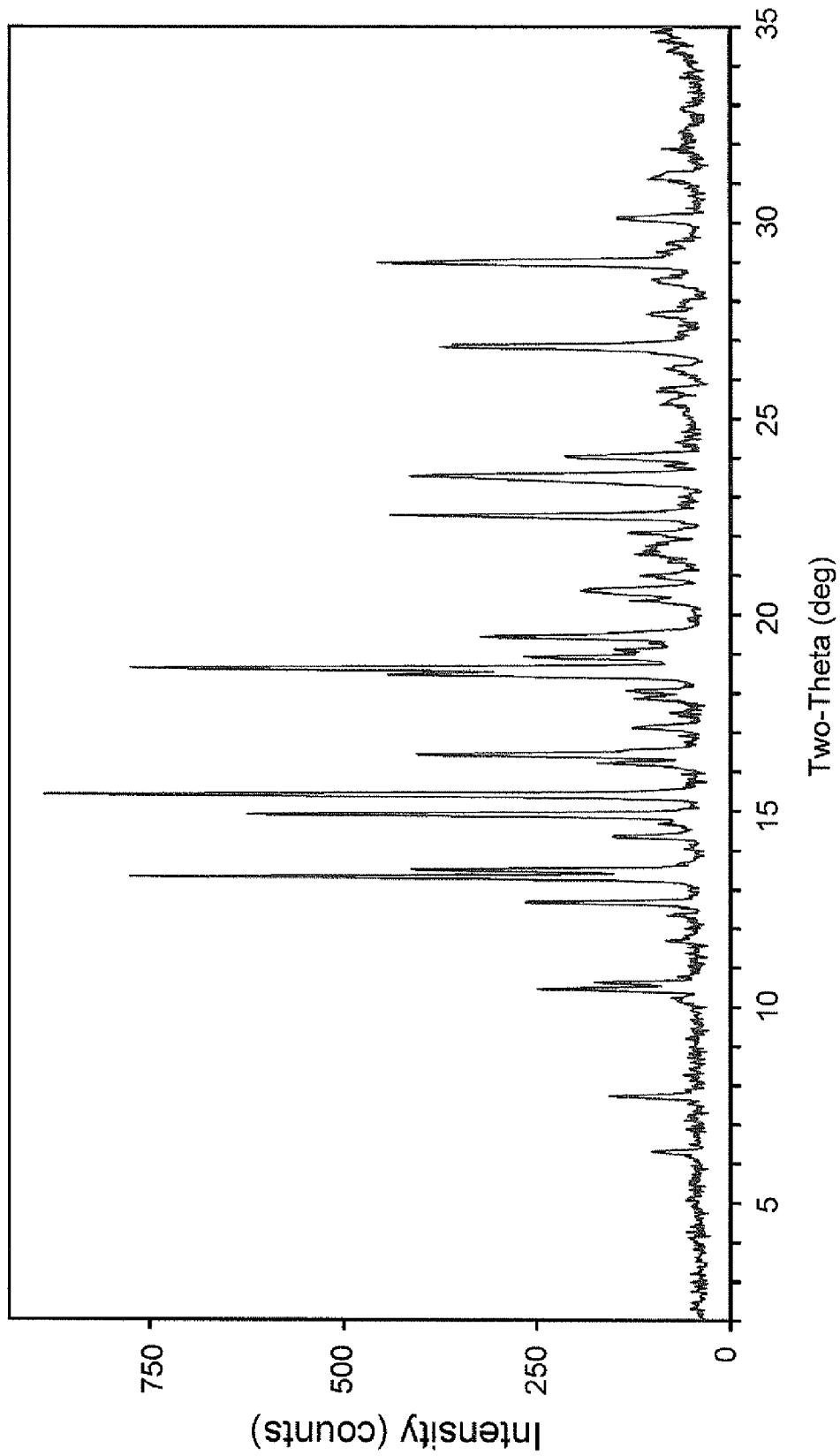
FIG. 18 shows an illustrative PXRD pattern for the pattern B hydrate of compound IB-L1-1.1.
Figure 19:
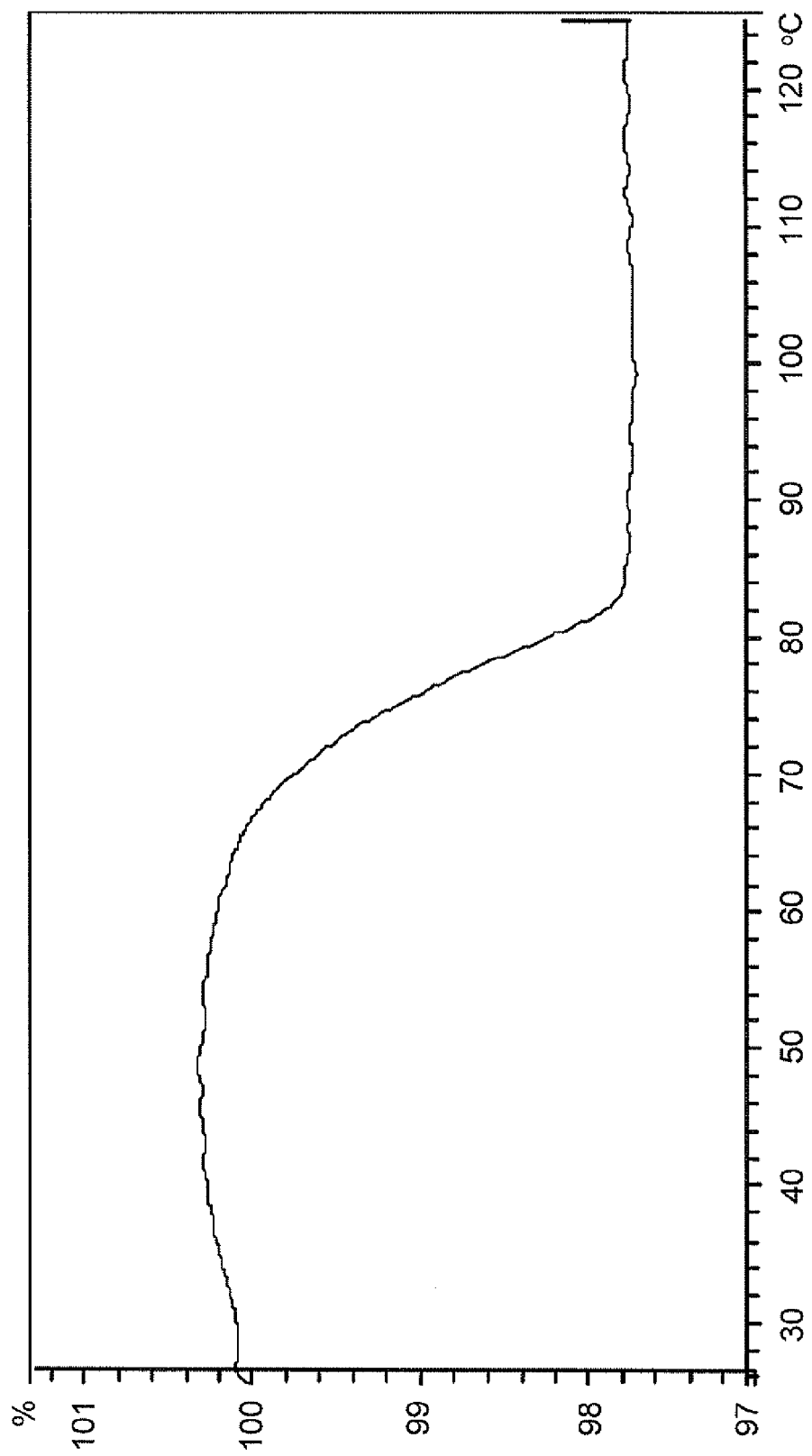
FIG. 19 shows an illustrative TGA profile of the pattern B hydrate of compound IB-L1-1.1.

In some embodiments, the pattern B hydrate has an X-ray powder diffraction pattern substantially as shown in FIG. 18. The 2θ values for the peaks in FIG. 18 (and their intensities) are as follows: 6.31 (7), 7.72 (14), 10.45 (24), 12.67 (26), 13.30 (88), 13.50 (44), 14.89 (70), 15.40 (100), 16.43 (43), 18.46 (47), 18.63 (86), 18.91 (26), 19.42 (33), 22.52 (47), 23.52 (44), 24.02 (20), 26.82 (40), and 28.97 (49).

This invention also relates, in part, to a process for preparing the pattern B hydrate by suspending pattern A polymorph (discussed above) in acetonitrile/water (9/1 v/v). The recovered pattern B hydrate contains ~0.7 water molecules per molecule of compound IB-L1-1.1.

This invention also relates, in part, to a pattern C (E)-N-(4-(3-tert-butyl-5-(2,4-dioxo-3,4-dihydropyrimidin-1(2H)-yl)-2-methoxystyryl)phenyl)methanesulfonamide hydrate.

In some embodiments, the pattern C hydrate has an X-ray powder diffreaction pattern comprising one or more peaks selected from the group consisting of 10.5±0.2, 13.3±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ. In some such embodiments, the pattern C hydrate has an X-ray powder diffraction pattern comprising three or more peaks selected from the group consisting of 10.5±0.2, 13.3±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ. In other such embodiments, the pattern C hydrate has an X-ray powder diffraction pattern comprising five or more peaks selected from the group consisting of 10.5±0.2, 13.3±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ.

In some embodiments, the pattern C hydrate has an X-ray powder diffraction pattern comprising one or more peaks selected from the group consisting of 10.5±0.2, 13.3±0.2, 13.5±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ. In some such embodiments, the pattern C hydrate has an X-ray powder diffraction pattern comprising three or more peaks selected from the group consisting of 10.5±0.2, 13.3±0.2, 13.5±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ. In other such embodiments, the pattern C hydrate has an X-ray powder diffraction pattern comprising five or more peaks selected from the group consisting of 10.5±0.2, 13.3±0.2, 13.5±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ.

Figure 20:
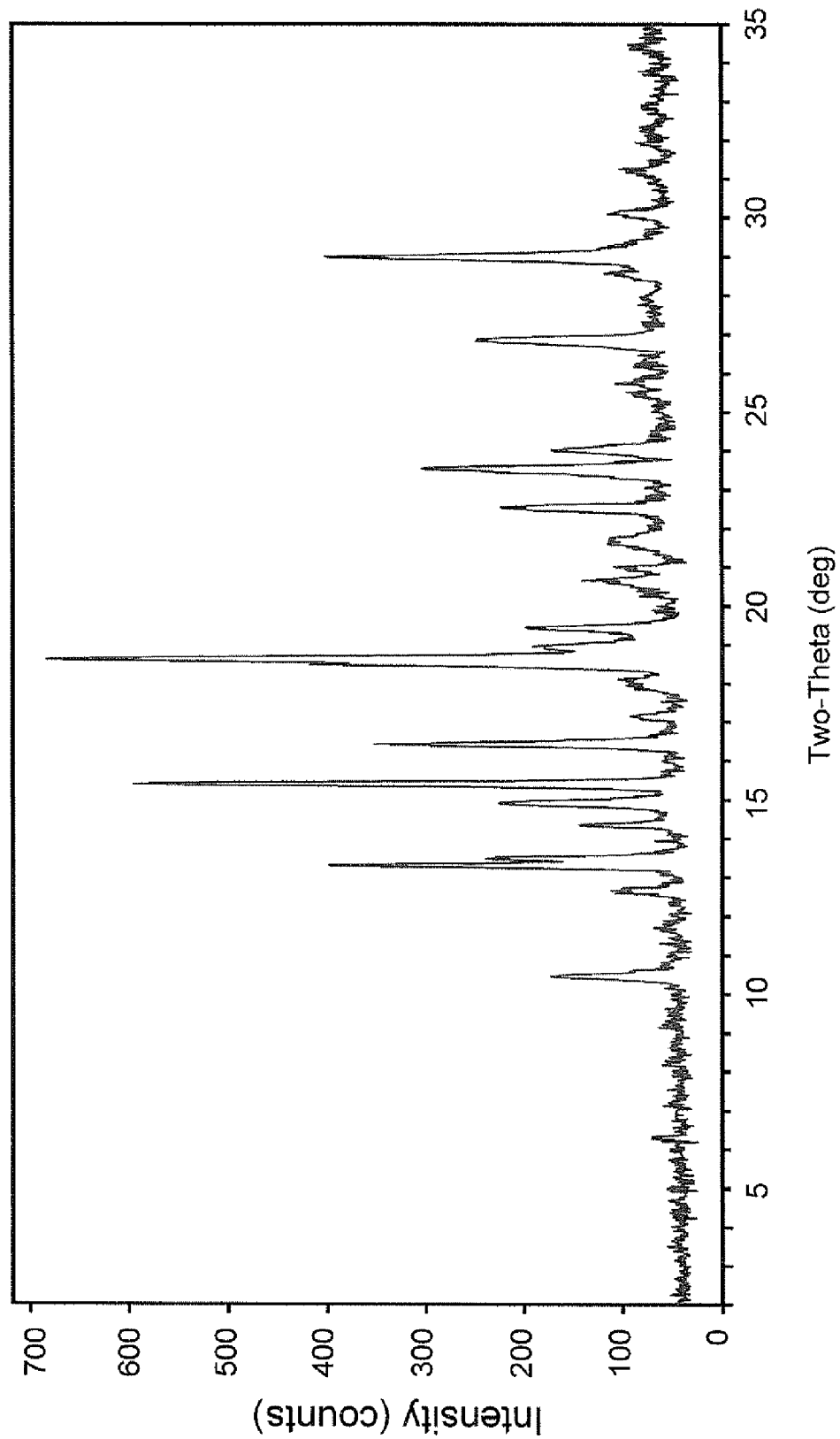
FIG. 20 shows an illustrative PXRD pattern for the pattern C hydrate of compound IB-L1-1.1.
Figure 21:
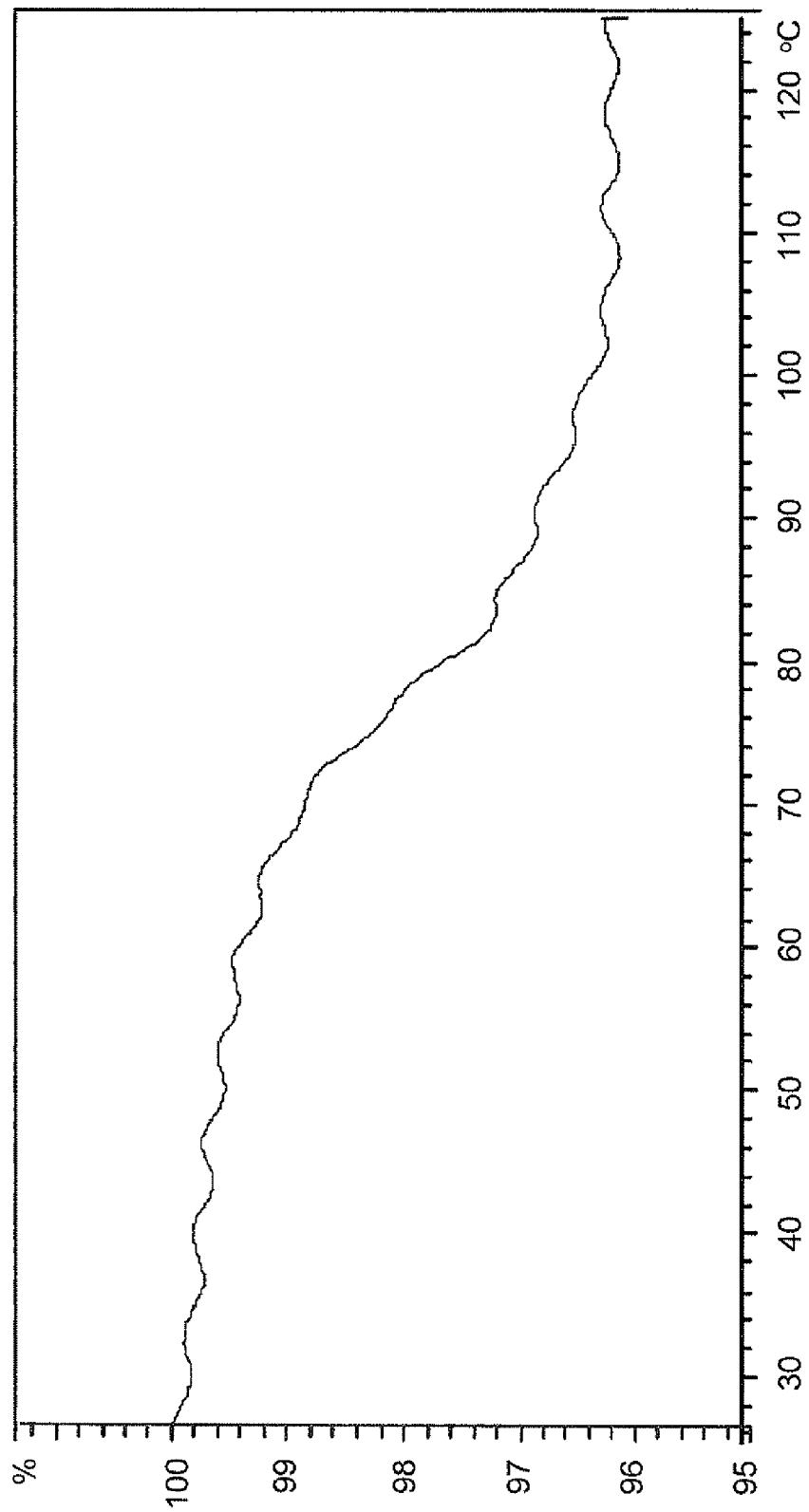
FIG. 21 shows an illustrative TGA profile of the pattern C hydrate of compound IB-L1-1.1.

In some embodiments, the pattern C hydrate has an X-ray powder diffraction pattern substantially as shown in FIG. 20. The 2θ values for the peaks in FIG. 20 (and their intensities) are as follows: 10.47 (21), 13.31 (56), 13.49 (31), 14.91 (28), 15.40 (86), 16.43 (48), 18.61 (100), 18.96 (20), 19.44 (19), 22.55 (26), 23.54 (39), 26.84 (29), and 28.99 (54).

This invention also relates, in part, to a process for preparing the pattern C hydrate by suspending pattern A polymorph (discussed above) in water. The recovered pattern C hydrate contains ~1 water molecules per molecule of compound IB-L1-1.1.

This invention also relates, in part, to a pattern D (E)-N-(4-(3-tert-butyl-5-(2,4-dioxo-3,4-dihydropyrimidin-1(2H)-yl)-2-methoxystyryl)phenyl)methanesulfonamide hydrate.

The crystallographic unit cell parameters of the pattern D hydrate salt have been determined to be as follows: a is 17.8 Å, b is 9.6 Å, and c is 27.0 Å (more precisely, a is 17.783(2)Å, b is 9.5651(12)Å, and c is 27.014(4)Å); the cell angle is: β—93.3° (more precisely, β is 93.256(2)°; and the cell volume is 4588 Å$^3$ (more precisely, 4587.5(10)Å$^3$). The salt crystallizes in the C2/c space group.

In some embodiments, the pattern D hydrate has an X-ray powder diffraction pattern comprising one or more peaks selected from the group consisting of 6.6±0.2, 10.0±0.2, 10.5±0.2, 11.1±0.2, 11.6±0.2, 12.2±0.2, 14.2±0.2, 16.6±0.2, 17.1±0.2, 17.7±0.2, 18.5±0.2, 18.8±0.2, 19.3±0.2, 21.4±0.2, 22.7±0.2, 23.1±0.2, 23.6±0.2, 24.6±0.2, 25.2±0.2, 27.2±0.2, 29.1±0.2, and 31.0±0.2 degrees 2θ. In some such embodiments, the pattern D hydrate has an X-ray powder diffraction pattern comprising three or more peaks selected from the group consisting of 6.6±0.2, 10.0±0.2, 10.5±0.2, 11.1±0.2, 11.6±0.2, 12.2±0.2, 14.1±0.2, 16.6±0.2, 17.1±0.2, 17.7±0.2, 18.5±0.2, 18.8±0.2, 19.3±0.2, 21.4±0.2, 22.7±0.2, 23.1±0.2, 23.6±0.2, 24.6±0.2, 25.2±0.2, 27.2±0.2, 29.1±0.2, and 31.0±0.2 degrees 2θ. In other such embodiments, the pattern D hydrate has an X-ray powder diffraction pattern comprising five or more peaks selected from the group consisting of 6.6±0.2, 10.0±0.2, 10.5±0.2, 11.1±0.2, 11.6±0.2, 12.2±0.2, 14.2±0.2, 16.6±0.2, 17.1±0.2, 17.7±0.2, 18.5±0.2, 18.8±0.2, 19.3±0.2, 21.4±0.2, 22.7±0.2, 23.1±0.2, 23.6±0.2, 24.6±0.2, 25.2±0.2, 27.2±0.2, 29.1±0.2, and 31.0±0.2 degrees 2θ.

In some embodiments, the pattern D hydrate has an X-ray powder diffraction pattern comprising one or more peaks selected from the group consisting of 6.6±0.2, 10.0±0.2, 10.5±0.2, 11.1±0.2, 11.6±0.2, 12.2±0.2, 12.5±0.2, 14.2±0.2, 16.6±0.2, 17.1±0.2, 17.7±0.2, 18.5±0.2, 18.8±0.2, 19.3±0.2, 21.4±0.2, 22.7±0.2, 22.8±0.2, 23.1±0.2, 23.6±0.2, 24.6±0.2, 24.9±0.2, 25.2±0.2, 27.1±0.2, 29.1±0.2, and 31.0±0.2 degrees 2θ. In some such embodiments, the pattern D hydrate has an X-ray powder diffraction pattern comprising three or more peaks selected from the group consisting of 6.6±0.2, 10.0±0.2, 10.5±0.2, 11.1±0.2, 11.6±0.2, 12.2±0.2, 12.5±0.2, 14.2±0.2, 16.6±0.2, 17.1±0.2, 17.7±0.2, 18.5±0.2, 18.8±0.2, 19.3±0.2, 21.4±0.2, 22.7±0.2, 22.8±0.2, 23.1±0.2, 23.6±0.2, 24.6±0.2, 24.9±0.2, 25.2±0.2, 27.2±0.2, 29.1±0.2, and 31.0±0.2 degrees 2θ. In other such embodiments, the pattern D hydrate has an X-ray powder diffraction pattern comprising five or more peaks selected from the group consisting of 6.6±0.2, 10.0±0.2, 10.5±0.2, 11.1±0.2, 11.6±0.2, 12.2±0.2, 12.5±0.2, 14.2±0.2, 16.6±0.2, 17.1±0.2, 17.7±0.2, 18.5±0.2, 18.8±0.2, 19.3±0.2, 21.4±0.2, 22.7±0.2, 22.8±0.2, 23.1±0.2, 23.6±0.2, 24.6±0.2, 24.9±0.2, 25.2±0.2, 27.2±0.2, 29.1±0.2, and 31.0±0.2 degrees 2θ.

Figure 22:
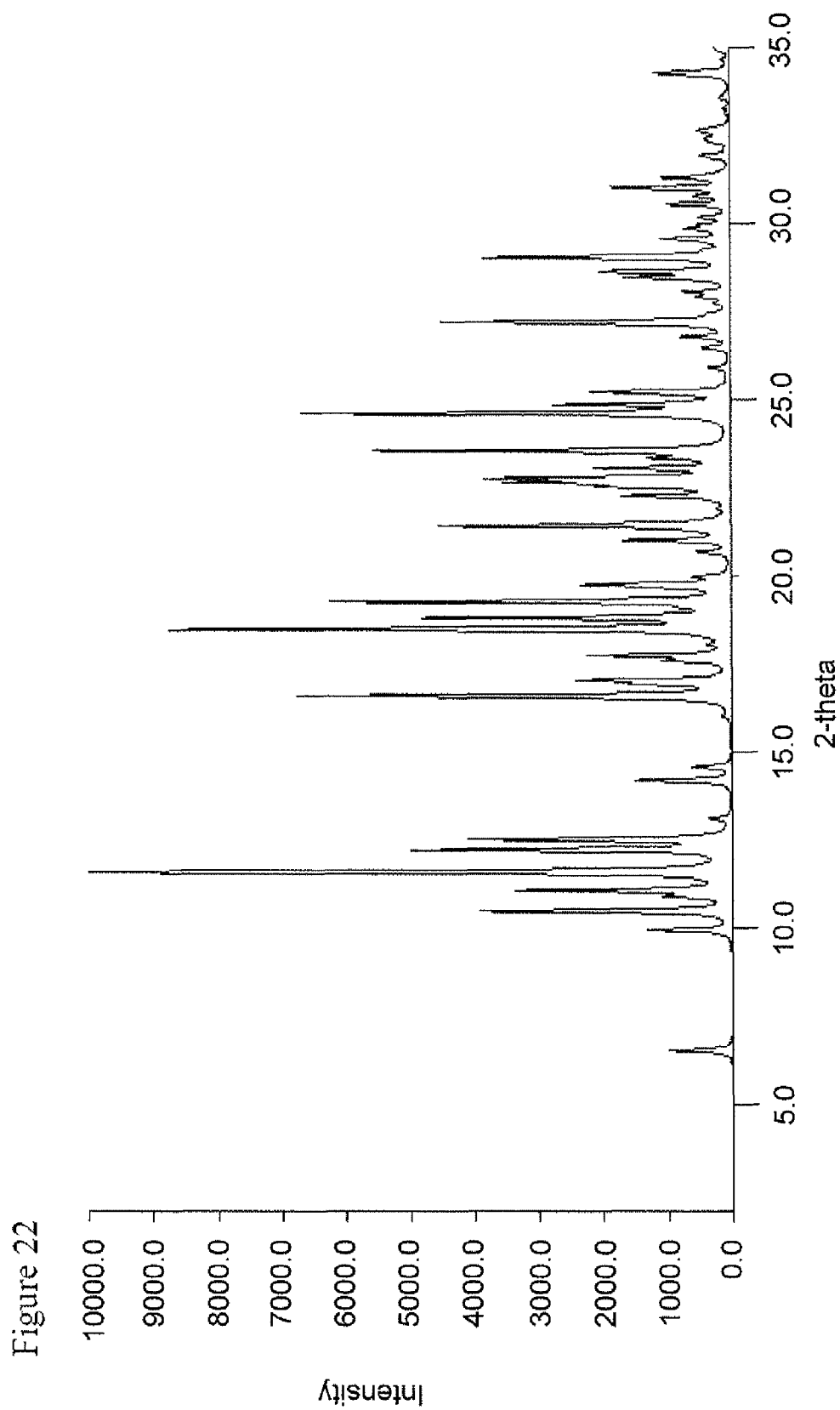
FIG. 22 shows an illustrative PXRD pattern for the pattern D hydrate of compound IB-L1-1.1.

In some embodiments, the pattern D hydrate has an X-ray powder diffraction pattern substantially as shown in FIG. 22. The 2θ values for the peaks in FIG. 22 (and their intensities) are as follows: 6.55 (10), 9.96 (12), 10.51 (37), 11.09 (31), 11.62 (100), 12.24 (44), 12.54 (40), 14.22 (15), 16.62 (68), 17.07 (22), 17.77 (21), 18.52 (82), 18.84 (47), 19.30 (63), 21.45 (34), 22.67 (30), 22.80 (34), 23.08 (20), 23.57 (58), 24.63 (73), 24.88 (26), 25.24 (21), 27.23 (36), 29.06 (41), and 31.04 (21).

This invention also relates, in part, to a process for preparing the pattern D hydrate. It was prepared by suspending pattern A polymorph (discussed above) in ethanol. Alternatively, it was prepared by suspending compound IB-L1-1.1 (103.03 mg) in 400 ul THF while heated to about 55° C. Aqueous NaOH (1M, 264 ul, 1.2 molar equivalent) was added. The solid dissolved completely to yield a clear solution. Ethanol (1.6 ml) was added to the solution. The solution was allowed to cool naturally to ambient temperatures. Crystals were formed during the slow evaporation process. Although it appears that the lattice can accommodate as much as 0.5 water molecules per molecule of compound IB-L1-1.1, the recovered pattern D hydrate contained ~0.2 water molecules per molecule of compound IB-L1-1.1.

This invention also relates, in part, to a pattern E (E)-N-(4-(3-tert-butyl-5-(2,4-dioxo-3,4-dihydropyrimidin-1(2'-1)-yl)-2-methoxystyryl)phenyl)methanesulfonamide hydrate.

The crystallographic unit cell parameters of the pattern E hydrate crystalline disodium salt have been determined to be as follows: a is 9.5 Å, b is 14.5 Å, and c is 17.3 Å (more precisely, a is 9.462(2)Å, b is 14.462(3)Å, and c is 17.281(4) Å); the cell angles are: α—84.9°, β—80.8°, and γ—81.8° (more precisely, α is 84.863(4)°, β is 80.760(4)°, and γ is 81.751(4)°; and the cell volume is 2304 Å$^3$ (more precisely, 2304.4(9)Å$^3$). The salt crystallizes in the P-1 space group.

In some embodiments, the pattern E hydrate has an X-ray powder diffraction pattern comprising one or more peaks selected from the group consisting of 6.2±0.2, 7.8±0.2, 10.2±0.2, 10.7±0.2, 12.1±0.2, 16.3±0.2, 19.7±0.2, 20.9±0.2, 21.8±0.2, 24.5±0.2, and 28.0±0.2 degrees 2θ. In some such embodiments, the pattern E hydrate has an X-ray powder diffreaction pattern comprising three or more peaks selected from the group consisting of 6.2±0.2, 7.8±0.2, 10.2±0.2, 10.7±0.2, 12.1±0.2, 16.3±0.2, 19.7±0.2, 20.9±0.2, 21.8±0.2, 24.5±0.2, and 28.0±0.2 degrees 2θ. In other such embodiments, the pattern E hydrate has an X-ray powder diffraction pattern pattern comprising five or more peaks selected from the group consisting of 6.2±0.2, 7.8±0.2, 10.2±0.2, 10.7±0.2, 12.1±0.2, 16.3±0.2, 19.7±0.2, 20.9±0.2, 21.8±0.2, 24.5±0.2, and 28.0±0.2 degrees 2θ.

In some embodiments, the pattern E hydrate has an X-ray powder diffraction pattern comprising one or more peaks selected from the group consisting of 6.1±0.2, 7.8±0.2, 10.2±0.2, 10.4±0.2, 10.7±0.2, 12.1±0.2, 16.3±0.2, 19.7±0.2, 20.9±0.2, 21.8±0.2, 24.5±0.2, and 28.0±0.2 degrees 2θ. In some such embodiments, the pattern E hydrate has an X-ray powder diffraction pattern comprising three or more peaks selected from the group consisting of 6.2±0.2, 7.8±0.2, 10.2±0.2, 10.4±0.2, 10.7±0.2, 12.1±0.2, 16.3±0.2, 19.7±0.2, 20.9±0.2, 21.8±0.2, 24.5±0.2, and 28.0±0.2 degrees 2θ. In other such embodiments, the pattern E hydrate has an X-ray powder diffraction pattern comprising five or more peaks selected from the group consisting of 6.2±0.2, 7.8±0.2, 10.2±0.2, 10.4±0.2, 10.7±0.2, 12.1±0.2, 16.3±0.2, 19.7±0.2, 20.9±0.2, 21.8±0.2, 24.5±0.2, and 28.0±0.2 degrees 2θ.

Figure 23:
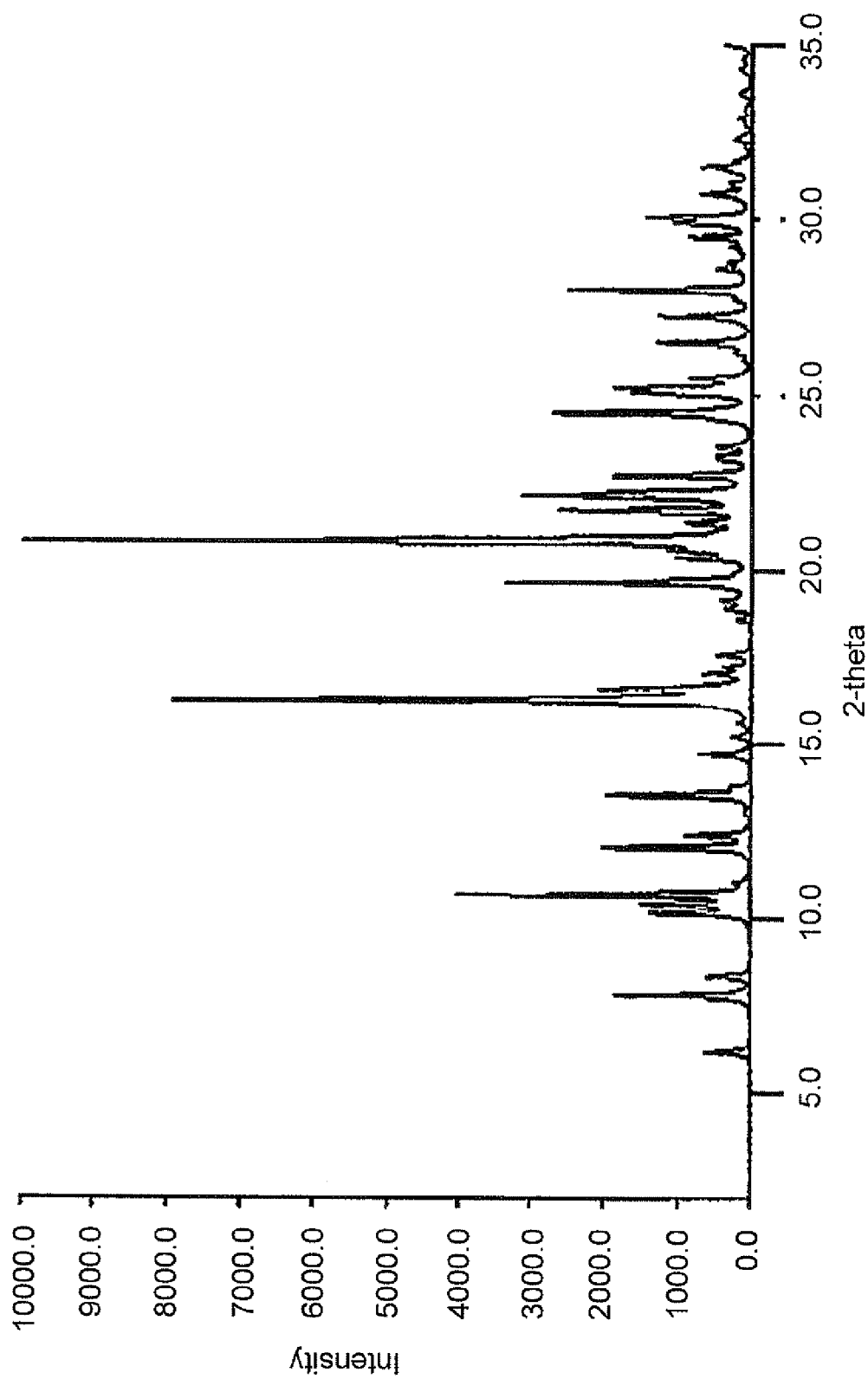
FIG. 23 shows an illustrative PXRD pattern for the pattern E hydrate of compound IB-L1-1.1.

In some embodiments, the pattern E hydrate has an X-ray powder diffraction pattern substantially as shown in FIG. 23. The 2θ values for the peaks in FIG. 23 (and their intensities) are as follows: 6.19 (6), 7.81 (18), 10.17 (13), 10.40 (14), 10.68 (39), 12.06 (20), 16.29 (78), 19.72 (32), 20.88 (100), 21.77 (27), 24.52 (25), and 28.01 (27).

This invention also relates, in part, to a process for preparing the pattern E hydrate. It was prepared by suspending compound IB-L1-1.1 (56.76 mg) in 200 ul THF while heated. Aqueous NaOH (1M, 146 uL, 1.2 molar equivalent) was added, which yielded a clear solution. Ethanol (800 ul) was added to the solution. The solution was allowed to cool naturally to ambient temperatures. Crystals were formed during the slow evaporation process. Although it appears that the lattice can accommodate as much as one water molecule per molecule of compound IB-L1-1.1, the recovered pattern D hydrate contained ~0.25 water molecules per molecule of compound IB-L1-1.1.

H. Compositions

This invention also is directed, in part, to compositions comprising one or more compounds and/or salts of the invention (including the crystalline compounds and salts discussed in section G above). In some embodiments, the compositions comprise one or more substantially phase pure crystalline forms (compounds/salts/solvates/hydrates) discussed in section G above. The compositions can be pharmaceutical compositions.

In some embodiments, the compositions further comprise one or more additional therapeutic agents. Such therapeutic agents can, but need not be, additional HCV inhibitors.

The preferred composition depends on the method of administration, and typically comprises one or more conventional pharmaceutically acceptable carriers, adjuvants, and/or vehicles (together referred to as "excipients"). Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions also can comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration can be prepared by, for example, mixing a compound or salt of the invention with a suitable nonirritating excipient that is solid at ordinary temperatures, but liquid at the rectal temperature, and will therefore melt in the rectum to release the drug. Suitable excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other excipients and modes of administration known in the pharmaceutical art also may be used.

Applicants have discovered that some I-L1 compounds in which $R^6$ and the phenyluracil are in trans-position relative to the double bond, when in solution, tend to convert into the corresponding cis-isomer upon exposure to light; thus, it may be desirable to store such solutions under conditions that reduce exposure to light (e.g., in an amber bottle or in a dark place).

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

I. Kits

This invention also is directed, in part, to a kit comprising one or more compounds and/or salts of the in invention. The kit can optionally contain one or more additional therapeutic agents and/or instructions for, for example, using the kit.

J. Methods of Use

This invention also is directed, in part, to a method for inhibiting replication of an RNA virus. The method comprises exposing the virus to one or more compounds and/or salts of this invention. In some embodiments, replication of the RNA virus is inhibited in vitro. In other embodiments, replication of the RNA virus is inhibited in vivo. In some embodiments, the RNA virus whose replication is being inhibited is a single-stranded, positive sense RNA virus. In some such embodiments, the RNA virus whose replication is being inhibited is a virus from the Flaviviridae family. In some such embodiments, the RNA virus whose replication is being inhibited is HCV.

This invention also is directed, in part, to a method for inhibiting HCV RNA polymerase. The method comprises exposing the polymerase with one or more compounds and/or salts of this invention. In some embodiments, HCV RNA polymerase activity is inhibited in vitro. In other embodiments, HCV RNA polymerase activity is inhibited in vivo.

The term "inhibiting" means reducing the level of RNA virus replication/HCV polymerase activity either in vitro or in vivo. For example, if a compound/salt of the invention reduces the level of RNA virus replication by at least about 10% compared to the level of RNA virus replication before the virus was exposed to the compound/salt, then the compound/salt inhibits RNA virus replication. In some embodiments, the compound/salt can inhibit RNA virus replication by at least about 20%, at least about 30%, at least about 40%, at least about 50%, at least about 60%, at least about 70%, at least about 80%, at least about 90%, or at least about 95%.

This invention also is directed, in part, to a method for treating a disease that can be treated by inhibiting HCV RNA polymerase. Thus, this invention also is directed, in part, to a method for treating hepatitis C in an animal in need of such treatment. These methods comprise administering to the animal one or more compounds and/or salts of the invention, and, optionally, one or more additional therapeutic agents. In some embodiments, a therapeutically effective amount of the compound(s) and/or salt(s) is administered to the animal. "Treating" means ameliorating, suppressing, eradicating, preventing, reducing the risk of, and/or delaying the onset of the disease being treated. Applicants specifically intend that the term "treating" encompass administration of the compounds and/or salts of the invention to an HCV-negative patient that is a candidate for an organ transplant. The methods of treatment are particularly suitable for use with humans, but may be used with other animals, particularly mammals. A "therapeutically-effective amount" or "effective amount" is an amount that will achieve the goal of treating the targeted condition.

In some embodiments, the methods comprise combination therapy, wherein the compound(s) and/or salt(s) of the invention is/are co-administered with a second (or even a third, fourth, etc.) compound, such as, for example, another therapeutic agent used to treat hepatitis C (e.g., interferon or interferon/ribavirin combination, or an HCV inhibitor such as, for example, an HCV polymerase inhibitr or an HCV protease inhibitor). The compound(s) and/or salt(s) of this invention can also be co-administered with therapeutic agents other than therapeutic agents used to treat hepatitis C (e.g., anti-HIV agents). In these co-administration embodiments, the compound(s) and/or salt(s) of the invention and the second, etc. therapeutic agent(s) may be administered in a substantially simultaneous manner (e.g., or within about 5 minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. The compound(s) and/or salt(s) of this invention and the second, etc. therapeutic agent may also be administered in a single formulation.

This invention also is directed, in part, to a use of one or more compounds and/or salts of the invention, and, optionally one or more additional therapeutic agents to prepare a medicament. In some embodiments, the medicament is for co-administration with one or more additional therapeutic agents.

In some embodiments, the medicament is for inhibiting replication of an RNA virus.

In some embodiments, the medicament is for treating hepatitis C.

This invention also is directed, in part, to one or more compounds and/or salts of the invention, and, optionally one or more additional therapeutic agents, for use as a medicament. In some embodiments, the medicament is for inhibiting replication of an RNA virus. In other embodiments, the medicament is for treating hepatitis C.

K. Intermediate Compounds

This invention also is directed, in part, to intermediates that correspond in structure to formula II that can be used to prepare the compounds of formula I (and their salts)(although some intermediates can also be used, just like the compounds of formula I, as HCV inhibitors, and one skilled in the art can determine such ability of the compounds of formula II by utilizing, for example, the methods discussed below):

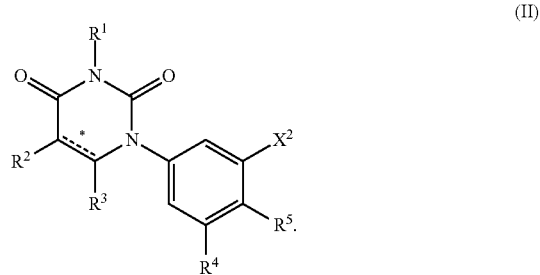

(II)

In formula II:

⋯∗⋯, $R^1$, $R^2$, $R^3$, $R^4$, and $R^5$ are as discussed above for the compounds of formula I; and $X^2$ is halo.

The various embodiments for ⋯∗⋯, $R^1$, $R^2$, $R^3$, $R^4$, and $R^5$ (as well as their combinations) discussed above apply to the compounds of formula II. As to $X^2$, in some embodiments, $X^2$ is selected from the group consisting of chloro, bromo, and iodo. In other embodiments, $X^2$ is selected from the group consisting of chloro and bromo. In yet other embodiments, $X^2$ is selected from the group consisting of chloro and iodo. In yet other embodiments, $X^2$ is selected from the group consisting of iodo and bromo. In further embodiments, $X^2$ is fluoro. In yet further embodiments, $X^2$ is chloro. In yet further embodiments, $X^2$ is bromo. And in yet further embodiments, $X^2$ is iodo.

The various embodiments for ⋯∗⋯, $R^1$, $R^2$, $R^3$, $R^4$, $R^5$, and $X^2$ discussed above can be combined to form various embodiments of compounds of formula II, and all embodiments of compounds of formula II so formed are within the scope of Applicants' invention. Some exemplary embodiments of the compounds (and salts thereof) of formula II are discussed below.

In some embodiments, the compounds of formula II correspond in structure to formula IIA:

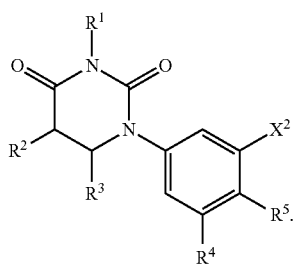

(IIA)

In other embodiments, the compounds of formula II correspond in structure to formula IIB:

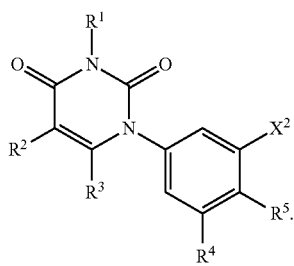

(IIB)

In some embodiments of the compounds of formula II:

$R^1$ is selected from the group consisting of hydrogen, methyl, and nitrogen-protecting group;
$R^2$ is selected from the group consisting of hydrogen and halo;
$R^3$ is selected from the group consisting of hydrogen and halo;
$R^4$ is selected from the group consisting of $C_1$-$C_4$-alkyl, $C_3$-$C_6$-carbocyclyl, and 5-6-membered heterocyclyl, wherein:
  (a) the $C_1$-$C_4$-alkyl optionally is substituted with up to three substituents independently selected from the group consisting of halo, oxo, hydroxy, alkyloxy, and trimethylsilyl, and
  (b) the $C_3$-$C_6$-carbocyclyl and 5-6-membered heterocyclyl optionally are substituted with one or two substituents independently selected from the group consisting of alkyl, halo, and alkylsulfonylamino;
$R^5$ is selected from the group consisting of hydrogen, hydroxy, alkyloxy, and halo; and
$X^2$ is selected from the group consisting of chloro, bromo, and iodo.

In some embodiments of the compounds of formula II:

⋯∗⋯ is a double carbon-carbon bond;
$R^1$ is hydrogen;
$R^2$ is selected from the group consisting of hydrogen and halo;
$R^3$ is hydrogen;
$R^4$ is tert-butyl;
$R^5$ is selected from the group consisting of hydrogen, hydroxy, and methoxy; and
$X^2$ is selected from the group consisting of bromo and iodo.

In some embodiments of the compounds of formula II:

$R^1$ is selected from the group consisting of hydrogen and methyl;
$R^2$ is selected from the group consisting of hydrogen and methyl;
$R^3$ is selected from the group consisting of hydrogen and methyl;
$R^4$ is tert-butyl;
$R^5$ is selected from the group consisting of hydroxy and methoxy; and
$X^2$ is selected from the group consisting of chloro, bromo, and iodo.

In some embodiments of the compounds of formula II:

⋯∗⋯ is a double carbon-carbon bond;
$R^1$ is hydrogen;
$R^2$ is hydrogen;
$R^3$ is hydrogen;
$R^4$ is tert-butyl;
$R^5$ is selected from the group consisting of hydroxy and methoxy; and
$X^2$ is selected from the group consisting of chloro, bromo, and iodo.

In some embodiments, the compound of formula II is selected from the group consisting of

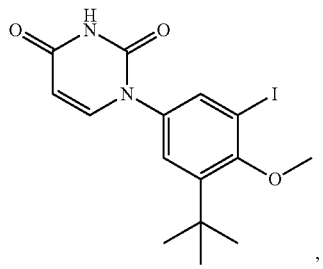

(II-I)

,

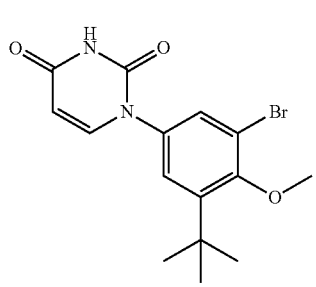

(II-Br)

, and

-continued (II-Cl)

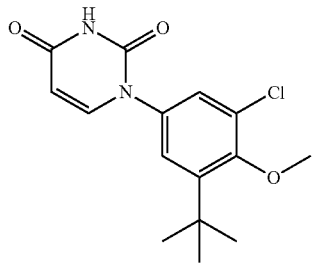

The discussion below provides instructions for the preparation of intermediate compounds of formula II (and salts thereof).

L. Starting Compounds

This invention also is directed, in part, to starting compounds that correspond in structure to formula III that can be used to prepare the compounds of formulas II and I (and their salts):

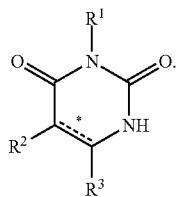

(III)

In formula III, $\cdots$, $R^1$, $R^2$, and $R^3$ are as discussed above for the compounds of formula I and II. The various embodiments for $\cdots$, $R^1$, $R^2$, and $R^3$ (as well as their combinations) discussed above apply to the compounds of formula III. The various embodiments for $\cdots$, $R^1$, $R^2$, and $R^3$ discussed above can be combined to form various embodiments of compounds of formula III, and all embodiments of compounds of formula III so formed are within the scope of Applicants' invention. Some exemplary embodiments of the compounds (and salts thereof) of formula III are discussed below.

In some embodiments of the compounds of formula III:
$R^1$ is selected from the group consisting of hydrogen, methyl, and nitrogen-protecting group;
$R^2$ is selected from the group consisting of hydrogen and halo; and
$R^3$ is selected from the group consisting of hydrogen and halo.

In some embodiments of the compounds of formula III:
$\cdots$ is a double carbon-carbon bond;
$R^1$ is selected from the group consisting of hydrogen;
$R^2$ is selected from the group consisting of hydrogen and halo; and
$R^3$ is selected from the group consisting of hydrogen.

In some embodiments of the compounds of formula III:
$R^1$ is selected from the group consisting of hydrogen and methyl;
$R^2$ is selected from the group consisting of hydrogen and methyl; and
$R^3$ is selected from the group consisting of hydrogen and methyl.

In some embodiments, the compound of formula III is uracil.

This invention also is directed, in part, to starting compounds that correspond in structure to formula IV that can be used to prepare the compounds of formulas II and I (and their salts):

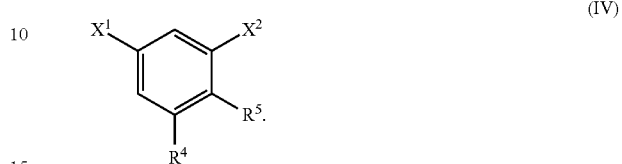

(IV)

In formula IV:
$R^4$, $R^5$, and $X^2$ are as discussed above for the compounds of formula I and II; and
$X^1$ is halo.

The various embodiments for $R^1$, $R^5$, and $X^2$ (as well as their combinations) discussed above apply to the compounds of formula IV. As to $X^1$, in some embodiments, $X^1$ is selected from the group consisting of chloro, bromo, and iodo. In other embodiments, $X^1$ is selected from the group consisting of chloro and bromo. In yet other embodiments, $X^1$ is selected from the group consisting of chloro and iodo. In yet other embodiments, $X^1$ is selected from the group consisting of iodo and bromo. In further embodiments, $X^1$ is fluoro. In yet further embodiments, $X^1$ is chloro. In yet further embodiments, $X^1$ is bromo. And in yet further embodiments, $X^1$ is iodo. As to $X^1$ and $X^2$, in some embodiments, $X^1$ and $X^2$ are identical.

The various embodiments for $R^4$, $R^5$, $X^1$, and $X^2$ discussed above can be combined to form various embodiments of compounds of formula IV, and all embodiments of compounds of formula III so formed are within the scope of Applicants' invention. Some exemplary embodiments of the compounds (and salts thereof) of formula IV are discussed below.

In some embodiments of the compounds of formula IV:
$R^4$ is selected from the group consisting of $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with one or two substituents independently selected from the group consisting of alkyl, halo, and alkylsulfonylamino;
$R^5$ is selected from the group consisting of hydrogen, hydroxy, and alkyloxy;
$X^1$ is selected from the group consisting of chloro, bromo, and iodo; and
$X^2$ is selected from the group consisting of chloro, bromo, and iodo.

In some embodiments of the compounds of formula IV:
$R^4$ is selected from the group consisting of tert-butyl;
$R^5$ is selected from the group consisting of hydrogen, hydroxy, and methoxy;
$X^1$ is selected from the group consisting of bromo and iodo; and
$X^2$ is selected from the group consisting of bromo and iodo.

In some embodiments of the compounds of formula IV:
$R^4$ is selected from the group consisting of tert-butyl;

$R^5$ is selected from the group consisting of hydroxy and methoxy;

$X^1$ is selected from the group consisting of chloro, bromo, and iodo; and $X^2$ is selected from the group consisting of chloro, bromo, and iodo.

In some embodiments of the compounds of formula IV:

$R^4$ is tert-butyl;

$R^5$ is selected from the group consisting of hydroxy and methoxy;

$X^1$ is selected from the group consisting of chloro, bromo, and iodo; and $X^2$ is selected from the group consisting of chloro, bromo, and iodo.

In some embodiments, the compound of formula IV is selected from the group consisting of

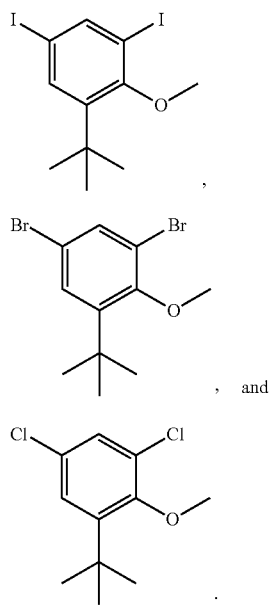

The discussion below provides instructions for the preparation of starting compounds of formula IV (and salts thereof).

L. Methods for Preparation

This invention also is directed, in part, to a process for preparing compounds of formula II. The process comprises reacting a compound of formula III with a compound of formula IV in the presence of (i) copper (I) salt catalyst and (ii) nitrogenous heteroaryl ligand:

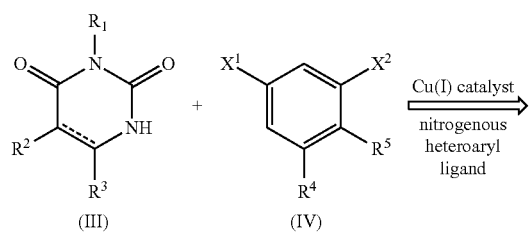

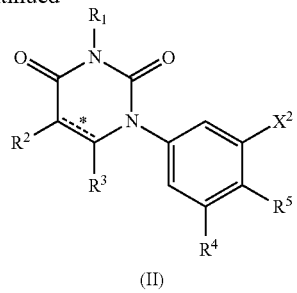

In the above process, $R^1$, $R^2$, $R^3$, $R^4$, $R^5$, $X^1$, and $X^2$ are as discussed above. Applicants have discovered that the process generally results in the substitution of the N1 hydrogen of uracil derivative compound III thus resulting in intermediate compound II. When $X^2$ in intermediate compound II is chloro, bromo, or iodo, then compound II is suitable for subsequent reaction (e.g., Suzuki coupling with an appropriate boronic acid or boronate ester) to provide compound of formula I. In other words, when $X^2$ in intermediate compound II is chloro, bromo, or iodo, the above process is suitable for preparing compounds of formula I as well.

In some embodiments, compound III is uracil, and compound IV corresponds in structure to a compound selected from the group consisting of compound IV-I, IV-Br, and IV-Cl, with compounds IV-I and IV-Br typically resulting in better yield than compound IV-Cl.

Suitable Cu(I) catalysts include, for example, CuI, CuBr, CuCl, Cu$_2$O, and CH$_3$C(O)OCu. In some embodiments, the catalyst is selected from the group consisting of CuI and CuBr. In some such embodiments, the catalyst is CuI. In other such embodiments, the catalyst is CuBr.

In some embodiments, the process is conducted in the presence of a base. In some such embodiments, the base is an inorganic base. Suitable inorganic bases include, for example, potassium, sodium, and cesium salts (e.g., K$_2$CO$_3$, K$_3$PO$_4$, Cs$_2$CO$_3$, Na, CO$_3$). In some embodiments, the base is selected from the group consisting of potassium salt and cesium salt. In some such embodiments, the salt is selected from the group consisting of K$_3$PO$_4$ and Cs$_2$CO$_3$. In some embodiments, the base comprises a potassium salt. In some such embodiments, the potassium salt is K$_2$CO$_3$. In other such embodiments, the potassium salt is K$_3$PO$_4$. In some embodiments, the base comprises a cesium salt. In some such embodiments, the potassium salt is Cs$_2$CO$_3$.

Typically, the process is conducted in the presence of a solvent. Suitable solvents include, for example, dimethylsulfoxide (DMSO), dimethylformamide (DMF), and acetonitrile (MeCN). In some embodiments, the solvent is DMSO.

Typically, the process is conducted at a temperature of from about 40 to about 130° C.

In some embodiments, the nitrogenous heteroaryl ligand comprises 8-hydroxyquinoline. In other embodiments, the ligand comprises 2-(2-pyridyl)-benzimidazole. In yet other embodiments, the ligand comprises a picolinamide compound corresponding in structure to formula V:

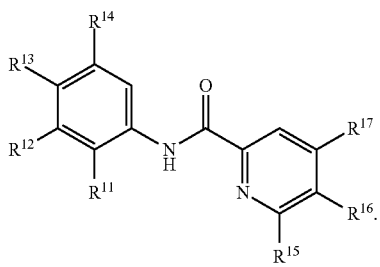
(V)

In formula V, $R^{11}$, $R^{12}$, $R^{14}$, $R^{15}$, $R^{16}$ and $R^{17}$ are independently selected from the group consisting of hydrogen, $C_{1-4}$-perfluoroalkyl, $C_{1-4}$-alkyloxy, $C_{1-4}$-haloalkyl, chloro, or cyano. In some embodiments, $R^{11}$, $R^{12}$, $R^{13}$, $R^{14}$, $R^{15}$, $R^{16}$, and $R^{17}$ are independently selected from the group consisting of hydrogen, methyl, methoxy, trifluoromethyl, chloro, and cyano. In some embodiments, the ligand of formula V comprises N-(4-cyanophenyl)picolinamide. In other embodiments, the ligand of formula V comprises N-(2-cyanophenyl)picolinamide.

In some embodiments, the process comprises (a) preparing a compound of formula IV; and (b) reacting a compound of formula III with a compound of formula IV in the presence of (i) copper (I) salt catalyst and (ii) nitrogenous heteroaryl ligand, optionally in the presence of inorganic base.

Compound of formula IV-I can be prepared by, for example, converting 2-tert-butylphenol into 2-tert-butyl-4,6-diiodophenol (by, for example, reacting it with NaI and NaOCl), and then converting the 2-tert-butyl-4,6-diiodophenol into 1-tert-butyl-3,5-diiodo-2-methoxybenzene (by, for example, treating it with $CH_3I$ in the presence of a base, such as, for example, NaOH).

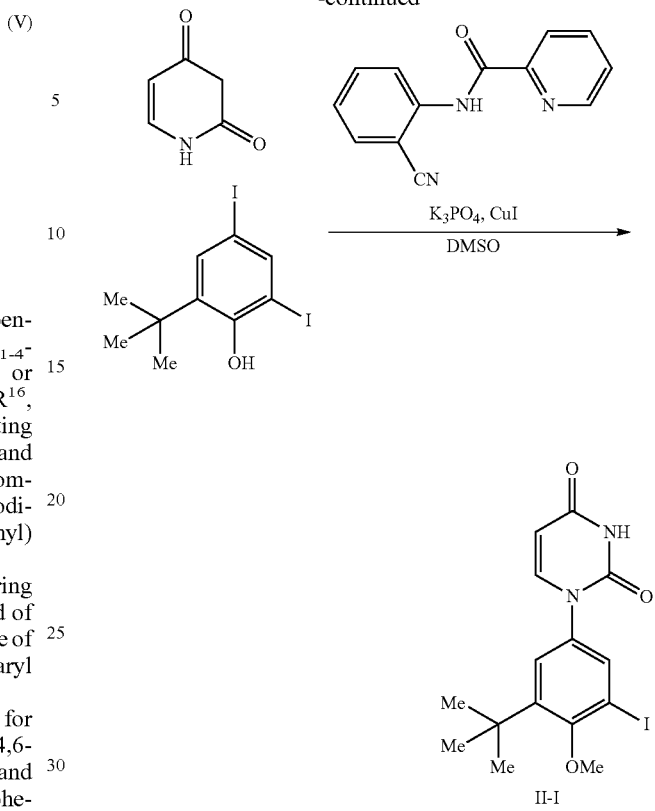

Compound of formula IV-Br can be prepared by, for example, converting 2-tert-butylphenol into 2,4-dibromo-6-tert-butylphenol (by, for example, reacting it with 1,3-dibromo-5,5-dimethylimidazo-lidine-2,4-dione), and then converting the 2,4-dibromo-6-tert-butylphenol into 1,5-dibromo-3-tert-butyl-2-methoxybenzene (by, for example, treating it with $CH_3I$ in the presence of KOtBu).

Additional information about the preparation of compounds of formulas I and II (and their salts) is provided in the general discussion and/or specific synthesis examples below. In the discussion below, $R^1$, $R^2$, $R^3$, $R^4$, $R^5$, L, $R^A$, $R^B$, $R^C$, $R^D$, $R^6$, $R^E$, $R^F$, $R^G$, $R^H$, $R^I$, $R^J$, $R^K$, $X^1$, and $X^2$ have the meaning discussed above unless otherwise stated.

SCHEME 1

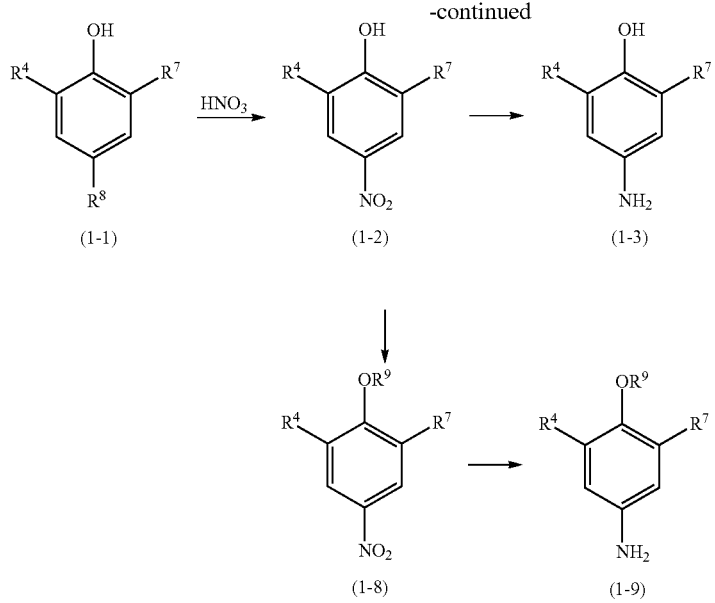

Compound (1-1), wherein $R^7$ is, for example, hydrogen or —$CO_2Me$, and $R^8$ is, for example, hydrogen or t-butyl, may be treated with nitric acid in solvents such as, for example, acetic acid or water in a temperature range of about 0 to about 35° C. over about 1 to about 5 h to provide compound (1-2). Compound (1-2) may then be reduced using conditions known to those skilled in the art to furnish the corresponding aniline (1-3). Typical conditions for this reduction include using hydrogen at a pressure of about 1 to about 5 atmospheres in the presence of a catalyst such as, for example, palladium or platinum on charcoal in a solvent such as, for example, tetrahydrofuran, ethyl acetate, ethanol, or hexane at or near ambient temperature over a period of about 1 to about 12 h. Dependent on the functional groups present, an alternative reduction procedure may be more appropriate such as, for example, using iron powder in the presence of a mild acid such as, for example, ammonium chloride or dilute hydrochloric acid at reflux temperatures in a mixture of solvents containing, for example, methanol, water, and/or tetrahydrofuran over about 1 to about 12 h. Another set of reduction conditions includes the use of sodium borohydride in a solvent mixture such as, for example, water and tetrahydrofuran. Yet another set of reduction conditions includes the use of tin(II) chloride in the presence of hydrochloric acid in such solvents as, for example, water and methanol or mixtures thereof.

Compound (1-2) may be modified prior to reduction. For example, treatment of compound (1-2), wherein $R^7$ is hydrogen, with iodine monochloride in a mixture of methanol and water at or near ambient temperature over a period of about 8 to about 24 h supplies compound (1-4), wherein $X^1$ is iodine. Alternatively, compound (1-2) can be treated with pyridinium hydrobromide perbromide in a solvent such as, for example, acetic acid at or near ambient temperature over a period of about 2 to about 16 h to provide compound (1-4), wherein $X^1$ is bromine. Modifications may be introduced at the phenol moiety in compound (1-4). For example, the phenol may be alkylated with alkyl halides (e.g., methyl iodide), alkyl sulfates (e.g., methyl sulfate), alkenyl halides (e.g., allyl bromide), alkynyl halides (e.g., propargyl bromide) in the presence of a base such as, for example, potassium carbonate in acetone, sodium hydride in dimethylformamide, or potassium t-butoxide in tetrahydrofuran, at temperatures from about 0 to about 35° C. over a period of about 1 to about 24 h to provide compound (1-5), wherein $R^9$ is, for example, alkyl, alkenyl, or alkynyl. Alternatively, alkylation may be achieved by using a reagent such as (trimethylsilyl) diazomethane in solvents such as, for example, methanol or t-butyl methyl ether, or mixtures thereof in a sealed tube at or near room temperature over about 8 to about 24 h. Compound (1-5) may subsequently be reduced to compound (1-6) using the iron powder or tin(II) chloride conditions described above. An alternative reduction procedure employs hydrogenation at approximately 1 atmosphere pressure with a catalyst such as 5% platinum on sulfided carbon in a solvent such as methanol. Protection of the resultant aniline of compound (1-6) with, for example, a t-butyl carbamate can be achieved by treatment with di-tert-butyl dicarbonate in a solvent such as, for example, tetrahydrofuran or dioxane at a temperature of about 50 to about 65° C. for about 1 to about 8 h provides compound (1-7).

Modifications may also occur at the phenol moiety in compound (1-2). One skilled in the art may alkylate the phenol of compound (1-2) using, for example, the conditions described above to obtain compound (1-8). Compound (1-8) is transformed into compound (1-9) using, for example, one or more of the appropriate reduction conditions described above.

Another modification of the phenol group in compound (1-2) is sulfonylation to furnish compound (1-8), wherein $R^9$ is alkylsulfonyl, carbocyclylsulfonyl, or haloalkylsulfonyl. Such a compound may be prepared by exposing compound (1-2) to sulfonyl chlorides such as, for example, methanesulfonyl chloride, cyclohexanesulfonyl chloride, benzenesulfonyl chloride, or 3-chloropropane sulfonyl chloride in the presence of a base such as, for example, triethylamine, diisopropylethylamine, or pyridine in a solvent such as, for example, dichloromethane at or near ambient temperature for a period of about 1 to about 24 h. One skilled in the art can then transform compound (1-8) into compound (1-9) with an appropriate set of reduction conditions.

SCHEME 2

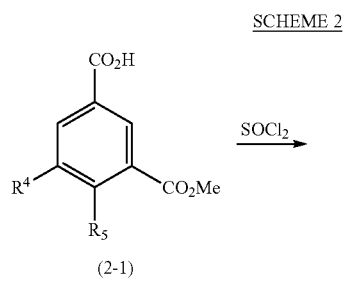

(2-1)

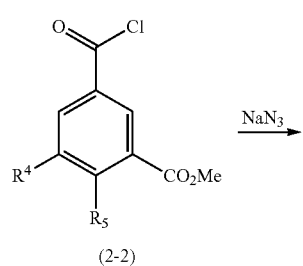

(2-2)

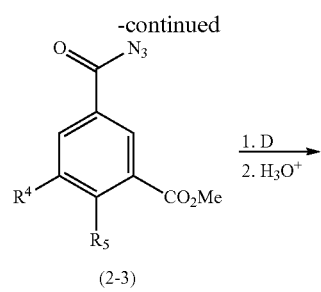

(2-3)

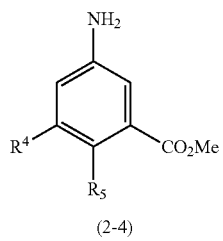

(2-4)

Aniline (2-4) can be prepared through use of the Curtius rearrangement. To this end, compound (2-1), wherein $R^4$ is not amino, can be treated in refluxing thionyl chloride with a catalytic amount of dimethylformamide for about 1 to about 4 h to obtain acid chloride (2-2). Treatment with thionyl chloride at the reflux temperature in solvents such as, for example, chloroform or toluene also furnishes compound (2-2). Compound (2-2) can be reacted with an aqueous solution of sodium azide in a solvent such as, for example, acetone over about 1 to about 8 h to provide acyl azide (2-3). Compound (2-3) can then undergo a Curtius rearrangement in refluxing solvents such as dioxane or toluene. The intermediate isocyanate is hydrolyzed with an aqueous acid such as dilute hydrochloric acid in a solvent such as dimethoxyethane to provide compound (2-4).

SCHEME 3

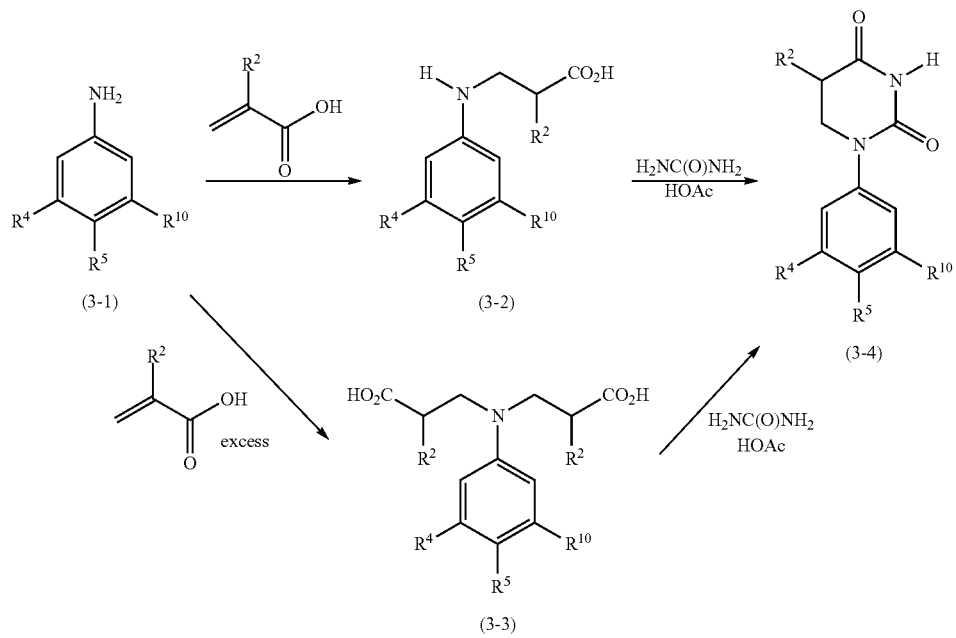

Compound (3-1), wherein $R^{10}$ is, for example, hydrogen, bromine, iodine, or —$CO_2Me$, can be treated with an acrylic acid either neat at or near ambient temperature in a solvent such as, for example, toluene and heated to reflux over a period of about 15 to about 48 h to supply compound (3-2). When excess of an acrylic acid is used, compound (3-3) is produced. Compound (3-2) or (3-3) can be treated with urea in a solvent such as, for example, acetic acid at about 100 to about 120° C. over about 2 to about 48 h to supply compound (3-4).

SCHEME 4

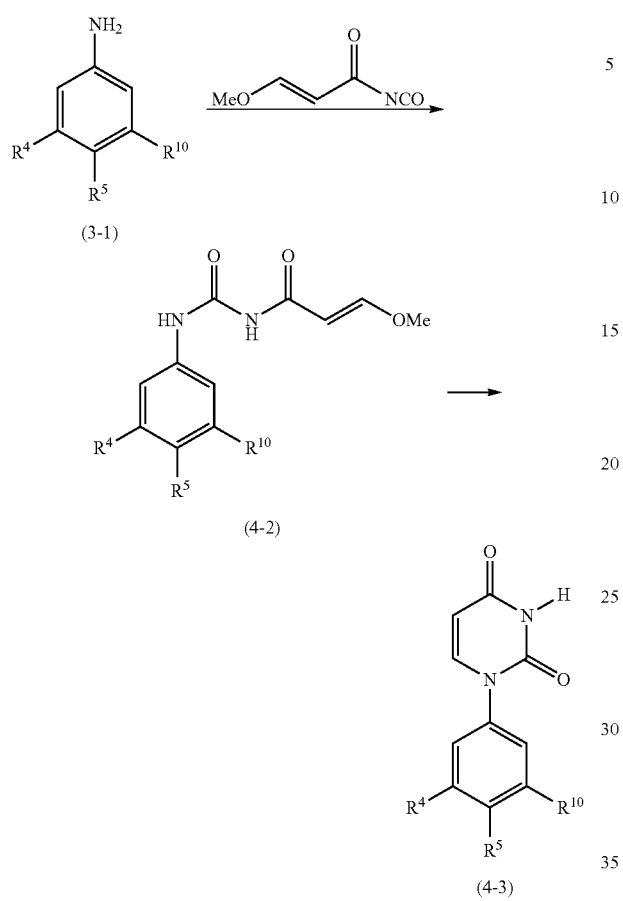

Compound (4-2) can be prepared from compound (3-1) dissolved in solvents such as, for example, dimethylformamide or dimethylacetamide by the addition of a benzene solution of (E)-3-methoxyacryloyl isocyanate (prepared as described by Santana, L.; et al. J. Heterocyclic Chem. 1999, 36, 293-295.) at a temperature of about −40 to about −15° C. under an inert atmosphere and then warming to ambient temperature for from about 30 min to about 4 h. Compound (4-2) can be treated with an acid such as, for example, sulfuric acid in mixtures of water and ethanol in a temperature range of from about 90 to about 110° C. for about 1 to about 8 h to supply compound (4-3). Alternatively, compound (4-2) can be cyclized to uracil (4-3) under the basic conditions described by Ueno, Y.; et al. J. Org. Chem. 70:7925-7935 (2005).

SCHEME 5

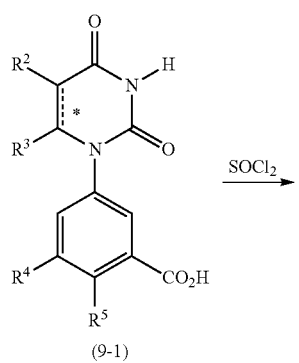

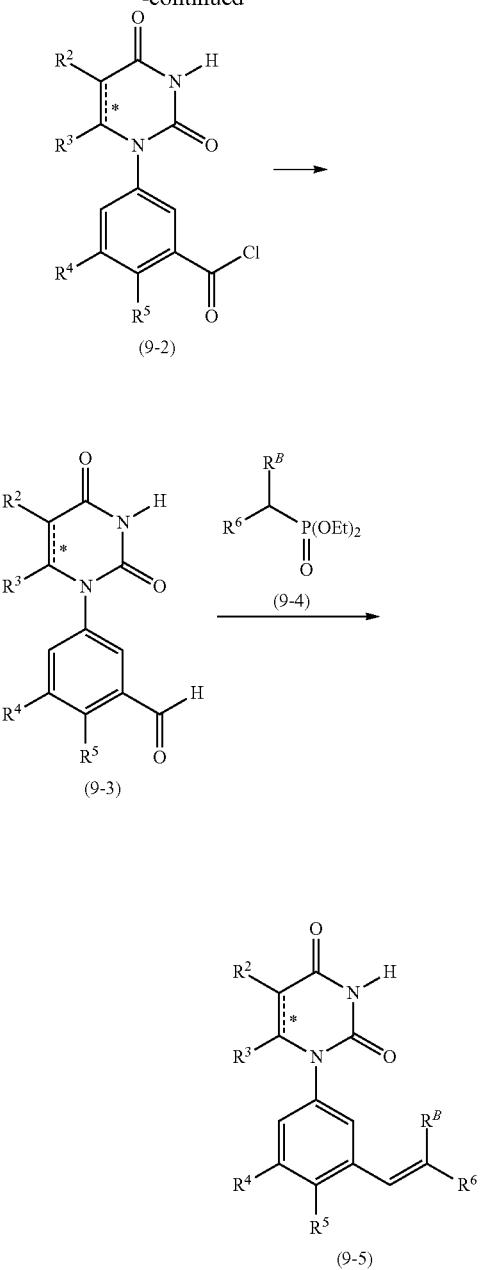

Compound (9-1) can be treated in refluxing thionyl chloride for about 1 to about 4 h to obtain acid chloride (9-2). Treatment with thionyl chloride at the reflux temperature in solvents such as, for example, chloroform or toluene also furnishes compound (9-2). Compound (2) is converted to the corresponding aldehyde (9-3) by reduction with lithium tri-t-butoxyaluminum hydride in a solvent such as, for example, tetrahydrofuran at about −78° C. over from about 1 to about 8 h. The reduction can also be achieved by treatment with indium chloride and tributyltin hydride in the presence of triphenylphosphine in a solvent such as tetrahydrofuran or toluene at temperatures from about −40 to about 0° C. Compound (9-3) can be treated with compound (9-4) in the presence of a base such as potassium t-butoxide in a solvent such as dichloromethane at or near room temperature over a period of about 1 to about 8 h to provide compound (9-5).

SCHEME 6

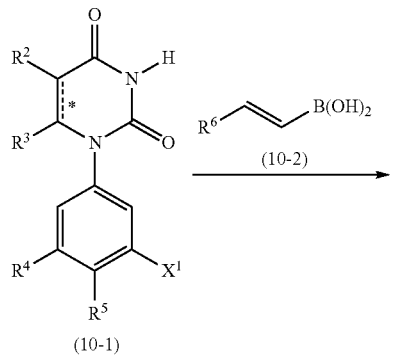

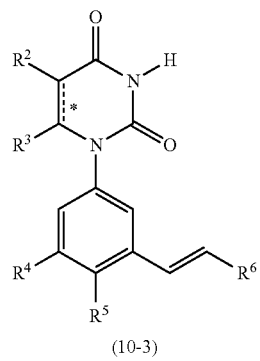

Compound (10-1), wherein $X^1$ is halo (e.g., bromine, iodine) can undergo a Suzuki reaction with vinyl boronic acid (10-2) to provide compound (10-3). The reaction typically requires the use of a base and a catalyst. Examples of bases include, for example, potassium carbonate, potassium phosphate, potassium t-butoxide, sodium carbonate, cesium carbonate, and cesium fluoride. Examples of catalysts include, for example, tris(dibenzylidineacetone)dipalladium (0), palladium acetate, bis(triphenyl phosphine)palladium (II) chloride, tetrakis(triphenylphosphine)palladium, dichloro[1,1'-bis(di-tert-butylphosphino)ferrocene]palladium (II), or dichloro[1,1'-bis(diphenylphosphino)ferrocene]palladium (II) dichloromethane adduct. The reaction may be conducted in a solvent such as, for example, water, dioxane, dimethoxyethane, dimethylformamide, toluene, ethanol, tetrahydrofuran and the like or mixtures thereof. The reaction may be conducted at ambient or elevated temperatures.

SCHEME 7

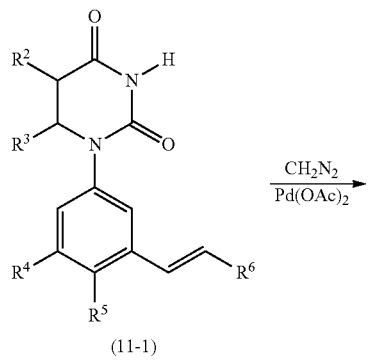

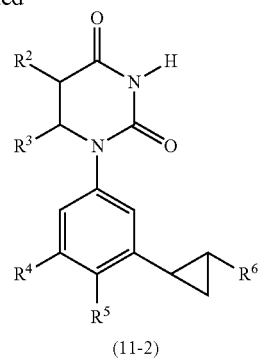

Compound (11-1) can be converted to compound (11-2) by treatment with diazomethane in a solvent such as, for example, tetrahydrofuran in the presence of palladium acetate at or near room temperature over a period of about 30 min to about 4 h.

SCHEME 8

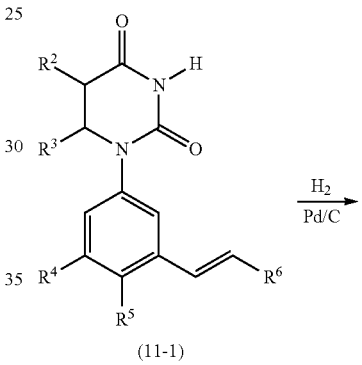

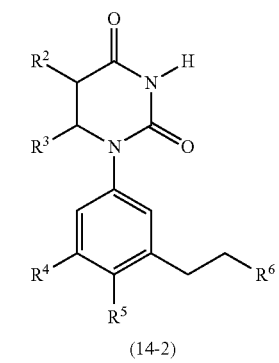

Compound (11-1) is reduced to supply compound (14-2). Typical conditions for this reduction include using hydrogen at a pressure of about 1 to about 5 atmospheres in the presence of a catalyst such as, for example, palladium or platinum on charcoal in a solvent such as, for example, tetrahydrofuran, ethyl acetate, ethanol, or hexane at or near ambient temperature over a period of about 1 to about 12 h.

SCHEME 9

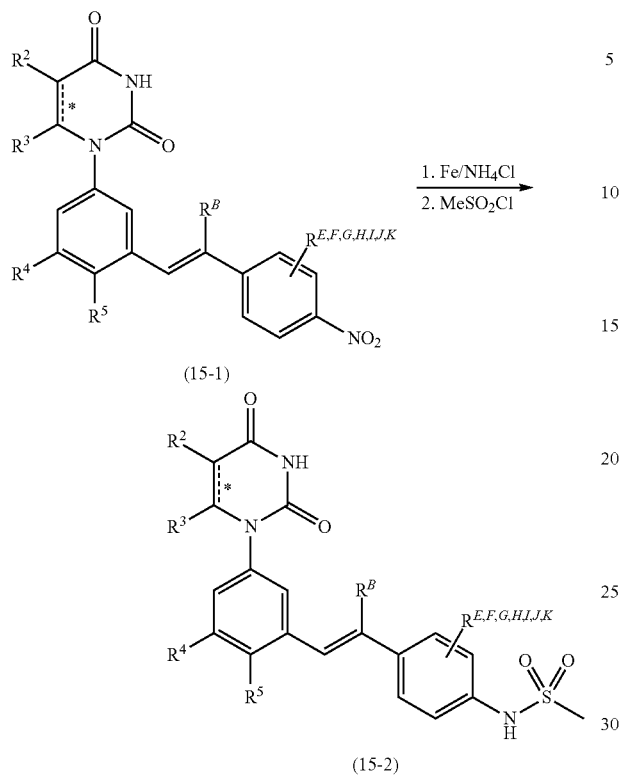

Compound (15-1) can be converted in a two-step sequence to compound (15-2). The initial step involves reduction of the aromatic nitro moiety with iron powder in the presence of a mild acid such as, for example, ammonium chloride or dilute hydrochloric acid at temperatures from about 60 to about 80° C. in a mixture of solvents containing, for example, methanol, water, and tetrahydrofuran over about 1 to about 12 h. The second step consists of exposure of the aniline, prepared in the first step, to methanesulfonyl chloride in the presence of a base such as pyridine in a solvent such as dichloromethane at or near ambient temperature.

Compound (17-1) can be mesylated to provide compound (17-2) by treatment with methanesulfonyl chloride in the presence of a base such as, for example, pyridine in a solvent such as, for example, dichloromethane. Compound (17-3) can be exposed to borane dimethyl sulfide complex in a solvent such as, for example, tetrahydrofuran at approximately about 0 to about 10° C. to supply compound (17-4). Compounds (17-2) and (17-4) can be combined with acetaldehyde in refluxing tetrahydrofuran. Subsequent treatment with water at room temperature yields compound (17-5).

SCHEME 11

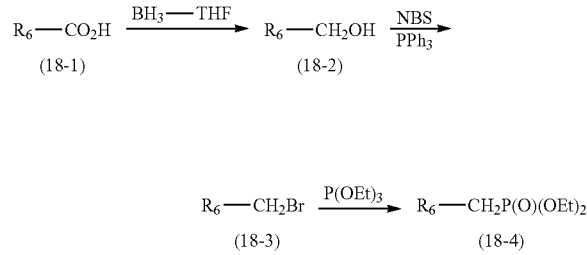

Carboxylic acid (18-1) can be reduced with boron tetrahydrofuran complex with heating to provide alcohol (18-2). Compound (18-2) is converted to the corresponding bromide (18-3) with N-bromosuccinimide and triphenylphosphine in solvents such as, for example, dichloromethane at room temperature in several hours. Treatment of compound (18-3) with triethyl phosphite at about 120° C. for about 1 to about 3 h supplies compound (18-4). Compound (18-4) can be used for example to make compound (9-5) as described in Scheme 5.

SCHEME 10

SCHEME 12

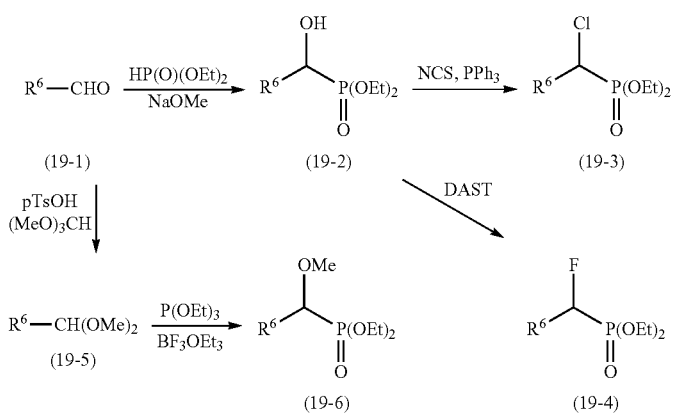

Benzaldehyde (19-1) can be treated with diethyl phosphonate in the presence of a base such as, for example, sodium methoxide in a solvent such as, for example, methanol at room temperature to provide compound (19-2). Compound (19-2) can be treated with N-chlorosuccinimide and triphenylphosphine in dichloromethane at room temperature to yield compound (19-3). Compound (19-2) can also be reacted with (diethylamino)sulfur trifluoride (DAST) to supply compound (19-4).

Compound (19-1) can also be treated with p-toluenesulfonic acid and trimethyl orthoformate in methanol at about 50° C. to provide acetal (19-5). Compound (19-5) can be converted to compound (19-6) by exposure to triethyl phosphite and boron trifluoride diethyl etherate at about −20° C. to about ambient temperature.

Compounds (19-3), (19-4), and (19-6) can be used for example to make compound (9-5) as described in Scheme 5.

SCHEME 13

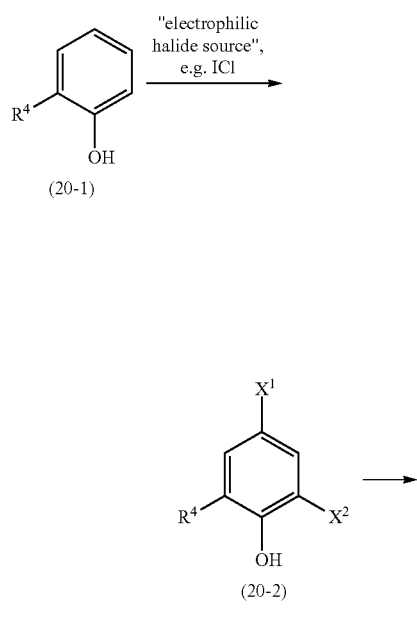

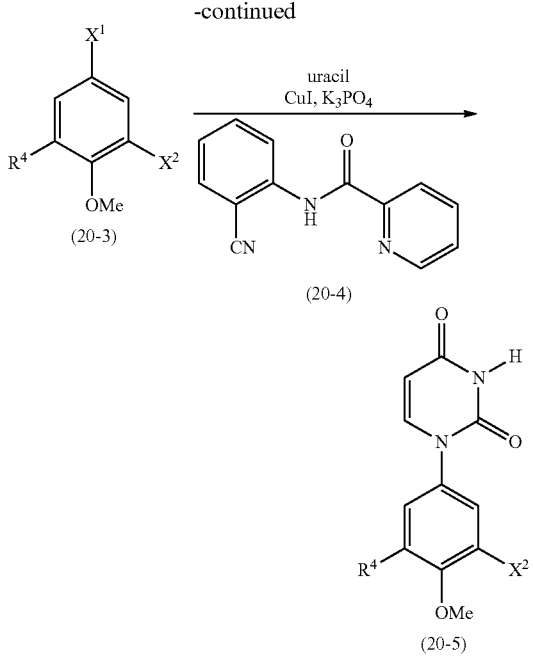

Phenol (20-1), wherein $R^4$ is other than amino, is treated with a source of electrophilic halide, such as, for example, iodine monochloride to provide dihalogenated compound (20-2), wherein $X^1$ and $X^2$ are independently bromine or iodine. Compound (20-2) is transformed to compound (20-3) by reaction of an alkylating agent such as, for example, methyl sulfate with a base such as, for example, potassium carbonate in refluxing acetone. Alternatively, methyl iodide in the presence of a base such as, for example, potassium t-butoxide in a solvent such as, for example, tetrahydrofuran, or dimethylformamide also furnish compound (20-3). In yet another alternative, compound (20-2) can be methylated with (trimethylsilyl)diazomethane in a solvent such as, for example, t-butyl methyl ether. Compound (20-3) can be reacted with uracil, ligand (20-4), copper (1) iodide, and potassium phosphate in dimethyl sulfoxide at about 40° C. to about 100° C. to supply compound (20-5).

For example, when in compound (20-3), $R^4$ is tert-butyl, $X^1$ is iodo, and $X^2$ is iodo or bromo, compound (20-3) can be stirred with uracil and compound (20-4) in the presence of CuI and $K_2PO_4$ in DMSO for about 15 to about 24 h at about 60° C. to supply compound (20-5). Alternatives to ligand (20-4) for making (20-5) are 8-hydroxyquinoline and 2-(2-pyridyl)-benzimidazole.

SCHEME 14

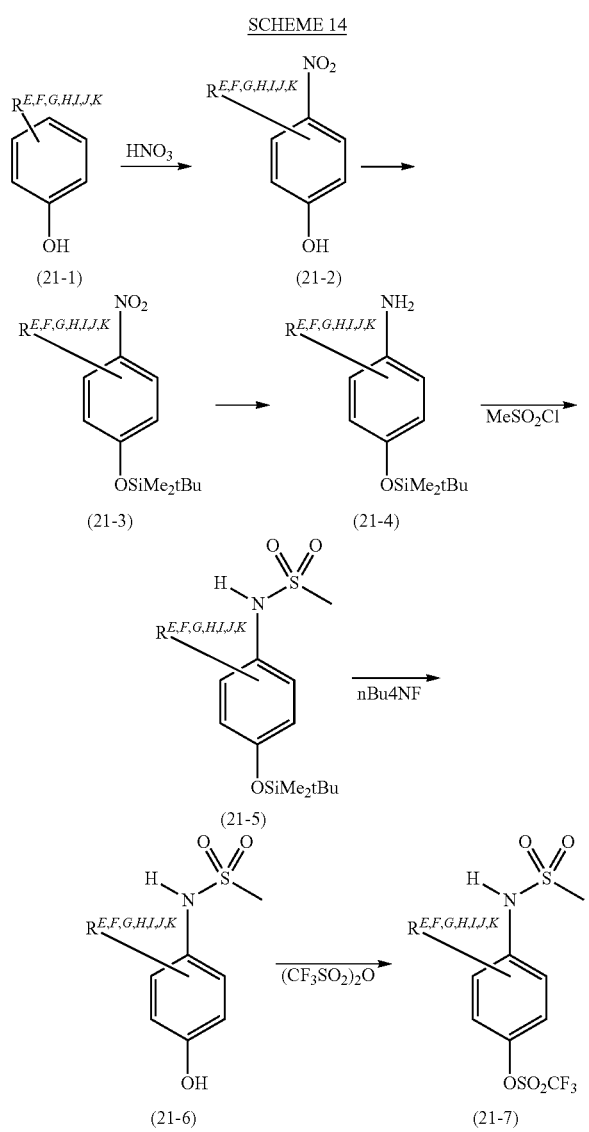

Compound (21-1) can be nitrated with nitric acid in acetic acid in a temperature range of about 10 to about 15° C. to give compound (21-2). The phenol moiety of compound (21-2) can be protected as a silyl ether, e.g. t-butyldimethylsilyl ether, by treatment with a sillyl chloride such as, for example, t-butyl dimethylsilyl chloride and imidazole in a solvent such as, for example, dimethyl formamide at ambient temperature to furnish compound (21-3). Compound (21-3) may then be reduced using conditions known to those skilled in the art to furnish the corresponding aniline (21-4).

Typical conditions for this reduction include using hydrogen at a pressure of about 1 to about 5 atmospheres in the presence of a catalyst such as, for example, palladium or platinum on charcoal in a solvent such as, for example, tetrahydrofuran, ethyl acetate, ethanol, methanol, or hexane at or near ambient temperature over a period of about 1 to about 12 h. Dependent on the functional groups present, an alternative reduction procedure may be more appropriate such as, for example, using iron powder in the presence of a mild acid such as, for example, ammonium chloride or dilute hydrochloric acid at reflux temperatures in a mixture of solvents containing, for example, methanol, water, and tetrahydrofuran over about 1 to about 12 h.

Aniline (21-4) can then by sulfonylated with methanesulfonyl chloride in the presence of pyridine in a solvent such as, for example, dichloromethane. The starting material and reagents are combined at about 0° C. and then allowed to gradually warm to ambient temperature over the course of the reaction to supply compound (21-5). The silyl ether protecting group is removed under conditions familiar to one skilled in the art. For example, tetrabutylammonium fluoride in tetrahydrofuran at room temperature transforms compound (21-5) to compound (21-6). The phenol group of compound (21-6) may be sulfonylated with trifluoromethanesulfonic anhydride in the presence of a base such as, for example, pyridine in a solvent such as, for example, dichloromethane at room temperature to provide compound (21-7). Compound (21-7) can be used as described in Scheme 12 to make compound (12-3).

SCHEME 15

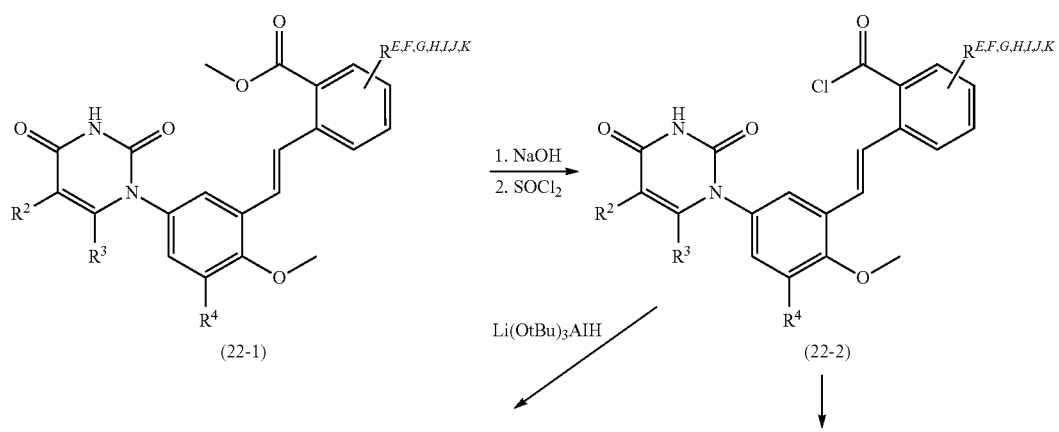

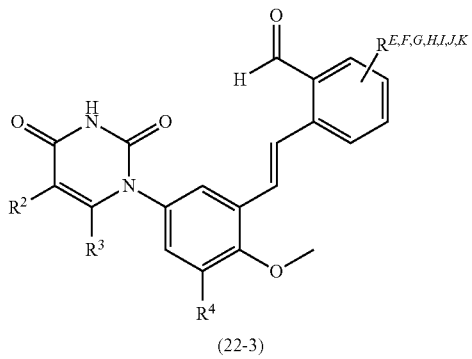

(22-3)

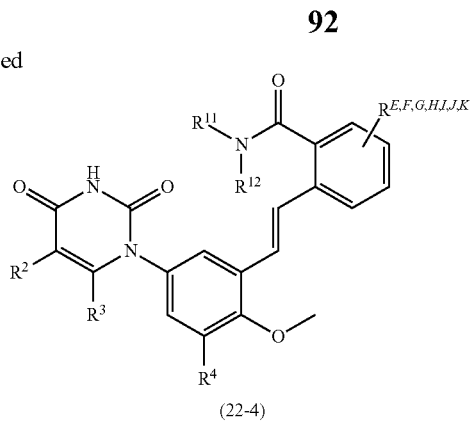

(22-4)

Compound (22-1) is converted to compound (22-2) in a two-step sequence. First, compound (22-1) can be hydrolyzed with a base such as, for example, sodium hydroxide, lithium hydroxide, or potassium hydroxide in a solvent such as, for example, methanol, ethanol, or tetrahydrofuran, or mixtures thereof. The resultant reaction mixture can be stirred for a period of about 6 to about 48 h at ambient temperature. Second, the intermediate carboxylic acid is treated in refluxing thionyl chloride with or without a catalytic amount of dimethylformamide for about 1 to about 4 h to deliver acid chloride (22-2). Treatment with thionyl chloride at reflux temperature in solvents such as, for example, chloroform or toluene also furnishes compound (22-2). Treatment of the carboxylic acid with oxalyl chloride in dichloromethane with a catalytic amount of dimethylformamide also furnishes compound (22-2).

Compound (22-2) can be treated with an amine or the corresponding salt in a solvent such as, for example, dioxane, dimethylformamide, dimethylacetamide, or dichloromethane optionally in the presence of a base such as, for example, pyridine, triethylamine or diisopropylethylamine at temperatures ranging from at or near ambient to about 100° C. for between about 1 and about 24 h to provide compound (22-4) wherein $R^{11}$ and $R^{12}$ are independently hydrogen or $R^F$, or taken together with the nitrogen to which they are attached form a 5-6-membered heterocyclyl or a fused 2-ring heterocyclyl.

Compound (22-2) is converted to the corresponding aldehyde (22-3) by reduction with lithium tri-t-butoxyaluminum hydride in a solvent such as, for example, tetrahydrofuran at about −60° C. to about −78° C.

SCHEME 16

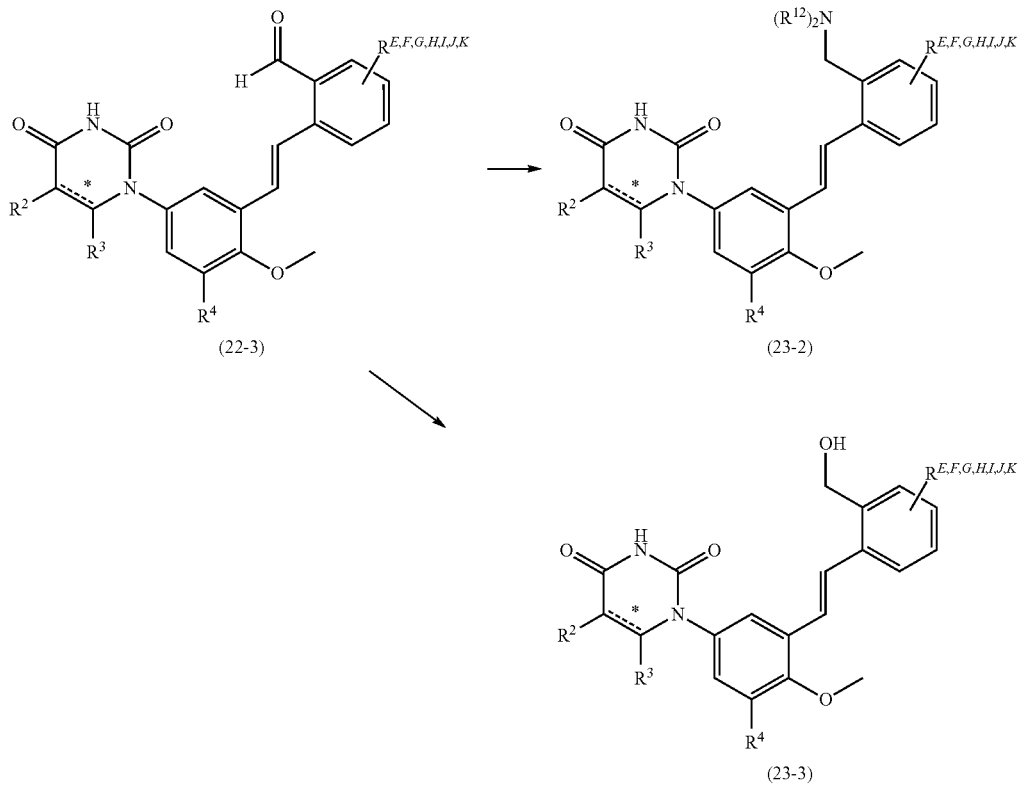

Compound (22-3) can be converted to compound (23-2) wherein $R^{11}$ and $R^{12}$ are independently hydrogen or $R^F$, or taken together with the nitrogen to which they are attached form a 5-6-membered heterocyclyl or a fused 2-ring heterocyclyl by treatment with an amine, $N(R^{11})(R^{12})$, in the presence of a reductant such as, for example, sodium triacetoxyborohydride or sodium cyanoborohydride in a solvent such as, for example, methanol, ethanol, dichloromethane, dimethylacetamide, or dimethylformamide over a period of about 1 to about 24 h. The reaction often proceeds best at an acidic pH that can be maintained by the addition of acetic acid or hydrochloric acid.

Compound (22-3) can also be converted to compound (23-3) by reduction with lithium tri-t-butoxyaluminum hydride in a solvent such as tetrahydrofuran at room temperature.

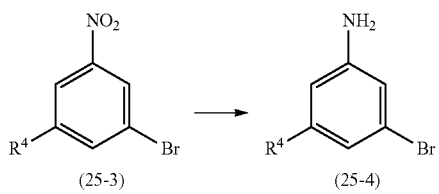

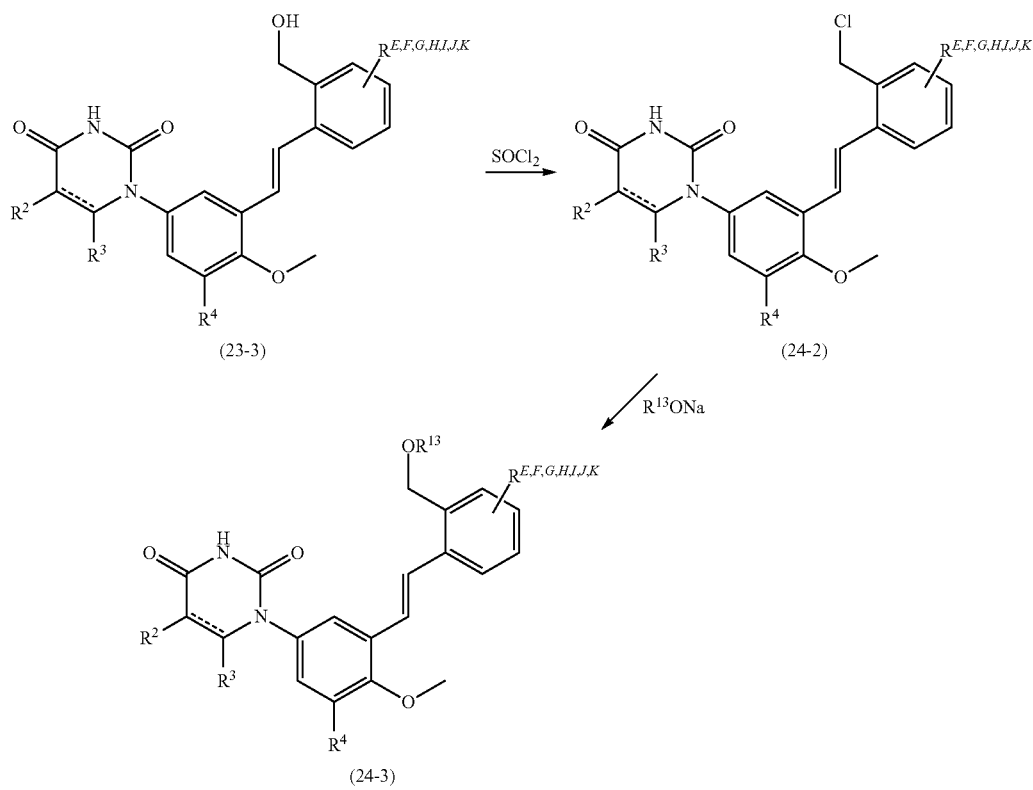

Compound (23-3) can be converted to compound of formula (24-2) by treatment with thionyl chloride in dichloromethane at room temperature. Compound (24-2) can be treated with a sodium alkoxide, $R^{13}ONa$, in a heated solution of the corresponding alcohol to provide compound (24-3), wherein $R^{13}$ is hydrogen or $R^F$.

Compound (25-1) can be brominated by treatment with, for example, pyridinium hydrobromide perbromide in a solvent such as, for example, acetic acid at or near ambient temperature over a period of about 1 to about 8 h to give compound (25-2). The amino group of compound (25-2) can be removed by exposure to t-butyl nitrite in a solvent such as, for example, dimethylformamide at a temperature initially at ambient temperature and then increased to the range of about 50 to about 65° C. to give compound (25-3). Additional aliquots of t-butyl nitrite can be added at ambient temperature followed by heating until the transformation is complete. Compound (25-3) can be reduced to compound (25-4) by, for example, treatment with iron and ammonium chloride.

EXAMPLES

The following examples are merely illustrative, and not limiting to this disclosure in any way.

Example A

Preparation of (E)-N-(3-tert-butyl-5-iodo-4-methoxyphenylcarbamoyl)-3-methoxy acrylamide

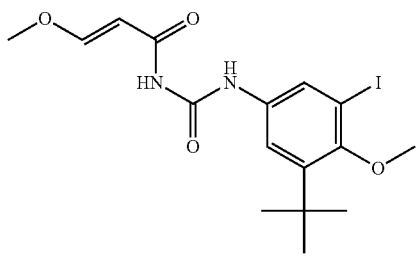

Part A. Preparation of 2-tert-butyl-4-nitrophenol

To a vigorously stirred solution of 2-tert-butylphenol (10 g, 66.6 mmol) in heptane (67 ml) was added at a fast drip a solution of 70% nitric acid (4.25 ml, 66.6 mmol) diluted with water (4.25 ml). The resulting dark red/brown mixture was stirred vigorously for 2 h. The suspended solid was collected by filtration washed with hexane (300 mL), water (200 mL) and once again with hexane (200 mL) to give a cocoa colored powder that was dried to constant mass (4.65 g, 35.6%).

Part B. Preparation of 2-tert-butyl-6-iodo-4-nitrophenol

To the product from Part A (4.5 g, 23.05 mmol) dissolved in MeOH (120 ml) and water (30 mL) was added iodine monochloride (1.155 ml, 23.05 mmol) drop wise over a period of 10 min. The mixture was stirred for 2 h and diluted into 1 L of water and allowed to stand overnight. The solid material was collected by filtration and washed 3×50 mL with water and dried under vacuum overnight to give a tan solid (7.14 g, 96%).

Part C. Preparation of 1-tert-butyl-3-iodo-2-methoxy-5-nitrobenzene

To an ice bath cooled solution of the product from Part B (5.5 g, 17.13 mmol) in MTBE (15 ml) in a 50 mL pressure vessel was added 2.0M TMS diazomethane (12.85 ml, 25.7 mmol) followed by drop-wise addition of methanol (1.0 mL) resulting in calm bubbling. The vessel was sealed and stirred at room temperature for 16 h, cooled and the pressure was released. The solution was partitioned between EtOAc and water. The organic layer was washed with 1.0M HCl, saturated potassium carbonate solution, and saturated NaCl. The organic layer was dried over sodium sulfate, filtered and concentrated to give a red oil that was used without purification (5.4 g, 84%).

Part D. Preparation of 3-tert-butyl-5-iodo-4-methoxyaniline

A mixture of the product from Part C (5.80 g, 17.31 mmol), ammonium chloride (1.389 g, 26.0 mmol), and iron (4.83 g, 87 mmol) in THF/MeOH/water (200 mL total, 2/2/1) was refluxed for 2 h, cooled and filtered through Celite. The filtrate was evaporated and the residue was partitioned between water and EtOAc. The organic layer was washed with saturated brine, dried with sodium sulfate, filtered and evaporated to give a brown oil (5.28 g, 100% yield).

Part E. Preparation of (E)-N-(3-tert-butyl-5-iodo-4-methoxyphenylcarbamoyl)-3-methoxy acrylamide To a solution of the product from Part E (3.05 g, 10 mmol) in DMF (50 ml) at −20° C. under $N_2$ was added at a fast drip a 0.4M solution in benzene of (E)-3-methoxyacryloyl isocyanate (50.0 ml, 20.00 mmol, prepared by the method of Santana et al., J. Heterocyclic Chem. 36:293 (1999). The solution was stirred for 15 min at −20° C., warmed to room temperature for 45 min and diluted into EtOAc. The EtOAc layer was washed 4×300 mL with water, 2×100 mL with brine, dried ($Na_2SO_4$) and concentrated to a brown solid. The residue was triturated in $Et_2O$/hexane to give a fine powder that was collected by filtration and dried to give a tan powder (2.46 g, 57%).

Example B

Preparation of 1-(3-tert-butyl-5-iodo-4-methoxyphenyl)dihydropyrimidine-2,4(1H, 3H)-dione

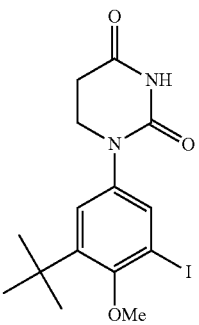 [SMILES: COc1c(I)cc(N2CCC(=O)NC2=O)cc1C(C)(C)C]

To a suspension of the product from Example A (2.46 g, 5.69 mmol) in ethanol (50 ml) was added a solution of 5.5 mL of $H_2SO_4$ in 50 mL water and the mixture was heated at 110° C. for 2.5 h to give a clear solution. The solution was cooled and diluted with 50 mL of water while stirring to give an off-white solid that was collected by filtration, washed with water and dried (2.06 g, 90%).

Example C

Preparation of 1-(3-tert-butyl-5-iodo-4-methoxyphenyl)pyrimidine-2,4(1H,3H)-dione

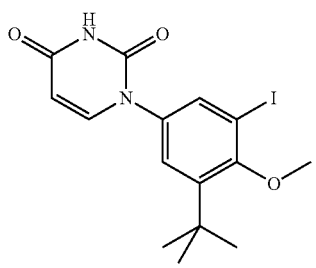 [SMILES: COc1c(I)cc(-n2ccc(=O)[nH]c2=O)cc1C(C)(C)C]

Part A. Preparation of 2-tert-butyl-4,6-diiodophenol

A solution of 2-tert-butylphenol (20.0 g, 133 mmol) in methanol (266 mL) was treated with sodium hydroxide pellets (6.39 g, 160 mmol). The mixture was stirred until all the sodium hydroxide had dissolved and was then cooled in an ice-salt bath to −2° C. Sodium iodide (15.0 g, 100 mmol) was added and then 10% sodium hypochlorite solution (45 mL, 73.3 mmol) was added drop wise at a rate such that the solution temperature rose no higher than 1.3° C. This sequence of events was repeated (3×) until a total of 60 g (400 mmol) of sodium iodide had been added and the sodium hypochlorite solution was added until the solution color changed from a light green-yellow color to the color of weak iced tea. This required all but 16 mL of the 180 mL total sodium hypochlorite solution measured out. With continued cooling at ca. 2° C., a solution of sodium thiosulfate pentahydrate (20 g) in water (100 mL) was added drop wise over 20 min. After addition, the solution was acidified to pH 3 by drop wise addition of concentrated hydrochloric acid (ca. 35 mL required of 40 mL placed in the addition funnel). The precipitate was collected by filtration and washed with >1 liter of water. The salmon-colored solid was sucked as dry as possible, and dried in a vacuum oven at 50° C. for 18 h. These procedures afforded the product (49.61 g, 93%) as a tan solid.

Part B. Preparation of 1-tert-butyl-3,5-diiodo-2-methoxybenzene

A solution of the product from Part A (20.0 g, 49.7 mmol) in acetone (140 mL) was treated with methyl iodide (3.9 mL, 8.83 g, 62.2 mmol) and 50% (w/w) sodium hydroxide solution (3.02 mL, 4.58 g, 57.2 mmol) followed by stirring at ambient temperature for 48 h. The mixture was concentrated in vacuo to a volume of ca. 50-60 mL, followed by dilution with heptane (80 mL) and water (50 mL). The layers were separated and the organic layer was extracted with saturated sodium chloride solution. Drying ($Na_2SO_4$) and concentration in vacuo afforded the product (20.59 g, 99%) as a light yellow oil.

Part C. Preparation of 1-(3-tert-butyl-5-iodo-4-methoxyphenyl)pyrimidine-2,4(1H,3H)-dione A suspension of the product from Part B (12.04 g, 28.9 mmol), uracil (3.89 g, 34.7 mmol), N-(2-cyanophenyl)picolinamide (1.29 g, 5.79 mmol) and tribasic potassium phosphate (12.9 g, 60.8 mmol) in DMSO (181 mL) was degassed by nitrogen sparge for 1 h. The mixture was then treated with copper (1) iodide (551 mg, 2.89 mmol) and degassing was continued for another 10 min. The mixture was then warmed at 60° C. for 18 h. The mixture was then poured into water (600 mL) and acidified to pH 3 by addition of 4N hydrochloric acid solution. The mixture was diluted with ethyl acetate, and the organic layer was extracted with water (3×), saturated ammonium chloride solution (1×) and saturated sodium chloride solution. The solution was dried and treated with (3-mercaptopropyl) silica gel, followed by stirring for 2 h. The mixture was filtered and concentrated in vacuo. The solid obtained was triturated with ether-ethyl acetate (>10:1) and collected by filtration and washed with ether. After drying in a vacuum oven at 50° C. for 2 h, these procedures afforded the product (2.75 g) as a white solid. The mother liquors were concentrated in vacuo to afford an amber solid. This material was chromatographed over a Flash 65 silica gel cartridge, eluting with 20-100% ethyl acetate in hexanes. These procedures afforded a nearly white solid, which was triturated with ether-hexanes and collected by filtration. After drying in a vacuum oven for 3 h, these procedures afforded another 4.31 g of the product as a white solid. Total yield: 7.06 g (61%).

Example D

Preparation of 1-(3-tert-Butyl-5-iodo-4-methoxyphenyl)pyrimidine-2,4(1H,3H)-dione

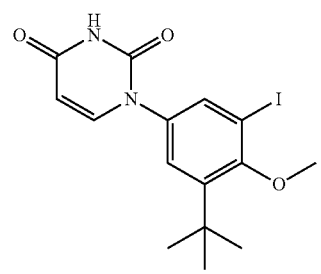 [SMILES: COc1c(I)cc(-n2ccc(=O)[nH]c2=O)cc1C(C)(C)C]

Part A. Preparation of 2-tert-butyl-4,6-diiodophenol 2-tert-Butylphenol (99.95 g, 665.36 mmol) was dissolved in 1250 mL methanol and converted to the corresponding phenoxide with 31.96 g (799.0 mmol, 1.2 equiv.) of sodium hydroxide by stirring the sodium hydroxide pellets at room temperature, and then cooling the reaction mixture in an ice/salt bath. Sodium iodide (299.34 g, 1997.07 mmol, 3.0 equiv.) and 8.3% bleach (1265.83 g, 1411.39 mmol, 2.1 equiv.) were added to the cold reaction solution in four equal portions, the bleach being added while keeping the reaction mixture at <0° C. 500 mL of 20% (w/w) sodium thiosulfate solution was added over an 18-minute period, with the temperature rising from −0.6° C. to 2.5° C. The pH of the reaction mixture was adjusted to approximately 3 by adding 197.5 mL of conc. HCl over a period of 97 min with the reaction temperature going from 1.2° C. to 4.1° C. The resulting slurry was filtered, and the wet cake washed with ~2 L of water. The wet cake was left on the Buchner funnel under vacuum overnight (approximately 15 h) to yield 289.33 g (potency adjusted yield=254.61 g) of the title product.

Part B. Preparation of 1-tert-butyl-3,5-diiodo-2-methoxybenzene

The product from Part A (93% assay, 21.6 g, 50 mmol) was dissolved in 140 mL of acetone. Methyl iodide (4.2 mL, 67.5 mmol, 1.35 equiv.) was added, followed by 50% aqueous sodium hydroxide (5.0 g, 62.5 mmol, 1.25 equiv.). The reaction was stirred overnight, then concentrated to approximately 50-60 mL. 80 mL of heptanes was added followed by 50 mL of water, and the layers were shaken and separated, and the aqueous layer was back extracted with 20 mL of heptanes. The organic layers were combined and washed twice with 50 mL each of 10% aqueous NaCl to afford 91.1 grams of a heptane solution, which assayed to 19.1 g of the title compound.

Part C. Preparation of 1-(3-tert-Butyl-5-iodo-4-methoxyphenyl)pyrimidine-2,4(1H,3H)-dione Uracil (33.3 g, 297 mmol, 1.2 equiv.), $K_3PO_4$ (106 g, 500 mmol, 2.1 equiv.), CuI (4.6 g, 24.2 mmol, 0.1 equiv.), and N-(2-cyanophenyl)picolinamide (6.4 g, 28.7 mmol, 0.12 equiv.) were charged to a flask and inerted with argon. The 1-tert-butyl-3,5-diiodo-2-methoxybenzene was solvent switched into MeCN, dissolved in 1 L DMSO and sparged with argon and added to the solids. The reaction was heated to 60° C. for 16 h. After cooling, the reaction was diluted with 2 L EtOAc and washed with 2.6 L water (back extracted with 3×1 L EtOAc). The combined organic layers were washed with 2×1 L of 0.25M (CuOAc)$_2$ then 2×830 mL 15% NH$_4$Cl then 800 mL brine. The organic layer was then concentrated and chased with 1 L heptane, then triturated with refluxing 85:15 (v/v) heptane:iPrOAc for 4 h. After cooling, the product was collected by filtration and washed with an additional 330 mL of 85:15 v/v heptanes:EtOAc to yield after drying 66.9 g (70% yield) of the product as a white solid.

Example E

Preparation of (E)-N-(4-(3-tert-butyl-5-(2,4-dioxo-3,4-dihydropyrimidin-1(2H)-yl)-2-methoxystyryl)phenyl)methanesulfonamide

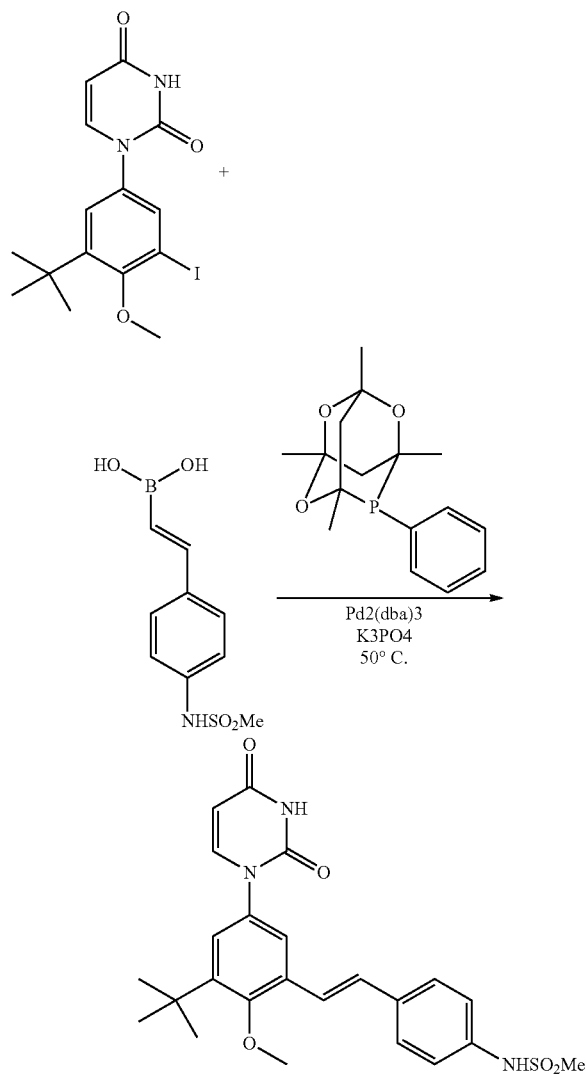

The boronic acid (96% potency) (3.75 g, 15.6 mmol, 1.2 eq), product from Example D (5.0 g, 12.5 mmol), Cytec ligand (175 mg, 5 mol %), Pd2(dba)$_3$ (46 mg, 0.4 mol %) and potassium phosphate (5.25 g, 25.0 mmol, 2 eq.) were charged to a 3 neck RB flask. The solids were purged with nitrogen for 10 min. 75 mL 4:1 THF:water was sparged 10 min and charged to the flask. The mixture was stirred to dissolve the solids followed by heating the mixture at 50° C. in darkness overnight. HPLC showed the reaction was not complete after stirring overnight (~2% iodouracil remained). The reaction mixture was diluted with 375 mL DCM and 250 ml 10% citric acid. The mixture was shaken in a sep funnel and the layers were separated. The DCM layer was washed with a solution of 0.6 g L-cysteine in 250 ml 5% NaHCO$_3$ for 30 min which changed the DCM layer color from orange to yellow. Repeated the 0.6 g L-cysteine in 250 ml 5% NaHCO3 for 30 min treatment followed by a 250 ml 5% NaHCO$_3$ wash, and a 250 ml 10% NaCl wash. The DCM layer was treated with 2 gm thiourea silica for 30 min. Added 1 gm carbon to decolorize mixed 5 min and filtered through hy-flo. The wet cake was washed with DCM. The DCM solution was then stripped to give 6.74 g of a light yellow solid. The solids were ~92% pure. The solids were heated in a mixture of 192 ml DCM and 9 mL MeOH. They never completely dissolved. Cooled to room temp with mixing. 80 ml heptane was added and more product began to crystallize. The slurry stirred over the weekend. Added 50 ml heptane in portions until a total of 230 ml heptane was added. The product was filtered. Filtrate was measured at 1.21 mg/mL at 210 nm and 1.35 at 220 nm, which equals a 522-582 mg loss in the liquors or 9-10% loss vs. theoretical. The wet cake was washed with 50 ml of a 27 ml Heptane:22 ml DCM: 1 ml MeOH mixture. The wash contained 0.5 mg/mL product or 25 mg (0.4% vs. theoretical). Product yield 5.22 gm (88.9%), purity 99.2% PA. Iodouracil was removed in the crystallization. Samples were submitted to solid state for analysis and analytical for Pd determination. NMR did not show any residual solvent.

Example 1

Preparation of (E)-N-(4-(3-tert-butyl-5-(2,4-dioxotetrahydropyrimidin-1(2H)-yl)-2-methoxystyryl)phenyl)methanesulfonamide (compound IA-L1-1.9)

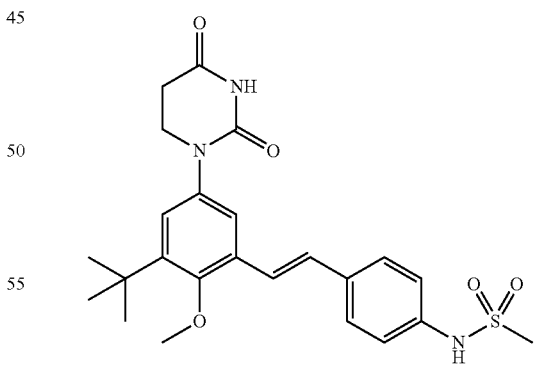

Part A. Preparation of methyl 3-tert-butyl-2-hydroxy-5-nitrobenzoate

Methyl 3,5-di-tert-butyl-2-hydroxybenzoate (28.66 g, 108.4 mmol) was dissolved with stirring in 430 mL glacial acetic acid and the resulting mixture was treated drop wise with fuming nitric acid (90%, 179.26 mL). When the addition was complete, the resulting mixture was stirred for 2.5 h. The reaction mixture was poured into a 2.0 L of crushed ice and allowed to stand 30 min. Afterwards, 1.0 L of water was added and the ice water mixture was allowed to melt. The mixture was then filtered, washed with water and dried to provide the title compound (24.57 g, 89%).

Part B. Preparation of methyl 3-tert-butyl-2-methoxy-5-nitrobenzoate

Methyl 3-tert-butyl-2-hydroxy-5-nitrobenzoate (11.41 g, 45.0 mmol), potassium carbonate (9.34 g, 67.6 mmol), acetone (200 mL), and dimethyl sulfate (6.46 g, 67.6 mmol) were added together. The resultant mixture was then heated to reflux for 16 h. The mixture was then filtered and the solid was washed with ethyl acetate. The resulting organic liquid was then concentrated under vacuum to an oil and redissolved in ethyl acetate (600 mL). The organic solution was then washed with water, dried, filtered and concentrated under vacuum to an oil that was then subjected to purification via column chromatography (gradient of 5% to 40% EtOAc/Hexanes) to yield the title compound as an oil (10.42, 87%).

Part C. Preparation of methyl 5-amino-3-tert-butyl-2-methoxybenzoate

Methyl 3-tert-butyl-2-methoxy-5-nitrobenzoate (10.42 g, 39.0 mmol), iron powder (325 mesh, 10.89 g, 195 mmol), ammonium chloride (3.13 g, 58.5 mmol), water (30 mL), and methanol (150 mL) were added together. The resultant mixture was then refluxed for 1 h. The mixture was then cooled to room temperature, filtered through celite, and the celite washed with methanol. The filtrate was then concentrated under vacuum and dissolved in ethyl acetate (600 mL). The resultant solution was then washed with water and brine. The organic extract was then dried, filtered and concentrated under vacuum to yield the title compound as an oil (9.25 g, 100%).

Part D. Preparation of 3-(3-tert-butyl-4-methoxy-5-(methoxycarbonyl)phenylamino) propanoic acid The product from Part C (16.44 g, 69.3 mmol) was dissolved in toluene (200 mL). This mixture was heated to reflux and acrylic acid added over time (1 mL of acrylic acid added every 3 h, 5.23 mL total, 76.2 mmol). The mixture was then refluxed for 24 h. The mixture was then cooled and concentrated under vacuum to dryness to yield an oil as the crude title compound that was used directly in the next reaction.

Part E. Preparation of methyl 3-tert-butyl-5-(2,4-dioxotetrahydropyrimidin-1(2H)-yl)-2-methoxybenzoate The product from Part D (21.43 g, 69.3 mmol), urea (10.4 g, 173 mmol) and acetic acid (glacial, 200 mL) were added together. The mixture was then heated to 120° C. for 18.5 h followed by concentration under vacuum to give an oil. To this oil was added methanol (13 mL), and ethyl acetate (350 mL). The resultant mixture was allowed to stand for 24-48 h whereby a precipitate formed. The resulting solid was filtered off and washed with a small amount of methanol (10 mL) and then air dried to yield the title compound as a solid (15.26 g, 66%).

Part F. Preparation of 3-tert-butyl-5-(2,4-dioxotetrahydropyrimidin-1(2H)-yl)-2-methoxy benzoic acid The product from Part D (4.52 g, 13.52 mmol), methanol (70 mL), and tetrahydrofuran (70 mL) were added together. The mixture was then stirred vigorously until a homogenous solution resulted. Once homogenous, a solution of aqueous sodium hydroxide (1.0M, 68 mL) was added. The mixture was then stirred for 12 h, the mixture was then concentrated under vacuum to remove the organic solvent, followed by the addition of aqueous hydrochloric acid (1.0M, 80 mL) that resulted in solid formation. The mixture was then concentrated under vacuum. To this material was added hydrochloric acid (12M, 100 mL) and the resultant material heated to 100° C. for 1.5 h. The reaction was then cooled and water added. The resulting solid was filtered, washed with water, and dried to yield the title compound as a solid (3.55 g, 82%).

Part G. Preparation of 3-tert-butyl-5-(2,4-dioxotetrahydropyrimidin-1(2H)-yl)-2-methoxy-benzaldehyde The product obtained in Part F (4.07 g, 12.71 mmol) and thionyl chloride (40.82 mL, 559 mmol) were combined and the mixture was refluxed for 2 h, followed by concentration under vacuum to provide a light yellow colored solid product. The solid was dissolved in tetrahydrofuran (125 mL), the solution cooled to −78° C. and LiAlH(OtBu)$_3$ (1M, 14 mL) was added slowly over 10 min while maintaining the temperature at −78° C. The mixture was stirred at −78° C. for 2 h, and the reaction was quenched with hydrochloric acid (aq., 1M, 25 mL) at −78° C. The mixture was warmed to room temperature and ethyl acetate was added. The layers were separated and the aqueous layer was washed with ethyl acetate. The organic extracts were combined and washed with half saturated sodium bicarbonate solution. The organic layer was dried, filtered and concentrated under vacuum to yield the title compound as a solid (3.73 g, 96%).

Part H. Preparation of 1-(3-tert-butyl-4-methoxy-5-(4-nitrostyryl)phenyl)dihydro-pyrimidine-2,4(1H,3H)-dione The product prepared in Part G (1.00 g, 3.29 mmol) and diethyl 4-nitrobenzyl-phosphonate (0.853 g, 3.12 mmol) were dissolved in dichloromethane (50 mL). Solid potassium tert-butoxide (0.737 g, 6.57 mmol) was added portion wise at room temperature. The resultant dark red solution was stirred for 1.5 h at room temperature. 1N aqueous HCl (50 mL) solution was added and the mixture was stirred 30 min, and then diluted with dichloromethane (50 mL). The resultant organic layer was separated and dried. The material was purified by column chromatography on silica gel using 99/1 dichloromethane/methanol as eluent to obtain the title compound as a solid (1.12 g, 80%).

Part I. Preparation of Preparation of (E)-N-(4-(3-tert-butyl-5-(2,4-dioxotetrahydropyrimidin-1(2H)-yl)-2-methoxystyryl)phenyl)methanesulfonamide The product obtained in Part H (1.1 g, 2.60 mmol), iron (0.725 g, 12.99 mmol), and ammonium chloride (0.208 g, 3.90 mmol) was added to a mixture of tetrahydrofuran (40 mL), ethanol (40 mL) and water (12 mL). The slurry was heated to 90° C. for 45 min, and then cooled to ambient temperature. The solution was filtered through a pad of celite (10 g), washed with ethanol (20 mL), and the filtrate concentrated under vacuum to a solid. The resulting solid was dissolved in ethyl acetate (100 mL), and the solution was washed with water (50 mL) and dried over Na$_2$SO$_4$. The drying agent was filtered off and the solvent removed under vacuum to give the aniline adduct as a yellow solid (830 mg).

The solid (830 mg, 2.109 mmol) was dissolved in dichloromethane (50 mL), and pyridine (0.512 mL, 6.33 mmol) and methanesulfonyl chloride (0.181 mL, 2.32 mmol) were added and the resulting solution was stirred at room temperature 16 h. Dichloromethane (100 mL) was added followed by extraction with a 1N aq. HCl solution (2×50 mL). The organic layer was dried, concentrated under vacuum and purified by column chromatography on silica gel using 98/2 CH$_2$Cl$_2$/MeOH to provide the title compound as a solid (480 mg, 39%, two steps). m.p.=260-261° C. (trans-isomer) NMR (500 MHz, DMSO-d$_6$): δ ppm 1.37 (s, 9H), 2.71 (t, J=6.7 Hz, 2H), 3.01 (s, 3H), 3.75 (s, 3H), 3.79 (t, J=6.6 Hz, 2H), 7.13 (d, J=16.5 Hz, 1H), 7.15 (d, J=2.4 Hz, 2H), 7.23 (d, J=8.5 Hz, 2H), 7.25 (d, J=16.5 Hz, 1H), 7.51 (d, J=2.4 Hz, 1H), 7.61 (d, J=8.6 Hz, 2H), 9.80 (bs, 1H), 10.30 (s, 1H). (trans-isomer).

Example 2

Preparation of (Z)-N-(4-(2-(3-tert-butyl-5-(2,4-dioxotetrahydropyrimidin-1(2H)-yl)-2-methoxyphenyl)-1-chlorovinyl)phenyl)methanesulfonamide (compound IA-L1-1.3)

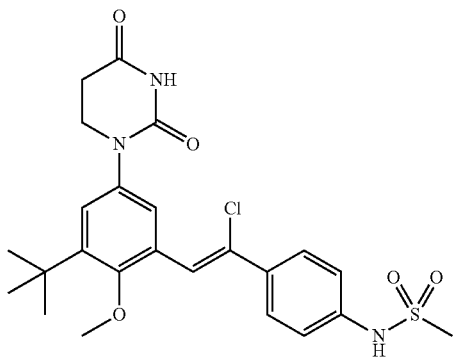

Part A. Preparation of diethyl hydroxy(4-nitrophenyl)methylphosphonate

The title compound was prepared as described in Taylor, W P, et. Al, Bioorg. Med. Chem. 4:1515-1520 (1996). 4-Nitrobenzaldehyde (3.0 g, 19.85 mmol) and diethyl phosphonate (2.74 g, 19.85 mmol) were combined and treated with a 0.5N solution of sodium methoxide in methanol (0.993 mL, 0.496 mmol). The resulting red-orange solution was stirred 12 h at room temperature. The reaction mixture was extracted with dichloromethane (20 mL) followed by half saturated ammonium chloride (20 mL). The organic layer was separated, dried and concentrated under vacuum to provide the title compound as a semi-solid (5.1 g, 89%).

Part B. Preparation of diethyl chloro(4-nitrophenyl)methylphosphonate

The product prepared in Part A (500 mg, 1.729 mmol) was dissolved in dichloromethane (±0 mL) and treated with triphenylphosphine (998 mg, 3.80 mmol), followed by N-chlorosuccinimide (462 mg, 3.46 mmol). The mixture was stirred at room temperature for 18 h. The solution was concentrated under vacuum and the residue was purified by column chromatography using silica gel eluting with a 1/1 mixture of hexanes/ethyl acetate to provide the title compound as an oil (262 mg, 49%).

Part C. Preparation of (Z)-N-(4-(2-(3-tert-butyl-5-(2,4-dioxotetrahydropyrimidin-1(2H)-yl)-2-methoxyphenyl)-1-chlorovinyl)phenyl)methanesulfonamide The product prepared in Example 1, Part G (100 mg, 0.329 mmole) was treated with the product obtained from Part B using the procedures described in Example 1, Part H and Example 1, Part I to provide 39 mg of the title compound. $^1$H NMR (300 MHz, DMSO-d$_6$): δ ppm 1.36 (s, 9H), 2.71 (t, J=6.8 Hz, 2H), 3.06 (s, 3H), 3.71 (s, 3H), 3.78 (t, J=6.8 Hz, 2H), 7.23 (d, J=2.6 Hz, 1H), 7.27 (s, 1H), 7.28 (d, J=8.6 Hz, 2H), 7.48 (d, J=2.6 Hz, 1H), 7.78 d, J=8.8 Hz, 1H), 10.05 (s, 1H), 10.34 (s, 1H).

Example 3

Preparation of (E)-1-(3-tert-butyl-5-(4-fluorostyryl)-4-methoxyphenyl) dihydropyrimidine-2,4(1H,3H)-dione (compound IA-L1-1.12)

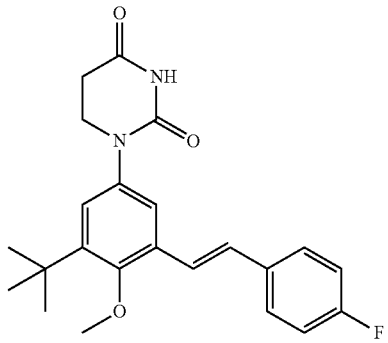 [SMILES: COc1c(/C=C/c2ccc(F)cc2)cc(N2CCC(=O)NC2=O)cc1C(C)(C)C]

The title compound was prepared according the procedures described in Example 1, Part H and Example 1, Part I using the product obtained in Example 1, Part G (50 mg, 0.164 mmol) and diethyl 4-fluorobenzylphosphonate (40.5 mg, 0.164 mmol). The title compound was obtained as a solid (30 mg, 46%). $^1$H NMR (300 MHz, DMSO-d$_6$): δ ppm 1.37 (s, 9H), 2.72 (t, J=6.6 Hz, 2H), 3.76 (s, 3H), 3.79 (t, =6.6 Hz, 2H), 7.21 (m, 4H), 7.30 (d, J=16.3 Hz, 1H), 7.53 (d, J=2.6 Hz, 1H), 7.73 (m, 2H), 10.35 (s, 1H).

Example 4

Preparation of (Z)-N-(4-(2-(3-tert-butyl-5-(2,4-dioxotetrahydropyrimidin-1(2H)-yl)-2-methoxyphenyl)-1-fluorovinyl)phenyl)methanesulfonamide (compound IA-L1-1.4).

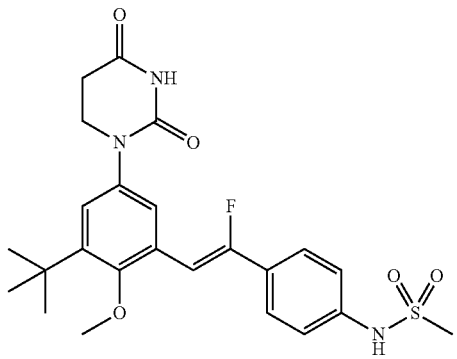 [SMILES: COc1c(/C=C(\F)c2ccc(NS(C)(=O)=O)cc2)cc(N2CCC(=O)NC2=O)cc1C(C)(C)C]

Part A. Preparation of diethyl fluoro(4-nitrophenyl)methylphosphonate

The title compound was prepared as described in Taylor, W P, et. Al, Bioorg. Med. Chem. 4:1515-1520 (1996). The product from Example 2, Part A (500 mg, 1.729 mmol) was dissolved in dichloromethane (10 mL) and treated by drop wise addition of (diethylamino)sulfur trifluoride (DAST) (2.5 mL, 18.9 mmol). The mixture was stirred at room temperature for 18 h. A solution of half saturated sodium phosphate monobasic (20 mL) was added followed by dichloromethane (20 mL) addition and separation of the resulting organic phase. The organic solution was dried and concentrated under vacuum, and then subjected to column chromatography using silica gel eluting with a 1/1 mixture of hexanes/ethyl acetate to provide the title compound as an oil (215 mg, 43%).

Part B. Preparation of (Z)-N-(4-(2-(3-tert-butyl-5-(2,4-dioxotetrahydropyrimidin-1(2H)-yl)-2-methoxyphenyl)-1-fluorovinyl)phenyl)methanesulfonamide The product prepared as described in Part A (100 mg, 0.329 mmole) was treated with the product prepared in Example 1, Part G (96 mg, 0.329 mmole) according to the procedures described in Example 1, Part H and Example 1, Part I to provide 53 mg of the title compound as a 1/1 mixture of cis/trans isomers. Reverse phase HPLC chromatographic separation using a 40-100% gradient of acetonitrile in 0.1% aqueous trifluoroacetic acid provided the title compound as a solid (20 mg). $^1$H NMR (300 MHz, DMSO-d$_6$): δ ppm 1.37 (s, 9H), 2.71 (t, J=6.8 Hz, 2H), 3.06 (s, 3H), 3.77 (s, 3H), 3.78 (m, 2H), 6.62 (d, J=40.4 Hz, 1H), 7.18 (d, J=2.6 Hz, 1H), 7.30 (d, J=8.4 Hz, 2H), 7.55 (d, J=2.6 Hz, 1H), 7.75 (d, J=8.8 Hz, 2H), 10.08 (s, 1H), 10.33 (s, 1H).

Example 5

Preparation of (E)-N-(4-(2-(3-tert-butyl-5-(2,4-dioxotetrahydropyrimidin-1(2H)-yl)-2-methoxyphenyl)-1-fluorovinyl)phenyl)methanesulfonamide (compound IA-L1-1.5)

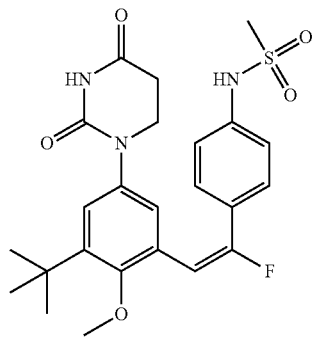 [SMILES: COc1c(/C=C(/F)c2ccc(NS(C)(=O)=O)cc2)cc(N2CCC(=O)NC2=O)cc1C(C)(C)C]

Reverse phase HPLC chromatographic separation of the 1/1 mixture of cis/trans isomeric material (53 mg) from Example 4, Part A using a 40-100% gradient of acetonitrile in 0.1% aqueous trifluoroacetic acid provided the title compound as a solid (16.5 mg). $^1$H NMR (300 MHz, DMSO-d$_6$): δ ppm 1.33 (s, 9H), 2.60 (t, J=6.6 Hz, 2H), 3.01 (s, 3H), 3.57 (t, J=6.6 Hz, 2H) 3.79 (s, 3H), 6.46 (d, J=21.3 Hz, 1H), 6.87 (d, J=2.2 Hz, 1H), 7.14 (m, 3H), 7.36 (d, J=8.8 Hz, 2H), 10.02 (s, 1H), 10.24 (s, 1H).

Example 6

Preparation of (E)-N-(4-(3-tert-butyl-5-(2,4-dioxotetrahydropyrimidin-1(2H)-yl)-2-methoxystyryl)-2-fluorophenyl)methanesulfonamide (compound IA-L1-1.26)

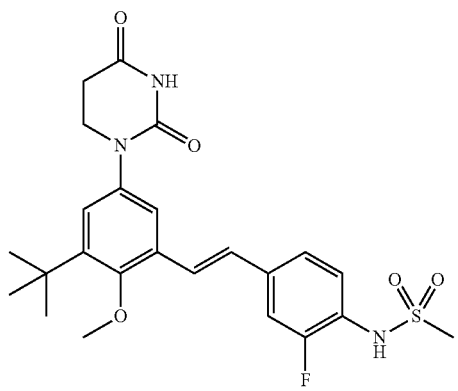 [SMILES: COc1c(/C=C/c2ccc(NS(C)(=O)=O)c(F)c2)cc(N2CCC(=O)NC2=O)cc1C(C)(C)C]

Part A. Preparation of 4-(bromomethyl)-2-fluoro-1-nitrobenzene (3-Fluoro-4-nitrophenol)methanol (1.24 g, 7.25 mmol) was dissolved in dichloromethane (25 mL) and treated with triphenylphosphine (2.281 g, 8.70 mmol) followed by N-bromosuccinimide (1.548 g, 8.70 mmol). The mixture was stirred at room temperature for 2 h. Water (50 mL) and dichloromethane (40 mL) were added, and the organic layer was separated and dried. The solution was concentrated under vacuum and purified by column chromatography using silica gel eluting with a 5/1 mixture of hexanes/ethyl acetate to provide the title compound as a solid (1.27 g, 75%).

Part B. Preparation of diethyl 3-fluoro-4-nitrobenzylphosphonate

The product prepared in Part A (1.27 g, 5.43 mmol) was added to triethyl phosphite (8 mL, 54.3 mmol) and the solution heated to 120° C. for 1 hr. After cooling, the excess triethyl phosphite was removed by heating under vacuum and the residue subjected to column chromatography on silica gel using 99/1 dichloromethane/methanol as eluent to obtain the crude title compound as an oil (800 mg).

Part C. Preparation of (E)-N-(4-(3-tert-butyl-5-(2,4-dioxotetrahydropyrimidin-1(2H)-yl)-2-methoxystyryl)-2-fluorophenyl)methanesulfonamide The product described in Example 1, Part G (533 mg, 1.751 mmole) was treated with the product described in Part B (510 mg, 1.751 mmole) according to the procedures described in Example 1, Part H and Example 1, Part I to provide 80 mg of the title compound. $^1$H NMR (300 MHz, DMSO-d$_6$): δ ppm 1.37 (s, 9H), 2.71 (t, J=6.5 Hz, 2H), 3.05 (s, 3H), 3.76 (s, 3H), 3.79 (t, J=6.6 Hz, 2H), 7.18 (m, 2H), 7.36 (d, J=16.5 Hz, 1H), 7.39 (m, 1H), 7.44 (m, 1H), 7.52 (d, J=2.6 Hz, 1H), 7.63 (m, 1H), 9.65 (s, 1H), 10.35 (s, 1H).

Example 7

Preparation of N-(4-(2-(3-tert-butyl-5-(2,4-dioxotetrahydropyrimidin-1(2H)-yl)-2-methoxyphenyl)cyclopropyl)phenyl)methanesulfonamide (compound IA-L8-1.1)

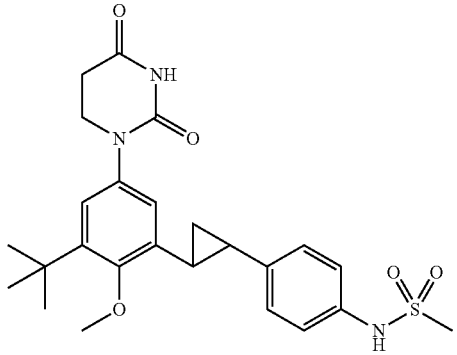 [SMILES: COc1c(C2CC2c2ccc(NS(C)(=O)=O)cc2)cc(N2CCC(=O)NC2=O)cc1C(C)(C)C]

The product obtained as described in Example 1, Part 1 (30 mg, 0.064 mmol) was dissolved in tetrahydrofuran (2 mL) and treated with 0.95 mL of a 0.67M ether solution of diazomethane (0.636 mmol) followed by palladium acetate (0.7 mg, 0.0031 mmol). The mixture was stirred for 30 min at room temperature followed by removal of the solid by filtration and concentration of the filtrate. The filtrate was purified by column chromatography on silica gel using 98/2 dichloromethane/methanol as eluent to obtain the title compound as a solid (21.6 mg, 70%). m.p. 265-266° C. $^1$H NMR (300 MHz, DMSO-$d_6$): δ ppm 1.33 (s, 9H) 1.50 (m, 2H), 2.13 (m, 1H), 2.27 (m, 1H), 2.69 (t, J=6.6 Hz, 2H), 2.94 (s, 3H), 3.63 (s, 3H), 3.74 (t, J=6.6 Hz, 2H), 6.84 (d, J=2.6 Hz, 1H), 7.04 (d, J=2.6 Hz, 1'-1), 7.14 (d, J=8.8 Hz, 2H), 7.20 (d, J=8.8 Hz, 2H), 9.60 (s, 1H), 10.29 (s, 1H).

Example 8

Preparation of N-(4-(3-tert-butyl-5-(2,4-dioxotetrahydropyrimidin-1(2H)-yl)-2-methoxyphenethyl)phenyl)methanesulfonamide (compound IA-L5-2-1.1)

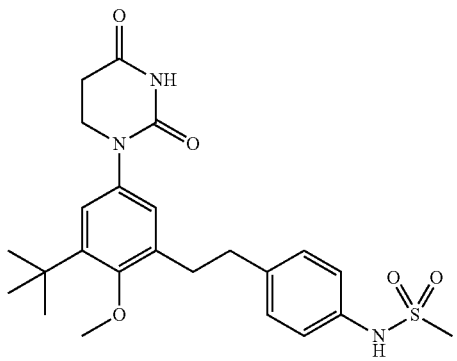 [SMILES: COc1c(CCc2ccc(NS(C)(=O)=O)cc2)cc(N2CCC(=O)NC2=O)cc1C(C)(C)C]

The product obtained as described in Example 1, Part I (415 mg, 0.88 mmol) was dissolved in methanol (30 mL) and treated with 50 mg of 10% palladium on carbon. The slurry was stirred for 48 h at room temperature under 1 atm of hydrogen. The reaction mixture was filtered through celite and concentrated in vacuo to provide the title compound as a solid (230 mg, 55%). m.p. 233-234° C. $^1$H NMR (300 MHz, DMSO-$d_6$): δ ppm 1.34 (s, 9H), 2.68 (t, J=6.8 Hz, 2H), 2.86 (s, 4H), 2.93 (s, 3H), 3.70 (m, 2H), 3.74 (s, 3H), 7.11 (m, 4H), 7.23 (m, 2H), 9.59 (s, 1H), 10.29 (s,).

Example 9

Preparation of (E)-N-(4-(3-tert-butyl-5-(2,4-dioxotetrahydropyrimidin-1(2H)-yl)styryl)phenyl)methanesulfonamide (compound IA-L1-1.16)

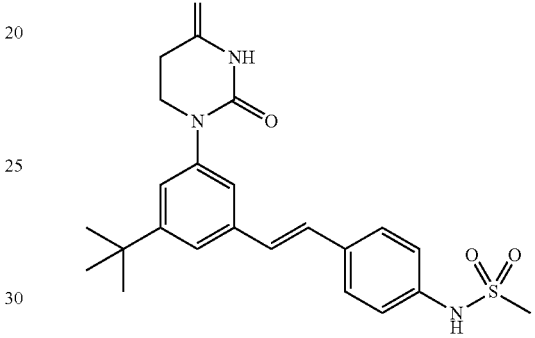

Part A. Preparation of methyl 3-tert-butyl-5-(chlorocarbonyl)benzoate

A mixture of 3-tert-butyl-5-(methoxycarbonyl)benzoic acid (9.18 g, 38.9 mmol, prepared by the method of Carter et. al., WO2005021500A1), thionyl chloride (75 mL) and 1 drop of DMF in toluene (200 mL) was heated at reflux for 2 h, cooled and concentrated. The residue was azeotroped with toluene (3×50 mL) and dried under high vacuum to give the title compound as an off-white waxy solid (9.9 g, quantitative yield).

Part B. Preparation of methyl 3-(azidocarbonyl)-5-tert-butylbenzoate

To the product of Part A (9.9 g, 38.9 mmol) in acetone (200 ml) was added at a fast drip a solution of sodium azide (10.12 g, 156 mmol) dissolved in water (20 mL). The mixture was stirred for 2 h and diluted with EtOAc. The organic layer was washed with $H_2O$, saturated brine, dried ($Na_2SO_4$), filtered and concentrated to give the title compound as a white solid (9.9 g, 97%).

Part C. Preparation of methyl 3-amino-5-tert-butylbenzoate

The product from Part B (9.9 g, 37.9 mmol) in toluene (100 mL) was heated at reflux for 1 h and concentrated to give the intermediate isocyanate which was dissolved in DME (60 mL) treated with 8% HCl (150 mL) and stirred for 16 h. The mixture was concentrated and the residue was dissolved in water, neutralized with solid sodium bicarbonate and extracted 3×100 mL with EtOAc. The organics were combined, washed with saturated NaCl, dried ($Na_2SO_4$), filtered and concentrated. The crude product was chromatographed on silica eluting with 2:1 hexane/EtOAc to give the title compound as an oil (2.7 g, 35%).

Part D. Preparation of methyl 3-tert-butyl-5-(2,4-dioxotetrahydropyrimidin-1(2H)-yl)-2-methoxybenzoate A mixture of the product of Part C (2.34 g, 11.29 mmol) and acrylic acid (2.32 ml, 33.9 mmol) in toluene (60 ml) was heated at reflux under nitrogen for 24 h, cooled and concentrated. The resulting residue was then treated with urea (2.03 g, 33.9 mmol) in acetic acid (35 ml) and heated at 120° C. for 24 h, cooled and concentrated. The residue was azeotroped 3×50 mL with toluene and dissolved in 100 mL of EtOAc. The organic layer was washed with dilute aqueous $NaHCO_3$, $H_2O$, saturated brine, dried ($Na_2SO_4$), filtered and concentrated to give the title compound as a white solid (2.1 g, 61%).

Part E. Preparation of 3-tert-butyl-5-(2,4-dioxotetrahydropyrimidin-1(2H)-yl)benzoic acid A mixture of the product from Part D (1.8 g, 5.91 mmol) and 1M NaOH (29.6 ml, 29.6 mmol) in MeOH (15 ml) and THF (15 mL) was stirred for 24 h and concentrated. The residue was treated with 50 mL of 1M HCl and extracted into EtOAc. The EtOAc layer was washed with $H_2O$, saturated brine, dried ($Na_2SO_4$), filtered and concentrated to give a white solid. This intermediate urea was combined with 20 mL of concentrated HCl and heated at 100° C. for 1 h, cooled and diluted with 75 mL of ice water to give a white powder which was collected by filtration and dried to constant mass to give the title compound (1.6 g, 93%).

Part F. Preparation of (E)-N-(4-(3-tert-butyl-5-(2,4-dioxotetrahydropyrimidin-1(2H)-yl) styryl)phenyl) methanesulfonamide The product described in Part E was treated with thionyl chloride and lithium tri-tert-butoxyaluminum hydride according to procedures described in Example 1, Part G to produce 3-tert-butyl-5-(2,4-dioxotetrahydropyrimidin-1 (2H)-yl)benzaldehyde. The aldehyde was treated with diethyl 4-nitrobenzylphosphonate according to the procedures described in Example 1, Part H and Example 1, Part 1 to provide the title compound (85 mg). $^1$H NMR (300 MHz, DMSO-$d_6$): δ ppm 1.32 (s, 9H) 2.72 (t, J=6.43 Hz, 2H) 3.01 (s, 3H) 3.82 (t, J=6.62 Hz, 2H) 7.18-7.25 (m, 5H) 7.39 (s, 1H) 7.46 (s, 1H) 7.58 (d, J=8.46 Hz, 2H) 9.84 (s, 1H) 10.37 (s, 1H).

Example 10

Preparation of (Z)-N-(4-(2-(3-tert-butyl-5-(2,4-dioxotetrahydropyrimidin-1(2H)-yl)-2-methoxyphenyl)-1-methoxyvinyl)phenyl)methanesulfonamide (compound IA-L1-1.17)

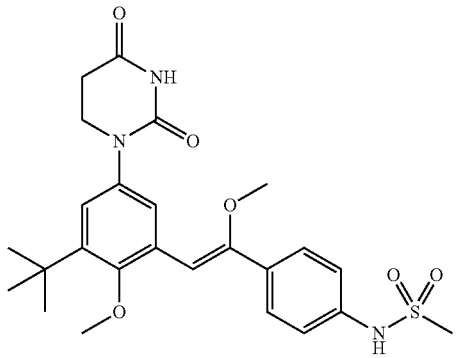 [SMILES: CO/C(=C\c1cc(N2CCC(=O)NC2=O)cc(C(C)(C)C)c1OC)c1ccc(NS(C)(=O)=O)cc1]

Part A. Preparation of 1-(dimethoxymethyl)-4-nitrobenzene

A flask equipped with a magnetic stir bar and vigreux column was charged with 4-nitro-benzaldehyde (5.0 g, 33.1 mmol), pyridinium p-toluenesulfonate (1.66 g, 6.62 mmol), trimethoxymethane (3.51 g, 33.1 mmol) and methanol (100 mL). The mixture was heated at 50° C. for 12 h and was concentrated in vacuo. The residue was redissolved in EtOAc and washed with aq. NaOH (1M), $H_2O$ and brine. The mixture was dried ($Na_2SO_4$), filtered and concentrated in vacuo to yield the title compound as a clear, light yellow oily product (6.36 g, 97%).

Part B. Preparation of diethyl methoxy(4-nitrophenyl)methylphosphonate

The product from Part A (3.0 g, 15.2 mmol) and triethyl phosphite (2.53 g, 15.2 mmol) were dissolved in dichloromethane (30 mL) under a nitrogen atmosphere, cooled to −20° C. and treated with drop wise addition of boron trifluoride etherate (2.27 g, 16 mmol). The mixture was allowed to slowly warm to room temperature overnight with stirring. Water was added and the resulting mixture was stirred 5 min, separated and the organic layer was dried ($Na_2SO_4$), filtered and concentrated in vacuo to a solid residue. The residue was purified on silica gel (100% EtOAc to 3% $CH_3OH$/EtOAc) to yield the title compound as a light yellow oily product (3.78 g, 82%).

Part C. Preparation of (Z)-N-(4-(2-(3-tert-butyl-5-(2,4-dioxotetrahydropyrimidin-1(2H)-yl)-2-methoxyphenyl)-1-methoxyvinyl)phenyl)methanesulfonamide The product obtained according to the procedure described in Example 1, Part G (400 mg, 1.314 mmole) was treated with the product obtained in Part B (399 mg, 1.314 mmole) according to the procedures described in Example 1, Part H and Example 1, Part Ito provide the title compound (17 mg, 6%). $^1$H NMR (300 MHz, DMSO-$d_6$): δ ☐ ppm 1.36 (s, 9H) 2.71 (t, J=6.62 Hz, 2H) 3.05 (s, 3H) 3.58 (s, 3H) 3.75 (s, 3H) 3.76-3.81 (m, 2H) 6.25 (s, 1H) 7.11 (d, J=2.57 Hz, 1H) 7.27 (d, J=8.46 Hz, 2H) 7.60 (d, J=8.82 Hz, 2H) 7.67 (d, J=2.57 Hz, 1H) 9.96 (s, 1H) 10.32 (s, 1H).

Example 11

Preparation of (E)-1-(3-tert-butyl-4-methoxy-5-styrylphenyl)dihydro-pyrimidine-2,4(1H,3H)-dione (compound IA-L1-1.18)

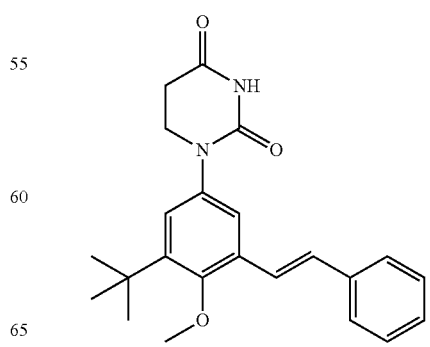

The product obtained according to procedure described in Example 1, Part G (50 mg, 0.164 mmole) was treated with diethyl benzylphosphonate (0.034 ml, 0.164 mmole) according to the procedure described in Example 1, Part H to provide the title compound (13 mg, 19%). $^1$H NMR (300 MHz, DMSO-$d_6$): δ ppm 1.37 (s, 9H) 2.72 (t, J=6.62 Hz, 2H) 3.76 (s, 3H) 3.80 (t, J=6.80 Hz, 2H) 7.16-7.18 (m, 1H) 7.21-7.23 (m, 1H) 7.29-7.33 (m, 2H) 7.36-7.43 (m, 2H) 7.54 (d, J=2.57 Hz, 1H) 7.64 (d, J=7.35 Hz, 2H) 10.35 (s, 1H).

Example 12

Preparation of (E)-1-(3-tert-butyl-4-methoxy-5-(4-methoxystyryl)phenyl)dihydro pyrimidine-2,4(1H,3H)-dione (compound IA-L1-14)

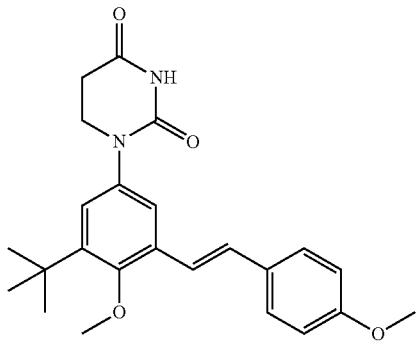 [SMILES: COc1ccc(/C=C/c2cc(N3CCC(=O)NC3=O)cc(C(C)(C)C)c2OC)cc1]

The product obtained according to procedure described in Example 1, Part G. (50 mg, 0.164 mmole) was treated with diethyl 4-methoxybenzylphosphonate (0.028 ml, 0.164 mmole) according to the procedure described in Example 1, Part H to provide the title compound (4 mg, 4%). $^1$H NMR (300 MHz, DMSO-$d_6$): δ ppm 1.37 (s, 9H) 2.71 (t, J=6.62 Hz, 2H) 3.70-3.81 (m, 8H) 6.96 (d, J=8.82 Hz, 2H) 7.13 (d, J=2.21 Hz, 1H) 7.15 (d, J=2.57 Hz, 2H) 7.50 (d, J=2.57 Hz, 1H) 7.58 (d, J=8.46 Hz, 2H) 10.34 (s, 1H).

Example 13A

Preparation of (E)-N-(4-(3-tert-butyl-5-(2,4-dioxo-3,4-dihydropyrimidin-1(2H)-yl)-2-methoxystyryl)phenyl)methanesulfonamide (compound IB-L1-1.1)

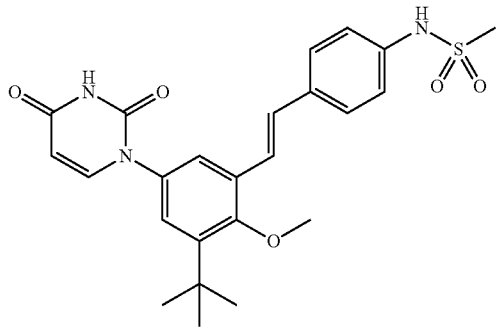 [SMILES: COc1c(/C=C/c2ccc(NS(C)(=O)=O)cc2)cc(-n2ccc(=O)[nH]c2=O)cc1C(C)(C)C]

Part A. Preparation of (E)-methyl 3-tert-butyl-2-methoxy-5-(3-(3-methoxyacryloyl)ureido) benzoate The product obtained as described in Example 1, Part C (2.0 g, 8.43 mmol) was dissolved in 30 mL of N,N-dimethylacetamide and cooled to −25° C. A 0.5 Molar solution of E-3-methoxyacryloyl isocyanate in benzene (21.9 mL, 10.96 mmol) was added drop wise and the resulting solution was stirred at ambient temperature for 4 h, and then poured into water. The product was extracted into dichloromethane, washed with brine, dried over sodium sulfate, filtered and evaporated under vacuum to give the title compound.

Part B. Preparation of methyl 3-tert-butyl-5-(2,4-dioxo-3,4-dihydropyrimidin-1(2H)-yl)-2-methoxy-benzoate The product from Part A (3.1 g, 8.51 mmol) was dissolved in ethanol (60 mL). To this solution was added a mixture of concentrated sulfuric acid (6 mL) and water (60 mL). The heterogeneous mixture was heated at 100° C. for 3 h. The ethanol was removed under vacuum, and then the aqueous solution was extracted with dichloromethane and evaporated to dryness. This residue was purified by column chromatography on silica gel, eluting with 1% methanol/dichloromethane to yield the title compound (1.23 g, 44%).

Part C. Preparation of 3-tert-butyl-5-(2,4-dioxo-3,4-dihydropyrimidin-1(2H)-yl)-2-methoxy benzoic acid The product from Part B (1.23 g, 3.7 mmol) was taken up in ethanol (5 mL) and 1M sodium hydroxide solution (±0 mL) and stirred at ambient temperature for 18 h. The solution was acidified with 1M HCl and the resulting solid was filtered and dried to give the title compound (0.945 g, 80%).

Part D. Preparation of 3-tert-butyl-5-(2,4-dioxo-3,4-dihydropyrimidin-1(2H)-yl)-2-methoxy benzaldehyde The product from Part C (0.945 g, 2.97 mmol) was taken up in thionyl chloride (4.5 mL) and the mixture was heated at 80° C. for 40 min. After evaporation to dryness, the acid chloride was dissolved in dry THF (8 mL) and cooled to −78° C. A 1 M solution of lithium tri-tert-butoxyaluminum hydride in THF (3.0 mL, 3.0 mmol) was added drop wise. After 45 min the cold reaction was quenched with 1M HCl (5 mL), extracted into ethyl acetate, and purified by column chromatography on silica gel, eluting with dichloromethane followed by 1% methanol/dichloromethane to give the title compound (0.635 g, 71%).

Part E. Preparation of (E)-1-(3-tert-butyl-4-methoxy-5-(4-nitrostyryl)phenyl)pyrimidine-2,4(1H,3H)-dione The product of Part D (0.634 g, 2.1 mmol) and diethyl 4-nitrobenzylphosphonate (0.573 g, 2.1 mmol) were combined in dichloromethane (25 mL) at ambient temperature. Potassium tert-butoxide (0.494 g, 4.4 mmol) was added portion wise and the resulting red/brown heterogeneous mixture was stirred for 1.5 h. This mixture was quenched with 1M HCl (15 mL), poured into water and extracted into ethyl acetate, and the crude product was purified by column chromatography on silica gel, eluting with 1% methanol/dichloromethane to give the title compound (0.735 g, 83%).

Part F. Preparation of (E)-1-(3-(4-aminostyryl)-5-tert-butyl-4-methoxyphenyl)pyrimidine-2,4(1H,3H)-dione The product from Part E (0.735 g, 1.74 mmol), ammonium chloride (0.14 g, 2.62 mmol), and iron (0.487 g, 8.72 mmol) were combined in a solution of ethanol (10 mL), water (5 mL), and THF (10 mL) and heated at 75° C. for 1 h. The mixture was filtered through diatomaceous earth, rinsing well with THF and concentrated to give the title compound.

Part G. Preparation of (E)-N-(4-(3-tert-butyl-5-(2,4-dioxo-3,4-dihydropyrimidin-1(2H)-yl)-2-methoxystyryl)phenyl)methanesulfonamide The product from Part F (0.683 g, 1.75 mmol) and pyridine (0.564 mL, 6.98 mmol) were combined in dichloromethane (15 mL) at ambient temperature. Methane sulfonylchloride (0.163 mL, 2.1 mmol) was added drop wise and the solution was stirred for 18 h. The mixture was poured into 1M HCl and extracted into dichloromethane, concentrated, and purified by column chromatography on silica gel, eluting with 1%, 2% methanol/dichloromethane. Trituration from dichloromethane provided a solid that was filtered and dried to give the title compound as a colorless powder (0.465 g, 57%). $^1$H NMR (300 MHz, DMSO-D6) δ ppm 1.38 (s, 9H), 3.01 (s, 3H), 3.79 (s, 3H) 5.65 (d, J=7.72 Hz, 1H), 7.17-7.28 (m, 5H), 7.58-7.70 (m, 3H), 7.75 (d, J=7.72 Hz, 1H), 9.86 (s, 1H), 11.42 (s, 1H).

Example 13B

Preparation of (E)-N-(4-(3-tert-butyl-5-(2,4-dioxo-3,4-dihydropyrimidin-1(2H)-yl)-2-methoxystyryl)phenyl)methanesulfonamide (compound IB-L1-1.1)

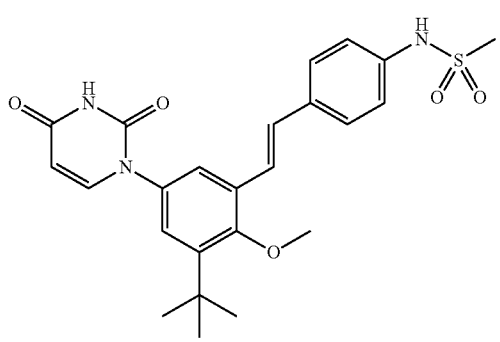 [SMILES: COc1c(/C=C/c2ccc(NS(C)(=O)=O)cc2)cc(-n2ccc(=O)[nH]c2=O)cc1C(C)(C)C]

Part A. Preparation of N-(4-ethynylphenyl)methanesulfonamide

In a 2 L, 3-neck round-bottom flask equipped with an overhead stirrer was added 4-ethynylaniline (30 g, 256 mmol) and pyridine (42.5 ml, 525 mmol) in dichloromethane (512 ml) to give an orange solution. The mixture was cooled to 5° C. and methanesulfonyl chloride (19.96 ml, 256 mmol) was added drop wise over 15 min. The reaction solution was stirred at 5° C. for 2 h and washed with 1M aqueous HCl (3×250 mL). The dichloromethane layer was then washed sequentially with saturated aqueous NaHCO$_3$, water, and saturated aqueous NaCl. The dichloromethane layer was dried over sodium sulfate and treated simultaneously with decolorizing charcoal for 30 min, the solution then filtered through Celite and the filtrate was concentrated. The pink/orange solid was dissolved in a minimal amounrof hot ethyl acetate (50-75 mL) and slowly diluted with hexanes (500-600 ml) to give orange crystals that were collected by filtration and dried to provide the title compound (40.0 g, 80%).

Part B. Preparation of (E)-4-(methylsulfonamido)styrylboronic acid (Reference: *Org. Prep. Proc. Int.*, 2004, 36, 573-579) To a flask was added borane-methyl sulfide complex (8.03 mL, 85 mmol) followed by tetrahydrofuran (16 mL) and the mixture then cooled to 0° C. (1R)-(+)-alpha-pinene (26.2 mL, 169 mmol) was then added drop wise (over 10 min) to the ice-cooled solution. The mixture was then stirred at 0° C. for 1 h followed by stirring 2 h at room temperature. The resulting thick white slurry was cooled to −40° C. in a dry ice/acetone bath, followed by the addition of the product from Part A (15.0 g, 77 mmol) dissolved in 60 mL of THF, drop wise over 30 min. After the addition was complete, the mixture was stirred for an additional hour at −35° C., then 1 h at room temperature. The light yellow solution was then cooled to 0° C. and acetaldehyde (61.4 mL, 1088 mmol) added, then the mixture refluxed at 50° C. for 18 h. The solvent was then removed under vacuum to provide an orange syrup, to which water (115 mL) was added and the heterogeneous mixture stirred for 3 h at room temperature. The light yellow solid generated was collected and washed with water (250 mL) then dried in a vacuum oven overnight. The resultant material was then dissolved in boiling acetone (190 mL), which provided a homogenous yellow solution, followed by removal of the solution from heating and the addition of hexanes (365 ml) over 5 min time. A white solid formed in the solution and the mixture was stirred until the solution cooled to room temperature, then the white solid was collected and dried in a vacuum oven for 1 hr to provide the title compound (12.1 g, 85%).

Part C. Preparation of 2-tert-butyl-4-nitrophenol

To a vigorously stirred solution of 2-tert-butylphenol (10 g, 66.6 mmol) in heptane (67 ml) was added at a fast drip a solution of 70% nitric acid (4.25 ml, 66.6 mmol) diluted with water (4.25 ml). The resulting dark red/brown mixture was stirred vigorously for 2 h. The suspended solid was collected by filtration washed with hexane (300 mL), water (200 mL) and once again with hexane (200 mL) to give a cocoa colored powder that was dried to constant mass (4.65 g, 35.6%).

Part D. Preparation of 2-bromo-6-tert-butyl-4-nitrophenol

A solution of the product from Part C (1.0 g, 5.12 mmol) in glacial acetic acid (10.25 mL) was treated portion wise with pyridine hydrobromide perbromide (1.80 g, 5.63 mmol) followed by stirring at room temperature for 2 h. Additional pyridinium hydrobromide perbromide (3.6 g) was added in two portions and after another 3 h of stirring, the reaction was complete. The mixture was poured into ice water, and the mixture treated with a small amount of sodium sulfite. The resulting solid was filtered and dried under vacuum to give the title compound as a brown solid (1.40 g, 100%).

Part E. Preparation of 1-bromo-3-tert-butyl-2-methoxy-5-nitrobenzene

A solution of the product from Part D (1.40 g, 5.11 mmol) in 10:1 t-butylmethylether-methanol (25.5 mL) was treated with 2.0M trimethylsilyldiazomethane in ether (5.1 mL, 10.21 mmol), followed by stirring at room temperature for 18 h. The mixture was concentrated under vacuum to afford a yellow oil, which was purified by silica gel column chromatography eluting with EtOAc/hexanes to give the title compound as a yellow oil (1.36 g, 92%).

Part F. Preparation of tert-butyl 3-bromo-5-tert-butyl-4-methoxyphenylcarbamate

A solution of the product from Part E (960 mg, 3.33 mmol) in methanol (17 mL) was treated with 5% platinum on sulfided carbon (100 mg), followed by hydrogenation under balloon pressure for 3 h, and then filtered through celite and concentrated under vacuum to afford the 3-bromo-5-tert-butyl-4-methoxyaniline as a yellow oil (860 mg, 3.33 mmol, 100%). A solution of this material in THF (17 mL) was treated with di-tert-butyl dicarbonate (800 mg, 3.66 mmol) followed by warming at reflux for 2 h. Concentration under vacuum afforded a beige solid, which was purified by silica gel column chromatography eluting with EtOAc/hexanes. Solid was triturated with hexanes, collected by filtration, and dried under vacuum to give the title compound as a nearly white solid (890 mg, 75%).

Part G. Preparation of (E)-N-(3-bromo-5-tert-butyl-4-methoxyphenylcarbamoyl)-3-methoxy acrylamide The product from Part F (2.0 g, 5.58 mmol) was dissolved in dichloromethane (10 mL) and trifluoroacetic acid (5 mL) added. The solution was stirred at room temperature for 1 h followed by concentration under vacuum and the addition of 10% aqueous sodium bicarbonate (50 mL), followed by extraction with ethyl acetate (3×50 mL). The combined organic extracts were dried and concentrated to provide a residue that was dissolved in 10 mL of N,N-dimethylacetamide and cooled to −25° C. A 0.5 molar solution of E-3-methoxyacryloyl isocyanate in benzene (20.3 mL, 11.16 mmol) was added drop wise and the resulting solution was stirred at ambient temperature for 4 h, and then poured into water. The product was extracted into dichloromethane, washed with brine, dried over sodium sulfate, filtered and evaporated under vacuum to give the title compound.

Part H. Preparation of 1-(3-bromo-5-tert-butyl-4-methoxyphenyl)pyrimidine-2,4(1H,3H)-dione The product from Part G (2.15 g, 5.58 mmol) was dissolved in ethanol (10 mL). To this solution was added a mixture of concentrated sulfuric acid (1 mL) and water (10 mL). The heterogeneous mixture was heated at 100° C. for 2 h. The ethanol was removed under vacuum, and then the aqueous solution was extracted with dichloromethane and evaporated to dryness. This residue was purified by column chromatography on silica gel, eluting with 1% methanol/dichloromethane to yield the title compound (1.35 g, 69%).

Part I. Preparation of (E)-N-(4-(3-tert-butyl-5-(2,4-dioxo-3,4-dihydropyrimidin-1(2H)-yl)-2-methoxystyryl)phenyl)methanesulfonamide The product from Part H (8.0 g, 22.65 mmol), the product from Part B (5.90 g, 24.46 mmol), 1,1'-bis(di-tert-butylphosphino)ferrocene palladium dichloride (0.738 g, 1.132 mmol), and potassium phosphate (9.62 g, 45.3 mmol) were dissolved in a mixture of tetrahydrofuran (128 mL) and water (32 mL). Nitrogen gas was bubbled through the resultant mixture for 10 min followed by heating the solution at 50° C. for 5 h in darkness. The reaction was allowed to cool to room temperature followed by the addition of saturated aqueous ammonium chloride (50 mL), water (200 mL), and the solution extracted with dichloromethane (600 mL). To the organic extract was added magnesium sulfate, and 3-mercaptopropyl-functionalized silica gel (20 g) and the resultant solution stirred in darkness for 18 h. The solids were then removed by filtration and the filtrate concentrated under vacuum and subjected to silica gel column chromatography using a 99/1 to 99/2 dichloromethane/methanol gradient to provide the title compound (7.4 g, 70%). $^1$H NMR (300 MHz, DMSO-D6) δ ppm 1.38 (s, 9H), 3.01 (s, 3H), 3.79 (s, 3H) 5.65 (d, J=7.72 Hz, 1H), 7.17-7.28 (m, 5H), 7.58-7.70 (m, 3H), 7.75 (d, J=7.72 Hz, 1H), 9.86 (s, 1H), 11.42 (s, 1H).

Example 14

Preparation of (E)-N-(4-(3-tert-butyl-5-(5-fluoro-2,4-dioxo-3,4-dihydro-pyrimidin-1(2H)-yl)-2-methoxystyryl)phenyl)methanesulfonamide (compound IB-L1-1.2)

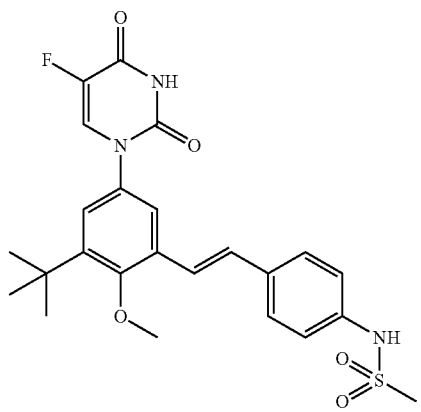 [SMILES: COc1c(/C=C/c2ccc(NS(C)(=O)=O)cc2)cc(-n2cc(F)c(=O)[nH]c2=O)cc1C(C)(C)C]

Part A. Preparation of methyl 3-tert-butyl-5-(5-fluoro-6-methoxy-2,4-dioxotetrahydro-pyrimidin-1(2H)-yl)-2-methoxybenzoate The fluorination procedure was performed as described in Lal, G S, et al. J. Org Chem., 60:7340-7342 (1995). The product from Example 13 Å, Part B (0.42 g, 1.26 mmol) and Selectfluor™ (0.672 g, 1.9 mmol) were combined in a mixture of acetonitrile (8 mL) and methanol (1 mL) and heated at 90° C. under $N_2$ for 5 h. The solution was diluted with water, extracted into ethyl acetate, washed with sodium bicarbonate solution, concentrated and purified by column chromatography on silica gel to give the title compound (0.138 g, 29%).

Part B. Preparation of methyl 3-tert-butyl-5-(5-fluoro-2,4-dioxo-3,4-dihydropyrimidin-1(2H)-yl)-2-methoxybenzoate The product from Part A (0.134 g, 0.35 mmol) and triethylamine (1 mL) were combined in methanol (4 mL) and stirred at ambient temperature for 18 h. The solution was quenched with 1M HCl, extracted into dichloromethane and concentrated to give the title compound (0.113 g, 92%).

Part C. Preparation of 3-tert-butyl-5-(5-fluoro-2,4-dioxo-3,4-dihydropyrimidin-1(2H)-yl)-2-methoxybenzoic acid The product from Part B (0.113 g, 0.32 mmol) was treated as described in Example 13 Å, Part C to give the title compound (0.088 g, 81%).

Part D. Preparation of 3-tert-butyl-5-(5-fluoro-2,4-dioxo-3,4-dihydropyrimidin-1(2H)-yl)-2-methoxybenzaldehyde The product from Part C (0.088 g, 0.26 mmol) was treated as described in Example 13 Å, Part D to give the title compound (0.075 g, 90%).

Part E. Preparation of (E)-1-(3-tert-butyl-4-methoxy-5-(4-nitrostyryl)phenyl)-5-fluoropyrimidine-2,4(1H,3H)-dione The product of Part D (0.075 g, 0.23 mmol) was treated as described in Example 13 Å, Part E to give 0.077 g (75%).

Part F. Preparation of (E)-1-(3-(4-aminostyryl)-5-tert-butyl-4-methoxyphenyl)-5-fluoro pyrimidine-2,4(1H,3H)-dione The product of Part E (0.077 g, 0.18 mmol) was treated as described in Example 13 Å, Part F to give the title compound (0.071 g, 94%).

Part G. Preparation of (E)-N-(4-(3-tert-butyl-5-(5-fluoro-2,4-dioxo-3,4-dihydropyrimidin-1(2H)-yl)-2-methoxystyryl)phenyl)methanesulfonamide The product of Part F (0.071 g, 0.17 mmol) was treated as described in Example 13 Å, Part G to give the title compound (0.048 g, 57%). NMR (300 MHz, DMSO-D6): δ ppm 1.38 (s, 9H), 3.01 (s, 3H), 3.79 (s, 3H) 7.19-7.27 (m, 5H), 7.62 (d, J=8.82 Hz, 2H), 7.66 (d, J=2.57 Hz, 1H), 8.25 (d, J=6.99 Hz, 1H).

Example 15

Preparation of (E)-N-(4-(3-bromo-5-(2,4-dioxo-3,4-dihydropyrimidin-1(2H)-yl)-2-methoxystyryl)phenyl)methanesulfonamide (compound IB-L1-1.52)

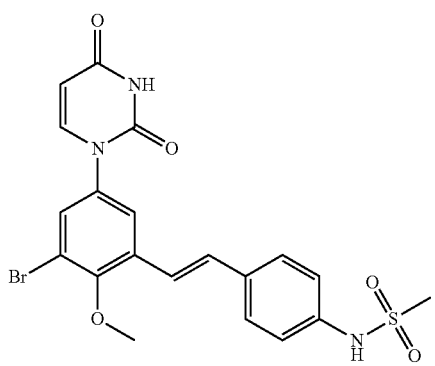 [SMILES: COc1c(Br)cc(-n2ccc(=O)[nH]c2=O)cc1/C=C/c1ccc(NS(C)(=O)=O)cc1]

Part A. Preparation of 2-bromo-4,6-diiodophenol

A 1 L round-bottom flask was charged with 2-bromophenol (8.65 g, 50 mmol) and methanol (100 ml) to give a colorless solution. Sodium hydroxide (2.40 g, 60.0 mmol) was added and stirred until the hydroxide pellets had dissolved. The solution was cooled in an ice water bath and sodium iodide (5.6 g, 37.4 mmol) was added followed by drop-wise addition of sodium hypochlorite (17 mL, 27.5 mmol) to give a transparent brown/red solution and gradual precipitation of a thick, white solid. The addition of sodium iodide and bleach was repeated 3 times to give an orange mixture that was stirred for 2 h, treated with a solution of sodium thiosulfate in water (20 g in 100 mL), stirred for 15 min and treated drop-wise with concentrated HCl to a constant pH of 1. The mixture was stirred for 15 min and filtered to collect a white solid that was washed repeatedly with water and dried to constant mass (14.7 g, 69%).

Part B. Preparation of 1-bromo-3,5-diiodo-2-methoxybenzene

A 500 mL round-bottom flask was charged with the product from Part A (14.7 g, 34.6 mmol), iodomethane (2.70 ml, 43.3 mmol), and sodium hydroxide (2.101 ml, 39.8 mmol) in acetone (96 ml) to give a tan solution. The mixture was stirred for 24 h and concentrated. The residue was dissolved in ethyl acetate, washed with water and saturated sodium chloride, dried over sodium sulfate, filtered and concentrated to give a white solid. The solid was recrystallized from hot hexane to give a white solid that was collected by filtration (12.3 g, 81%).

Part C. Preparation of 1-(3-bromo-5-iodo-4-methoxyphenyl)pyrimidine-2,4(1H,3H)-dione A 250 mL round-bottom flask was charged with the product from Part B (8.09 g, 18.44 mmol), pyrimidine-2,4(1H,3H)-dione (2.273 g, 20.28 mmol), N-(2-cyanophenyl)picolinamide (0.823 g, 3.69 mmol), copper (1) iodide (0.351 g, 1.844 mmol) and potassium phosphate (8.22 g, 38.7 mmol) in DMSO (70 ml). The mixture was sealed, sparged with nitrogen for 15 min and heated at 60° C. for 16 h. The mixture was partitioned with ethyl acetate and water. The organic layer was washed with 1M HCl, water, brine, dried with sodium sulfate, and filtered. The filtrate was treated with 3-mercaptopropyl functionalized silica gel (Aldrich catalog #538086), filtered through celite and evaporated to give an off-white solid (3.92 g, 50%).

Part D. Preparation of (E)-N-(4-(3-bromo-5-(2,4-dioxo-3,4-dihydropyrimidin-1(2H)-yl)-2-methoxystyryl)phenyl)methanesulfonamide To a 100 ml round-bottom flask was added the product from Part C (846 mg, 2.0 mmol), the product from Example 13B, Part B (482 mg, 2.000 mmol), potassium phosphate (892 mg, 4.20 mmol), 1,3,5,7-tetramethyl-6-phenyl-2,4,8-trioxa-6-phosphaadamante (PA-Ph) (CAS 97739-46-3) (17.54 mg, 0.060 mmol) and tris(dibenzylideneacetone)dipalladium(0) (18.31 mg, 0.020 mmol) in THF (12.0 ml) and water (4.0 ml). The flask was sealed and the mixture was sparged with nitrogen for 5 min and stirred at ambient temperature for 72 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered and evaporated. The residue was triturated with a minimal amount of methanol/$CH_2Cl_2$ to give the title compound as a white solid (595 mg, 60%). $^1$H NMR (300 MHz, DMSO-$d_6$) δ ppm 3.03 (s, 3H) 3.82 (s, 3H) 5.69 (dd, J=7.72, 1.50 Hz, 1H) 7.24 (d, J=8.46 Hz, 2H) 7.35 (m, 2H) 7.61 (d, J=8.46 Hz, 2H) 7.69 (d, J=2.21 Hz, 1H) 7.78 (d, J=8.09 Hz, 1H) 7.87 (d, J=2.21 Hz, 1H) 9.90 (s, 1H) 11.50 (s, 1H). MS (ESI−) m/z 490,492 (M−H)+.

Example 16

Preparation of (E)-N-(4-(5-(2,4-dioxo-3,4-dihydro-pyrimidin-1(2H)-yl)-2-methoxy-3-(thiophen-2-yl)styryl)phenyl)methanesulfonamide (compound IB-L1-1.48)

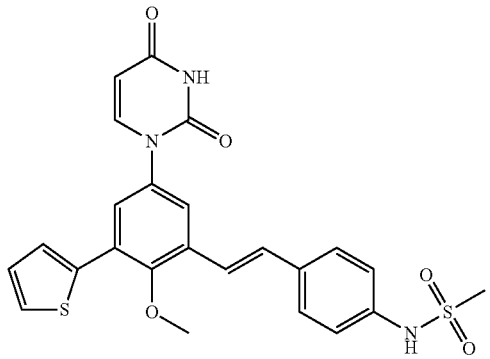 [SMILES: COc1c(/C=C/c2ccc(NS(C)(=O)=O)cc2)cc(-n2ccc(=O)[nH]c2=O)cc1-c1ccco1]

To a 5 ml microwave tube was added the product from Example 15, Part D (40 mg, 0.081 mmol), thiophen-2-ylboronic acid (10.40 mg, 0.081 mmol), 1,1'-bis(di-tert-butylphosphino)ferrocene palladium dichloride (2.65 mg, 4.06 µmol) and potassium phosphate (34.5 mg, 0.162 mmol) in THF (3.0 ml) and water (1.0 ml). The vessel was sealed and the mixture was sparged by nitrogen for 5 min and heated at 50° C. for 3 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered through celite and evaporated. The residue was purified by reverse phase chromatography to give the title compound as a white solid (20 mg, 50%). $^1$H NMR (300 MHz, DMSO-$d_6$) δ ppm 3.03 (s, 3H) 3.70 (s, 3H) 5.70 (dd, J=7.72, 2.21 Hz, 1H) 7.18 (dd, J=5.43, 4.05 Hz, 1H) 7.25 (d, J=8.82 Hz, 2H) 7.35 (s, 2H) 7.63 (d, J=8.82 Hz, 2H) 7.68 (m, 2H) 7.77 (m, 2H) 7.83 (d, J=7.72 Hz, 1H) 9.89 (s, 1H) 11.49 (d, J=2.21 Hz, 1H). MS (ESI+) m/z 496 (M+H)+.

Example 17

Preparation of (E)-N-(4-(5-(2,4-dioxo-3,4-dihydro-pyrimidin-1(2H)-yl)-3-(furan-2-yl)-2-methoxystyryl)phenyl)methanesulfonamide (compound IB-L1-1.46)

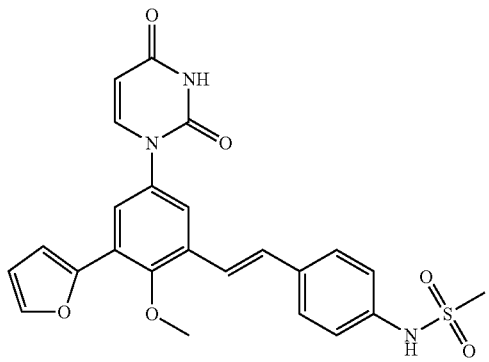

The title compound was prepared according to the procedure of Example 16 substituting furan-2-ylboronic acid for thiophen-2-ylboronic acid to give a white solid (22 mg, 56%). $^1$H NMR (300 MHz, DMSO-$d_6$) δ ppm 3.03 (s, 3H) 3.76 (s, 3H) 5.69 (d, J=7.72 Hz, 1H) 6.69 (dd, J=3.31, 1.84 Hz, 1H) 7.08 (d, J=2.57 Hz, 1H) 7.25 (d, J=8.46 Hz, 2H) 7.36 (m, 2H) 7.63 (d, J=8.82 Hz, 2H) 7.67 (d, J=2.57 Hz, 1H) 7.77 (d, J=2.57 Hz, 1H) 7.82 (m, J=7.72 Hz, 2H) 9.88 (s, 1H) 11.48 (s, 1H). MS (ESI+) m/z 497 (M+NH4)+.

Example 18

Preparation of (E)-N-(4-(5-(2,4-dioxo-3,4-dihydro-pyrimidin-1(2H)-yl)-2-methoxy-3-(pyridin-4-yl)styryl)phenyl)methanesulfonamide (compound IB-L1-1.55)

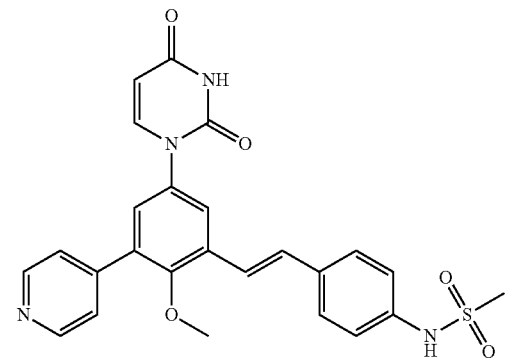 [SMILES: COc1c(/C=C/c2ccc(NS(C)(=O)=O)cc2)cc(-n2ccc(=O)[nH]c2=O)cc1-c1ccncc1]

The title compound was prepared according to the procedure of Example 16 substituting 4-(4,4,5,5-tetramethyl-1,3,2-dioxaborolan-2-yl)pyridine for thiophen-2-ylboronic acid to give a white solid (15 mg, 38%). $^1$H NMR (300 MHz, DMSO-$d_6$) δ ppm 3.03 (s, 3H) 3.49 (s, 3H) 5.72 (dd, J=7.72, 2.21 Hz, 1H) 7.25 (d, J=8.46 Hz, 2H) 7.38 (d, J=4.41 Hz, 2H) 7.51 (d, J=2.57 Hz, 1H) 7.63 (d, J=8.82 Hz, 2H) 7.80 (d, J=5.88 Hz, 2H) 7.85 (d, J=7.72 Hz, 1H) 7.97 (d, J=2.57 Hz, 1H) 8.77 (d, J=6.25 Hz, 2H) 9.90 (s, 1H) 11.51 (d, J=2.21 Hz, 1H). MS (ESI+) m/z 491 (M+H)+.

Example 19

Preparation of (E)-N-(4-(5-(2,4-dioxo-3,4-dihydro-pyrimidin-1(2H)-yl)-2-methoxy-3-(pyridin-3-yl)styryl)phenyl)methanesulfonamide (compound IB-L1-1.53)

The title compound was prepared according to the procedure of Example 16 substituting 3-(4,4,5,5-tetramethyl-1,3,2-dioxaborolan-2-yl)pyridine for thiophen-2-ylboronic acid to give a white solid (19 mg, 48%). $^1$H NMR (300 MHz, DMSO-$d_6$) δ ppm 3.02 (s, 3H) 3.45 (s, 3H) 5.71 (dd, J=8.09, 2.21 Hz, 1H) 7.24 (d, J=8.46 Hz, 2H) 7.37 (d, J=2.94 Hz, 2H) 7.47 (d, J=2.57 Hz, 1H) 7.63 (m, 3H) 7.85 (d, J=7.72 Hz, 1H) 7.93 (d, J=2.57 Hz, 1H) 8.15 (m, 1H) 8.68 (dd, J=4.80 Hz, 1.47 Hz, 1H) 8.86 (d, J=1.84 Hz, 1H) 9.89 (s, 1H) 11.50 (d, J=2.21 Hz, 1H). MS (ESI+) m/z 491 (M+H)+.

Example 20

Preparation of (E)-N-(4-(5-(2,4-dioxo-3,4-dihydropyrimidin-1(2H)-yl)-2-methoxy-3-(thiophen-3-yl)styryl)phenyl)methanesulfonamide (compound IB-L1-1.47)

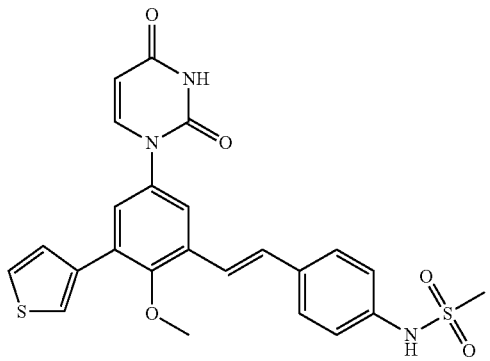 [SMILES: COc1c(/C=C/c2ccc(NS(C)(=O)=O)cc2)cc(-n2ccc(=O)[nH]c2=O)cc1-c1ccsc1]

The title compound was prepared according to the procedure of Example 16 substituting thiophen-3-ylboronic acid for thiophen-2-ylboronic acid to give a white solid (19 mg, 38%). $^1$H NMR (300 MHz, DMSO-$d_6$) δ ppm 3.02 (s, 3H) 3.55 (s, 3H) 5.69 (d, J=8.09 Hz, 1H) 7.24 (d, J=8.46 Hz, 2H) 7.36 (s, 2H) 7.55 (m, 2H) 7.61 (d, J=8.46 Hz, 2H) 7.67 (dd, J=5.15, 2.94 Hz, 1H) 7.78 (d, J=2.57 Hz, 1H) 7.83 (d, J=7.72 Hz, 1H) 7.93 (dd, J=2.57, 0.96 Hz, 1H) 9.88 (s, 1H) 11.48 (s, 1H). MS (ESI−) m/z 494 (M−H)+.

Example 21

Preparation of (E)-N-(4-(5-(2,4-dioxo-3,4-dihydropyrimidin-1(2H)-yl)-3-(furan-3-yl)-2-methoxystyryl)phenyl)methanesulfonamide (compound IB-L1-1.50)

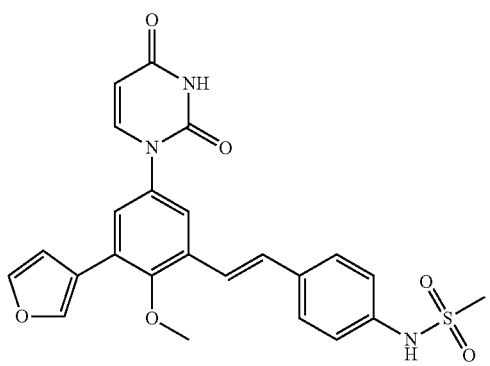 [SMILES: COc1c(/C=C/c2ccc(NS(C)(=O)=O)cc2)cc(-n2ccc(=O)[nH]c2=O)cc1-c1ccoc1]

The title compound was prepared according to the procedure of Example 16 substituting furan-3-ylboronic acid acid for thiophen-2-ylboronic acid to give a white solid (14 mg, 29%). NMR (300 MHz, DMSO-$d_6$) δ ppm 3.02 (s, 3H) 3.69 (s, 3H) 5.69 (d, J=8.09 Hz, 1H) 7.05 (dd, J=2.57, 0.90 Hz, 1H) 7.24 (d, J=8.82 Hz, 2H) 7.34 (s, 2H) 7.61 (m, 3H) 7.74 (d, J=2.57 Hz, 1H) 7.80 (m, 2H) 8.25 (s, 1H) 9.88 (s, 1H) 11.49 (s, 1H). MS (ESI−) m/z 478 (M−H)+.

Example 22

Preparation of (E)-N-(4-(5-(2,4-dioxo-3,4-dihydropyrimidin-1(2H)-yl)-3-(1-hydroxy-2-methylpropan-2-yl)-2-methoxystyryl)phenyl)methanesulfonamide (compound IB-L1-1.45)

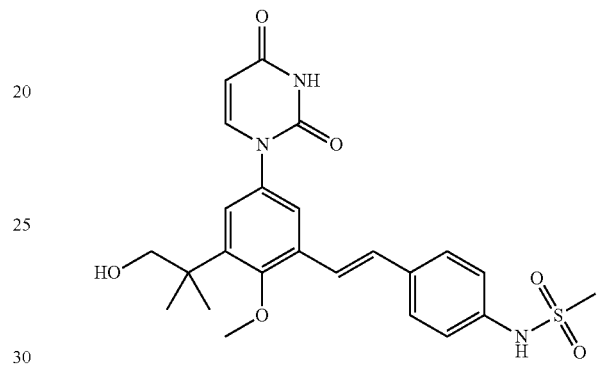

Part A. Preparation of 2-(2-hydroxy-3,5-diiodophenyl)acetic acid

To a 250 mL round-bottom flask was added 2-(2-hydroxyphenyl)acetic acid (Aldrich, 3.04 g, 20 mmol) in acetonitrile (50 ml) to give a colorless solution. N-iodosuccinimide (9.00 g, 40.0 mmol) was added portionwise over 15 min to give a red/brown transparent solution that was stirred for 16 h. The mixture was concentrated and the resulting solid was triturated in 75 mL of water and filtered to collect an orange solid that was dried under vacuum. The crude solid was recrystallized from toluene to give a light orange powder (6.0 g, 74%).

Part B. Preparation of methyl 2-(3,5-diiodo-2-methoxyphenyl)acetate

To a 250 mL round-bottom flask was added the product from Part A (6 g, 14.85 mmol), potassium carbonate (6.16 g, 44.6 mmol), and dimethyl sulfate (4.12 g, 32.7 mmol) in acetone (49.5 ml) to give a brown suspension. The suspension was heated at reflux for 16 h, cooled, concentrated and the residue was partitioned between EtOAc and water. The EtOAc layer was washed with brine, dried (Na$_2$SO$_4$) and concentrated to a brown oil that was chromatographed on a 40 g silica cartridge eluting with 3:1 hexane/EtOAc to give a yellow oil (6.0 g, 94%).

Part C. Preparation of methyl 2-(3,5-diiodo-2-methoxyphenyl)-2-methylpropanoate

To a 100 mL round-bottom flask under nitrogen was added the product from Part B (1.728 g, 4 mmol) in anhydrous THF (20 ml) and HMPA (2 ml) to give a colorless solution. Methyl iodide (1.251 ml, 20.00 mmol) was added and the solution was cooled to −40° C. Potassium t-butoxide(12.00 ml, 12.00 mmol) was added drop-wise and the mixture was stirred at −40 to −20° C. for 30 min and quenched with 1M HCl to a pH of 1. The mixture was extracted 3×40 ml with EtOAc. The extracts were combined, washed with brine, dried ($Na_2SO_4$) and concentrated. The crude product was flash chromatographed on a 40 g ISCO silica cartridge eluting with 9:1 hexane/EtOAc to give the bis-methylated product as a yellow oil (1.63 g, 89%).

Part D. Preparation of 2-(3,5-diiodo-2-methoxyphenyl)-2-methylpropanoic acid

A suspension of the product from Part C (2.63 g, 5.72 mmol) in MeOH (40 ml) and THF (40 ml) was treated with 4.0M sodium hydroxide (28 ml, 112 mmol) and heated at 80° C. for 48 h. The organic solvent was evaporated and the remaining aqueous solution was acidified with 1M HCl producing a solid that was collected by filtration, washed with water and dried to give the desired carboxylic acid (2.46 g, 96%).

Part E. Preparation of 2-(3,5-diiodo-2-methoxyphenyl)-2-methylpropan-1-ol

A solution of the product from Part D (1.00 g, 2.242 mmol) in THF (40 ml) was treated drop-wise with borane THF complex 1.0M (20 ml, 20 mmol) and then heated at 50° C. for 24 h. The mixture was treated with methanol (20 mL), refluxed for 30 min and concentrated. The resulting residue was washed with water, brine, dried with sodium sulfate, filtered and evaporated. The residue was chromatographed on silica gel eluting with hexane/EtOAc (4:1) to give the desired product (810 mg, 84%).

Part F. Preparation of tert-butyl(2-(3,5-diiodo-2-methoxyphenyl)-2-methylpropoxy)-dimethylsilane A solution of the product from Part E (432 mg, 1.000 mmol) in DMF (5 ml) was treated with tert-butyldimethyl-chlorosilane (301 mg, 2.000 mmol), and imidazole (204 mg, 3.00 mmol) and stirred for 2 h. The mixture was partitioned between 1M HCl and ethyl acetate. The organic layer was washed with saturated sodium bicarbonate, brine, dried with sodium sulfate, filtered and evaporated. The residue was chromatographed on silica gel eluting with hexane/EtOAc (9:1) to give the desired product (522 mg, 96%).

Part G. Preparation of 1-(3-(1-(tert-butyldimethylsi-lyloxy)-2-methylpropan-2-yl)-5-iodo-4-methoxyphenyl)pyrimidine-2,4(1H,3H)-dione To a 50 mL round-bottom flask was added the product from Part F (520 mg, 0.952 mmol), pyrimidine-2,4(1H,3H)-dione (117 mg, 1.047 mmol), N-(2-cyanophenyl)picolinamide (42.5 mg, 0.190 mmol), copper(I) iodide (18.13 mg, 0.095 mmol) and potassium phosphate (424 mg, 1.999 mmol) in DMSO (5 ml). The vessel was sealed, sparged with nitrogen and then heated at 60° C. for 24 h. The mixture was partitioned between 1M HCl and ethyl acetate. The organic layer was washed with saturated sodium bicarbonate, brine, dried with sodium sulfate, and filtered. The filtrate was treated with 3-mercaptopropyl functionalized silica gel, filtered and evaporated. The residue was chromatographed on silica gel eluting with hexane/EtOAc (3:2) to give the product as a solid (285 mg, 65%).

Part H. Preparation of (E)-N-(4-(3-(1-(tert-butyldim-ethylsilyloxy)-2-methylpropan-2-yl)-5-(2,4-dioxo-3, 4-dihydropyrimidin-1(2H)-yl)-2-methoxystyryl)phenyl)methanesulfonamide To a 5 ml microwave tube was added the product from Part G (53 mg, 0.1 mmol), the product from Example 13B, Part B (24 mg, 0.1 mmol), potassium phosphate (44.0 mg, 0.2 mmol), PA-Ph (CAS 97739-46-3) (0.87 mg, 3.0 mmol) and tris(dibenzylideneacetone)palladium(0) (0.9 mg, 1 μmol) in THF (3.0 ml) and water (1.0 ml). The vessel was sealed and the mixture was sparged with nitrogen for 5 min and then heated at 50° C. for 2 h. The mixture was partitioned between 1M HCl and ethyl acetate. The organic layer was washed with saturated sodium bicarbonate, brine, dried with sodium sulfate and filtered. The filtrate was treated with 3-mercaptopropyl functionalized silica gel, filtered and evaporated. The residue was chromatographed on silica gel eluting with hexane/EtOAc (1:1) to give a solid (50 mg, 83%).

Part I. Preparation of (E)-N-(4-(5-(2,4-dioxo-3,4-dihydropyrimidin-1(2H)-yl)-3-(1-hydroxy-2-methyl-propan-2-yl)-2-methoxystyryl)phenyl)methane-sulfonamide A solution of the product from Part H (120 mg, 0.20 mmol) in THF (5.0 ml) was treated with 1 M TBAF (0.800 ml, 0.800 mmol) in THF and stirred for 16 h. The mixture was partitioned with water and ethyl acetate. The organic layer was washed (3× brine), dried with sodium sulfate, filtered and evaporated. The residue was chromatographed on silica gel eluting with 4% methanol in $CH_2Cl_2$ to give a solid (85 mg, 88%). $^1$H NMR (300 MHz, DMSO-$d_6$) δ ppm 1.30 (s, 6H) 3.01 (s, 3H) 3.62 (d, J=5.52 Hz, 2H) 3.77 (s, 3H) 4.67 (t, J=5.33 Hz, 1H) 5.66 (d, J=8.09 Hz, 1H) 7.21 (m, 5H) 7.62 (m, 3H) 7.72 (d, J=8.09 Hz, 1H) 9.85 (s, 1H) 11.42 (s, 1H). MS (ESI+) m/z 503 (M+NH4)+.

Example 23

Preparation of (E)-N-(4-(5-(2,4-dioxo-3,4-dihydro-pyrimidin-1(2H)-yl)-3-iodo-2-methoxystyryl)phe-nyl)methanesulfonamide (compound IB-L1-1.51)

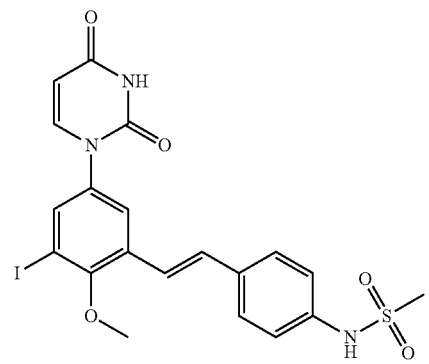 [SMILES: COc1c(I)cc(-n2ccc(=O)[nH]c2=O)cc1/C=C/c1ccc(NS(C)(=O)=O)cc1]

Part A. Preparation of 1,3,5-triiodo-2-methoxybenzene

In a 250 mL pressure vessel was added 2,4,6-triiodophenol (5 g, 10.60 mmol) in MTBE (60 ml) to give a yellow solution. The solution was cooled in an ice bath and 2.0M trimethyl-silyldiazomethane (7.95 ml, 15.90 mmol) was added at a fast drip followed by dropwise addition of methanol (6 mL) resulting in calm bubbling. The vessel was sealed and stirred at room temperature for 4 h. The reaction solution was partitioned between EtOAc and water and the organic layer was washed with 1M HCl, saturated $NaHCO_3$, and saturated NaCl. The EtOAc was dried ($MgSO_4$), filtered and concentrated to give a tan solid that was used without purification (4.8 g, 94%).

Part B. Preparation of 1-(3,5-diiodo-4-methoxyphenyl)pyrimidine-2,4(1H,3H)-dione To a 100 mL round-bottom flask under $N_2$ was added the product from Part A (3.5 g, 7.2 mmol), 1H-pyrimidine-2,4-dione (0.97 g, 8.64 mmol), and potassium phosphate tribasic (3.2 g, 15.0 mmol) in DMSO (50 ml) to give a colorless suspension. N-(2-cyanophenyl)picolinamide (320 mg, 1.44 mmol) was added and the mix was sparged with $N_2$ for 5 min. Copper(I) iodide (137 mg, 0.72 mmol) was added and the mix was sparged once again for 10 min, placed under $N_2$ and heated at 60° C. for 18 h. The mixture was cooled and partitioned between EtOAc and water adjusting the pH to 1 with HCl. The aqueous layer was extracted 2× with EtOAc. The organics were combined, washed with water, saturated $NaHCO_3$, and saturated NaCl, dried ($Na_2SO_4$), treated with 3-mercaptopropyl functionalized silica, filtered and concentrated. The resulting solid was triturated in 2:1 hexane/EtOAc to give an off white powder (2.2 g, 62%).

Part C. Preparation of (E)-N-(4-(5-(2,4-dioxo-3,4-dihydropyrimidin-1(2H)-yl)-3-iodo-2-methoxystyryl)phenyl)methanesulfonamide In a 5 ml microwave tube was mixed the product from Part B (141 mg, 0.30 mmol), the product from Example 13B, Part B (72.3 mg, 0.300 mmol), 1,1'-bis(diphenylphosphino)ferrocene-palladium(II)dichloride $CH_2Cl_2$ complex (12.25 mg, 0.015 mmol) and potassium phosphate (70.0 mg, 0.330 mmol) in THF (3.0 ml) and water (1.0 ml). The mixture was sparged with nitrogen for 5 min and heated at 50° C. for 2 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered and evaporated. The residue was chromatographed on silica eluting with 5% methanol in $CH_2Cl_2$ to give a solid (47 mg, 29%). $^1$H NMR (300 MHz, DMSO-d$_6$) δ ppm 3.02 (s, 3H) 3.77 (s, 3H) 5.67 (d, J=7.72 Hz, 1H) 7.28 (m, 4H) 7.60 (d, J=8.82 Hz, 2H) 7.76 (d, J=8.09 Hz, 1H) 7.81 (d, J=2.57 Hz, 1H) 7.86 (d, J=2.21 Hz, 1H) 9.90 (s, 1H) 11.48 (s, 1H). MS (ESI−) m/z 538 (M−H)+.

Example 24

Preparation of (E)-N-(4-(5-(2,4-dioxo-3,4-dihydropyrimidin-1(2H)-yl)-2-methoxy-3-(methylsulfonyl) styryl)phenyl)methanesulfonamide (compound IB-L1-1.49)

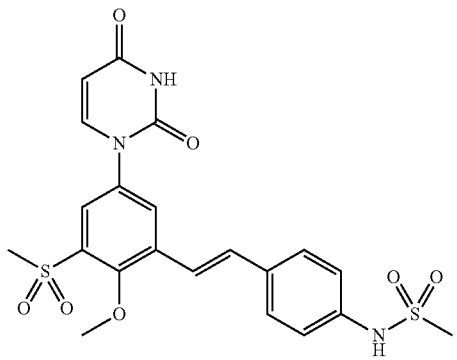

Part A. Preparation of 4-nitrobenzene-2-diazo-1-oxide

To a 250 mL round-bottom flask was added 2-amino-4-nitrophenol (6.165 g, 40.0 mmol) in 48% tetrafluoroboric acid (15 ml). Sodium nitrite (2.76 g, 40.0 mmol) in water (6 ml) was added dropwise at 0° C. and the mixture was stirred at room temperature for 30 min. The solid was collected by filtration, washed with tetrafluoroboric acid and water. The solid was suspended in acetone (50 ml), filtered and dried to give a solid (3.31 g, 50%).

Part B. Preparation of 2-(methylthio)-4-nitrophenol

To a 1 L beaker was added the product from Part A (2.70 g, 16.35 mmol) in ice water (250 g) to give a brown suspension. Copper (0.520 g, 8.18 mmol) was added, followed by addition of sodium thiomethoxide (2.292 g, 32.7 mmol) in water (50 ml) slowly. The mixture was stirred at room temperature for 24 h. The mixture was filtered and the filtrate was acidified with 1M HCl producing a solid that was collected by filtration and dried (2.53 g, 84%).

Part C. Preparation of 2-(methylsulfonyl)-4-nitrophenol

To a 250 mL round-bottom flask was added the product from Part B (1.111 g, 6.00 mmol) in MeOH (20 ml) to give a brown suspension. Oxone (7.746 g, 12.60 mmol) in water (20 ml) was added slowly at 0° C. The mixture was warmed to room temperature, stirred for 1 h and partitioned with ethyl acetate and 1 M HCl. The organic layer was washed with brine, dried with sodium sulfate, filtered and evaporated. The residue was chromatographed on silica gel eluting with 1% to 5% methanol in $CH_2Cl_2$ to give a solid (0.472 g, 36%).

Part D. Preparation of 2-iodo-6-(methylsulfonyl)-4-nitrophenol

To a 50 mL round-bottom flask was added the product from Part C (470 mg, 2.164 mmol) in MeOH (10 ml) and water (2.5 ml). Iodine monochloride (0.130 ml, 2.60 mmol) in $CH_2Cl_2$ (2.0 mL) was added drop-wise and the mixture was stirred at room temperature, poured into water (200 mL) and stirred for 10 min. The resulting solid was collected by filtration and dried (636 mg, 86%).

Part E. Preparation of 1-iodo-2-methoxy-3-(methylsulfonyl)-5-nitrobenzene

To a 50 mL pressure vessel was added the product from Part D (630 mg, 1.836 mmol) in MTBE (6 ml) to give a yellow solution. The mixture was cooled in an ice bath and 2M trimethylsilyl-diazomethane (1.377 ml, 2.75 mmol) was added at a fast drip followed by drop-wise addition of MeOH (0.4 ml) resulting in calm bubbling. The vessel was sealed and stirred at room temperature for 1 h. The mixture was partitioned with ethyl acetate and 1M HCl. The organic layer was washed with saturated sodium bicarbonate, brine, dried with sodium sulfate, filtered and evaporated to give an off-white solid (655 mg, 100%).

Part F. Preparation of 3-iodo-4-methoxy-5-(methylsulfonyl)aniline

To a 250 mL round-bottom flask was added the product from Part E (0.650 g, 1.820 mmol), ammonium chloride (0.146 g, 2.73 mmol), and iron (0.508 g, 9.10 mmol) in THF/MeOH/water (50 ml, 2/2/1). The mixture was refluxed for 2 h, cooled and filtered. The filtrate was evaporated and the residue was partitioned with ethyl acetate and water. The organic layer was washed with brine, dried with sodium sulfate, filtered and evaporated to give a solid (590 mg, 99%).

Part G. Preparation of (E)-N-(3-iodo-4-methoxy-5-(methylsulfonyl)phenylcarbamoyl)-3-methoxyacrylamide To a 100 mL round-bottom flask was added the product from Part F (500 mg, 1.528 mmol) in DMF (15.0 ml). The solution was cooled under nitrogen to −20° C. and (E)-3-methoxyacryloyl isocyanate (15.28 ml, 6.11 mmol; prepared as described by Santana, L.; et al. J. Heterocyclic Chem. 1999, 36, 293-295) was added dropwise. The mixture was stirred at this temperature for 15 min, then warmed to room temperature and stirred for 45 min. The mixture was diluted with ethyl acetate and washed by water (3×50 ml), brine (3×50 ml), dried with sodium sulfate, filtered and evaporated. The residue was triturated with ethyl acetate/hexane to give a solid (425 mg, 61%).

Part H. Preparation of 1-(3-iodo-4-methoxy-5-(methylsulfonyl)phenyl)pyrimidine-2,4(1H,3H)-dione To a 100 mL round-bottom flask was added the product from Part G (420 mg, 0.925 mmol) in ethanol (10 ml) to give a suspension. Concentrated sulfuric acid (1 mL, 18.76 mmol) in water (10 ml) was added and the mixture was heated at 110° C. for 2 h. The reaction mix was cooled, diluted with water (50 ml) and stirred for 10 min. The solid material was collected by filtration, washed with water and dried to give a white solid (325 mg, 83%).

Part I. Preparation of (E)-N-(4-(5-(2,4-dioxo-3,4-dihydropyrimidin-1(2H)-yl)-2-methoxy-3-(methylsulfonyl)styryl)phenyl)methanesulfonamide In a 5 ml microwave tube was added the product from Part H (63.3 mg, 0.15 mmol), the product from Example 13B, Part B (36.2 mg, 0.150 mmol), potassium phosphate (66.9 mg, 0.315 mmol), PA-Ph (CAS 97739-46-3) (1.315 mg, 4.50 µmol) and tris(dibenzylideneacetone)dipalladium(0) (1.374 mg, 1.500 µmol) in THF (3.0 ml) and water (1.0 ml). The vessel was sealed and the mixture was sparged with nitrogen for 5 min and heated at 50° C. for 2 h. The mixture was partitioned with ethyl acetate and 1M HCl. The organic layer was washed with saturated sodium bicarbonate, brine, dried with sodium sulfate and filtered. The filtrate was treated with 3-mercaprpropyl functionalized silica gel, filtered and evaporated. The residue was triturated with methanol/CH$_2$Cl$_2$ to give a solid (62 mg, 84%). $^1$H NMR (300 MHz, DMSO-d$_6$) δ ppm 3.03 (s, 3H) 3.37 (s, 3H) 3.94 (s, 3H) 5.72 (d, J=7.72 Hz, 1H) 7.26 (m, 3H) 7.45 (m, 1H) 7.65 (d; J=8.46 Hz, 2H) 7.77 (d, J=2.57 Hz, 1H) 7.81 (d, J=8.09 Hz, 1H) 8.21 (d, J=2.57 Hz, 1H) 9.93 (s, 1H) 11.52 (s, 1H). MS (ESI+) m/z 509 (M+NH4)+.

Example 25

Preparation of (E)-methyl 2-(3-tert-butyl-5-(2,4-dioxo-3,4-dihydropyrimidin-1(2H)-yl)-2-methoxystyryl)-5-(methylsulfonamido)benzoate (compound IB-L1-1.7)

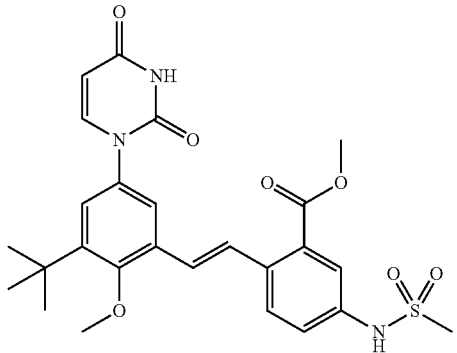 [SMILES: COC(=O)c1cc(NS(C)(=O)=O)ccc1/C=C/c1cc(-n2ccc(=O)[nH]c2=O)cc(C(C)(C)C)c1OC]

Part A. Preparation of methyl 2-((diethoxyphosphoryl)methyl)-5-nitrobenzoate

To a solution of methyl 2-methyl-5-nitrobenzoate (0.40 g, 2.05 mmol) in CCl$_4$ (20 ml) was added N-bromosuccinimide (365 mg, 2.05 mmol) and 2,2'-azobisisobutyronitrile (34 mg, 0.21 mmol). The resulting mixture was stirred at reflux for 18 h, cooled to room temperature and partitioned between EtOAc (50 ml) and H$_2$O (50 ml). The organic layer was dried over Na$_2$SO$_4$, filtered and concentrated in vacuo. The crude product was purified by column chromatography on silica gel using 1:3 EtOAc:hexanes as the eluent to give the bromide as an oil (345 mg, 61%). The oil was placed in triethylphosphite (5 ml) and heated with stirring at 120° C. for 3 h. The mixture was allowed to cool to room temperature, and the crude product was purified by column chromatography on silica gel using 5% MeOH in CH$_2$Cl$_2$ as the eluent. The title compound was obtained as an oil (313 mg, 75%).

Part B. Preparation of (E)-methyl 2-(3-tert-butyl-5-(2,4-dioxo-3,4-dihydropyrimidin-1(2H)-yl)-2-methoxystyryl)-5-nitrobenzoate To a solution of the product from Part A (360 mg, 1.09 mmol) and the product from Example 13 Å, Part D (329 mg, 1.09 mmol) in anhydrous CH$_2$Cl$_2$ (10 ml) was added potassium tert-butoxide (305 mg, 2.72 mmol). The resulting dark red solution was stirred at room temperature for 1 h, and then poured into 1 N aq. HCl (10 ml). The resulting mixture was extracted with CH$_2$Cl$_2$ (10 ml), dried over Na$_2$SO$_4$, filtered and concentrated in vacuo to give a solid. A solution of the solid in thionyl chloride (2.3 ml) was heated at 85° C. for 30 min, and the thionyl chloride was removed in vacuo. The residue was stirred in a 2:1 mixture of CH$_2$Cl$_2$ and MeOH (3 ml) for 30 min, and evaporated to dryness in vacuo. The crude product was purified by column chromatography on silica gel using 3% MeOH in CH$_2$Cl$_2$ as the eluent to give the title compound (350 mg, 69%).

Part C. Preparation of (E)-methyl 2-(3-tert-butyl-5-(2,4-dioxo-3,4-dihydropyrimidin-1(2H)-yl)-2-methoxystyryl)-5-(methylsulfonamido)benzoate To a solution of the product from Part B (465 mg, 0.97 mmol) in a 2:2:1 mixture of THF:MeOH:H$_2$O (±0 ml) was added iron powder (271 mg, 4.85 mmol), and ammonium chloride (78 mg, 1.46 mmol). The mixture was heated at 80° C. for 45 min, filtered through celite, and concentrated to dryness in vacuo. The residue was combined with methanesulfonyl chloride (0.16 ml, 2.0 mmol) and triethylamine (0.392 ml, 4.85 mmol) in anhydrous CH$_2$Cl$_2$ (10 ml) and the resulting mixture was stirred at room temperature for 3 h. The mixture was partitioned between 1 N HCl (20 ml) and CH$_2$Cl$_2$ (20 ml), and the organic layer was dried over Na$_2$SO$_4$, filtered and concentrated in vacuo. The crude product was purified by column chromatography on silica gel using 3% MeOH in CH$_2$Cl$_2$ as the eluent to give the title compound (270 mg, 53%). $^1$H NMR (300 MHz, DMSO-d$_6$) δ 11.42 (s, 1H) 10.07 (s, 1H) 7.90 (d, J=8.82 Hz, 1H) 7.66-7.79 (m, 3H) 7.52 (d, J=2.57 Hz, 1H) 7.44 (dd, J=8.64, 2.39 Hz, 1H) 7.14-7.26 (m, 2H) 5.65 (dd, J=7.72, 1.84 Hz, 1H) 3.86 (s, 3H) 3.79 (s, 3H) 3.04 (s, 3H) 1.38 (s, 9H).

Example 26

Preparation of (E)-2-(3-tert-butyl-5-(2,4-dioxo-3,4-dihydropyrimidin-1(2H)-yl)-2-methoxystyryl)-5-(methylsulfonamido)benzoic acid (compound IB-L1-1.4)

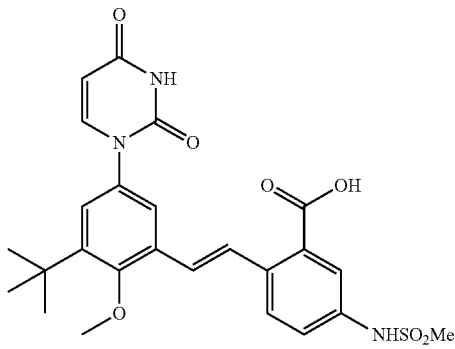

A solution of the product from Example 25 (55 mg, 0.104 mmol) in THF (1 ml) and 1N aq. NaOH (1 ml) was stirred in the dark at room temperature for 1.5 h. 1N aqueous HCl was added until pH 3, and the resulting mixture was extracted with EtOAc (2×2 ml). The combined organic layers were dried over $Na_2SO_4$, filtered and concentrated to give the title compound (53 mg, 99%). $^1H$ NMR (300 MHz, DMSO-$d_6$) δ 13.22 (br s, 1H) 11.40 (d, J=2.21 Hz, 1H) 10.02 (s, 1H) 7.72-7.91 (m, 3H) 7.68 (d, J=2.57 Hz, 1H) 7.49 (d, J=2.57 Hz, 1H) 7.42 (dd, J=8.64, 2.39 Hz, 1H) 7.21 (d, J=2.57 Hz, 1H) 7.16 (d, J=16.18 Hz, 1H) 5.64 (dd, J=7.72, 2.21 Hz, 1H) 3.79 (s, 3H) 3.04 (s, 3H) 1.38 (s, 9H).

Example 27

Preparation of (E)-N-(4-(3-tert-butyl-5-(2,4-dioxo-3,4-dihydropyrimidin-1(2H)-yl)-2-methoxystyryl)-3-(morpholine-4-carbonyl)phenyl)methanesulfonamide (compound IB-L1-1.23)

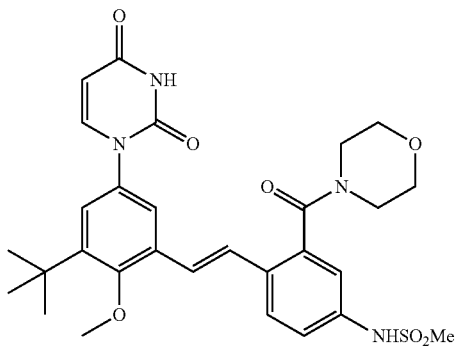

Part A. Preparation of (E)-2-(3-tert-butyl-5-(2,4-dioxo-3,4-dihydropyrimidin-1(2H)-yl)-2-methoxystyryl)-5-(methylsulfonamido)benzoyl chloride A solution of the product from Example 26 (257 mg, 0.50 mmol) in thionyl chloride (1.5 ml) was heated at 85° C. for 40 min and then concentrated and dried in vacuo to give the title compound as a solid (0.27 g).

Part B. Preparation of (E)-N-(4-(3-tert-butyl-5-(2,4-dioxo-3,4-dihydropyrimidin-1(2H)-yl)-2-methoxystyryl)-3-(morpholine-4-carbonyl)phenyl)methanesulfonamide To a solution of the product from Part A (24 mg, 0.045 mmol) in anhydrous $CH_2Cl_2$ (1 ml) was added morpholine (0.02 ml, 0.226 mmol). The mixture was stirred at room temperature for 2 h, and then partitioned between 1 N aq. HCl (5 ml) and EtOAc (2×5 ml). The combined organic layers were dried over $Na_2SO_4$, filtered and concentrated in vacuo. The crude product was purified by column chromatography on silica gel using 4% MeOH in $CH_2Cl_2$ as the eluent to give the title compound (19 mg, 71%). $^1H$ NMR (300 MHz, DMSO-$d_6$) δ ppm 11.41 (d, J=1.84 Hz, 1 μl) 10.04 (s, 1H) 7.85 (d, J=8.46 Hz, 1H) 7.75 (d, J=8.09 Hz, 1H) 7.52 (d, J=2.57 Hz, 1H) 6.99-7.34 (m, 5H) 5.65 (dd, J=7.72, 1.84 Hz, 1H) 3.76 (s, 3H) 3.56-3.71 (m, 4H) 3.40-3.51 (m, 2H) 3.11-3.22 (m, 2H) 3.06 (s, 3H) 1.38 (s, 9H).

Example 28

Preparation of (E)-N-(4-(3-tert-butyl-5-(2,4-dioxo-3,4-dihydropyrimidin-1(2H)-yl)-2-methoxystyryl)-3-(hydroxymethyl)phenyl)methanesulfonamide (compound IB-L1-1.10)

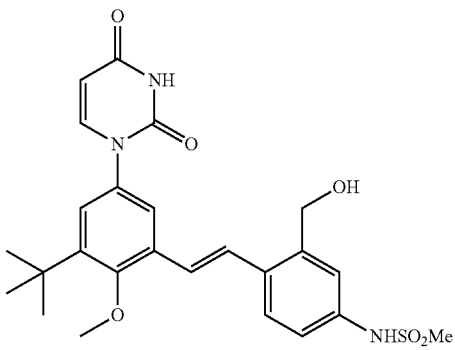

To a solution of the product from Example 27, Part A (375 mg, 0.705 mmol) in anhydrous THF (5 ml) at 0° C. under $N_2$ gas was added a 1.0 M solution of lithium tert-butoxyaluminiumhydride (1.8 ml, 1.8 mmol) dropwise. The resulting mixture was stirred at 0° C. for 30 min, and then allowed to warm to room temperature and was stirred for 1 h. The mixture was partitioned between 1 N aq. HCl (10 ml) and EtOAc (2×10 ml). The combined organic layers were dried over $Na_2SO_4$, filtered and concentrated in vacuo. The crude product was purified by column chromatography on silica gel using 3% MeOH in $CH_2Cl_2$ as the eluent to give the title compound (220 mg, 63%). $^1H$ NMR (300 MHz, DMSO-$d_6$) δ ppm 11.41 (s, 1H) 9.82 (s, 1H) 7.73 (t, J=8.27 Hz, 2H) 7.66 (d, J=2.57 Hz, 1H) 7.31-7.39 (m, 2H) 7.20 (d, J=2.57 Hz, 1H) 7.12-7.19 (m, 2H) 5.65 (d, J=8.09 Hz, 1H) 5.28 (t, J=5.52 Hz, 1H) 4.65 (d, J=5.52 Hz, 2H) 3.79 (s, 3H) 3.00 (s, 3H) 1.38 (s, 9H).

Example 29

Preparation of (E)-N-(4-(3-tert-butyl-5-(2,4-dioxo-3,4-dihydropyrimidin-1(2H)-yl)-2-methoxystyryl)-3-(methoxymethyl)phenyl)methanesulfonamide (compound IB-L1-1.13)

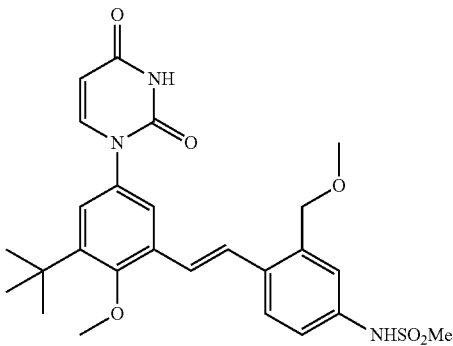

To a solution of the product from Example 28 (32 mg, 0.064 mmol) in anhydrous CH$_2$Cl$_2$ (1 ml) was added thionyl chloride (23 µL, 0.32 mmol), and the resulting mixture was stirred at room temperature for 30 min. The mixture was partitioned between saturated aq. NaHCO$_3$ (5 ml) and CH$_2$Cl$_2$ (5 ml) and the organic layer was dried over Na$_2$SO$_4$, filtered and concentrated. The residue was dissolved in MeOH (1 ml), and a solution of 25% NaOMe in MeOH (584, 0.254 mmol) was added. The resulting mixture was stirred at 50° C. for 2 h. The mixture was partitioned between 1 N aq. HCl (10 ml) and EtOAc (2×10 ml). The combined organic layers were dried over Na$_2$SO$_4$, filtered and concentrated in vacuo. The crude product was purified by column chromatography on silica gel using 3% MeOH in CH$_2$Cl$_2$ as the eluent to give the title compound (15 mg, 46%). $^1$H NMR (300 MHz, DMSO-d$_6$) δ 11.43 (s, 1H) 9.86 (s, 1H) 7.62-7.87 (m, 3H) 7.12-7.39 (m, 5H) 5.66 (d, J=1.72 Hz, 1H) 4.58 (s, 2H) 3.78 (s, 3H) 3.35 (s, 3H) 3.00 (s, 3H) 1.38 (s, 9H).

Example 30

Preparation of (E)-N-(4-(3-tert-butyl-5-(2,4-dioxo-3,4-dihydropyrimidin-1(2H)-yl)-2-methoxystyryl)-3-((isopentylamino)methyl)phenyl)methanesulfonamide (compound IB-L1-1.31)

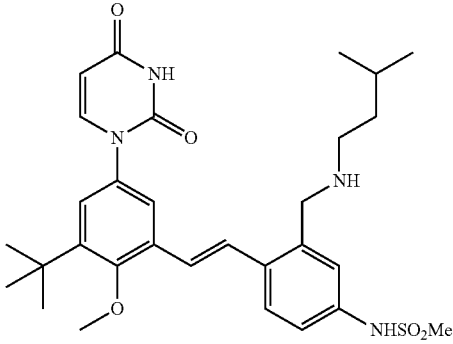

Part A. Preparation of (E)-N-(4-(3-tert-butyl-5-(2,4-dioxo-3,4-dihydropyrimidin-1(2H)-yl)-2-methoxystyryl)-3-formyl-phenyl)methanesulfonamide To a solution of the product from Example 28 (0.60 g, 1.20 mmol) in anhydrous DMA (15 ml) was added 2-iodoxybenzoic acid (336 mg, 1.20 mmol). The mixture was stirred at room temperature for 1 h, and then partitioned between EtOAc (20 ml) and H$_2$O (2×20 ml). The organic layer was dried over Na$_2$SO$_4$, filtered and concentrated in vacuo. The crude product was purified by column chromatography on silica gel using 2% MeOH in CH$_2$Cl$_2$ as the eluent to give the title compound as a colorless solid (395 mg, 66%). $^1$H NMR (300 MHz, DMSO-d$_6$) δ ppm 11.43 (d, J=2.21 Hz, 1H) 10.45 (s, 1H) 10.15 (s, 1H) 8.06 (d, J=16.18 Hz, 1H) 7.97 (d, J=8.82 Hz, 1H) 7.73-7.78 (m, 2H) 7.69 (d, J=2.57 Hz, 1H) 7.51 (dd, J=8.64, 2.39 Hz, 1H) 7.30 (d, J=16.18 Hz, 1H) 7.26 (d, J=2.57 Hz, 1H) 5.66 (dd, J=7.72, 2.21 Hz, 1H) 3.81 (s, 3H) 3.07 (s, 3H) 1.39 (s, 9H).

Part B. Preparation of (E)-N-(4-(3-tert-butyl-5-(2,4-dioxo-3,4-dihydropyrimidin-1(2H)-yl)-2-methoxystyryl)-3-((isopentylamino)methyl)phenyl)methanesulfonamide To a solution of the product from Part A (50 mg, 0.10 mmol) and 3-methylbutan-1-amine (14 µL, 0.10 mmol) in anhydrous THF (3 ml) was added sodium triacetoxyborohydride (32 mg, 0.15 mmol) and AcOH (94, 0.15 mmol). The resulting mixture was stirred at room temperature for 4 h, and then partitioned between H$_2$O (10 ml) and EtOAc (2×10 ml). The combined organic layers were dried over Na$_2$SO$_4$, filtered and concentrated in vacuo. The crude product was purified by column chromatography on silica gel using 3% MeOH in CH$_2$Cl$_2$ as the eluent to give the title compound (37 mg, 65%). $^1$H NMR (300 MHz, DMSO-d$_6$) δ 11.45 (d, J=1.84 Hz, 1H) 10.04 (s, 1H) 8.80-8.87 (m, 1H) 7.88 (d, J=8.46 Hz, 1H) 7.71-7.77 (m, 2H) 7.41-7.48 (m, 1H) 7.37 (d, J=2.21 Hz, 1H) 7.21-7.29 (m, 3H) 5.67 (dd, J=7.91, 2.02 Hz, 1H) 4.30-4.38 (m, 2H) 3.80 (s, 3H) 3.10 (s, 3H) 2.95-3.04 (m, 2H) 1.49-1.67 (m, 3H) 1.38 (s, 9H) 0.86 (d, J=6.25 Hz, 6H).

Example 31

Preparation of N-(4-(3-tert-butyl-5-(2,4-dioxo-3,4-dihydropyrimidin-1(2H)-yl)-2-methoxystyryl)-3-((E)-(methoxyimino)methyl)phenyl)methanesulfonamide (compound IB-L1-1.19)

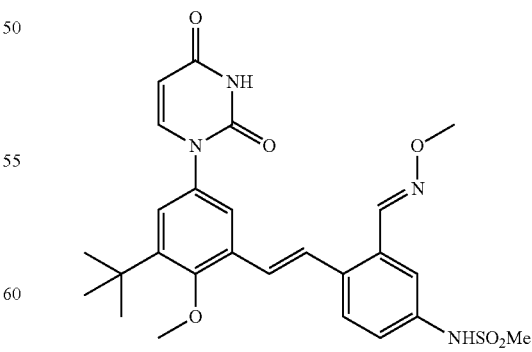

To a solution of the product from Example 30, Part A (35 mg, 0.070 mmol) in EtOH (2 ml) was added O-methoxylamine hydrochloride (29 mg, 0.35 mmol) and sodium bicarbonate (30 mg, 0.35 mmol). The resulting mixture was stirred at 70° C. for 2 h. To the mixture was added 1 N aq. HCl (1 ml) to give a colorless precipitate that was filtered and dried to give the title compound as a colorless solid (24 mg, 64%). $^1$H NMR (300 MHz, DMSO-d$_6$) δ ppm 11.43 (d, J=2.21 Hz, 1H) 9.94 (s, 1H) 8.74 (s, 1H) 7.79-7.85 (m, 2H) 7.76 (d, J=7.72 Hz, 1H) 7.57-7.65 (m, 2H) 7.32 (dd, J=8.64, 2.39 Hz, 1H) 7.23 (d, J=2.57 Hz, 1H) 7.18 (d, J=16.18 Hz, 1H) 5.66 (dd, J=7.72, 2.21 Hz, 1H) 3.93 (s, 3H) 3.79 (s, 3H) 3.03 (s, 3H) 1.38 (s, 9H).

Example 32

Preparation of (E)-N-(4-(3-tert-butyl-5-(2,4-dioxo-3,4-dihydropyrimidin-1(2H)-yl)-2-methoxystyryl)-3-(oxazol-2-yl)phenyl)methanesulfonamide (compound IB-L1-1.26)

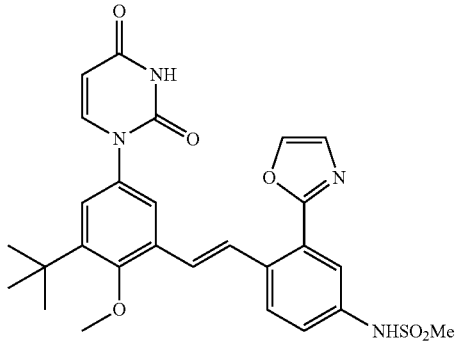

To a solution of the product from Example 27, Part A (80 mg, 0.15 mmol) in tetramethylene sulfone (1.5 ml) was added 1H-1,2,3-triazole (10 μL, 0.17 mmol) and potassium carbonate (73 mg, 0.53 mmol). The mixture was heated for 35 min at 130° C. in a microwave reactor. After cooling to room temperature, the mixture was partitioned between 1 N aqueous HCl (10 ml) and EtOAc (2×10 ml). The combined organic layers were dried over Na$_2$SO$_4$, filtered and concentrated in vacuo. The crude product was purified by column chromatography on silica gel using 3% MeOH in CH$_2$Cl$_2$ as the eluent to give the title compound (37 mg, 46%). $^1$H NMR (300 MHz, DMSO-d$_6$) δ 11.41 (d, J=1.84 Hz, 1H) 10.10 (s; 1H) 8.29 (d, J=1.10 Hz, 1H) 8.05 (d, J=16.18 Hz, 1H) 7.95 (d, J=8.82 Hz, 1H) 7.82 (d, J=2.21 Hz, 1H) 7.74 (d, J=8.09 Hz, 1H) 7.51 (d, J=2.57 Hz, 1H) 7.46 (d, J=0.74 Hz, 1H) 7.39 (dd, J=8.64, 2.39 Hz, 1H) 7.20-7.30 (m, 2H) 5.65 (dd, J=7.91, 2.02 Hz, 1H) 3.80 (s, 3H) 3.07 (s, 3H) 1.38 (s, 9H).

Example 33

Preparation of (E)-N-(4-(3-tert-butyl-5-(2,4-dioxo-3,4-dihydropyrimidin-1(2H)-yl)-2-methoxystyryl)-3-(1H-imidazol-2-yl)phenyl)methanesulfonamide (compound IB-L1-1.16)

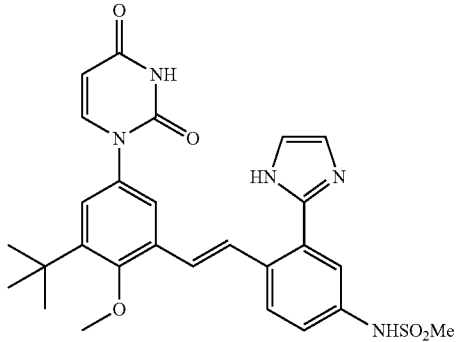

To a solution of the product from Example 30, Part A (50 mg, 0.10 mmol) in EtOH (2 ml) was added glyoxal (57 uL, 0.50 mmol) and concentrated aqueous NH$_4$OH (70 uL, 0.50 mmol). The resulting mixture was stirred at room temperature for 16 h. To the mixture was added 1 N aq. HCl until pH=7, and the mixture was partitioned between H$_2$O (10 ml) and EtOAc (2×10 ml). The combined organic layers were dried over Na$_2$SO$_4$, filtered and concentrated in vacuo. The crude product was purified by column chromatography on silica gel using 5% MeOH in CH$_2$Cl$_2$ as the eluent to give the title compound (27 mg, 50%). NMR (300 MHz, DMSO-d$_6$) δ 12.39 (s, 1H) 11.40 (d, J=1.84 Hz, 1H) 9.98 (s, 1H) 7.89 (d, J=8.82 Hz, 1H) 7.66-7.76 (m, 2H) 7.38 (t, J=2.21 Hz, 2H) 7.23-7.31 (m, 2H) 7.06-7.21 (m, 3H) 5.63 (dd, J=8.09, 1.84 Hz, 1H) 3.78 (s, 3H) 3.07 (s, 3H) 1.37 (s, 9H).

Example 34

Preparation of (E)-tert-butyl 2-(3-tert-butyl-5-(2,4-dioxo-3,4-dihydropyrimidin-1(2H)-yl)-2-methoxystyryl)-5-(methylsulfonamido)phenylcarbamate (compound IB-L1-1.32)

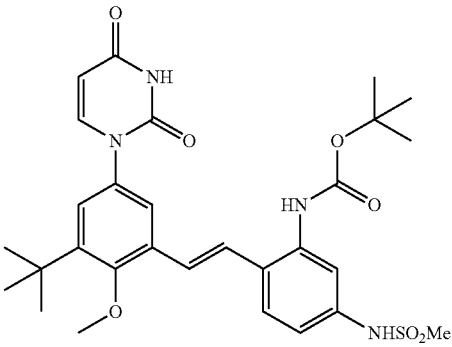

To a solution of the product from Example 26 (75 mg, 0.146 mmol) in tert-butanol (4 ml) was added diphenylphosphoryl azide (47 μL 0.219 mmol) and triethylamine (31 μL, 0.219 mmol). The resulting mixture was stirred at 80° C. for 18 h. The cooled mixture was partitioned between H$_2$O (10 ml) and EtOAc (2×10 ml). The combined organic layers were dried over Na$_2$SO$_4$, filtered and concentrated in vacuo. The crude product was purified by column chromatography on silica gel using 3% MeOH in CH$_2$Cl$_2$ as the eluent to give the title compound (16 mg, 19%). $^1$H NMR (300 MHz, DMSO-d$_6$) δ 11.45 (d, J=1.84 Hz, 1H) 9.86 (s, 1H) 9.03 (s, 1H) 7.75 (d, J=7.72 Hz, 2H) 7.55 (d, J=2.57 Hz, 1H) 7.10-7.33 (m, 4H) 7.04 (dd, J=8.64, 2.39 Hz, 1H) 5.66 (dd, J=7.91, 2.02 Hz, 1H) 3.78 (s, 3H) 3.02 (s, 3H) 1.45 (s, 9H) 1.38 (s, 9H).

Example 35

Preparation of (E)-N-(3-amino-4-(3-tert-butyl-5-(2,4-dioxo-3,4-dihydropyrimidin-1(2H)-yl)-2-methoxystyryl)phenyl)methanesulfonamide (compound IB-L1-1.28)

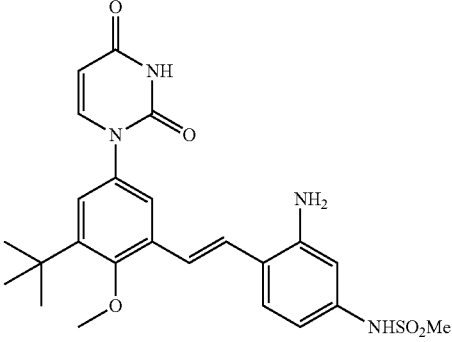

The procedure described for the preparation of Example 34 provided the title compound, which was purified by column chromatography on silica gel using 5% methanol in $CH_2Cl_2$ as the eluent (6 mg, 9%). $^1H$ NMR (300 MHz, DMSO-$d_6$) δ 11.44 (d, J=2.21 Hz, 1H) 9.55 (s, 1H) 7.77 (d, J=2.57 Hz, 1H) 7.75 (d, J=8.09 Hz, 1H) 7.45 (d, J=8.46 Hz, 1H) 7.33 (d, J=15.81 Hz, 1H) 7.15 (d, J=2.57 Hz, 1H) 7.00 (d, J=16.18 Hz, 1H) 6.56 (d, J=2.21 Hz, 1H) 6.44 (dd, J=8.46, 2.21 Hz, 1H) 5.66 (dd, J=7.91, 2.02 Hz, 1H) 5.56 (s, 2H) 3.78 (s, 3H) 2.97 (s, 3H) 1.37 (s, 9H).

Example 36

Preparation of (E)-N-(4-(3-tert-butyl-5-(2,4-dioxo-3,4-dihydropyrimidin-1(2H)-yl)-2-methoxystyryl)-2-fluorophenyl)methanesulfonamide (compound IB-L1-1.5)

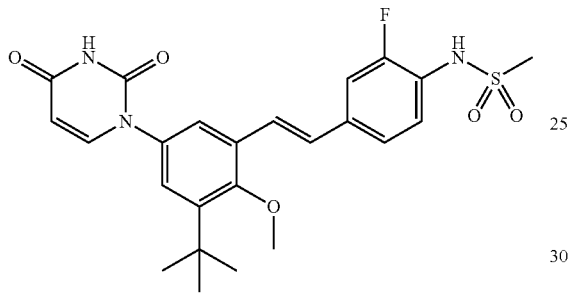

Part A. Preparation of (3-fluoro-4-nitrophenyl)methanol

To a solution of 3-fluoro-4-nitrobenzoic acid (2.0 g, 10.8 mmol) in THF (50 ml) at 0° C. was added $BH_3.Me_2S$ complex (2.215 ml, 22.15 mmol) drop-wise. The mixture was stirred at 0° C. for 3 h, and was then stirred at 65° C. for 18 h. To the cooled mixture was added ice (50 g), followed by 1 N aq. HCl (100 ml), and the resulting mixture was extracted with EtOAc (200 ml). The organic layer was dried over $Na_2SO_4$, filtered and concentrated in vacuo to provide the title compound as a white solid (1.79 g, 97%).

Part B. Preparation of 4-(bromomethyl)-2-fluoro-1-nitrobenzene

A solution of the product from Part A (1.79 g, 10.46 mmol), N-bromosuccinimide (2.234 g, 12.55 mmol) and triphenylphosphine (3.29 g, 12.55 mmol) in $CH_2Cl_2$ (100 ml) and THF (50 ml) was stirred at room temperature for 3 h. The mixture was partitioned between $H_2O$ (200 ml) and EtOAc (400 ml), and the organic layer was dried over $Na_2SO_4$, filtered and concentrated in vacuo. The crude product was purified by column chromatography on silica gel using 1:1 EtOAc:hexanes as the eluent to give the title compound (1.14 g, 47%).

Part C. Preparation of diethyl 3-fluoro-4-nitrobenzylphosphonate

The product from Part B (1.25 g, 5.34 mmol) was subjected to the conditions described for Example 6, Part B to provide the title product (0.75 g, 48%)., Part D. Preparation of (E)-N-(4-(3-tert-butyl-5-(2,4-dioxo-3,4-dihydropyrimidin-1(2H)-yl)-2-methoxystyryl)-2-fluorophenyl)methanesulfonamide The product from Part C (0.193 g, 0.662 mmol) was subjected to the conditions described for Example 13 A, Part E, Part F, and Part G to provide the title product as a colorless solid (15 mg, 5%). $^1H$ NMR (300 MHz, DMSO-$d_6$) δ 11.43(s, 1H), 9.67 (s, 1H), 7.76 (d, J=8.1 Hz, 1H), 7.62 (m, 2H), 7.41 (m, 2H), 7.38 (m, 1H), 7.23 (m, 2H), 5.66(dd, J=8.0, 2.0 Hz, 1H), 3.80 (s, 3H), 3.05 (s, 3H), 1.38(s, 9H).

Example 37

Preparation of (E)-N-(4-(3-tert-butyl-5-(2,4-dioxo-3,4-dihydropyrimidin-1(2H)-yl)-2-methoxystyryl)-2-fluoro-5-methylphenyl)methanesulfonamide (compound IB-L1-1.15)

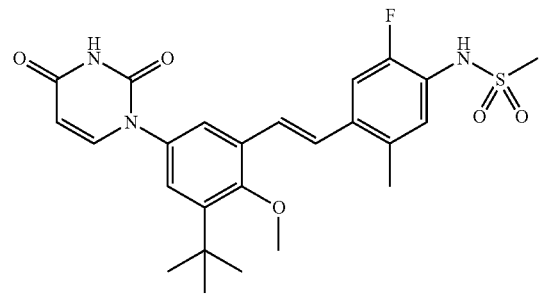 [SMILES: COc1c(/C=C/c2cc(F)c(NS(C)(=O)=O)cc2C)cc(-n2ccc(=O)[nH]c2=O)cc1C(C)(C)C]

Part A. Preparation of N-(4-bromo-2-fluoro-5-methylphenyl)methanesulfonamide

To a solution of 4-bromo-2-fluoro-5-methylaniline (2.04 g, 10.0 mmol) in anhydrous $CH_2Cl_2$ (20 ml) and pyridine (3.23 ml, 40.0 mmol) was added methanesulfonyl chloride (0.86 ml, 11.0 mmol) and the resulting mixture was stirred at room temperature for 2 h. Solvent was removed in vacuo, and the residue was partitioned between EtOAc and 1M aq. HCl. The organic layer was washed with saturated aqueous $NaHCO_3$, brine and then dried over $Na_2SO_4$. The drying agent was filtered off, and the filtrate was concentrated to give the title compound as a solid (2.80 g, 99%).

Part B. Preparation of N-(4-ethynyl-2-fluoro-5-methylphenyl)methanesulfonamide

A mixture of the product from Part A (3.0 g, 10.63 mmol), triphenylphosphine (0.279 g, 1.06 mmol), trimethylsilylacetate (6.0 ml, 42.5 mmol) and palladium(II) acetate (0.12 g, 0.53 mmol) in triethylamine (30 ml) and toluene (15 ml) under $N_2$ was heated at 80° C. for 5 h. The mixture was allowed to cool to room temperature, and was partitioned between EtOAc and 1M aq. HCl. The organic layer was washed with saturated $NaHCO_3$ and brine, dried over $Na_2SO_4$, filtered and concentrated in vacuo. The crude product was purified by column chromatography on silica gel using a solvent gradient of 10% to 35% EtOAc in hexanes to give an oil (3.0 g, 94%). To a solution of the oil (3.0 g, 10.0 mmol) in MeOH (50 ml) was added 1M aq. NaOH (21 ml, 21.0 mmol), and the resulting mixture was stirred at room temperature for 45 min. The mixture was partitioned between EtOAc and 1M aq. HCl, and the organic layer was washed with brine and dried over $Na_2SO_4$. The drying agent was filtered off, and the filtrate was concentrated in vacuo to give the title compound as a solid (2.3 g, quant.).

Part C. Preparation of (E)-5-fluoro-2-methyl-4-(methylsulfonamido)styrylboronic acid The product from Part B (0.20 g, 0.88 mmol) was subjected to the conditions described for the preparation of Example 13B, Part B to give the title compound (42 mg, 17%).

Part D. Preparation of (E)-N-(4-(3-tert-butyl-5-(2,4-dioxo-3,4-dihydropyrimidin-1(2H)-yl)-2-methoxystyryl)-2-fluoro-5-methyl-phenyl)methanesulfonamide The product from Part C (40 mg, 0.15 mmol) was subjected to the conditions described for the preparation of Example 13B, Part I to give the title compound (51 mg, 83%). $^1$H NMR (300 MHz, DMSO-$d_6$) δ 11.42 (d, J=2.21 Hz, 1H) 9.59 (s, 1H) 7.70-7.78 (m, 2H) 7.66 (d, J=11.77 Hz, 1H) 7.20-7.32 (m, 3H) 5.65 (dd, J=7.72, 2.21 Hz, 1H) 3.79 (s, 3H) 3.05 (s, 3H) 2.38 (s, 3H) 1.38 (s, 9H).

Example 38

Preparation of methyl 2-(3-tert-butyl-5-(2,4-dioxo-3,4-dihydropyrimidin-1(2H)-yl)-2-methoxyphenethyl)-5-(methylsulfonamido)benzoate (compound IB-L5-2-1.1)

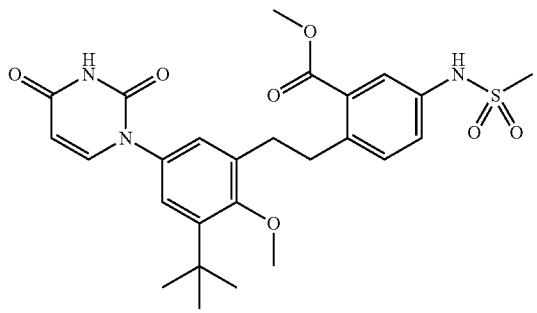 [SMILES: COC(=O)c1cc(NS(C)(=O)=O)ccc1CCc1cc(-n2ccc(=O)[nH]c2=O)cc(C(C)(C)C)c1OC]

To a solution of the product from Example 25 (40 mg, 0.076 mmol) in MeOH (2 ml) and THF (2 ml) was added 10% Pd/C (20 mg) and the resulting mixture was stirred at room temperature under 1 atm H$_2$ for 16 h. The mixture was filtered through celite and concentrated in vacuo to give a solid (27.5 mg, 68%). $^1$H NMR (300 MHz, DMSO-$d_6$) δ □11.39 (s, 1H) 9.88 (s, 1H) 7.61-7.71 (m, 2H) 7.28-7.36 (m, 2H) 7.20 (d, J=2.57 Hz, 1H) 7.13 (d, J=2.94 Hz, 1H) 5.64 (d, J=7.72 Hz, 1H) 3.83 (s, 3H) 3.75 (s, 3H) 3.14 (dd, J=10.30, 5.88 Hz, 2H) 2.96 (s, 3H) 2.83-2.92 (m, 2H) 1.34 (s, 9H).

Example 39

Preparation of N-(4-(3-tert-butyl-5-(2,4-dioxo-3,4-dihydropyrimidin-1(2H)-yl)-2-methoxyphenethyl)phenyl)methanesulfonamide (compound IB-L5-2-1.2)

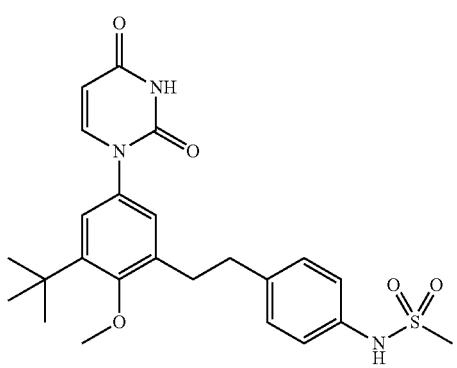

The product from Example 13B, Part M (200 mg, 0.426 mmol) was dissolved in MeOH (10 ml) followed by the addition of 10% Palladium on activated Carbon (50 mg). The resultant mixture was evacuated and a hydrogen balloon attached then stirred at room temperature for 48 h. The mixture was then filtered through celite and the filtrate concentrated under vacuum to an oil which was dissolved in ethanol (4 ml) then a 1N solution of aqueous sodium hydroxide (3.8 ml, 3.8 mmol) was added and the solution stirred at room temperature for 18 h. The ethanol was then removed under vacuum and a 1N solution of aqueous hydrochloric acid (4 ml) was added to acidify the mixture followed by extraction with EtOAc (2×10 mL). The organic extracts were combined, dried and purified by column chromatography on silica gel using 5% MeOH in CH$_2$Cl$_2$ as the eluent to provide the title compound as a colorless solid (82 mg, 41%). $^1$H NMR (300 MHz, DMSO-$d_6$) δ 011.39 (s, 1H), 9.60 (s, 1H), 7.65 (d, J=8.1 Hz, 1H), 7.23 (m, 3H), 7.17 (m, 3H), 5.64 (d, J=7.7 Hz, 1H), 3.77 (s, 3H), 2.93 (s, 3H), 2.88 (br s, 4H), 1.35 (s, 9H).

Example 40

Preparation of (E)-N-(4-(3-tert-butyl-5-(2,4-dioxo-3,4-dihydropyrimidin-1(2H)-yl)-2-ethoxystyryl)phenyl)methanesulfonamide (compound IB-L1-1.30)

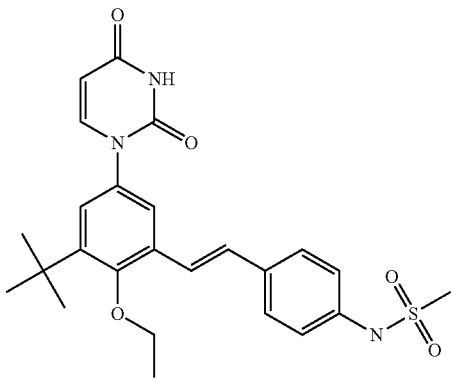 [SMILES: CCOc1c(/C=C/c2ccc(NS(C)(=O)=O)cc2)cc(-n2ccc(=O)[nH]c2=O)cc1C(C)(C)C]

Part A. Preparation of 2-tert-butyl-4-iodophenol

To a 250 mL round-bottom flask was added 2-tert-butylphenol (3.76 g, 25 mmol) in MeOH (50.0 ml) to give a colorless solution. Sodium hydroxide (1.200 g, 30.0 mmol) was added and the mix was stirred until the hydroxide was completely dissolved. The solution was cooled to 0° C. and treated with sodium iodide (1.75 g, 11.6 mmol) followed by drop-wise addition of 10% sodium hypochlorite solution (7.2 ml, 11.6 mmol). The addition of sodium iodide followed by sodium hypochlorite was repeated twice and the mixture was stirred at 0° C. for 30 min. The mixture was treated with 10% w/w solution of sodium thiosulfate, stirred for 30 min and treated with concentrated HCl dropwise to a constant pH of 1. The mixture was extracted 3× with EtOAc. The extracts were combined, washed with brine, dried (MgS04), filtered and concentrated. The crude oil was flash chromatographed on an Isco 80 g silica cartridge eluting with hexane to >4:1 hexane/EtOAc to give a yellow oil (5.2 g, 75%).

Part B. Preparation of 2-bromo-6-tert-butyl-4-iodophenol

To a 250 mL round-bottom flask was added the product from Part A (4.8 g, 17.38 mmol) and 1,3-dibromo-5,5-dimethylhydantoin (2.61 g, 9.13 mmol) in chloroform (87 ml) to give an orange solution. The reaction mixture was stirred for 2 h resulting in a black solution that was washed with water, brine, dried (Na$_2$SO$_4$) and concentrated. The black oil was flash chromatographed on a 120 g Isco silica cartridge eluting with hexane to give a pinkish solid (4.84 g, 78%).

Part C. Preparation of 1-bromo-3-tert-butyl-2-ethoxy-5-iodobenzene

To a 50 mL round-bottom flask was added the product from Part B (888 mg, 2.5 mmol), ethyl iodide (409 mg, 2.63 mmol), and potassium carbonate (415 mg, 3.00 mmol) in acetone (12 ml) to give a green suspension. The mixture was heated at reflux for 16 h, cooled and concentrated. The residue was partitioned between water and EtOAc. The organic layer was washed twice with brine, dried over Na$_2$SO$_4$, filtered and concentrated to a red oil. The oil was flash chromatographed on an Isco 40 g silica cartridge eluting with hexane to give a clear oil (820 mg, 86%).

Part D. Preparation of 1-(3-bromo-5-tert-butyl-4-ethoxyphenyl)pyrimidine-2,4(1H,3H)-dione In a 20 mL microwave tube under nitrogen flush was added the product from Part C (0.4 g, 1.044 mmol), 1H-Pyrimidine-2,4-dione (0.140 g, 1.253 mmol), and potassium phosphate tribasic (0.465 g, 2.193 mmol) in DMSO (5 ml) to give a colorless suspension. N-(2-cyanophenyl)picolinamide (0.047 g, 0.209 mmol) was added and the mix was sparged with nitrogen for 10 min. Copper(I) iodide (0.020 g, 0.104 mmol) was added and the mix was sparged once again for 10 min, placed under nitrogen and heated at 60° C. for 18 h. The mixture was cooled and partitioned between EtOAc and water adjusting the pH to 1 with HCl. The aqueous layer was extracted 2× with EtOAc. The organics were combined, washed with water, saturated NaHCO$_3$, and saturated NaCl. The organic layer was dried (Na$_2$SO$_4$), stirred with 3-mercaptopropyl functionalized silica for 1 h, filtered and concentrated. The crude product was purified by chromatography on an Isco 12 g silica cartridge eluting with 2% MeOH in CH$_2$Cl$_2$ to give a white powder (266 mg, 69%).

Part E. Preparation of (E)-N-(4-(3-tert-butyl-5-(2,4-dioxo-3,4-dihydropyrimidin-1(2H)-yl)-2-ethoxystyryl)phenyl)methanesulfonamide A mixture of the product from Part D (55.1 mg, 0.15 mmol), the product from Example 13B, Part B (36.2 mg, 0.150 mmol), potassium phosphate tribasic (63.7 mg, 0.300 mmol) and 1,1'-bis(di-tert-butylphosphino)ferrocene palladium dichloride (4.89 mg, 7.50 mmol) in THF (3 ml) water (1 ml) was sparged for 10 min with nitrogen, and then sealed and heated at 50° C. for 4 h. The mixture was cooled to room temperature and diluted into EtOAc. The EtOAc layer was washed with 1M HCl, saturated NaHCO3, saturated NaCl, dried (Na$_2$SO$_4$) and treated simultaneously with mercaptopropyl silica gel, filtered and concentrated. The crude product was purified by column chromatography on silica gel using 2% MeOH in CH$_2$Cl$_2$ as the eluent to give the title compound as a solid (40 mg, 55%) m.p. 265-266° C. $^1$H NMR (300 MHz, DMSO-d$_6$) δ 11.42 (s, 1H) 9.87 (s, 1H) 7.76 (d, J=8.09 Hz, 1H) 7.55-7.66 (m, 3H) 7.17-7.27 (m, 5H) 5.65 (dd, J=7.72, 1.47 Hz, 1H) 3.89 (q, J=6.74 Hz, 2H) 3.02 (s, 3H) 1.45 (t, J=6.99 Hz, 3H) 1.39 (s, 9H).

The following compounds were prepared utilizing the above discussion:

(E)-N-(4-(1-(3-tert-butyl-5-(2,4-dioxotetrahydropyrimidin-1(2H)-yl)-2-methoxyphenyl) prop-1-en-2-yl)phenyl) methanesulfonamide (compound IA-L1-1.6). $^1$H NMR (300 MHz, DMSO-d$_6$) δ 2.14 (s, 3H) 2.70 (t, J=6.62 Hz, 2H) 3.01 (s, 3H) 3.68 (s, 3H) 3.78 (t, J=6.62 Hz, 2H) 6.82 (s, 1H) 7.10-7.17 (m, 2H) 7.23 (d, J=8.46 Hz, 2H) 7.59 (d, J=8.46 Hz, 2H) 9.78 (s, 1H) 10.32 (s, 1H).

(Z)-N-(4-(3-tert-butyl-5-(2,4-dioxotetrahydropyrimidin-1(2H)-yl)-2-methoxystyryl)phenyl) methanesulfonamide (compound IA-L1-1.10). $^1$H NMR (300 MHz, DMSO-d$_6$) δ 10.23 (s, 1H) 9.74 (s, 1H) 7.23 (d, J=8.46 Hz, 2H) 7.13 (d, J=2.57 Hz, 1H) 7.06 (d, J=8.82 Hz, 2H) 6.92 (d, J=2.57 Hz, 1H) 6.54-6.67 (m, 2H) 3.78 (s, 3H) 3.57 (t, J=6.62 Hz, 2H) 2.96 (s, 3H) 2.60 (t, J=6.80 Hz, 2H) 1.34 (s, 9H).

(E)-N-(4-(3-tert-butyl-5-(2,4-dioxotetrahydropyrimidin-1(2H)-yl)-2-methoxystyryl)phenyl)-N-(methylsulfonyl)acetamide (compound IA-L1-1.11). $^1$H NMR (300 MHz, DMSO-d$_6$) δ 10.36 (s, 1H) 7.77 (d, J=8.46 Hz, 2H) 7.56 (d, J=2.21 Hz, 1H) 7.39-7.50 (m, 3H) 7.25 (d, J=16.55 Hz, 1H) 7.19 (d, J=2.57 Hz, 1H) 3.74-3.85 (m, 5H) 3.54 (s, 3H) 2.72 (t, J=6.62 Hz, 2H) 1.94 (s, 3H) 1.38 (s, 9H).

(E)-1-(3-(4-aminostyryl)-5-tert-butyl-4-methoxyphenyl) dihydropyrimidine-2,4(1H,3H)-dione (compound IA-L1-1.13). $^1$H NMR (300 MHz, DMSO-d$_6$) δ 1.36 (s, 9H) 2.70 (t, J=6.62 Hz, 2H) 3.74 (s, 3H) 3.77 (t, J=6.62 Hz, 2H) 5.34 (s, 1H) 6.57 (d, J=8.46 Hz, 2H) 6.98 (s, 1H) 7.07 (d, J=2.21 Hz, 1H) 7.17 (s, 2H) 7.30 (d, J=8.09 Hz, 2H) 7.45 (d, J=2.21 Hz, 1H) 10.32 (s, 1H).

(Z)-N-(4-(3-tert-butyl-5-(2,4-dioxotetrahydropyrimidin-1(2H)-y 0-2-methoxystyryl)phenyl) methanesulfonamide (compound IA-L1-1.2θ). $^1$H NMR (500 MHz, DMSO-d$_6$): δ ppm 1.37 (s, 9H), 2.71 (t, J=6.7 Hz, 2H), 3.01 (s, 3H), 3.75 (s, 3H), 3.79 (t, J=6.6 Hz, 2H), 7.13 (d, J=16.5 Hz, 1H), 7.15 (d, J=2.4 Hz, 2H), 7.23 (d, J=8.5 Hz, 2H), 7.25 (d, J=16.5 Hz, 1H), 7.51 (d, J=2.4 Hz, 1H), 7.61 (d, J=8.6 Hz, 2H), 9.80 (bs, 1H), 10.30 (s, 1H).

N-(4-(2-(3-tert-butyl-5-(2,4-dioxotetrahydropyrimidin-1(2H)-yl)-2-methoxyphenyl)-1-fluorovinyl)phenyl)methanesulfonamide (compound IA-L1-1.21). (racemic mixture (1:1) of compounds IA-L1-1.4 and IA-L1-1.5).

(E)-1-(3-tert-butyl-4-methoxy-5-(4-nitrostyryl)phenyl)dihydropyrimidine-2,4(1H,3H)-dione (compound IA-L1-1.22).

1-{3-tert-butyl-5-[(Z)-2-chloro-2-(4-nitro-phenyl)-vinyl]-4-methoxy-phenyl}-dihydro-pyrimidine-2,4-dione (compound IA-L1-1.23).

1-{3-tert-butyl-4-methoxy-5-[(E)-2-(4-nitro-phenyl)-propenyl]-phenyl}-dihydro-pyrimidine-2,4-dione (compound IA-L1-1.24).

1-{3-tert-Butyl-5-[(E)-2-(4-nitro-phenyl)-vinyl]-phenyl}-dihydro-pyrimidine-2,4-dione (compound IA-L1-1.25). $^1$H NMR (300 MHz, DMSO-D6) δ ppm 1.33 (s, 9H) 2.70-2.77 (m, 2H) 3.84 (t, J=6.80 Hz, 2H) 7.33 (s, 1H) 7.49 (d, J=4.04 Hz, 2H) 7.56 (d, 1=5.88 Hz, 2H) 7.89 (d, J=8.82 Hz, 2H) 8.25 (d, J=8.82 Hz, 2H) 10.40 (s, 1H)

N-(4-{(E)-2-[3-tert-Butyl-5-(dioxo-tetrahydro-pyrimidin-1-yl)-2-methoxy-phenyl]-vinyl}-3-methoxy-phenyl)-methanesulfonamide (compound IA-L1-1.27). $^1$H NMR (300 MHz, DMSO-D6) δ ppm 10.33 (s, 1H) 9.86 (s, 1H) 7.64 (d, J=8.46 Hz, 1H) 7.45 (d, J=2.21 Hz, 1H) 7.26 (s, 2H) 7.12 (d, J=2.21 Hz, 1H) 6.89 (s, 1H) 6.85 (dd, J=8.46, 1.84 Hz, 1H) 3.84 (s, 3H) 3.78 (t, J=6.80 Hz, 2H) 3.74 (s, 3H) 3.04 (s, 3H) 2.71 (t, J=6.62 Hz, 2H) 1.37 (s, 9H)

N-(4-{(E)-2-[3-tert-Butyl-5-(2,4-dioxo-3,4-dihydro-2H-pyrimidin-1-yl)-2-methoxy-phenyl]-vinyl}-3-formyl-phenyl)-methanesulfonamide (compound IB-L1-1.6). $^1$H NMR (300 MHz, DMSO-D6) δ ppm 1.39 (s, 9H) 3.07 (s, 3H) 3.81 (s, 3H) 5.66 (dd, J=7.72, 2.21 Hz, 1H) 7.26 (d, J=2.57 Hz, 1H) 7.30 (d, J=16.18 Hz, 1H) 7.51 (dd, J=8.64, 2.39 Hz, 1H) 7.69 (d, J=2.57 Hz, 1H) 7.73-7.78 (m, 2H) 7.97 (d, J=8.82 Hz, 1H) 8.06 (d, J=16.18 Hz, 1H) 10.15 (s, 1H) 10.45 (s, 1H) 11.43 (d, 1=2.21 Hz, 1H)

N-[4-{(E)-2-[3-tert-Butyl-5-(2,4-dioxo-3,4-dihydro-2H-pyrimidin-1-yl)-2-methoxy-phenyl]-vinyl}-3-(hydroxyimino-methyl)-phenyl]-methanesulfonamide (compound IB-L1-1.8). $^1$H NMR (300 MHz, DMSO-d$_6$) δ 1.38 (s, 9H) 3.03 (s, 3H) 3.79 (s, 3H) 5.66 (dd, J=7.91, 2.02 Hz, 1H) 7.16

(d, J=15.81 Hz, 1H) 7.22 (d, J=2.57 Hz, 1H) 7.26 (dd, J=8.64, 2.39 Hz, 1H) 7.59 (d, J=16.18 Hz, 1H) 7.63 (d, J=2.21 Hz, 1H) 7.73-7.83 (m, 3H) 8.64 (s, 1H) 9.96 (s, 1H) 11.42 (d, J=2.21 Hz, 1H) 11.50 (s, 1H).

2-{(E)-2-[3-tert-Butyl-5-(2,4-dioxo-3,4-dihydro-2H-pyrimidin-1-yl)-2-methoxy-phenyl]-vinyl}-5-methanesulfonylamino-N-(2-methoxy-ethyl)-benzamide (compound IB-L1-1.9). NMR (300 MHz, DMSO-D6) δ 1.38 (s, 9H) 3.05 (s, 3H) 3.20 (s, 3H) 3.37-3.49 (m, 4H) 3.78 (s, 3H) 5.64 (d, 1=7.72 Hz, 1H) 7.15 (d, J=2.57 Hz, 1H) 7.20 (d, J=2.57 Hz, 1H) 7.24 (s, 2H) 7.28 (dd, J=8.46, 2.21 Hz, 1H) 7.42 (d, J=2.57 Hz, 1H) 7.73 (d, J=7.72 Hz, 1H) 7.87 (d, J=8.82 Hz, 1H) 8.49 (t, J=5.15 Hz, 1H) 9.99 (s, 1H) 11.42 (s, 1H).

2-{(E)-2-[3-tert-Butyl-5-(2,4-dioxo-3,4-dihydro-2H-pyrimidin-1-yl)-2-methoxy-phenyl]-viny}-5-methanesulfonylamino-benzoic acid ethyl ester (compound IB-L1-1.11). $^1$H NMR (300 MHz, DMSO-d$_6$) δ 1.31 (t, J=7.17 Hz, 3H) 1.38 (s, 9H) 3.05 (s, 3H) 3.79 (s, 3H) 4.33 (q, J=7.23 Hz, 2H) 5.65 (dd, J=7.72, 2.21 Hz, 1H) 7.15-7.25 (m, 2H) 7.46 (dd, J=8.64, 2.39 Hz, 1H) 7.52 (d, J=2.57 Hz, 1H) 7.68 (d, J=2.57 Hz, 1H) 7.71-7.81 (m, 2H) 7.90 (d, J=8.46 Hz, 1H) 10.06 (s, 1H) 11.42 (d, J=1.84 Hz, 1H).

N-(4-{(E)-2-[3-tert-Butyl-2-chloro-5-(2,4-dioxo-3,4-dihydro-2H-pyrimidin-1-yl)-phenyl]-vinyl}-phenyl)-methanesulfonamide (compound IB-L1-1.12). $^1$H NMR (300 MHz, DMSO-d$_6$) δ ppm 1.49 (s, 9H) 3.02 (s, 3H) 5.69 (d, J=7.72 Hz, 1H) 7.22 (m, 3H) 7.41 (d, J=2.21 Hz, 1H) 7.51 (d, J=16.18 Hz, 1H) 7.59 (d, J=8.82 Hz, 2H) 7.78 (d, J=2.21 Hz, 1H) 7.80 (d, J=8.09 Hz, 1H) 9.90 (s, 1H) 11.47 (s, 1H).

2-{(E)-2-[3-tert-Butyl-5-(2,4-dioxo-3,4-d hydro-2H-pyrimidin-1-yl)-2-methoxy-phenyl]-vinyl}-5-methanesulfonylamino-N,N-dimethyl-benzamide (compound IB-L1-1.14). $^1$H NMR (300 MHz, DMSO-d$_6$) δ 1.37 (s, 9H) 2.76 (s, 3H) 3.03 (s, 3H) 3.05 (s, 3H) 3.76 (s, 3H) 5.64 (dd, J=7.91, 1.65 Hz, 1H) 6.95 (d, J=16.55 Hz, 1H) 7.02 (d, J=2.21 Hz, 1H) 7.17-7.25 (m, 2H) 7.27 (dd, J=8.64, 2.39 Hz, 1H) 7.48 (d, J=2.57 Hz, 1H) 7.74 (d, J=8.09 Hz, 1H) 7.82 (d, J=8.82 Hz, 1H) 10.03 (s, 1H) 11.39-11.43 (m, 1H).

2-{(E)-2-[3-tert-Butyl-5-(2,4-dioxo-3,4-dihydro-2H-pyrimidin-1-yl)-2-methoxy-phenyl]-vinyl}-5-methanesulfonylamino-N-methyl-benzamide (compound IB-L1-1.17). $^1$H NMR (300 MHz, DMSO-d$_6$) δ 1.38 (s, 9H) 2.77 (d, J=4.41 Hz, 3H) 3.06 (s, 3H) 3.77 (s, 3H) 5.64 (dd, J=7.72, 1.84 Hz, 1H) 7.16-7.33 (m, 5H) 7.43 (d, 1=2.21 Hz, 1H) 7.73 (d, J=7.72 Hz, 1H) 7.84 (d, J=8.46 Hz, 1H) 8.37 (q, J=4.41 Hz, 1H) 10.00 (s, 1H) 11.40 (d, J=1.84 Hz, 1H).

2-{(E)-2-[3-tert-butyl-5-(2,4-dioxo-3,4-dihydro-2H-pyrimidin-1-yl)-2-methoxy-phenyl]-vinyl}-N-(1,1-dioxo-tetrahydro-1 lambda*6*-thiophen-3-yl)-5-methanesulfonylamino-N-methyl-benzamide (compound IB-L1-1.18). $^1$H NMR (300 MHz, DMSO-d$_6$) δ 1.37 (s, 9H) 2.17-2.47 (m, 2H) 2.70 (s, 3H) 3.06 (s, 3H) 3.15-3.31 (m, 2H) 3.36-3.51 (m, 2H) 3.77 (s, 3H) 5.37 (dt, J=17.74, 8.96 Hz, 1H) 5.65 (dd, J=7.91, 2.02 Hz, 1H) 6.93 (d, J=16.18 Hz, 1H) 7.05 (d, J=2.21 Hz, 1H) 7.19-7.35 (m, 3H) 7.50 (d, J=2.57 Hz, 1H) 7.76 (d, J=8.09 Hz, 1H) 7.87 (d, J=8.82 Hz, 1H) 10.04 (s, 1H) 11.38 (d, J=2.21 Hz, 1H).

N-(4-{(E)-2-[3-tert-butyl-5-(5-chloro-2,4-dioxo-3,4-dihydro-2H-pyrimidin-1-yl)-2-methoxy-phenyl]-vinyl}-phenyl)-methanesulfonamide (Compound 1B-1-1.20). $^1$H NMR (300 MHz, DMSO-D6) δ ppm 11.31 (s, 1H) 9.77 (s, 1H) 7.53 (d, J=8.09 Hz, 1H) 7.23 (d, J=8.46 Hz, 2H) 7.17 (d, J=2.57 Hz, 1H) 7.06 (d, J=8.82 Hz, 2H) 7.01 (d, J=2.57 Hz, 1H) 6.53-6.71 (m, 2H) 5.56 (d, J=7.72 Hz, 1H) 3.81 (s, 3H) 2.96 (s, 3H) 1.35 (s, 9H)

2-{(E)-2-[3-tert-Butyl-5-(2,4-dioxo-3,4-dihydro-2H-pyrimidin-1-yl)-2-methoxy-phenyl]-vinyl}-5-methanesulfonylamino-benzamide (compound IB-L1-1.21). $^1$H NMR (300 MHz, DMSO-d$_6$) δ 1.38 (s, 9H) 3.07 (s, 3H) 3.78 (s, 3H) 5.64 (d, J=7.72 Hz, 1H) 7.18-7.34 (m, 5H) 7.43 (d, J=2.21 Hz, 1H) 7.54 (s, 1H) 7.73 (d, 1=7.72 Hz, 1H) 7.84 (d, J=8.46 Hz, 1H) 7.93 (s, 1H).

N-(3-(azetidine-1-carbonyl)-4-{(E)-2-[3-tert-butyl-5-(2,4-dioxo-3,4-dihydro-2H-pyrimidin-1-yl)-2-methoxy-phenyl]-vinyl}-phenyl)-methanesulfonamide (compound (compound IB-L1-1.22). $^1$H NMR (300 MHz, DMSO-d$_6$) δ 1.38 (s, 9H) 3.07 (s, 3H) 3.78 (s, 3H) 5.64 (d, J=7.72 Hz, 1H) 7.18-7.34 (m, 5H) 7.43 (d, J=2.21 Hz, 1H) 7.54 (s, 1H) 7.73 (d, J=7.72 Hz, 1H) 7.84 (d, J=8.46 Hz, 1H) 7.93 (s, 1H).

2-{(E)-2-[3-tert-Butyl-5-(2,4-dioxo-3,4-dihydro-2H-pyrimidin-1-yl)-2-methoxy-phenyl]-vinyl}-5-methanesulfonylamino-N-(2-methoxy-ethyl)-N-methyl-benzamide (compound IB-L1-1.24). $^1$H NMR (300 MHz, DMSO-d$_6$) δ 1.40 (s, 9H) 2.81 (s, 3H) 3.07 (s, 3H) 3.23 (s, 3H) 3.29 (t, J=5.33 Hz, 1H) 3.39 (t, J=4.96 Hz, 1H) 3.62 (t, J=4.78 Hz, 2H) 3.82 (s, 3H) 5.68 (d, J=8.09 Hz, 1H) 6.96-7.07 (m, 1H) 7.09-7.17 (m, 1H) 7.23-7.38 (m, 3H) 7.49 (dd, J=16.55, 2.57 Hz, 1H) 7.71-7.76 (m, 1H) 7.83-7.94 (m, 1H).

N-(4-{(E)-2-[3-tert-butyl-5-(2,4-dioxo-3,4-dihydro-2H-pyrimidin-1-yl)-2-methoxy-phenyl]-vinyl}-3-isopropoxymethyl-phenyl)-methanesulfonamide (compound IB-L1-1.25). $^1$H NMR (300 MHz, DMSO-d$_6$) δ 1.16 (d, J=5.88 Hz, 6H) 1.38 (s, 9H) 3.01 (s, 3H) 3.69 (dt, J=12.13, 6.07 Hz, 1H) 3.79 (s, 3H) 4.59 (s, 2H) 5.65 (dd, J=7.91, 2.02 Hz, 1H) 7.13-7.29 (m, 4H) 7.32-7.40 (m, 1H) 7.59 (d, J=2.57 Hz, 1H) 7.75 (d, J=8.09 Hz, 2H) 9.86 (s, 1H) 11.43 (d, J=1.84 Hz, 1H).

N-[4-{(E)-2-[3-tert-butyl-5-(2,4-dioxo-3,4-dihydro-2H-pyrimidin-1-yl)-2-methoxy-phenyl]-vinyl}-3-(pyrrolidine-1-carbonyl)-phenyl]-methanesulfonamide (compound IB-L1-1.27). $^1$H NMR (300 MHz, DMSO-d$_6$) δ 1.37 (s, 9H) 1.73-1.89 (m, 4H) 3.03-3.12 (m, 5H) 3.51 (t, J=6.80 Hz, 2H) 3.76 (s, 3H) 5.64 (dd, J=7.91, 2.02 Hz, 1H) 6.99-7.06 (m, 1H) 7.08 (d, J=2.21 Hz, 1H) 7.19-7.31 (m, 3H) 7.46 (d, J=2.57 Hz, 1H) 7.75 (d, J=8.09 Hz, 1H) 7.82 (d, J=8.82 Hz, 1H) 10.01 (s, 1H) 11.41 (d, J=2.21 Hz, 1H).

N-[4-{(E)-2-[3-tert-butyl-5-(2,4-dioxo-3,4-dihydro-2H-pyrimidin-1-yl)-2-methoxy-phenyl]-vinyl}-3-(3-hydroxy-azetidin-1-ylmethyl)-phenyl]-methanesulfonamide (compound IB-L1-1.29). $^1$H NMR (300 MHz, DMSO-d$_6$) δ 1.38 (s, 9H) 2.78-2.85 (m, 2H) 2.99 (s, 3H) 3.50-3.58 (m, 2H) 3.71 (s, 3H) 3.79 (s, 3H) 4.19 (td, J=12.41, 6.07 Hz, 1H) 5.29 (d, J=6.25 Hz, 1H) 5.66 (d, J=8.09 Hz, 1H) 7.10-7.18 (m, 2H) 7.20 (t, J=2.21 Hz, 2H) 7.35-7.42 (m, 1H) 7.63 (d, J=2.57 Hz, 1H) 7.69 (d, J=8.46 Hz, 1H) 7.76 (d, J=7.72 Hz, 1H) 9.78 (s, 1H) 11.42 (s, 1H).

N-(4-{(E)-2-[3-tert-Butyl-5-(2,4-dioxo-3,4-dihydro-2H-pyrimidin-1-yl)-2-methoxy-phenyl]-vinyl}-3-pyrrolidin-1-ylmethyl-phenyl)-methanesulfonamide (compound IB-L1-1.33). $^1$H NMR (500 MHz, DMSO-d$_6$) δ 1.40 (s, 9H) 1.72-1.95 (m, 4H) 2.84 (s, 2H) 2.88-2.98 (m, 2H) 3.01 (s, 3H) 3.81 (s, 3H) 3.86-4.23 (m, 2H) 5.63 (d, J=7.81 Hz, 1H) 7.17 (d, J=15.63 Hz, 1H) 7.21-7.28 (m, 2H) 7.32-7.38 (m, 1H) 7.47 (d, J=16.11 Hz, 1H) 7.53-7.59 (m, 1H) 7.61 (d, J=7.81 Hz, 1H) 7.70 (d, J=6.35 Hz, 1H) 9.42 (s, 1H) 10.88 (s, 1H).

N-(4-{(Z)-2-[3-tert-Butyl-5-(2,4-dioxo-3,4-dihydro-2H-pyrimidin-1-yl)-2-methoxy-phenyl]-vinyl}-phenyl)-methanesulfonamide (compound IB-L1-1.34 $^1$H NMR (300 MHz, DMSO-D6) δ ppm 11.31 (s, 1H) 9.77 (s, 1H) 7.53 (d, J=8.09 Hz, 1H) 7.23 (d, J=8.46 Hz, 2H) 7.17 (d, J=2.57 Hz, 1H) 7.06 (d, J=8.82 Hz, 2H) 7.01 (d, J=2.57 Hz, 1H) 6.53-6.71 (m, 2H) 5.56 (d, J=7.72 Hz, 1H) 3.81 (s, 3H) 2.96 (s, 3H) 1.35 (s, 9H)

N-(4-(3-tert-butyl-5-(2,4-dioxotetrahydropyrimidin-1 (2H)-yl)phenethyl)phenyl)methane sulfonamide (compound IA-L5-2-1.2). $^1$H NMR (300 MHz, DMSO-d$_6$) δ 1.25 (s, 9H) 2.69 (t, J=6.62 Hz, 2H) 2.83 (s, 4H) 2.91 (s, 3H) 3.75 (t, J=6.62 Hz, 2H) 6.99-7.21 (m, 7H) 9.60 (s, 1H) 10.31 (s, 1H).

methyl 2-(3-tert-butyl-5-(2,4-dioxo-3,4-dihydropyrimidin-1(2H)-yl)-2-methoxyphen ethyl)-5-(methylsulfonamido)benzoate (compound IB-L5-2-1.1). $^1$H NMR (300 MHz, DMSO-d$_6$) δ 1.34 (s, 9H) 2.83-2.92 (m, 2H) 2.96 (s, 3H) 3.14 (dd, J=10.30, 5.88 Hz, 2H) 3.75 (s, 3H) 3.83 (s, 3H) 5.64 (d, J=7.72 Hz, 1H) 7.13 (d, J=2.94 Hz, 1H) 7.20 (d, J=2.57 Hz, 1H) 7.28-7.36 (m, 2H) 7.61-7.71 (m, 2H) 9.88 (s, 1H) 11.39 (s, 1H)

N-(4-(3-tert-butyl-5-(2,4-dioxo-3,4-dihydropyrimidin-1 (2H)-yl)-2-methoxyphenethyl)phenyl) methanesulfonamide (compound IB-L5-2-1.2). $^1$H NMR (300 MHz, DMSO-d6): δ 11.39 (s, 1H), 9.60 (s, 1H), 7.65 (d, J=8.1 Hz, 1H), 7.23 (m, 3H), 7.17 (m, 3H), 5.64 (d, J=7.7 Hz, 1H), 3.77 (s, 3H), 2.93 (s, 3H), 2.88 (bs, 4H), 1.35 (s, 9H)

The following compounds can be prepared utilizing the above discussion:

TABLE A

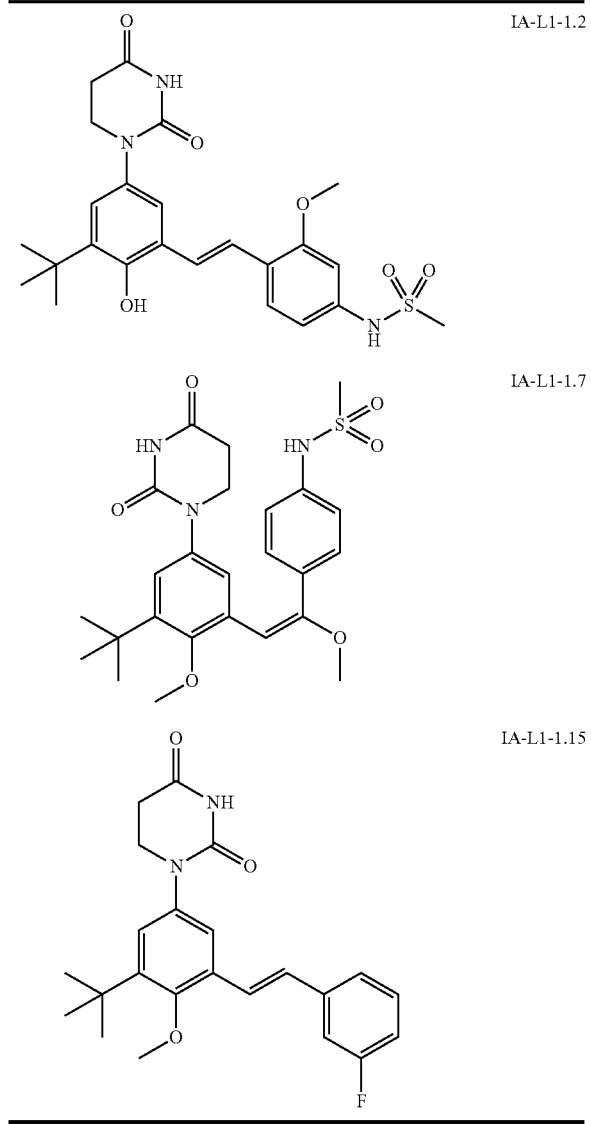

HCV Polymerase Inhibition Assay

Either two-fold serial dilutions (fractional inhibition assay) or a narrower range of dilutions spanning the IC$_{50}$ of the inhibitor (tight binding assay) of the inhibitors were incubated with 20 mM Tris-Cl pH 7.4, 2 mM MnCl$_2$, 1 mM dithiothreitol, 1 mM ethylene diamine tetraacetic acid (EDTA), 60 to 125 μM GTP and 20 to 50 nM Δ21 NS5B (HCV Strain 1B (BK, Genbank accession number M58335, or H77, Genbank accession number AF011751)) for 15 min at room temperature. The reaction was initiated by the addition of 20 μM CTP, 20 μM ATP, 1 μM $^3$H-UTP (10 mCi/umol), 5 nM template RNA and 0.1 U/μl RNase inhibitor (RNasin, Promega), and allowed to proceed for 2 to 4 h at room temperature. Reaction volume was 50 μl. The reaction was terminated by the addition of 1 volume of 4 mM spermine in 10 mM Tris-Cl pH 8.0, 1 mM EDTA. After incubation for at least 15 min at room temperature, the precipitated RNA was captured by filtering through a GF/B filter (Millipore) in a 96 well format. The filter plate was washed three times with 200 μl each of 2 mM spermine, 10 mM Tris-Cl pH 8.0, 1 mM EDTA, and 2 times with ethanol. After air-drying, 30 μl of Microscint 20 scintillation cocktail (Packard) was added to each well, and the retained cpm were determined by scintillation counting. IC$_{50}$ values were calculated by a two-variable nonlinear regression equation using an uninhibited control and a fully inhibited control sample to determine the minimum and maximum for the curve. Tight-binding assays were performed on those compounds exhibiting IC$_{50}$ values less than 0.005 μM in the fractional inhibition assay in order to more precisely measure the IC$_{50}$ values. Retained cpm were plotted vs. inhibitor concentration and fit to equation 1 using nonlinear regression (ref. 1) to obtain the IC$_{50}$ values:

$$\text{Retained cpm} = A[\text{sqrt}\{(IC_{50}+I_t-E_t)^2+4\cdot IC_{50}\cdot E_t\}-(IC_{50}+I_t-E_t)] \quad \text{(eqn 1)}$$

where $A=V_{max}[S]/2(K_m+[S])$; It=total inhibitor concentration and Et=total active concentration of enzyme.

Ref. Morrison, J. F. and S. R. Stone. 1985. Approaches to the study and analysis of the inhibition of enzymes by slow- and tight-binding inhibitors. Comments Mol. Cell. Biophys. 2: 347-368.

The sequence of the template RNA used was: 5'-GGGC-GAAUUG GGCCCUCUAG AUGCAUGCUC GAGCGGC-CGC CAGUGUGAUG GAUAUCUGCA GAAUUCGCCC UUGGUGGCUC CAUCUUAGCC CUAGUCACGG CUAGCUGUGA AAGGUCCGUG AGCCGCUUGA CUG-CAGAGAG UGCUGAUACU GGCCUCUCUG CAGAUCAAGUC-3'

When tested by the above method, the compounds of this invention inhibit HCV polymerase 1A and/or 1B. The legend in the table below is as follows: A—IC$_{50}$≤0.01 uM; B—0.1 uM≥IC$_{50}$>0.01 uM; C—1 uM≥IC$_{50}$>0.1 uM; and D—IC$_{50}$>1 uM; ND—not determined.

TABLE

| compound | IC$_{50}$ 1a | 1b | compound | 1a | 1b |
|---|---|---|---|---|---|
| IA-L1-1.3 | A | A | IA-L1-1.4 | A | A |
| IA-L1-1.5 | A | B | IA-L1-1.6 | A | B |
| IA-L1-1.9 | A | B | IA-L1-1.10 | B | B |
| IA-L1-1.11 | B | B | IA-L1-1.12 | C | C |
| IA-L1-1.13 | C | C | IA-L1-1.14 | D | D |
| IA-L1-1.16 | A | A | IA-L1-1.17 | B | B |
| IA-L1-1.18 | C | C | IA-L1-1.20 | A | B |
| IA-L1-1.21 | B | B | IA-L1-1.22 | C | C |
| IA-L1-1.23 | C | C | IA-L1-1.24 | D | D |
| IA-L1-1.25 | D | D | IA-L1-1.26 | B | B |
| IA-L1-1.27 | A | B | IB-L1-1.1 | A | A |
| IB-L1-1.2 | B | B | IB-L1-1.4 | A | A |
| IB-L1-1.5 | A | A | IB-L1-1.6 | A | B |
| IB-L1-1.7 | A | B | IB-L1-1.8 | A | B |
| IB-L1-1.9 | A | B | IB-L1-1.10 | A | B |
| IB-L1-1.11 | A | B | IB-L1-1.12 | A | B |
| IB-L1-1.13 | A | B | IB-L1-1.14 | A | B |
| IB-L1-1.15 | A | B | IB-L1-1.16 | A | B |
| IB-L1-1.17 | A | B | IB-L1-1.18 | A | B |
| IB-L1-1.19 | A | B | IB-L1-1.20 | A | B |
| IB-L1-1.21 | A | B | IB-L1-1.22 | B | B |
| IB-L1-1.23 | B | B | IB-L1-1.24 | B | B |
| IB-L1-1.25 | B | B | IB-L1-1.26 | B | B |
| IB-L1-1.27 | B | B | IB-L1-1.28 | B | B |
| IB-L1-1.29 | B | B | IB-L1-1.30 | B | B |
| IB-L1-1.31 | B | C | IB-L1-1.32 | C | C |
| IB-L1-1.33 | C | C | IB-L1-1.34 | D | D |
| IB-L1-1.45 | A | B | IB-L1-1.46 | B | B |
| IB-L1-1.47 | B | B | IB-L1-1.48 | B | B |
| IB-L1-1.49 | B | C | IB-L1-1.50 | B | B |
| IB-L1-1.51 | B | B | IB-L1-1.52 | C | C |

TABLE-continued

| | IC$_{50}$ | | | | |
|---|---|---|---|---|---|
| compound | 1a | 1b | compound | 1a | 1b |
| IB-L1-1.53 | D | D | IB-L1-1.55 | D | D |
| IA-L5-2-1.1 | B | B | IA-L5-2-1.2 | B | B |
| IB-L5-2-1.1 | A | B | IB-L5-2-1.2 | B | B |
| IA-L8-1.1 | C | C | | | |

HCV Polymerase Replicon Assay

Two stable subgenomic replicon cell lines were used for compound characterization in cell culture: one derived from genotype 1a-H77 and one derived from genotype 1b-Con1 (obtained from Apath, LLC, St. Louis, Mo.). All replicon constructs were bicistronic subgenomic replicons similar to those described by Bartenschlager and coworkers (Lohmann et al., *Replication of Subgenomic Hepatitis C Virus RNAs in a Hepatoma Cell Line*, SCIENCE 285:110-3 (1999)). The genotype 1a replicon construct contains NS3-NS5B coding region derived from the H77 strain of HCV (1a-H77) (Blight et al., *Efficient Replication of Hepatitis C Virus Genotype 1a RNAs in Cell Culture*, J. VIROL. 77:3181-90 (2003)). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and 522041. The 1b-Con1 replicon construct is identical to the 1a-H77 replicon, except that the NS3-NS5B coding region was derived from the 1b-Con1 strain, and the adaptive mutations are E1202G, T12801 and S22041. Replicon cell lines were maintained in Dulbecco's modified Eagles medium (DMEM) containing 10% (v/v) fetal bovine serum (FBS), 100 IU/ml penicillin, 100 mg/ml streptomycin (Invitrogen), and 200 mg/ml G418 (Invitrogen).

The inhibitory effects of compounds on HCV replication were determined by measuring activity of the luciferase reporter gene. Briefly, replicon-containing cells were seeded into 96 well plates at a density of 5000 cells per well in 100 ul DMEM containing 5% FBS. 16-24 h later, the compounds were diluted in dimethyl sulfoxide (DMSO) to generate a 200× stock in a series of eight half-log dilutions. The dilution series was then further diluted 100-fold in the medium containing 5% FBS. Medium with the inhibitor was added to the overnight cell culture plates already containing 100 ul of DMEM with 5% FBS. In assays measuring inhibitory activity in the presence of human plasma, the medium from the overnight cell culture plates was replaced with DMEM containing 40% human plasma and 5% FBS. The cells were incubated for three days in the tissue culture incubators and were then lysed for RNA extraction. For the luciferase assay, 30 ul of Passive Lysis buffer (Promega) was added to each well, and then the plates were incubated for 15 min with rocking to lyse the cells. Luciferin solution (50 to 100 ul, Promega) was added to each well, and luciferase activity was measured with a Victor II luminometer (Perkin-Elmer). The percent inhibition of HCV RNA replication was calculated for each compound concentration and the EC$_{50}$ value was calculated using nonlinear regression curve fitting to the 4-parameter logistic equation and GraphPad Prism 4 software.

When tested by the above method, the compounds of this invention inhibit HCV polymerase IA and/or 1B. The legend in the table below is as follows: A—EC$_{50}$<0.01 uM; B—0.1 uM≥EC$_{50}$<0.01 uM; C—1 uM≥EC$_{50}$>0.1 uM; and D—EC$_{50}$>1 uM; ND—not determined.

TABLE

| | EC$_{50}$ | | | | |
|---|---|---|---|---|---|
| compound | 1a | 1b | compound | 1a | 1b |
| IA-L1-1.3 | B | A | IA-L1-1.4 | A | A |
| IA-L1-1.5 | B | A | IA-L1-1.6 | B | B |
| IA-L1-1.9 | B | A | IA-L1-1.10 | B | B |
| IA-L1-1.11 | A | A | IA-L1-1.12 | C | C |
| IA-L1-1.13 | D | C | IA-L1-1.14 | D | D |
| IA-L1-1.16 | B | B | IA-L1-1.17 | B | B |
| IA-L1-1.18 | C | C | IA-L1-1.20 | B | B |
| IA-L1-1.21 | A | A | IA-L1-1.22 | D | C |
| IA-L1-1.23 | D | D | IA-L1-1.24 | D | D |
| IA-L1-1.25 | ND | ND | IA-L1-1.26 | B | B |
| IA-L1-1.27 | B | A | IB-L1-1.1 | A | A |
| IB-L1-1.2 | ND | B | IB-L1-1.4 | B | A |
| IB-L1-1.5 | B | A | IB-L1-1.6 | A | A |
| IB-L1-1.7 | A | A | IB-L1-1.8 | B | A |
| IB-L1-1.9 | B | A | IB-L1-1.10 | A | A |
| IB-L1-1.11 | B | A | IB-L1-1.12 | B | B |
| IB-L1-1.13 | B | A | IB-L1-1.14 | B | A |
| IB-L1-1.15 | A | A | IB-L1-1.16 | C | B |
| IB-L1-1.17 | B | A | IB-L1-1.18 | B | B |
| IB-L1-1.19 | B | A | IB-L1-1.20 | B | A |
| IB-L1-1.21 | B | A | IB-L1-1.22 | B | A |
| IB-L1-1.23 | C | A | IB-L1-1.24 | B | A |
| IB-L1-1.25 | B | A | IB-L1-1.26 | B | A |
| IB-L1-1.27 | B | A | IB-L1-1.28 | A | A |
| IB-L1-1.29 | C | C | IB-L1-1.30 | C | B |
| IB-L1-1.31 | D | D | IB-L1-1.32 | C | B |
| IB-L1-1.33 | C | B | IB-L1-1.34 | B | A |
| IB-L1-1.45 | B | A | IB-L1-1.46 | C | A |
| IB-L1-1.47 | C | B | IB-L1-1.48 | C | A |
| IB-L1-1.49 | D | D | IB-L1-1.50 | C | B |
| IB-L1-1.51 | D | B | IB-L1-1.52 | D | C |
| IB-L1-1.53 | ND | ND | IB-L1-1.55 | ND | ND |
| IA-L5-2-1.1 | C | B | IA-L5-2-1.2 | C | C |
| IB-L5-2-1.1 | B | A | IB-L5-2-1.2 | C | B |
| IA-L6-1.1 | C | B | IA-L8-1.1 | C | C |

All references (patent and non-patent) cited above are incorporated by reference into this patent application. The discussion of those references is intended merely to summarize the assertions made by their authors. No admission is made that any reference (or a portion of ay reference) is relevant prior art (or prior art at all). Applicants reserve the right to challenge the accuracy and pertinence of the cited references.

We claim:

1. (E)-N-(4-(3-tert-butyl-5-(2,4-dioxo-3,4-dihydropyrimidin-1(2H)-yl)-2-methoxystyryl)phenyl)methanesulfonamide crystalline form selected from the group consisting of:
   crystalline (E)-N-(4-(3-tert-butyl-5-(2,4-dioxo-3,4-dihydropyrimidin-1(2H)-yl)-2-methoxystyryl)phenyl) methanesulfonamide disodium salt nonahydrate;
   crystalline (E)-N-(4-(3-tert-butyl-5-(2,4-dioxo-3,4-dihydropyrimidin-1(2H)-yl)-2-methoxystyryl)phenyl) methanesulfonamide disodium salt tetrahydrate;
   crystalline (E)-N-(4-(3-tert-butyl-5-(2,4-dioxo-3,4-dihydropyrimidin-1(2H)-yl)-2-methoxystyryl)phenyl) methanesulfonamide dipotassium salt tetrahydrate;
   crystalline (E)-N-(4-(3-tert-butyl-5-(2,4-dioxo-3,4-dihydropyrimidin-1(2H)-yl)-2-methoxystyryl)phenyl) methanesulfonamide monopotassium salt trihydrate;
   crystalline (E)-N-(4-(3-tert-butyl-5-(2,4-dioxo-3,4-dihydropyrimidin-1(2H)-yl)-2-methoxystyryl)phenyl) methanesulfonamide monopotassium salt dihydrate;
   crystalline (E)-N-(4-(3-tert-butyl-5-(2,4-dioxo-3,4-dihydropyrimidin-1(2H)-yl)-2-methoxystyryl)phenyl) methanesulfonamide 1/7 potassium salt;
   crystalline (E)-N-(4-(3-tert-butyl-5-(2,4-dioxo-3,4-dihydropyrimidin-1(2H)-yl)-2-methoxystyryl)phenyl) methanesulfonamide monodiethylamine salt tetrahydrate;
   crystalline pattern A (E)-N-(4-(3-tert-butyl-5-(2,4-dioxo-3,4-dihydropyrimidin-1(2H)-yl)-2-methoxystyryl) phenyl)methanesulfonamide;
   crystalline pattern B (E)-N-(4-(3-tert-butyl-5-(2,4-dioxo-3,4-dihydropyrimidin-1(2H)-yl)-2-methoxystyryl) phenyl)methanesulfonamide;
   crystalline pattern C (E)-N-(4-(3-tert-butyl-5-(2,4-dioxo-3,4-dihydropyrimidin-1(2H)-yl)-2-methoxystyryl) phenyl)methanesulfonamide;
   crystalline pattern D (E)-N-(4-(3-tert-butyl-5-(2,4-dioxo-3,4-dihydropyrimidin-1(2H)-yl)-2-methoxystyryl) phenyl)methanesulfonamide;
   crystalline pattern A (E)-N-(4-(3-tert-butyl-5-(2,4-dioxo-3,4-dihydropyrimidin-1(2H)-yl)-2-methoxystyryl) phenyl)methanesulfonamide hydrate;
   crystalline pattern B (E)-N-(4-(3-tert-butyl-5-(2,4-dioxo-3,4-dihydropyrimidin-1(2H)-yl)-2-methoxystyryl) phenyl)methanesulfonamide hydrate;
   crystalline pattern C (E)-N-(4-(3-tert-butyl-5-(2,4-dioxo-3,4-dihydropyrimidin-1(2H)-yl)-2-methoxystyryl) phenyl)methanesulfonamide hydrate;
   crystalline pattern D (E)-N-(4-(3-tert-butyl-5-(2,4-dioxo-3,4-dihydropyrimidin-1(2H)-yl)-2-methoxystyryl) phenyl)methanesulfonamide hydrate; and
   crystalline pattern E (E)-N-(4-(3-tert-butyl-5-(2,4-dioxo-3,4-dihydropyrimidin-1(2H)-yl)-2-methoxystyryl) phenyl)methanesulfonamide hydrate.

2. The crystalline form of claim 1, wherein said crystalline form is crystalline (E)-N-(4-(3-tert-butyl-5-(2,4-dioxo-3,4-dihydropyrimidin-1(2H)-yl)-2-methoxystyryl)phenyl)methanesulfonamide monopotassium salt dihydrate.

3. The crystalline form of claim 1, wherein said crystalline form is crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate.

4. The crystalline form of claim 2, wherein said crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate has an X-ray powder diffraction pattern comprising one or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ.

5. The crystalline form of claim 2, wherein said crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate has an X-ray powder diffraction pattern comprising one or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 22.1±0.2, 22.5±0.2, 22.6±0.2, and 23.0±0.2 degrees 2θ.

6. The crystalline form of claim 2, wherein said crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate has an X-ray powder diffraction pattern comprising five or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ.

7. The crystalline form of claim 2, wherein said crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate has unit cell parameters, wherein a is 9.0 Å, b is 8.3 Å, and c is 18.6 Å.

8. A pharmaceutical composition comprising one or more crystalline forms recited in claim 1 and one or more excipients.

9. The pharmaceutical composition of claim 8, wherein said composition comprises crystalline (E)-N-(4-(3-tert-butyl-5-(2,4-dioxo-3,4-dihydropyrimidin-1(2H)-yl)-2-methoxystyryl) phenyl)methanesulfonamide monopotassium salt trihydrate.

10. The pharmaceutical composition of claim 8, wherein the pharmaceutical composition further comprises one or more additional therapeutic agents.

11. The pharmaceutical composition of claim 10, wherein the one or more additional therapeutic agents are selected from the group consisting of interferon agent, ribavirin, HCV inhibitor, and HIV inhibitor.

12. The pharmaceutical composition of claim 10, wherein the one or more additional therapeutic agents is an HCV inhibitor.

13. A method for inhibiting replication of a ribonucleic acid (RNA) virus, wherein the method comprises exposing the virus to one or more crystalline forms recited in claim 1.

14. The method of claim 13, wherein the RNA virus is hepatitis C virus (HCV).

15. The method of claim 13, wherein the crystalline form is crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate.

16. A method for treating hepatitis C in a mammal in need of such treatment, wherein the method comprises administering to the mammal one or more crystalline forms recited in claim 1.

17. The method of claim 16, wherein the mammal is human.

18. The method of claim 16, wherein the crystalline form is crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate.

19. The method of claim 16, wherein the method further comprises administering to the mammal one or more additional therapeutic agents.

20. The method of claim 19, wherein one or more additional therapeutic agents are selected from the group consisting of interferon agent, ribavirin, HCV inhibitor, and HIV inhibitor.

21. The method of claim 19, wherein the one or more additional therapeutic agents is an HCV inhibitor.

22. (E)-N-(4-(3-tert-butyl-5-(2,4-dioxo-3,4-dihydropyrimidin-1(2H)-yl)-2-methoxystyryl)phenyl)methanesulfonamide crystalline form selected from the group consisting of:

crystalline (E)-N-(4-(3-tert-butyl-5-(2,4-dioxo-3,4-dihydropyrimidin-1(2H)-yl)-2-methoxystyryl)phenyl)methanesulfonamide disodium salt nonahydrate having an X-ray powder diffraction pattern comprising one or more peaks selected from the group consisting of 4.3±0.2, 10.4±0.2, 10.9±0.2, 11.6±0.2, 12.9±0.2, 14.7±0.2, 16.4±0.2, 17.8±0.2, 19.4±0.2, 19.8±0.2, 20.8±0.2, 21.9±0.2, and 23.5±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide disodium salt nonahydrate having an X-ray powder diffraction pattern comprising one or more peaks selected from the group consisting of 4.3±0.2, 10.4±0.2, 10.9±0.2, 11.6±0.2, 12.9±0.2, 14.7±0.2, 14.9±0.2, 16.4±0.2, 17.8±0.2, 19.4±0.2, 19.7±0.2, 19.8±0.2, 20.8±0.2, 20.9±0.2, 21.9±0.2, 22.1±0.2, and 23.5±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide disodium salt nonahydrate having an X-ray powder diffraction pattern substantially as shown in FIG. 1;

crystalline (E)-N-(4-(3-tert-butyl-5-(2,4-dioxo-3,4-dihydropyrimidin-1(2H)-yl)-2-methoxystyryl)phenyl)methanesulfonamide nonahydrate disodium salt having cell unit parameters, wherein a is 8.9 Å, b is 9.4 Å, and c is 20.7 Å;

crystalline (E)-N-(4-(3-tert-butyl-5-(2,4-dioxo-3,4-dihydropyrimidin-1(2H)-yl)-2-methoxystyryl)phenyl)methanesulfonamide disodium salt tetrahydrate having an X-ray powder diffraction pattern comprising one or more peaks selected from the group consisting of 4.8±0.2, 12.1±0.2, 14.0±0.2, 17.0±0.2, 17.5±0.2, 20.9±0.2, 21.6±0.2, 25.0±0.2, and 29.5±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide disodium salt tetrahydrate having an X-ray powder diffraction pattern comprising one or more peaks selected from the group consisting of 4.8±0.2, 12.1±0.2, 14.0±0.2, 14.4±0.2, 17.0±0.2, 17.5±0.2, 20.9±0.2, 21.6±0.2, 25.0±0.2, 29.5±0.2, and 34.2±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide disodium salt tetrahydrate having an X-ray powder diffraction pattern substantially as shown in FIG. 2;

crystalline (E)-N-(4-(3-tert-butyl-5-(2,4-dioxo-3,4-dihydropyrimidin-1(2H)-yl)-2-methoxystyryl)phenyl)methanesulfonamide dipotassium salt tetrahydrate having an X-ray powder diffraction pattern comprising one or more peaks selected from the group consisting of 5.0±0.2, 11.9±0.2, 12.4±0.2, 13.7±0.2, 15.0±0.2, 16.5±0.2, 17.1±0.2, 20.8±0.2, 21.3±0.2, 22.2±0.2, 24.0±0.2, 26.4±0.2, and 29.3±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide dipotassium salt tetrahydrate having an X-ray powder diffraction pattern comprising one or more peaks selected from the group consisting of 5.0±0.2, 11.9±0.2, 12.4±0.2, 12.6±0.2, 13.7±0.2, 15.0±0.2, 16.5±0.2, 16.7±0.2, 17.1±0.2, 20.7±0.2, 20.8±0.2, 21.3±0.2, 22.2±0.2, 22.4±0.2, 24.0±0.2, 26.4±0.2, and 29.3±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide dipotassium salt tetrahydrate having an X-ray powder diffraction pattern substantially as shown in FIG. 4;

crystalline (E)-N-(4-(3-tert-butyl-5-(2,4-dioxo-3,4-dihydropyrimidin-1(2H)-yl)-2-methoxystyryl)phenyl)methanesulfonamide dipotassium salt tetrahydrate having unit cell parameters, wherein a is 14.5 Å, b is 10.8 Å, and c is 35.8 Å;

crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate having an X-ray powder diffraction pattern comprising one or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate having an X-ray powder diffraction pattern comprising one or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 22.1±0.2, 22.5±0.2, 22.6±0.2, and 23.0±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate having an X-ray powder diffraction pattern comprising five or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate having unit cell parameters, wherein a is 9.0 Å, b is 8.3 Å, and c is 18.6 Å;

crystalline (E)-N-(4-(3-tert-butyl-5-(2,4-dioxo-3,4-dihydropyrimidin-1(2H)-yl)-2-methoxystyryl)phenyl)methanesulfonamide monopotassium salt dihydrate having an X-ray powder diffraction pattern comprising one or more peaks selected from the group consisting of 7.7±0.2, 8.8±0.2, 16.1±0.2, and 19.7±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide monopotassium salt dihydrate having an X-ray powder diffraction pattern comprising one or more peaks selected from the group consisting of 7.7±0.2, 8.8±0.2, 12.4±0.2, 14.0±0.2, 16.1±0.2, 17.7±0.2, 19.2±0.2, 19.7±0.2, 23.1±0.2, and 29.2±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide monopotassium salt dihydrate having an X-ray powder diffraction pattern substantially as shown in FIG. 6;

crystalline (E)-N-(4-(3-tert-butyl-5-(2,4-dioxo-3,4-dihydropyrimidin-1(2H)-yl)-2-methoxystyryl)phenyl)methanesulfonamide 1/7 potassium salt having an X-ray powder diffraction pattern comprising one or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 21.2±0.2, 22.1±0.2, and 22.9±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide 1/7 potassium salt having an X-ray powder diffraction pattern comprising one or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 20.8±0.2, 21.2±0.2, 22.1±0.2, 22.9±0.2, 24.3±0.2, 24.9±0.2, and 25.1±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide 1/7 potassium salt having an X-ray powder diffraction pattern substantially as shown in FIG. 8;

crystalline (E)-N-(4-(3-tert-butyl-5-(2,4-dioxo-3,4-dihydropyrimidin-1(2H)-yl)-2-methoxystyryl)phenyl)methanesulfonamide monodiethylamine salt tetrahydrate having an X-ray powder diffraction pattern comprising one or more peaks selected from the group consisting of 9.5±0.2, 10.0±0.2, 11.8±0.2, 12.1±0.2, 14.4±0.2, 16.8±0.2, 17.6±0.2, 19.8±0.2, 20.8±0.2, 21.4±0.2, 21.8±0.2, and 29.8±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide monodiethylamine salt tetrahydrate having an X-ray powder diffraction pattern comprising one or more peaks selected from the group consisting of 9.5±0.2, 10.0±0.2, 11.8±0.2, 12.1±0.2, 14.4±0.2, 16.8±0.2, 17.6±0.2, 19.4±0.2, 19.8±0.2, 20.8±0.2, 21.4±0.2, 21.8±0.2, 21.9±0.2, and 29.8±0.2 degrees 2θ;

crystalline (E)-N-(4-(3-tert-butyl-5-(2,4-dioxo-3,4-dihydropyrimidin-1(2H)-yl)-2-methoxystyryl)phenyl)methanesulfonamide monodiethylamine salt tetrahydrate having an X-ray powder diffraction pattern substantially as shown in FIG. 9;

crystalline pattern A (E)-N-(4-(3-tert-butyl-5-(2,4-dioxo-3,4-dihydropyrimidin-1(2H)-yl)-2-methoxystyryl)phenyl)methanesulfonamide having an X-ray powder diffraction pattern comprising one or more peaks selected from the group consisting of 5.8±0.2, 9.9±0.2, 11.8±0.2, 12.4±0.2, 14.5±0.2, 18.8±0.2, 22.7±0.2, and 29.2±0.2 degrees 2θ;

crystalline pattern A (E)-N-(4-(3-tert-butyl-5-(2,4-dioxo-3,4-dihydropyrimidin-1(2H)-yl)-2-methoxystyryl)phenyl)methanesulfonamide having an X-ray powder diffraction pattern comprising one or more peaks selected from the group consisting of 5.8±0.2, 9.9±0.2, 11.8±0.2, 12.4±0.2, 14.0±0.2, 14.5±0.2, 15.3±0.2, 18.5±0.2, 18.8±0.2, 22.2±0.2, 22.7±0.2, 23.8±0.2, 26.0±0.2, and 29.2±0.2 degrees 2θ;

crystalline pattern A (E)-N-(4-(3-tert-butyl-5-(2,4-dioxo-3,4-dihydropyrimidin-1(2H)-yl)-2-methoxystyryl)phenyl)methanesulfonamide having an X-ray powder diffraction pattern substantially as shown in FIG. 11;

crystalline pattern B (E)-N-(4-(3-tert-butyl-5-(2,4-dioxo-3,4-dihydropyrimidin-1(2H)-yl)-2-methoxystyryl)phenyl)methanesulfonamide having an X-ray powder diffraction pattern comprising one or more peaks selected from the group consisting of 11.5±0.2, 13.3±0.2, 15.4±0.2, 16.4±0.2, 17.1±0.2, 18.6±0.2, 19.4±0.2, 20.4±0.2, 21.6±0.2, 22.4±0.2, 24.0±0.2, 26.8±0.2, and 29.0±0.2 degrees 2θ;

crystalline pattern B (E)-N-(4-(3-tert-butyl-5-(2,4-dioxo-3,4-dihydropyrimidin-1(2H)-yl)-2-methoxystyryl)phenyl)methanesulfonamide having an X-ray powder diffraction pattern substantially as shown in FIG. 13;

crystalline pattern C (E)-N-(4-(3-tert-butyl-5-(2,4-dioxo-3,4-dihydropyrimidin-1(2H)-yl)-2-methoxystyryl)phenyl)methanesulfonamide having an X-ray powder diffraction pattern comprising one or more peaks selected from the group consisting of 7.7±0.2, 10.1±0.2, 10.6±0.2, 12.0±0.2, 13.4±0.2, 16.2±0.2, 19.4±0.2, 20.5±0.2, 21.4±0.2, 22.0±0.2, 22.6±0.2, 24.3±0.2, and 27.6±0.2 degrees 2θ;

crystalline pattern C (E)-N-(4-(3-tert-butyl-5-(2,4-dioxo-3,4-dihydropyrimidin-1(2H)-yl)-2-methoxystyryl)phenyl)methanesulfonamide having an X-ray powder diffraction pattern substantially as shown in FIG. 14;

crystalline pattern D (E)-N-(4-(3-tert-butyl-5-(2,4-dioxo-3,4-dihydropyrimidin-1(2H)-yl)-2-methoxystyryl)phenyl)methanesulfonamide having an X-ray powder diffraction pattern comprising one or more peaks selected from the group consisting of 5.8±0.2, 10.7±0.2, 11.2±0.2, 15.2±0.2, 16.1±0.2, 16.9±0.2, 19.9±0.2, 22.1±0.2, 24.7±0.2, and 26.0±0.2 degrees 2θ;

crystalline pattern D (E)-N-(4-(3-tert-butyl-5-(2,4-dioxo-3,4-dihydropyrimidin-1(2H)-yl)-2-methoxystyryl)phenyl)methanesulfonamide having an X-ray powder diffraction pattern comprising one or more peaks selected from the group consisting of 5.8±0.2, 10.7±0.2, 11.2±0.2, 15.2±0.2, 16.1±0.2, 16.9±0.2, 17.1±0.2, 19.9±0.2, 20.1±0.2, 22.1±0.2, 24.7±0.2, and 26.0±0.2 degrees 2θ;

crystalline pattern D (E)-N-(4-(3-tert-butyl-5-(2,4-dioxo-3,4-dihydropyrimidin-1(2H)-yl)-2-methoxystyryl)phenyl)methanesulfonamide having an X-ray powder diffraction pattern substantially as shown in FIG. 15;

crystalline pattern A (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern comprising one or more peaks selected from the group consisting of 5.1±0.2, 7.9±0.2, 9.5±0.2, 10.3±0.2, 13.7±0.2, 16.5±0.2, 17.1±0.2, 17.5±0.2, 18.8±0.2, 19.2±0.2, 20.7±0.2, 21.3±0.2, 21.6±0.2, 25.8±0.2, 26.8±0.2, and 28.4±0.2 degrees 2θ;

crystalline pattern A (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern substantially as shown in FIG. 16;

crystalline pattern A (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern comprising one or more peaks selected from the group consisting of 6.3±0.2, 7.7±0.2, 10.4±0.2, 12.7±0.2, 13.3±0.2, 14.9±0.2, 15.4±0.2, 16.4±0.2, 18.6±0.2, 18.9±0.2, 19.4±0.2, 22.5±0.2, 23.5±0.2, 24.0±0.2, 26.8±0.2, and 29.0±0.2 degrees 2θ;

crystalline pattern B (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern comprising one or more peaks selected from the group consisting of 6.3±0.2, 7.7±0.2, 10.4±0.2, 12.7±0.2, 13.3±0.2, 13.5±0.2, 14.9±0.2, 15.4±0.2, 16.4±0.2, 18.5±0.2, 18.6±0.2, 18.9±0.2, 19.4±0.2, 22.5±0.2, 23.5±0.2, 24.0±0.2, 26.8±0.2, and 29.0±0.2 degrees 2θ;

crystalline pattern B (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern substantially as shown in FIG. 18;

crystalline pattern C (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern comprising one or more peaks selected from the group consisting of 10.5±0.2, 13.3±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ;

crystalline pattern C (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern comprising one or more peaks selected from the group consisting of 10.5±0.2, 13.3±0.2, 13.5±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ;

crystalline pattern C (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern substantially as shown in FIG. 20;

crystalline pattern D (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern comprising one or more peaks selected from the group consisting of 6.6±0.2, 10.0±0.2, 10.5±0.2, 11.1±0.2, 11.6±0.2, 12.2±0.2, 14.2±0.2, 16.6±0.2, 17.1±0.2, 17.7±0.2, 18.5±0.2, 18.8±0.2, 19.3±0.2, 21.4±0.2, 22.7±0.2, 23.1±0.2, 23.6±0.2, 24.6±0.2, 25.2±0.2, 27.2±0.2, 29.1±0.2, and 31.0±0.2 degrees 2θ;

crystalline pattern D (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern comprising one or more peaks selected from the group consisting of 6.6±0.2, 10.0±0.2, 10.5±0.2, 11.1±0.2, 11.6±0.2, 12.2±0.2, 12.5±0.2, 14.2±0.2, 16.6±0.2, 17.1±0.2, 17.7±0.2, 18.5±0.2, 18.8±0.2, 19.3±0.2, 21.4±0.2, 22.7±0.2, 22.8±0.2, 23.1±0.2, 23.6±0.2, 24.6±0.2, 24.9±0.2, 25.2±0.2, 27.2±0.2, 29.1±0.2, and 31.0±0.2 degrees 2θ;

crystalline pattern D (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern substantially as shown in FIG. 22;

crystalline pattern D (E)-N-(4-(3-tert-butyl-5-(2,4-dioxo-3,4-dihydropyrimidin-1(2H)-yl)-2-methoxystyryl)phenyl)methanesulfonamide hydrate having unit cell parameters, wherein a is 17.8 Å, b is 9.6 Å, and c is 27.0 Å;

crystalline pattern E (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern comprising one or more peaks selected from the group consisting of 6.2±0.2, 7.8±0.2, 10.2±0.2, 10.7±0.2, 12.1±0.2, 16.3±0.2, 19.7±0.2, 20.9±0.2, 21.8±0.2, 24.5±0.2, and 28.0±0.2 degrees 2θ;

crystalline pattern E (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern comprising one or more peaks selected from the group consisting of 6.2±0.2, 7.8±0.2, 10.2±0.2, 10.4±0.2, 10.7±0.2, 12.1±0.2, 16.3±0.2, 19.7±0.2, 20.9±0.2, 21.8±0.2, 24.5±0.2, and 28.0±0.2 degrees 2θ;

crystalline pattern E (E)-N-(4-(3-tert-butyl-5-(2,4-dioxo-3,4-dihydropyrimidin-1(2H)-yl)-2-methoxystyryl)phenyl)methanesulfonamide hydrate having an X-ray powder diffraction pattern substantially as shown in FIG. 23; and crystalline pattern E (E)-N-(4-(3-tert-butyl-5-(2,4-dioxo-3,4-dihydropyrimidin-1(2H)-yl)-2-methoxystyryl)phenyl)methanesulfonamide hydrate having unit cell parameters, wherein a is 9.5 Å, b is 14.5 Å, and c is 17.3 Å.

23. A pharmaceutical composition comprising one or more crystalline forms recited in claim 22 and one or more excipients.

24. The pharmaceutical composition of claim 23, wherein the pharmaceutical composition further comprises one or more additional therapeutic agents.

25. The pharmaceutical composition of claim 24, wherein the one or more additional therapeutic agents are selected from the group consisting of interferon agent, ribavirin, HCV inhibitor, and HIV inhibitor.

26. The pharmaceutical composition of claim 24, wherein the one or more additional therapeutic agents is an HCV inhibitor.

27. A method for inhibiting replication of a ribonucleic acid (RNA) virus, wherein the method comprises exposing the virus to one or more crystalline forms recited in claim 22.

28. The method of claim 27, wherein the RNA virus is hepatitis C virus (HCV).

29. A method for treating hepatitis C in a mammal in need of such treatment, wherein the method comprises administering to the mammal one or more crystalline forms recited in claim 22.

30. The method of claim 29, wherein the mammal is human.

31. The method of claim 29, wherein the method further comprises administering to the mammal one or more additional therapeutic agents.

32. The method of claim 31, wherein one or more additional therapeutic agents are selected from the group consisting of interferon agent, ribavirin, HCV inhibitor, and HIV inhibitor.

33. The method of claim 31, wherein the one or more additional therapeutic agents is an HCV inhibitor.

34. A process for preparing a crystalline (E)-N-(4-(3-tert-butyl-5-(2,4-dioxo-3,4-dihydropyrimidin-1(2H)-yl)-2-methoxystyryl)phenyl)methanesulfonamide monopotassium salt hydrate comprising contacting a potassium base and a mixture of (E)-N-(4-(3-tert-butyl-5-(2,4-dioxo-3,4-dihydropyrimidin-1(2H)-yl)-2-methoxystyryl)phenyl)methanesulfonamide in a first solvent to form a solution.

35. The process of claim 34, wherein the potassium base is potassium hydroxide.

36. The process of claim 34, wherein the first solvent is tetrahydrofuran.

37. The process of claim 34, further comprising adding a second solvent to the solution.

38. The process of claim 37, wherein the second solvent is selected from the group consisting of tetrahydrofuran and ethanol.

39. The process of claim 34, wherein the crystalline (E)-N-(4-(3-tert-butyl-5-(2,4-dioxo-3,4-dihydropyrimidin-1(2H)-yl)-2-methoxystyryl)phenyl)methanesulfonamide monopotassium salt hydrate is crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate.

40. The process of claim 39, wherein the crystalline (E)-N-(4-(3-tert-butyl-5-(2,4-dioxo-3,4-dihydropyrimidin-1(2H)-yl)-2-methoxystyryl)phenyl)methanesulfonamide monopotassium salt trihydrate has an X-ray powder diffraction pattern comprising one or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 22.1±0.2, 22.5±0.2, 22.6±0.2, and 23.0±0.2 degrees 2θ.

* * * * *

SEQUENCE LISTING

```
<160> NUMBER OF SEQ ID NOS: 1

<210> SEQ ID NO 1
<211> LENGTH: 171
<212> TYPE: RNA
<213> ORGANISM: Artificial
<220> FEATURE:
<223> OTHER INFORMATION: RNA template
```

```
<400> SEQUENCE: 1
gggcgaauug ggcccucuag augcaugcuc gagcggccgc cagugugaug gauaucugca        60
gaauucgccc uugguggcuc caucuuagcc cuagucacgg cuagcuguga aagguccgug       120
agccgcuuga cugcagagag ugcugauacu ggccucucug cagaucaagu c               171
```